(12) United States Patent
Gharat et al.

(10) Patent No.: US 9,006,257 B2
(45) Date of Patent: Apr. 14, 2015

(54) BICYCLIC COMPOUNDS AS MPGES-1 INHIBITORS

(71) Applicant: Glenmark Pharmaceuticals S.A., La Chaux-de-Fonds (CH)

(72) Inventors: Laxmikant Atmaram Gharat, Maharashtra (IN); Abhisek Banerjee, Howrah (IN); Neelima Khairatkar-Joshi, Maharashtra (IN); Vidya Ganapati Kattige, Maharashtra (IN)

(73) Assignee: Glenmark Pharmaceuticals S.A., La Chaux-de-Fonds (CH)

(*) Notice: Subject to any disclaimer, the term of this patent is extended or adjusted under 35 U.S.C. 154(b) by 16 days.

(21) Appl. No.: 13/761,937

(22) Filed: Feb. 7, 2013

(65) Prior Publication Data
US 2013/0210844 A1 Aug. 15, 2013

Related U.S. Application Data

(60) Provisional application No. 61/602,227, filed on Feb. 23, 2012, provisional application No. 61/645,193, filed on May 10, 2012, provisional application No. 61/707,838, filed on Sep. 28, 2012.

(30) Foreign Application Priority Data

| | | |
|---|---|---|
| Feb. 9, 2012 | (IN) | 372/MUM/2012 |
| Apr. 24, 2012 | (IN) | 1302/MUM/2012 |
| Sep. 5, 2012 | (IN) | 2576/MUM/2012 |

(51) Int. Cl.
*A01N 43/54* (2006.01)
*A61K 31/517* (2006.01)
*C07D 239/88* (2006.01)
*C07D 215/233* (2006.01)
*C07D 239/94* (2006.01)
*C07D 401/12* (2006.01)
*C07D 217/22* (2006.01)
*C07D 217/24* (2006.01)

(52) U.S. Cl.
CPC .......... *C07D 239/88* (2013.01); *C07D 215/233* (2013.01); *C07D 239/94* (2013.01); *C07D 401/12* (2013.01); *C07D 217/22* (2013.01); *C07D 217/24* (2013.01)

(58) Field of Classification Search
CPC ............. C07D 401/12; C07D 215/233; C07D 217/22; C07D 217/24; C07D 239/88; C07D 239/94

USPC .......... 514/266.2, 266.21, 266.3, 266.4, 312; 544/283, 284, 287, 293; 546/153
See application file for complete search history.

(56) References Cited

U.S. PATENT DOCUMENTS 8,519,149 B2 * 8/2013 Gharat et al. ............... 548/302.1

FOREIGN PATENT DOCUMENTS

| EP | 2495244 A1 * | 9/2012 | C07D 405/14 |
|---|---|---|---|
| WO | WO-2006063466 A1 | 6/2006 | |
| WO | WO-2007059610 A1 | 5/2007 | |
| WO | WO-2010034796 A1 | 4/2010 | |
| WO | WO-2010100249 A1 | 9/2010 | |
| WO | WO 2011023812 A1 * | 3/2011 | C07D 401/04 |
| WO | WO-2012055995 A1 | 5/2012 | |
| WO | WO-2012110860 A1 | 8/2012 | |

OTHER PUBLICATIONS

Gomez-Hernandez, *Atherosclerosis* 2006,187, 139-49.
Kojima, et. al, *The Journal of Immunology* 2008, 180, 8361-6.
Korotkova, et al., *Annals of the Rheumatic Diseases* 2008, 67, 1596-1602.
Nakanishi, et. al., *Cancer Research* 2008, 68(9), 3251-9.
Schroder, et al., *Journal of Lipid Research* 2006, 47, 1071-80.
Wang, et. al., *Circulation*, 2008, 117, 1302-1309.
Wang, *Proceedings of National Academy of Sciences* 2006, 103(39), 14507-12.
Xu, et. al., *The Journal of Pharmacology and Experimental Therapeutics* 2008, 326, 754-63.
International Search Report issued in PCT/IB2013/051004 on May 17, 2013.

* cited by examiner

*Primary Examiner* — My-Chau T Tran
(74) *Attorney, Agent, or Firm* — Blank Rome LLP

(57) ABSTRACT

The present disclosure is directed to compounds of formula (I), and pharmaceutically acceptable salts thereof, as mPGES-1 inhibitors. These compounds are inhibitors of the microsomal prostaglandin E synthase-1 (mPGES-1) enzyme and are therefore useful in the treatment of pain and/or inflammation from a variety of diseases or conditions, such as asthma, osteoarthritis, rheumatoid arthritis, acute or chronic pain and neurodegenerative diseases.

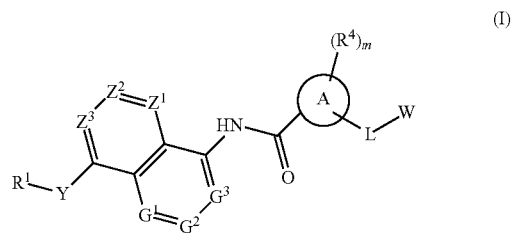

42 Claims, No Drawings

BICYCLIC COMPOUNDS AS MPGES-1 INHIBITORS

RELATED APPLICATIONS

This application claims the benefit of Indian Provisional Application Nos. 372/MUM/2012, filed on Feb. 9, 2012; 1302/MUM/2012, filed on Apr. 24, 2012; and 2576/MUM/2012, filed on Sep. 5, 2012 and U.S. Provisional Application Nos. 61/602,227, filed on Feb. 23, 2012; 61/645,193, filed on May 10, 2012; and 61/707,838 filed on Sep. 28, 2012, each of which is hereby incorporated by reference in its entirety.

TECHNICAL FIELD

The present application relates to bicyclic compounds which may be useful as microsomal prostaglandin E synthase-1 (mPGES-1) inhibitors.

BACKGROUND OF THE INVENTION

There are many diseases or disorders that are inflammatory in their nature. One of the major problems associated with existing treatments of inflammatory conditions is inadequate efficacy and/or the prevalence of side effects. Inflammatory diseases that affect the population include asthma, inflammatory bowel disease, rheumatoid arthritis, osteoarthritis, rhinitis, conjunctivitis and dermatitis. Inflammation is also a common cause of pain.

The enzyme cyclooxygenase (COX) converts arachidonic acid to an unstable intermediate, prostaglandin $H_2$ ($PGH_2$), which is further converted to other prostaglandins, including $PGE_2$, $PGF_{2\alpha}$, $PGD_2$, prostacyclin and thromboxane $A_2$. These arachidonic acid metabolites are known to have pronounced physiological and pathophysiological activity, including pro-inflammatory effects. The COX enzyme exists in two forms, one that is constitutively expressed in many cells and tissues (COX-1), and another that in most cells and tissues is induced by pro-inflammatory stimuli, such as cytokines, during an inflammatory response (COX-2).

Among all prostaglandin metabolites, $PGE_2$ is particularly known to be a strong pro-inflammatory mediator, and is also known to induce fever and pain. Consequently, numerous drugs have been developed with a view to inhibiting the formation of $PGE_2$, including "NSAIDs" (non-steroidal anti-inflammatory drugs) and "coxibs" (selective COX-2 inhibitors). These drugs act predominantly by inhibition of COX-1 and/or COX-2, thereby reducing the formation of $PGE_2$. However, the inhibition of COXs has the disadvantage in that it results in the reduction of the formation of all metabolites of $PGH_2$, thereby decreasing the beneficial properties of some of the metabolites. In view of this, drugs which act by inhibition of COXs are therefore suspected to cause adverse biological effects. For example, the non-selective inhibition of COXs by NSAIDs may give rise to gastrointestinal side-effects and affect platelet and renal function. Even the selective inhibition of COX-2 by coxibs, whilst reducing such gastrointestinal side-effects, is believed to give rise to cardiovascular problems.

A combination of pharmacological, genetic and neutralizing antibody approaches demonstrates the importance of $PGE_2$ in inflammation. The conversion of $PGH_2$ to $PGE_2$ by prostaglandin E synthases (PGES) may, therefore, represent a pivotal step in the propagation of inflammatory stimuli. Microsomal prostaglandin E synthase-1 (mPGES-1) is an inducible PGES after exposure to pro-inflammatory stimuli. mPGES-1 is induced in the periphery and CNS by inflammation, and represents therefore a target for acute and chronic inflammatory disorders. $PGE_2$ is a major prostanoid, produced from arachidonic acid liberated by phospholipases (PLAs), which drives the inflammatory processes. Arachidonic acid is transformed by the action of prostaglandin H synthase (PGH synthase, cycloxygenase) into $PGH_2$ which is a substrate for mPGES-1, the terminal enzyme transforming $PGH_2$ to the pro-inflammatory $PGE_2$.

$PGH_2$ may be transformed to $PGE_2$ by prostaglandin E synthases (PGES). There are two microsomal prostaglandin E synthases (mPGES-1 and mPGES-2), and one cytosolic prostaglandin E synthase (cPGES). Thus, agents that are capable of inhibiting the action of mPGES-1, and thus reducing the formation of the specific arachidonic acid metabolite $PGE_2$, are beneficial in the treatment of inflammation. Further, agents that are capable of inhibiting the action of the proteins involved in the synthesis of the leukotrienes are also beneficial in the treatment of asthma and COPD.

Blocking the formation of $PGE_2$ in animal models of inflammatory pain results in reduced inflammation, pain and fever response (Kojima et. al, *The Journal of Immunology* 2008, 180, 8361-6; Xu et. al., *The Journal of Pharmacology and Experimental Therapeutics* 2008, 326, 754-63). In abdominal aortic aneurism, inflammation leads to connective tissue degradation and smooth muscle apoptosis ultimately leading to aortic dilation and rupture. In animals lacking mPGES-1 a slower disease progression and disease severity has been demonstrated (Wang et. al., *Circulation,* 2008, 117, 1302-1309).

Several lines of evidence indicate that $PGE_2$ is involved in malignant growth. $PGE_2$ facilitates tumor progression by stimulation of cellular proliferation and angiogenesis and by modulation of immunosupression. In support of a role for $PGE_2$ in cancers, genetic deletion of mPGES-1 in mice suppresses intestinal tumourogenesis (Nakanishi et. al., *Cancer Research* 2008, 68(9), 3251-9). In human beings, mPGES-1 is also upregulated in cancers such as colorectal cancer (*Schroder Journal of Lipid Research* 2006, 47, 1071-80).

Myositis is chronic muscle disorder characterized by muscle weakness and fatigue. Proinflammatory cytokines and prostanoids have been implicated in the development of myositis. In skeletal muscle tissue from patients suffering from myositis an increase in cyclooxygenases and mPGES-1 has been demonstrated, implicating mPGES-1 as a target for treating this condition. (*Korotkova Annals of the Rheumatic Diseases* 2008, 67, 1596-1602).

In atherosclerosis inflammation of the vasculature leads to atheroma formation that eventually may progress into infarction. In patients with carotid atherosclerosis an increase in mPGES-1 in plaque regions has been reported (Gomez-Hernandez *Atherosclerosis* 2006, 187, 139-49). In an animal model of atherosclerosis, mice lacking the mPGES-1 receptor were found to show a retarded atherogenesis and a concomitant reduction in macrophage-derived foam cells together with an increase in vascular smooth muscle cells (Wang, *Proceedings of National Academy of Sciences* 2006, 103(39), 14507-12).

International Publication Nos. WO 2006/063466, WO 2007/059610, WO 2010/034796, WO 2010/100249, WO 2012/055995, and WO 2012/110860 disclose numerous heterocyclic compounds which are stated to be inhibitors of microsomal prostaglandin E synthase-1 (mPGES-1) enzyme.

The present application is directed to compounds that may be inhibitors of the mPGES-1 enzyme and would therefore be useful for the treatment of pain and inflammation in a variety of diseases or conditions.

SUMMARY OF THE INVENTION

In one aspect, the present invention relates to a compound of formula (I):

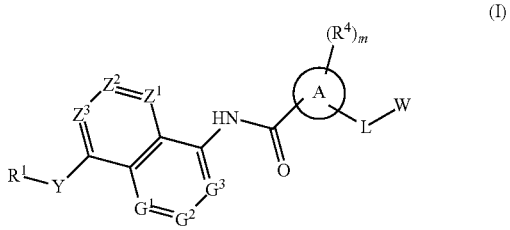

or a pharmaceutically acceptable salt thereof, wherein

Y is a bond or selected from $NR^c$, O and $CR^cR^d$;

A is selected from $C_{6-14}$aryl, 5-14 membered heteroaryl and 3-15 membered heterocyclyl;

$Z^1$, $Z^2$ and $Z^3$, which may be same or different, are independently selected from N and $CR^2$; with a proviso that $Z^1$, $Z^2$ and $Z^3$ are not N simultaneously;

$G^1$, $G^2$ and $G^3$, which may be same or different, are independently selected from N and $CR^3$; with a proviso that $G^1$, $G^2$ and $G^3$ are not N simultaneously; with another proviso that at least one of $Z^1$, $Z^2$, $Z^3$, $G^1$, $G^2$ and $G^3$ is N;

L is a bond or selected from $(CR^xR^y)_nNR^x$, $(CR^xR^y)_nC(O)NR^x$, $(CR^xR^y)_nC(O)O$, $(CR^xR^y)_nNR^xC(O)$, $(CR^xR^y)_nNR^xC(O)NR^y$, $(CR^xR^y)_nNR^xC(O)O$, $(CR^xR^y)_nNR^xSO_2$, $(CR^xR^y)_nOC(O)$, $(CR^xR^y)_nOC(O)O$, $(CR^xR^y)_nOC(O)NR^x$, $(CR^xR^y)_nS(O)$, $(CR^xR^y)_nSO_2$, $(CR^xR^y)_nS(O)NR^x$, $(CR^xR^y)_nSO_2NR^x$ and $(CR^xR^y)_nS$;

W is selected from hydrogen, substituted or unsubstituted $C_{1-8}$alkyl, substituted or unsubstituted $C_{2-10}$alkenyl, substituted or unsubstituted $C_{2-10}$alkynyl, substituted or unsubstituted $C_{1-8}$alkoxy$C_{1-8}$alkyl, substituted or unsubstituted halo$C_{1-8}$alkyl, substituted or unsubstituted hydroxy$C_{1-8}$alkyl, substituted or unsubstituted $C_{3-12}$cycloalkyl, substituted or unsubstituted $C_{3-8}$cycloalkenyl, substituted or unsubstituted $C_{6-14}$aryl, substituted or unsubstituted 3 to 15 membered heterocyclyl, and substituted or unsubstituted 5 to 14 membered heteroaryl;

$R^1$ is selected from hydrogen, substituted or unsubstituted $C_{1-8}$alkyl, substituted or unsubstituted $C_{2-10}$alkenyl, substituted or unsubstituted $C_{2-10}$alkynyl, substituted or unsubstituted $C_{1-8}$alkoxy$C_{1-8}$alkyl, substituted or unsubstituted halo$C_{1-8}$alkyl, substituted or unsubstituted hydroxy$C_{1-8}$alkyl, substituted or unsubstituted $C_{3-12}$cycloalkyl, substituted or unsubstituted $C_{3-8}$cycloalkyl$C_{1-8}$alkyl, substituted or unsubstituted $C_{3-8}$cycloalkenyl, substituted or unsubstituted $C_{3-8}$cycloalkenyl$C_{1-8}$alkyl, substituted or unsubstituted $C_{6-14}$aryl, substituted or unsubstituted $C_{6-14}$aryl$C_{1-8}$alkyl, substituted or unsubstituted 3-15 membered heterocyclyl, substituted or unsubstituted 3-15 membered heterocyclyl$C_{1-8}$alkyl, substituted or unsubstituted 5-14 membered heteroaryl and substituted or unsubstituted 5-14 membered heteroaryl$C_{1-8}$alkyl;

each occurrence of $R^2$ and $R^3$, which may be the same or different, are independently selected from hydrogen, halogen, nitro, cyano, hydroxyl, substituted or unsubstituted $C_{1-8}$alkyl, substituted or unsubstituted $C_{2-10}$alkenyl, substituted or unsubstituted $C_{2-10}$alkynyl, substituted or unsubstituted $C_{1-8}$alkoxy, substituted or unsubstituted $C_{1-8}$alkoxy$C_{1-8}$alkyl, substituted or unsubstituted halo$C_{1-8}$alkyl, substituted or unsubstituted halo$C_{1-8}$alkoxy, substituted or unsubstituted hydroxy$C_{1-8}$alkyl, substituted or unsubstituted $C_{3-12}$cycloalkyl, substituted or unsubstituted $C_{3-8}$cycloalkyl$C_{1-8}$alkyl, substituted or unsubstituted $C_{3-8}$cycloalkenyl, substituted or unsubstituted $C_{3-8}$cycloalkenyl$C_{1-8}$alkyl, substituted or unsubstituted $C_{6-14}$aryl, substituted or unsubstituted $C_{6-14}$aryloxy, substituted or unsubstituted $C_{6-14}$aryl$C_{1-8}$alkyl, substituted or unsubstituted 3-15 membered heterocyclyl, substituted or unsubstituted 3-15 membered heterocyclyl$C_{1-8}$alkyl, substituted or unsubstituted 5-14 membered heteroaryl, substituted or unsubstituted 5-14 membered heteroaryl$C_{1-8}$alkyl, $-C(O)R^a$, $-C(O)NR^aR^b$, $-C(O)OR^a$, $-NR^aR^b$, $-NR^aC(O)R^b$, $-NR^aC(O)NR^aR^b$, $-NR^aC(O)OR^b$, $-N(R^a)SO_2R^b$, $-OC(O)R^a$, $-OC(O)OR^a$, $-OC(O)NR^aR^b$, $-S(O)R^a$, $-SO_2R^a$, $-S(O)NR^aR^b$, $-SO_2NR^aR^b$ and $-SR^a$;

each occurrence of $R^4$ is independently selected from halogen, nitro, cyano, hydroxyl, substituted or unsubstituted $C_{1-8}$alkyl, substituted or unsubstituted $C_{2-10}$alkenyl, substituted or unsubstituted $C_{2-10}$alkynyl, substituted or unsubstituted $C_{1-8}$alkoxy, substituted or unsubstituted $C_{1-8}$alkoxy$C_{1-8}$alkyl, substituted or unsubstituted halo$C_{1-8}$alkyl, substituted or unsubstituted halo$C_{1-8}$alkoxy, substituted or unsubstituted hydroxy$C_{1-8}$alkyl, substituted or unsubstituted $C_{3-12}$cycloalkyl, substituted or unsubstituted $C_{3-8}$cycloalkyl$C_{1-8}$alkyl, substituted or unsubstituted $C_{3-8}$cycloalkenyl, substituted or unsubstituted $C_{3-8}$cycloalkenyl$C_{1-8}$alkyl, substituted or unsubstituted $C_{6-14}$aryl, $C_{6-14}$aryloxy, substituted or unsubstituted $C_{6-14}$aryl$C_{1-8}$alkyl, substituted or unsubstituted 3-15 membered heterocyclyl, substituted or unsubstituted 3-15 membered heterocyclyl$C_{1-8}$alkyl, substituted or unsubstituted 5-14 membered heteroaryl, substituted or unsubstituted 5-14 membered heteroaryl$C_{1-8}$alkyl; $-C(O)R^a$, $-C(O)NR^aR^b$, $-C(O)OR^a$, $-NR^aR^b$, $-NR^aC(O)R^b$, $-NR^aC(O)NR^aR^b$, $-NR^aC(O)OR^b$, $-N(R^a)SO_2R^b$, $-OC(O)R^a$, $-OC(O)OR^a$, $-OC(O)NR^aR^b$, $-S(O)R^a$, $-SO_2R^a$, $-S(O)NR^aR^b$, $-SO_2NR^aR^b$ and $-SR^a$;

at each occurrence, $R^a$ and $R^b$, which may be the same or different, are independently selected from hydrogen, substituted or unsubstituted $C_{1-8}$alkyl, substituted or unsubstituted $C_{1-8}$alkoxy$C_{1-8}$alkyl, substituted or unsubstituted halo$C_{1-8}$alkyl, substituted or unsubstituted hydroxy$C_{1-8}$alkyl, substituted or unsubstituted $C_{3-12}$cycloalkyl, substituted or unsubstituted $C_{3-8}$cycloalkyl$C_{1-8}$alkyl, substituted or unsubstituted $C_{6-14}$aryl, substituted or unsubstituted $C_{6-14}$aryl$C_{1-8}$alkyl, substituted or unsubstituted 3-15 membered heterocyclyl, substituted or unsubstituted 3-15 membered heterocyclyl$C_{1-8}$alkyl, substituted or unsubstituted 5-14 membered heteroaryl and substituted or unsubstituted 5-14 membered heteroaryl$C_{1-8}$alkyl; or $R^a$ and $R^b$ together with the atom to which they are attached, form a cyclic ring which is substituted or unsubstituted and wherein the cyclic ring optionally contains one or more hetero atoms selected from O, N or S;

at each occurrence, $R^c$ and $R^d$, which may be the same or different, are independently selected from hydrogen, substituted or unsubstituted $C_{1-8}$alkyl, substituted or unsubstituted $C_{1-8}$alkoxy$C_{1-8}$alkyl, substituted or unsubstituted halo$C_{1-8}$alkyl, substituted or unsubstituted hydroxy$C_{1-8}$alkyl, substituted or unsubstituted $C_{3-12}$cycloalkyl, substituted or unsubstituted $C_{3-8}$cycloalkyl$C_{1-8}$alkyl, substituted or unsubstituted $C_{6-14}$aryl, substituted or unsubstituted $C_{6-14}$aryl$C_{1-8}$alkyl, substituted or unsubstituted 3-15 membered heterocyclyl, substituted or unsubstituted 3-15 membered heterocyclyl$C_{1-8}$alkyl, substituted or unsubstituted 5-14 membered heteroaryl and substituted or unsubstituted 5-14 membered heteroaryl$C_{1-8}$alkyl; or, when Y is $CR^cR^d$, $R^c$ and $R^d$ together with the 'C' atom to which they are attached, form a cyclic ring which is substituted or unsubstituted and wherein the cyclic ring optionally contains one or more hetero atoms selected from O, N or S; or, when Y is $NR^c$, $R^c$ and $R^1$ together with the 'N' atom to which they are attached, form a cyclic ring which is substituted or unsubstituted and wherein the cyclic ring optionally contains another hetero atom selected from O, N or S;

at each occurrence, $R^x$ and $R^y$, which may be the same or different, are independently selected from hydrogen, substituted or unsubstituted $C_{1-8}$alkyl, substituted or unsubstituted $C_{1-8}$alkoxy$C_{1-8}$alkyl, substituted or unsubstituted halo$C_{1-8}$alkyl, substituted or unsubstituted hydroxy$C_{1-8}$alkyl, substituted or unsubstituted $C_{3-12}$cycloalkyl, substituted or unsubstituted $C_{3-8}$cycloalkyl$C_{1-8}$alkyl, substituted or unsubstituted $C_{6-14}$aryl, substituted or unsubstituted $C_{6-14}$aryl$C_{1-8}$alkyl, substituted or unsubstituted 3-15 membered heterocyclyl, substituted or unsubstituted 3-15 membered heterocyclyl$C_{1-8}$alkyl, substituted or unsubstituted 5-14 membered heteroaryl and substituted or unsubstituted 5-14 membered heteroaryl$C_{1-8}$alkyl; or $R^x$ and $R^y$ together with the atom to which they are attached, form a cyclic ring which is substituted or unsubstituted and wherein the cyclic ring optionally contains one or more hetero atoms selected from O, N or S;

'm' is an integer ranging from 0 to 4, both inclusive; and

'n' is an integer ranging from 0 to 6, both inclusive.

The compounds of formula (I) may involve one or more embodiments. Embodiments of formula (I) include compounds of formula (II) and compounds of formula (III), as described hereinafter. It is to be understood that the embodiments below are illustrative of the present invention and are not intended to limit the claims to the specific embodiments exemplified. It is also to be understood that the embodiments defined herein may be used independently or in conjunction with any definition of any other embodiment defined herein. Thus, the invention contemplates all possible combinations and permutations of the various independently described embodiments. For example, the invention provides compounds of formula (I) as defined above wherein Y is O (according to an embodiment defined below), $R^2$ is hydrogen, $C_{1-4}$alkyl or halo$C_{1-8}$alkyl (according to another embodiment defined below) and $R^3$ is hydrogen or $C_{1-4}$alkyl.

According to one embodiment, specifically provided are compounds of formula (I), in which at least one of $Z^1$, $Z^2$ and $Z^3$ is $CR^2$.

According to another embodiment, specifically provided are compounds of formula (I), in which at least one of $Z^1$, $Z^2$ and $Z^3$ is N.

According to yet another embodiment, specifically provided are compounds of formula (I), in which $Z^1$ is N or $CR^2$, $Z^2$ is $CR^2$ and $Z^3$ is N or $CR^2$.

According to yet another embodiment, specifically provided are compounds of formula (I), in which $G^1$ is N or $CR^3$, and $G^2$ and $G^3$ are $CR^3$.

According to yet another embodiment, specifically provided are compounds of formula (I), in which $Z^1$ is N or $CR^2$, $Z^2$ is $CR^2$, $Z^3$ is N or $CR^2$, $G^1$ is N or $CR^3$, and $G^2$ and $G^3$ are $CR^3$; with proviso that at least one of $Z^1$, $Z^2$, $Z^3$, $G^1$, $G^2$ and $G^3$ is N.

According to yet another embodiment, specifically provided are compounds of formula (I), in which each occurrence of $R^2$ is independently hydrogen, $C_{1-4}$alkyl (e.g. methyl, ethyl, or tert-butyl) or halo$C_{1-8}$alkyl (e.g. trifluoromethyl).

According to yet another embodiment, specifically provided are compounds of formula (I), in which each occurrence of $R^2$ is independently hydrogen, methyl or trifluoromethyl.

According to yet another embodiment, specifically provided are compounds of formula (I), in which each occurrence of $R^3$ is independently hydrogen or $C_{1-4}$alkyl (e.g. methyl, ethyl, or tert-butyl).

According to yet another embodiment, specifically provided are compounds of formula (I), in which each occurrence of $R^3$ is independently hydrogen or methyl.

According to yet another embodiment, specifically provided are compounds of formula (I), in which $Z^1$ is N, $Z^2$ is $CR^2$, $Z^3$ is N, and $G^1$, $G^2$ and $G^3$ are $CR^3$. In this embodiment, each occurrence of $R^2$ is independently hydrogen, methyl or trifluoromethyl and each occurrence of $R^3$ is independently hydrogen or methyl.

According to yet another embodiment, specifically provided are compounds of formula (I), in which $Z^1$ is N, $Z^2$ and $Z^3$ are $CR^2$, and $G^1$, $G^2$ and $G^3$ are $CR^3$. In this embodiment each occurrence of $R^2$ is independently hydrogen, methyl or trifluoromethyl and each occurrence of $R^3$ is independently hydrogen or methyl.

According to yet another embodiment, specifically provided are compounds of formula (I), in which $Z^1$ and $Z^2$ are $CR^2$, $Z^3$ is N, and $G^1$, $G^2$ and $G^3$ are $CR^3$. In this embodiment each occurrence of $R^2$ is independently hydrogen, methyl or trifluoromethyl and each occurrence of $R^3$ is independently hydrogen or methyl.

According to yet another embodiment, specifically provided are compounds of formula (I), in which $Z^1$, $Z^2$ and $Z^3$ are CH, and $G^1$ is N, $G^2$ and $G^3$ are CH.

According to yet another embodiment, specifically provided are compounds of formula (I), in which Y is O.

According to yet another embodiment, specifically provided are compounds of formula (I), in which Y is $NR^c$. In this embodiment, $R^c$ is hydrogen, $C_{1-4}$alkyl (e.g. methyl or ethyl) or $R^C$ and $R^1$, together with the N to which they are attached, form a morpholine ring.

According to yet another embodiment, specifically provided are compounds of formula (I), in which Y is NH.

According to yet another embodiment, specifically provided are compounds of formula (I), in which $R^1$ is substituted or unsubstituted $C_{1-8}$alkyl, preferably unsubstituted $C_{1-8}$alkyl, and more preferably unsubstituted $C_{1-4}$alkyl (e.g. methyl, ethyl, isopropyl, or tert-butyl).

According to yet another embodiment, specifically provided are compounds of formula (I), in which $R^1$ is methyl, ethyl, isopropyl or tert-butyl.

According to yet another embodiment, specifically provided are compounds of formula (I), in which $R^1$ is substituted or unsubstituted halo$C_{1-8}$alkyl, preferably unsubstituted halo$C_{1-8}$alkyl (e.g. 2,2,2-trifluoroethyl).

According to yet another embodiment, specifically provided are compounds of formula (I), in which $R^1$ is 2,2,2-trifluoroethyl.

According to yet another embodiment, specifically provided are compounds of formula (I), in which $R^1$ is substituted or unsubstituted $C_{6-14}$aryl, preferably substituted or unsubstituted phenyl, and more preferably substituted phenyl. In this embodiment, substituent(s) on the $C_{6-14}$aryl or phenyl may be one or more and are independently selected from halogen (e.g. F, Cl or Br), $C_{1-4}$alkyl (e.g. methyl or ethyl) and halo$C_{1-8}$alkyl (e.g. trifluoromethyl).

According to yet another embodiment, specifically provided are compounds of formula (I), in which $R^1$ is phenyl optionally substituted with one or more substituent(s) independently selected from halogen (e.g. F, Cl or Br), $C_{1-4}$alkyl (e.g. methyl or ethyl) and halo$C_{1-8}$alkyl (e.g. trifluoromethyl)

. In one preferred embodiment, the phenyl group in $R^1$ has a substituent at the 3-position, and optionally one or more other positions.

According to yet another embodiment, specifically provided are compounds of formula (I), in which $R^1$ is substituted phenyl and the substituent(s) are independently selected from fluoro, methyl, and trifluoromethyl.

According to yet another embodiment, specifically provided are compounds of formula (I), in which $R^1$ is substituted or unsubstituted $C_{3-12}$cycloalkyl, preferably substituted or unsubstituted $C_{3-6}$cycloalkyl, and more preferably substituted or unsubstituted cyclohexyl. In this embodiment, substituent(s) on the $C_{3-12}$cycloalkyl, $C_{3-6}$cycloalkyl or cyclohexyl may be one or more and are independently selected from halogen (e.g. F, Cl or Br), $C_{1-4}$alkyl (e.g. methyl), and halo$C_{1-8}$alkyl (e.g. trifluoromethyl).

According to yet another embodiment, specifically provided are compounds of formula (I), in which $R^1$ is cyclohexyl optionally substituted with one or more substituents independently selected from halogen (e.g. F, Cl or Br), $C_{1-4}$alkyl (e.g. methyl) and halo$C_{1-8}$alkyl (e.g. trifluoromethyl).

According to yet another embodiment, specifically provided are compounds of formula (I), in which $R^1$ is substituted cyclohexyl and the one or more substituent(s) are independently selected from fluorine, methyl and trifluoromethyl.

According to yet another embodiment, specifically provided are compounds of formula (I), in which $R^1$ is substituted or unsubstituted 5-14 membered heteroaryl, preferably substituted or unsubstituted pyridine, and more preferably substituted pyridine. In this embodiment, substituent(s) on the pyridine ring may be one or more and are independently selected from halogen (e.g. F, Cl or Br), $C_{1-4}$alkyl (e.g. methyl, ethyl) and halo$C_{1-8}$alkyl (e.g. trifluoromethyl).

According to yet another embodiment, specifically provided are compounds of formula (I), in which $R^1$ is pyridine, optionally substituted with one or more substituents independently selected from halogen (e.g. F, Cl or Br), $C_{1-4}$alkyl (e.g. methyl) and halo$C_{1-8}$alkyl (e.g. trifluoromethyl).

According to yet another embodiment, specifically provided are compounds of formula (I), in which $R^1$ is substituted pyridine and the one or more substituent(s) are trifluoromethyl.

According to yet another embodiment, specifically provided are compounds of formula (I), in which $R^1$ is methyl, ethyl, isopropyl, tert-butyl, 2,2,2-trifluoroethyl, 3-(trifluoromethyl)phenyl, 4-(trifluoromethyl)phenyl, 2-fluoro-5-(trifluoromethyl)phenyl, 4-fluoro-3-(trifluoromethyl)phenyl, 2-fluoro-4-(trifluoromethyl)phenyl, 6-(trifluoromethyl)pyridin-3-yl, 4,4-difluorocyclohexyl, 4,4-dimethylcyclohexyl, 4-(trifluoromethyl)cyclohexyl, (1s,4s)-4-(trifluoromethyl)cyclohexyl or (1r,4r)-4-(trifluoromethyl)cyclohexyl.

According to yet another embodiment, specifically provided are compounds of formula (I), in which A is $C_{6-14}$aryl, preferably phenyl.

According to yet another embodiment, specifically provided are compounds of formula (I), in which A is 5-14 membered heteroaryl, preferably pyridine.

According to yet another embodiment, specifically provided are compounds of formula (I), in which each occurrence of $R^4$ is independently halogen (e.g. F, Cl or Br), $C_{1-4}$alkyl (e.g. methyl, ethyl), halo$C_{1-8}$alkyl (e.g. difluoromethyl) or $C_{1-8}$alkoxy (e.g. methoxy).

According to yet another embodiment, specifically provided are compounds of formula (I), in which each occurrence of $R^4$ is independently $OCH_3$, $CH_3$, $CHF_2$, Cl or F.

According to yet another embodiment, specifically provided are compounds of formula (I), in which m is 0, 1 or 2.

According to yet another embodiment, specifically provided are compounds of formula (I), in which each occurrence of $R^4$ is independently $OCH_3$, $CH_3$, Cl or F and m is 1 or 2.

According to yet another embodiment, specifically provided are compounds of formula (I), in which L is $(CR^xR^y)_n$NR$^x$C(O).

According to yet another embodiment, specifically provided are compounds of formula (I), in which $R^x$ and $R^y$ are independently selected from hydrogen and $C_{1-8}$alkyl (e.g. methyl).

According to yet another embodiment, specifically provided are compounds of formula (I), in which L is $(CR^xR^y)_n$NR$^x$C(O). In this embodiment, each occurrence of $R^x$ and $R^y$ are independently selected from hydrogen and $C_{1-4}$alkyl (e.g. methyl), and n is 1 or 2.

According to yet another embodiment, specifically provided are compounds of formula (I), in which L is $CH_2NHC(O)$.

According to yet another embodiment specifically provided are compounds of formula (I), in which W is substituted or unsubstituted $C_{1-8}$alkyl (e.g. methyl, ethyl, isopropyl or tert-butyl), halo $C_{1-8}$alkyl (e.g. 1-fluoro-2-methylpropan-2-yl), hydroxy$C_{1-8}$alkyl (e.g. 1-hydroxy-2-methylpropan-2-yl), tetrahydrofuranyl or (S)-tetrahydrofuran-2-yl.

According to yet another embodiment, specifically provided are compounds of formula (I), in which W is isopropyl, tert-butyl, 1-fluoro-2-methylpropan-2-yl, 1-hydroxy-2-methylpropan-2-yl, tetrahydrofuranyl or (S)-tetrahydrofuran-2-yl.

According to yet another embodiment, specifically provided are compounds of formula (I), in which L is a bond and W is hydrogen.

According to yet another embodiment, specifically provided are compounds of formula (I), in which L is $CH_2NHC(O)$ and W is isopropyl, tert-butyl, 1-fluoro-2-methylpropan-2-yl, 1-hydroxy-2-methylpropan-2-yl, tetrahydrofuranyl or (S)-tetrahydrofuran-2-yl.

According to an embodiment, specifically provided are compounds of formula (I) with an $IC_{50}$ value of less than 500 nM, preferably, less than 100 nM, more preferably less than 50 nM, with respect to mPGES-1 activity.

Further embodiments relating to groups Y, A, $Z^1$, $Z^2$, $Z^3$, $G^1$, $G^2$, L, W, $R^1$, $R^2$, $R^3$, $R^4$, $R^a$, $R^b$, $R^c$, $R^d$, $R^x$, $R^y$, 'm' and 'n' (and groups defined therein) are described hereinafter in relation to the compounds of formula (II) and formula (III). It is to be understood that these embodiments are not limited to use in conjunction with formula (II) or formula (III), but apply independently and individually to the compounds of formula (I). For example, in an embodiment described hereinafter, the invention specifically provides compounds of formula (II) or formula (III), wherein $R^3$ is hydrogen or methyl and consequently there is also provided a compound of formula (I), wherein $R^3$ is hydrogen or methyl.

The invention also provides a compound of formula (II), which is an embodiment of a compound of formula (I).

Accordingly the invention provides a compound of formula (II):

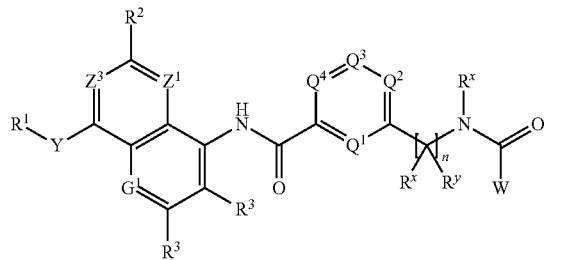

(II)

or a pharmaceutically acceptable salt thereof,
wherein,

Y is O, NH or $NR^c$;

$Z^1$ and $Z^3$, which may be same or different, are independently selected from N and $CR^2$;

$G^1$ is selected from N and $CR^3$; with a proviso that at least one of $Z^1$, $Z^3$ and $G^1$ is N;

$Q^1$, $Q^2$, $Q^3$ and $Q^4$, which may be same or different, are independently selected from N, CH and $CR^4$; with a proviso that $Q^2$, $Q^3$ and $Q^4$ are not N simultaneously;

W is selected from substituted or unsubstituted $C_{1-8}$alkyl, substituted or unsubstituted $C_{1-8}$alkoxy$C_{1-8}$alkyl, substituted or unsubstituted halo$C_{1-8}$alkyl, substituted or unsubstituted hydroxy$C_{1-8}$alkyl, substituted or unsubstituted $C_{3-12}$cycloalkyl and substituted or unsubstituted tetrahydrofuryl or tetrahydrofuranyl;

$R^1$ is selected from substituted or unsubstituted $C_{1-8}$alkyl, substituted or unsubstituted $C_{1-8}$alkoxy$C_{1-8}$alkyl, substituted or unsubstituted halo$C_{1-8}$alkyl, substituted or unsubstituted hydroxy$C_{1-8}$alkyl, substituted or unsubstituted $C_{3-12}$cycloalkyl, substituted or unsubstituted $C_{6-14}$aryl, substituted or unsubstituted 3-15 membered heterocyclyl, and substituted or unsubstituted 5-14 membered heteroaryl;

each occurrence of $R^2$ and $R^3$, which may be the same or different, are independently selected from hydrogen, halogen, nitro, cyano, hydroxyl, substituted or unsubstituted $C_{1-8}$alkyl, substituted or unsubstituted $C_{1-8}$alkoxy, substituted or unsubstituted halo$C_{1-8}$alkyl, substituted or unsubstituted hydroxy$C_{1-8}$alkyl, substituted or unsubstituted $C_{3-12}$cycloalkyl and substituted or unsubstituted $C_{3-8}$cycloalkyl$C_{1-8}$alkyl;

at each occurrence, $R^4$ is independently selected from halogen, nitro, cyano, hydroxyl, substituted or unsubstituted $C_{1-8}$alkyl, substituted or unsubstituted $C_{1-8}$alkoxy, substituted or unsubstituted $C_{1-8}$alkoxy$C_{1-8}$alkyl, substituted or unsubstituted halo$C_{1-8}$alkyl, substituted or unsubstituted hydroxy$C_{1-8}$alkyl, substituted or unsubstituted $C_{3-12}$cycloalkyl and substituted or unsubstituted $C_{3-8}$cycloalkyl$C_{1-8}$alkyl:

at each occurrence, $R^c$ is independently selected from substituted or unsubstituted $C_{1-8}$alkyl and substituted or unsubstituted $C_{6-14}$aryl$C_{1-8}$alkyl; or $R^c$ and $R^1$, together with the N to which they are attached, form a morpholine ring;

each occurrence of $R^x$ and $R^y$, which may be the same or different, are independently selected from hydrogen, substituted or unsubstituted $C_{1-8}$alkyl and substituted or unsubstituted $C_{6-14}$aryl$C_{1-8}$alkyl; and 'n' is an integer ranging from 1 to 4, both inclusive.

The compounds of formula (II) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition of any other embodiment defined herein. Thus, the invention contemplates all possible combinations and permutations of the various independently described embodiments. For example, the invention provides compounds of formula (II) as defined above wherein Y is NH (according to an embodiment defined below) and n is 1 (according to another embodiment defined below).

According to one embodiment, specifically provided are compounds of formula (II), in which Y is NH.

According to another embodiment, specifically provided are compounds of formula (II), in which Y is O.

According to yet another embodiment, specifically provided are compounds of formula (II), in which Y is $NR^c$. In this embodiment, $R^c$ is $C_{1-4}$alkyl (e.g. methyl or ethyl) or $R^c$ and $R^1$, together with the N to which they are attached, form a morpholine ring.

According to yet another embodiment, specifically provided are compounds of formula (II), in which $Z^1$ is N, $Z^3$ is $CR^2$ and $G^1$ is $CR^3$.

According to yet another embodiment, specifically provided are compounds of formula (II), in which $Z^1$ and $Z^3$ are N and $G^1$ is $CR^3$.

According to yet another embodiment, specifically provided are compounds of formula (II), in which $Z^1$ is $CR^2$, $Z^3$ is N and $G^1$ is $CR^3$. According to yet another embodiment, specifically provided are compounds of formula (II), in which $Z^1$ and $Z^3$ are $CR^2$ and $G^1$ is N.

According to yet another embodiment, specifically provided are compounds of formula (II), in which each occurrence of $R^2$ is independently hydrogen, $C_{1-4}$alkyl (e.g. methyl, ethyl, or tert-butyl) or halo$C_{1-8}$alkyl (e.g. trifluoromethyl).

According to yet another embodiment, specifically provided are compounds of formula (II), in which each occurrence of $R^2$ is independently hydrogen, methyl or trifluoromethyl.

According to yet another embodiment, specifically provided are compounds of formula (II), in which each occurrence of $R^3$ is independently hydrogen or $C_{1-4}$alkyl (e.g. methyl, ethyl, or tert-butyl).

According to yet another embodiment, specifically provided are compounds of formula (II), in which each occurrence of $R^3$ is independently hydrogen or methyl.

According to yet another embodiment, specifically provided are compounds of formula (II), in which $Z^1$ is N, $Z^3$ is CH and $G^1$ is CH.

According to yet another embodiment, specifically provided are compounds of formula (II), in which $Z^1$ and $Z^3$ are N and $G^1$ is CH.

According to yet another embodiment, specifically provided are compounds of formula (II), in which $Z^1$ is CH, $Z^3$ is N and $G^1$ is CH.

According to yet another embodiment, specifically provided are compounds of formula (II), in which $Z^1$ and $Z^3$ are CH and $G^1$ is N.

According to yet another embodiment, specifically provided are compounds of formula (II), in which $R^1$ is substituted or unsubstituted $C_{1-8}$alkyl, preferably unsubstituted $C_{1-8}$alkyl, more preferably unsubstituted $C_{1-4}$alkyl (e.g. methyl, ethyl, isopropyl, or tert-butyl).

According to yet another embodiment, specifically provided are compounds of formula (II), in which $R^1$ is methyl, ethyl, isopropyl or tert-butyl.

According to yet another embodiment, specifically provided are compounds of formula (II), in which $R^1$ is substituted or unsubstituted haloC$_{1-8}$alkyl, preferably unsubstituted haloC$_{1-8}$alkyl (e.g. 2,2,2-trifluoroethyl).

According to yet another embodiment, specifically provided are compounds of formula (II), in which R$^1$ is 2,2,2-trifluoroethyl.

According to yet another embodiment, specifically provided are compounds of formula (II), in which R$^1$ is substituted or unsubstituted C$_{6-14}$aryl, preferably substituted or unsubstituted phenyl, and more preferably substituted phenyl. In this embodiment, substituent(s) on the C$_{6-14}$aryl or phenyl may be one or more and are independently selected from halogen (e.g. F, Cl or Br), C$_{1-4}$alkyl (e.g. methyl, ethyl) and haloC$_{1-8}$alkyl (e.g. trifluoromethyl).

According to yet another embodiment, specifically provided are compounds of formula (II), in which R$^1$ is phenyl optionally substituted with one or more substituent(s) independently selected from halogen (e.g. F, Cl or Br), C$_{1-4}$alkyl (e.g. methyl, ethyl) and haloC$_{1-8}$alkyl (e.g. trifluoromethyl).

According to yet another embodiment, specifically provided are compounds of formula (II), in which R$^1$ is substituted phenyl and the one or more substituent(s) are independently selected from fluoro, methyl and trifluoromethyl.

According to yet another embodiment, specifically provided are compounds of formula (II), in which R$^1$ is substituted or unsubstituted C$_{3-12}$cycloalkyl, preferably substituted or unsubstituted C$_{3-6}$cycloalkyl, and more preferably substituted or unsubstituted cyclohexyl. In this embodiment, substituent(s) on C$_{3-12}$cycloalkyl, C$_{3-6}$cycloalkyl or cyclohexyl may be one or more and are independently selected from halogen (e.g. F, Cl or Br), C$_{1-4}$alkyl (e.g. methyl) and haloC$_{1-8}$alkyl (e.g. trifluoromethyl).

According to yet another embodiment, specifically provided are compounds of formula (II), in which R$^1$ is cyclohexyl optionally substituted with one or more substituents independently selected from halogen (e.g. F, Cl or Br), C$_{1-4}$alkyl (e.g. methyl) and haloC$_{1-8}$alkyl (e.g. trifluoromethyl).

According to yet another embodiment, specifically provided are compounds of formula (II), in which R$^1$ is substituted cyclohexyl and the one or more substituent(s) are independently selected from fluorine, methyl and trifluoromethyl.

According to yet another embodiment, specifically provided are compounds of formula (II), in which R$^1$ is substituted or unsubstituted 5-14 membered heteroaryl, preferably substituted or unsubstituted pyridine, more preferably substituted pyridine. In this embodiment, substituent(s) on the pyridine may be one or more and are independently selected from halogen (e.g. F, Cl or Br), C$_{1-4}$alkyl (e.g. methyl or ethyl) and haloC$_{1-8}$alkyl (e.g. trifluoromethyl).

According to yet another embodiment, specifically provided are compounds of formula (II), in which R$^1$ is pyridine, optionally substituted with one or more substituents independently selected from halogen (e.g. F, Cl or Br), C$_{1-4}$alkyl (e.g. methyl) and haloC$_{1-8}$alkyl (e.g. trifluoromethyl).

According to yet another embodiment, specifically provided are compounds of formula (II), in which R$^1$ is substituted pyridine and the one or more substituent(s) are trifluoromethyl.

According to yet another embodiment, specifically provided are compounds of formula (II), in which R$^1$ is methyl, ethyl, isopropyl, tert-butyl, 2,2,2-trifluoroethyl, 3-(trifluoromethyl)phenyl, 4-(trifluoromethyl)phenyl, 2-fluoro-5-(trifluoromethyl)phenyl, 4-fluoro-3-(trifluoromethyl)phenyl, 2-fluoro-4-(trifluoromethyl)phenyl, 6-(trifluoromethyl)pyridin-3-yl, 4,4-difluorocyclohexyl, 4,4-dimethylcyclohexyl, 4-(trifluoromethyl)cyclohexyl, (1s,4s)-4-(trifluoromethyl)cyclohexyl or (1r,4r)-4-(trifluoromethyl)cyclohexyl.

According to yet another embodiment, specifically provided are compounds of formula (II), in which n is 1.

According to yet another embodiment, specifically provided are compounds of formula (II), in which R$^x$ is hydrogen.

According to yet another embodiment, specifically provided are compounds of formula (II), in which R$^y$ is hydrogen.

According to yet another embodiment, specifically provided are compounds of formula (II), in which Q$^1$ is N.

According to yet another embodiment, specifically provided are compounds of formula (II), in which Q$^1$ is CH or CR$^4$.

According to yet another embodiment, specifically provided are compounds of formula (II), in which Q$^2$ is CH or CR$^4$.

According to yet another embodiment, specifically provided are compounds of formula (II), in which Q$^3$ is N or CH.

According to yet another embodiment, specifically provided are compounds of formula (II), in which Q$^4$ is CH or CR$^4$.

According to yet another embodiment, specifically provided are compounds of formula (II), in which Q$^1$ is N, CH or CR$^4$, Q$^2$ is CH or CR$^4$, Q$^3$ is N or CH, and Q$^4$ is CR$^4$.

According to yet another embodiment, specifically provided are compounds of formula (II), in which each occurrence of R$^4$ is independently halogen (e.g. F, Cl or Br), C$_{1-4}$alkyl (e.g. methyl or ethyl), haloC$_{1-8}$alkyl (e.g. difluoromethyl) or C$_{1-8}$alkoxy (e.g. methoxy).

According to yet another embodiment, specifically provided are compounds of formula (II), in which each occurrence of R$^4$ is independently OCH$_3$, CH$_3$, CHF$_2$, Cl or F.

According to yet another embodiment, specifically provided are compounds of formula (II), in which Q$^1$ is N, CH or CR$^4$, Q$^2$ is CH or CR$^4$, Q$^3$ is N or CH, and Q$^4$ is CR$^4$. In this embodiment, R$^4$ is OCH$_3$, CH$_3$, CHF$_2$, Cl or F.

According to yet another embodiment specifically provided are compounds of formula (II), in which W is substituted or unsubstituted C$_{1-8}$alkyl (e.g. methyl, ethyl, isopropyl or tert-butyl), halo C$_{1-8}$alkyl (e.g. 1-fluoro-2-methylpropan-2-yl), hydroxyC$_{1-8}$alkyl (e.g. 1-hydroxy-2-methylpropan-2-yl), tetrahydrofuranyl or (S)-tetrahydrofuran-2-yl.

According to yet another embodiment, specifically provided are compounds of formula (II), in which W is isopropyl, tert-butyl, 1-fluoro-2-methylpropan-2-yl, 1-hydroxy-2-methylpropan-2-yl, tetrahydrofuranyl or (S)-tetrahydrofuran-2-yl.

According to an embodiment, specifically provided are compounds of formula (II) with an IC$_{50}$ value of less than 500 nM, preferably, less than 100 nM, more preferably, less than 50 nM with respect to mPGES-1 activity.

Further embodiments relating to groups R$^1$, R$^2$, R$^3$, Z$^1$, Z$^3$, G$^1$, Q$^1$, Q$^2$, Q$^3$, Q$^4$, W, n, R$^x$ and R$^y$ (and groups defined therein) are described hereinafter in relation to the compounds of formula (III). It is to be understood that these embodiments are not limited to use in conjunction with formula (III), but apply independently and individually to the compounds of formula (I) and formula (II). For example, in an embodiment described hereinafter, the invention specifically provides compounds of formula (III) wherein Y is NH and consequently there is also provided a compound of formula (I) or formula (II) wherein Y is NH.

The invention also provides a compound of formula (III) which is an embodiment of a compound of formula (I).

Accordingly the invention provides a compound of formula (III):

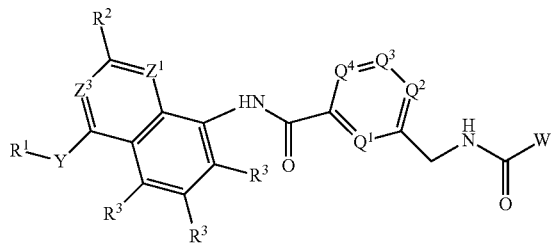

(III)

or a pharmaceutically acceptable salt thereof,
wherein,

Y is selected from NH and O;

$Z^1$ and $Z^3$, which may be same or different, are independently selected from N and $CR^2$; with a proviso that at least one of $Z^1$ and $Z^3$ is N;

$Q^1$, $Q^2$, $Q^3$ and $Q^4$, which may be same or different, are independently selected from N, CH and $CR^4$; with a proviso that $Q^2$, $Q^3$ and $Q^4$ are not N simultaneously;

W is selected from substituted or unsubstituted $C_{1-8}$alkyl, substituted or unsubstituted $C_{1-8}$ alkoxy$C_{1-8}$ alkyl, substituted or unsubstituted halo$C_{1-8}$alkyl, substituted or unsubstituted hydroxy$C_{1-8}$alkyl, substituted or unsubstituted $C_{3-12}$cycloalkyl and substituted or unsubstituted tetrahydrofuryl or tetrahydrofuranyl;

$R^1$ is selected from substituted or unsubstituted $C_{1-8}$alkyl, substituted or unsubstituted $C_{1-8}$alkoxy$C_{1-8}$alkyl, substituted or unsubstituted halo$C_{1-8}$alkyl, substituted or unsubstituted hydroxy$C_{1-8}$alkyl, substituted or unsubstituted $C_{3-12}$cycloalkyl, substituted or unsubstituted $C_{6-14}$aryl, substituted or unsubstituted 3-15 membered heterocyclyl, and substituted or unsubstituted 5-14 membered heteroaryl;

each occurrence of $R^2$ and $R^3$, which may be the same or different, are independently selected from hydrogen, halogen, hydroxyl, substituted or unsubstituted $C_{1-8}$alkyl, substituted or unsubstituted $C_{1-8}$alkoxy and substituted or unsubstituted halo$C_{1-8}$alkyl; and at each occurrence, $R^4$ is independently selected from halogen, nitro, cyano, hydroxyl, substituted or unsubstituted $C_{1-8}$alkyl, substituted or unsubstituted $C_{1-8}$alkoxy, substituted or unsubstituted halo$C_{1-8}$alkyl, and substituted or unsubstituted $C_{3-12}$cycloalkyl.

The compounds of formula (III) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition, or any other embodiment defined herein. Thus the invention contemplates all possible combinations and permutations of the various independently described embodiments. For example, the invention provides compounds of formula (III) as defined above wherein $R^2$ is hydrogen, methyl or trifluoromethyl (according to an embodiment defined below) and $R^3$ is hydrogen or methyl (according to another embodiment defined below).

According to one embodiment, specifically provided are compounds of formula (III), in which Y is NH.

According to another embodiment, specifically provided are compounds of formula (III), in which Y is O.

According to yet another embodiment, specifically provided are compounds of formula (III), in which $Z^1$ is N and $Z^3$ is $CR^2$.

According to yet another embodiment, specifically provided are compounds of formula (III), in which $Z^1$ and $Z^3$ are N.

According to yet another embodiment, specifically provided are compounds of formula (III), in which $Z^1$ is $CR^2$ and $Z^3$ is N.

According to yet another embodiment, specifically provided are compounds of formula (III), in which each occurrence of $R^2$ is independently hydrogen, $C_{1-4}$alkyl (e.g. methyl, ethyl, tert-butyl) or halo$C_{1-8}$alkyl (e.g. trifluoromethyl).

According to yet another embodiment, specifically provided are compounds of formula (III), in which each occurrence of $R^2$ is independently hydrogen, methyl or trifluoromethyl.

According to yet another embodiment, specifically provided are compounds of formula (III), in which $Z^1$ is N and $Z^3$ is CH or N.

According to yet another embodiment, specifically provided are compounds of formula (III), in which $Z^1$ is CH and $Z^3$ is N According to yet another embodiment, specifically provided are compounds of formula (III), in which each occurrence of $R^3$ is independently hydrogen or $C_{1-4}$alkyl (e.g. methyl, ethyl, or tert-butyl).

According to yet another embodiment, specifically provided are compounds of formula (III), in which each occurrence of $R^3$ is independently hydrogen or methyl.

According to yet another embodiment, specifically provided are compounds of formula (III), in which $R^1$ is substituted or unsubstituted $C_{1-8}$alkyl, preferably substituted or unsubstituted $C_{1-4}$alkyl, more preferably unsubstituted $C_{1-4}$alkyl (e.g. methyl, ethyl, isopropyl, or tert-butyl).

According to yet another embodiment, specifically provided are compounds of formula (III), in which $R^1$ is methyl, ethyl, isopropyl or tert-butyl.

According to yet another embodiment, specifically provided are compounds of formula (III), in which $R^1$ is substituted or unsubstituted halo$C_{1-8}$alkyl, preferably unsubstituted halo$C_{1-8}$alkyl (e.g. 2,2,2-trifluoroethyl).

According to yet another embodiment, specifically provided are compounds of formula (III), in which $R^1$ is 2,2,2-trifluoroethyl.

According to yet another embodiment, specifically provided are compounds of formula (III), in which $R^1$ is substituted or unsubstituted $C_{6-14}$aryl, preferably substituted or unsubstituted phenyl, and more preferably substituted phenyl. In this embodiment, substituent(s) on the $C_{6-14}$aryl or phenyl may be one or more and are independently selected from halogen (e.g. F, Cl or Br), $C_{1-4}$alkyl (e.g. methyl or ethyl) and halo$C_{1-8}$alkyl (e.g. trifluoromethyl).

According to yet another embodiment, specifically provided are compounds of formula (III), in which $R^1$ is phenyl optionally substituted with one or more substituent(s) independently selected from halogen (e.g. F, Cl or Br), $C_{1-4}$ alkyl (e.g. methyl or ethyl) and halo$C_{1-8}$alkyl (e.g. trifluoromethyl).

According to yet another embodiment, specifically provided are compounds of formula (III), in which $R^1$ is substituted phenyl and the one or more substituent(s) are independently selected from fluoro, methyl and trifluoromethyl.

According to yet another embodiment, specifically provided are compounds of formula (III), in which $R^1$ is substituted or unsubstituted $C_{3-12}$cycloalkyl, preferably substituted or unsubstituted $C_{3-6}$cycloalkyl, more preferably substituted or unsubstituted cyclohexyl. In this embodiment, substituent(s) on $C_{3-12}$cycloalkyl, $C_{3-6}$cycloalkyl or cyclohexyl may be one or more and are independently selected from halogen (e.g. F, Cl or Br), $C_{1-4}$alkyl (e.g. methyl) and halo$C_{1-8}$alkyl (e.g. trifluoromethyl).

According to yet another embodiment, specifically provided are compounds of formula (III), in which $R^1$ is cyclohexyl optionally substituted with one or more substituents independently selected from halogen (e.g. F, Cl or Br), $C_{1-4}$alkyl (e.g. methyl) and halo$C_{1-8}$alkyl (e.g. trifluoromethyl).

According to yet another embodiment, specifically provided are compounds of formula (III), in which $R^1$ is substituted cyclohexyl and the one or more substituent(s) are independently selected from fluorine, methyl and trifluoromethyl.

According to yet another embodiment, specifically provided are compounds of formula (III), in which $R^1$ is substituted or unsubstituted 5-14 membered heteroaryl, preferably substituted or unsubstituted pyridine, more preferably substituted pyridine. In this embodiment, substituent(s) on pyridine may be one or more and are independently selected from halogen (e.g. F, Cl or Br), $C_{1-4}$alkyl (e.g. methyl, ethyl) and halo$C_{1-8}$alkyl (e.g. trifluoromethyl).

According to yet another embodiment, specifically provided are compounds of formula (III), in which $R^1$ is pyridine, optionally substituted with one or more substituents selected from halogen (F, Cl or Br), $C_{1-4}$alkyl (e.g. methyl) and halo$C_{1-8}$alkyl (e.g. trifluoromethyl).

According to yet another embodiment, specifically provided are compounds of formula (III), in which $R^1$ is substituted pyridine and the one or more substituent(s) are trifluoromethyl.

According to yet another embodiment, specifically provided are compounds of formula (III), in which $R^1$ is methyl, ethyl, isopropyl, tert-butyl, 2,2,2-trifluoroethyl, 3-(trifluoromethyl)phenyl, 4-(trifluoromethyl)phenyl, 2-fluoro-5-(trifluoromethyl)phenyl, 4-fluoro-3-(trifluoromethyl)phenyl, 2-fluoro-4-(trifluoromethyl)phenyl, 6-(trifluoromethyl)pyridin-3-yl, 4,4-difluorocyclohexyl, 4,4-dimethylcyclohexyl, 4-(trifluoromethyl)cyclohexyl, (1s,4s)-4-(trifluoromethyl)cyclohexyl or (1r,4r)-4-(trifluoromethyl)cyclohexyl.

According to yet another embodiment, specifically provided are compounds of formula (III), in which $Q^1$ is N.

According to yet another embodiment, specifically provided are compounds of formula (III), in which $Q^1$ is CH or $CR^4$.

According to yet another embodiment, specifically provided are compounds of formula (III), in which $Q^2$ is CH or $CR^4$.

According to yet another embodiment, specifically provided are compounds of formula (III), in which $Q^3$ is N or CH.

According to yet another embodiment, specifically provided are compounds of formula (III), in which $Q^4$ is CH or $CR^4$.

According to yet another embodiment, specifically provided are compounds of formula (III), in which $Q^1$ is N, CH or $CR^4$, $Q^2$ is CH or $CR^4$, $Q^3$ is N or CH, and $Q^4$ is $CR^4$.

According to yet another embodiment, specifically provided are compounds of formula (III), in which each occurrence of $R^4$ is independently halogen (e.g. F, Cl or Br), $C_{1-4}$alkyl (e.g. methyl or ethyl), halo$C_{1-8}$alkyl (e.g. difluoromethyl) or $C_{1-8}$alkoxy (e.g. methoxy).

According to yet another embodiment, specifically provided are compounds of formula (III), in which each occurrence of $R^4$ is independently $OCH_3$, $CH_3$, $CHF_2$, Cl or F.

According to yet another embodiment, specifically provided are compounds of formula (III), in which $Q^1$ is N, CH or $CR^4$, $Q^2$ is CH or $CR^4$, $Q^3$ is N or CH, and $Q^4$ is $CR^4$. In this embodiment, $R^4$ is $OCH_3$, $CH_3$, $CHF_2$, Cl or F.

According to yet another embodiment specifically provided are compounds of formula (III), in which W is substituted or unsubstituted $C_{1-8}$alkyl (e.g. methyl, ethyl, isopropyl or tert-butyl), halo$C_{1-8}$alkyl (e.g. 1-fluoro-2-methylpropan-2-yl), hydroxy$C_{1-8}$alkyl (e.g. 1-hydroxy-2-methylpropan-2-yl), tetrahydrofuranyl or (S)-tetrahydrofuran-2-yl.

According to yet another embodiment, specifically provided are compounds of formula (III), in which W is isopropyl, tert-butyl, 1-fluoro-2-methylpropan-2-yl, 1-hydroxy-2-methylpropan-2-yl, tetrahydrofuranyl or (S)-tetrahydrofuran-2-yl.

According to yet another embodiment, specifically provided are compounds of formula (III), in which:
$Z^1$ is N;
$Z^3$ is $CR^2$ (e.g., CH) or N;
$R^1$ is substituted or unsubstituted phenyl, preferably having at least one substitution at the 3-position (e.g., a $—CF_3$ or halogen substitution);
$R^2$ and $R^3$ are defined as above with respect to formula (III), and are preferably hydrogen;
$Q^1$, $Q^2$, $Q^3$ and $Q^4$ are N, CH, or $CR^4$, where at most one of $Q^1$, $Q^2$, $Q^3$ and $Q^4$ is N, and preferably $Q^1$, $Q^2$, $Q^3$ and $Q^4$ are independently CH or $CR^4$ where each $R^4$ is halogen or methyl; and
W is as defined above with respect to formula (III) and is preferably a branched alkyl (e.g., tert-butyl or isopropyl).

According to yet another embodiment, specifically provided are compounds of formula (III), in which:
$Z^1$ is $CR^2$ (e.g., CH);
$Z^3$ is N;
$R^1$ is substituted or unsubstituted phenyl, preferably having at least one substitution at the 3-position (e.g., a $—CF_3$ or halogen substitution);
$R^2$ and $R^3$ are defined as above with respect to formula (III), and are preferably hydrogen;
$Q^1$, $Q^2$, $Q^3$ and $Q^4$ are N, CH, or $CR^4$, where at most one of $Q^1$, $Q^2$, $Q^3$ and $Q^4$ is N, and preferably $Q^1$, $Q^2$, $Q^3$ and $Q^4$ are independently CH or $CR^4$ where each $R^4$ is halogen or methyl; and
W is as defined above with respect to formula (III) and is preferably a branched alkyl (e.g., tert-butyl or isopropyl).

Compounds of the present invention include the compounds in Examples 1-80.

According to one embodiment, specifically provided are compounds of formula (III) with an $IC_{50}$ value of less than 500 nM, preferably, less than 100 nM, more preferably, less than 50 nM with respect to mPGES-1 activity.

It should be understood that the formulas (I), (II) and (III), structurally encompass all geometrical isomers, stereoisomers, enantiomers and diastereomers, N-oxides, and pharmaceutically acceptable salts that may be contemplated from the chemical structure of the genera described herein.

The present application also provides a pharmaceutical composition that includes at least one compound described herein and at least one pharmaceutically acceptable excipient (such as a pharmaceutically acceptable carrier or diluent). Preferably, the pharmaceutical composition comprises a therapeutically effective amount of at least one compound described herein. The compounds described herein may be associated with a pharmaceutically acceptable excipient (such as a carrier or a diluent) or be diluted by a carrier, or enclosed within a carrier which can be in the form of a capsule, sachet, paper or other container.

The compounds and pharmaceutical compositions of the present invention are useful for inhibiting the activity of mPGES-1, which is related to a variety of disease states.

The present invention further provides a method of inhibiting mPGES-1 in a subject in need thereof by administering to the subject one or more compounds described herein in an amount effective to cause inhibition of such receptor.

DETAILED DESCRIPTION OF THE INVENTION

Definitions

The terms "halogen" or "halo" means fluorine (fluoro), chlorine (chloro), bromine (bromo), or iodine (iodo).

The term "alkyl" refers to a hydrocarbon chain radical that includes solely carbon and hydrogen atoms in the backbone, containing no unsaturation, having from one to eight carbon atoms (i.e. $C_{1-8}$alkyl), and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "$C_{1-6}$ alkyl" refers to an alkyl chain having 1 to 6 carbon atoms. The term "$C_{1-4}$alkyl" refers to an alkyl chain having 1 to 4 carbon atoms. Unless set forth or recited to the contrary, all alkyl groups described or claimed herein may be straight chain or branched, substituted or unsubstituted.

The term "alkenyl" refers to a hydrocarbon chain containing from 2 to 10 carbon atoms (i.e. $C_{2-10}$alkenyl) and including at least one carbon-carbon double bond. Non-limiting examples of alkenyl groups include ethenyl, 1-propenyl, 2-propenyl (allyl), iso-propenyl, 2-methyl-1-propenyl, 1-butenyl, and 2-butenyl. Unless set forth or recited to the contrary, all alkenyl groups described or claimed herein may be straight chain or branched, substituted or unsubstituted.

The term "alkynyl" refers to a hydrocarbyl radical having at least one carbon-carbon triple bond, and having 2 to about 12 carbon atoms (with radicals having 2 to about 10 carbon atoms being preferred i.e. $C_{2-10}$alkynyl). Non-limiting examples of alkynyl groups include ethynyl, propynyl, and butynyl. Unless set forth or recited to the contrary, all alkynyl groups described or claimed herein may be straight chain or branched, substituted or unsubstituted.

The term "alkoxy" denotes an alkyl group attached via an oxygen linkage to the rest of the molecule (i.e. $C_{1-8}$ alkoxy). Representative examples of such groups are —OCH$_3$ and —OC$_2$H$_5$. Unless set forth or recited to the contrary, all alkoxy groups described or claimed herein may be straight chain or branched, substituted or unsubstituted.

The term "alkoxyalkyl" or "alkyloxyalkyl" refers to an alkoxy or alkyloxy group as defined above directly bonded to an alkyl group as defined above (i.e. $C_{1-8}$alkoxy$C_{1-8}$alkyl or $C_{1-8}$alkyloxy$C_{1-8}$alkyl). Example of such alkoxyalkyl moiety includes, but are not limited to, —CH$_2$OCH$_3$ and —CH$_2$OC$_2$H$_5$. Unless set forth or recited to the contrary, all alkoxyalkyl groups described herein may be straight chain or branched, substituted or unsubstituted.

The term "haloalkyl" refers to at least one halo group (selected from F, Cl, Br or I), linked to an alkyl group as defined above (i.e. halo$C_{1-8}$alkyl). Examples of such haloalkyl moiety include, but are not limited to, trifluoromethyl, difluoromethyl and fluoromethyl groups. Unless set forth or recited to the contrary, all haloalkyl groups described herein may be straight chain or branched, substituted or unsubstituted.

The term "haloalkoxy" refers to an alkoxy group substituted with one or more halogen atoms (i.e. halo$C_{1-8}$alkoxy). Examples of "haloalkoxy" include but are not limited to fluoromethoxy, difluoromethoxy, trifluoromethoxy, 2,2,2-trifluoroethoxy, pentafluoroethoxy, pentachloroethoxy, chloromethoxy, dichlorormethoxy, trichloromethoxy and 1-bromoethoxy. Unless set forth or recited to the contrary, all haloalkoxy groups described herein may be straight chain or branched, substituted or unsubstituted.

The term "hydroxyalkyl" refers to an alkyl group as defined above wherein one to three hydrogen atoms on different carbon atoms is/are replaced by hydroxyl groups (i.e. hydroxy$C_{1-8}$alkyl). Examples of hydroxyalkyl moieties include, but are not limited to —CH$_2$OH, —C$_2$H$_4$OH and —CH(OH)C$_2$H$_4$OH.

The term "cycloalkyl" denotes a non-aromatic mono or multicyclic ring system of 3 to about 12 carbon atoms, (i.e. $C_{3-12}$cycloalkyl). Examples of monocyclic cycloalkyl include but are not limited to cyclopropyl, cyclobutyl, cyclopentyl, and cyclohexyl. Examples of multicyclic cycloalkyl groups include, but are not limited to, perhydronapthyl, adamantyl and norbornyl groups, bridged cyclic groups or spirobicyclic groups, e.g., spiro(4,4)non-2-yl. The term "$C_{3-6}$cycloalkyl" refers to the cyclic ring having 3 to 6 carbon atoms. Unless set forth or recited to the contrary, all cycloalkyl groups described or claimed herein may be substituted or unsubstituted.

The term "cycloalkylalkyl" refers to a cyclic ring-containing radical having 3 to about 8 carbon atoms directly attached to an alkyl group (i.e. $C_{3-8}$cycloalkyl$C_{1-8}$alkyl). The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl. Unless set forth or recited to the contrary, all cycloalkylalkyl groups described or claimed herein may be substituted or unsubstituted.

The term "cycloalkenyl" refers to a cyclic ring-containing radical having 3 to about 8 carbon atoms with at least one carbon-carbon double bond, (i.e. $C_{3-8}$cycloalkenyl). Examples of "cycloalkenyl" include but are not limited to cyclopropenyl, cyclobutenyl, and cyclopentenyl. Unless set forth or recited to the contrary, all cycloalkenyl groups described or claimed herein may be substituted or unsubstituted.

The term "cycloalkenylalkyl" refers to a cyclic ring-containing radical having 3 to about 8 carbon atoms with at least one carbon-carbon double bond, directly attached to an alkyl group, (i.e. $C_{3-8}$cycloalkenyl$C_{1-8}$alkyl). The cycloalkenylalkyl group may be attached to the main structure at any carbon atom in the alkyl group that results in the creation of a stable structure. Unless set forth or recited to the contrary, all cycloalkenylalkyl groups described or claimed herein may be substituted or unsubstituted.

The term "aryl" refers to an aromatic radical having 6 to 14 carbon atoms (i.e. $C_{6-14}$aryl), including monocyclic, bicyclic and tricyclic aromatic systems, such as phenyl, naphthyl, tetrahydronapthyl, indanyl, and biphenyl. Unless set forth or recited to the contrary, all aryl groups described or claimed herein may be substituted or unsubstituted.

The term "aryloxy" refers to an aryl group as defined above attached via an oxygen linkage to the rest of the molecule (i.e. $C_{6-14}$aryloxy). Examples of aryloxy moieties include, but are not limited to phenoxy and naphthoxy. Unless set forth or recited to the contrary, all aryloxy groups described herein may be substituted or unsubstituted.

The term "arylalkyl" refers to an aryl group as defined above directly bonded to an alkyl group as defined above, i.e. $C_{6-14}$aryl$C_{1-8}$alkyl, such as —CH$_2$C$_6$H$_5$ and —C$_2$H$_4$C$_6$H$_5$. Unless set forth or recited to the contrary, all arylalkyl groups described or claimed herein may be substituted or unsubstituted.

The term "heterocyclic ring" or "heterocyclyl" unless otherwise specified refers to substituted or unsubstituted non-aromatic 3 to 15 membered ring radical (i.e. 3 to 15 membered heterocyclyl) which consists of carbon atoms and from one to five hetero atoms selected from nitrogen, phosphorus, oxygen and sulfur. The heterocyclic ring radical may be a mono-, bi- or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; also, unless otherwise constrained by the definition the heterocyclic ring or heterocyclyl may optionally contain one or more olefinic bond(s). Examples of such heterocyclic ring radicals include, but are not limited to azepinyl, azetidinyl, benzodioxolyl, benzodioxanyl, chromanyl, dioxolanyl, dioxaphospholanyl, decahydroisoquinolyl, indanyl, indolinyl, isoindolinyl, isochromanyl, isothiazolidinyl, isoxazolidinyl, morpholinyl, oxazolinyl, oxazolidinyl, oxadiazolyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisoquinolyl, tetrahydrofuryl or tetrahydrofuranyl, tetrahydropyranyl, thiazolinyl, thiazolidinyl, thiamorpholinyl, thiamorpholinyl sulfoxide and thiamorpholinyl sulfone. The heterocyclic ring radical may be attached to the main structure at any heteroatom or carbon atom that results in the creation of a stable structure. Unless set forth or recited to the contrary, all heterocyclyl groups described or claimed herein may be substituted or unsubstituted.

The term "heterocyclylalkyl" refers to a heterocyclic ring radical directly bonded to an alkyl group (i.e. 3 to 15 membered heterocyclyl$C_{1-8}$alkyl). The heterocyclylalkyl radical may be attached to the main structure at any carbon atom in the alkyl group that results in the creation of a stable structure. Unless set forth or recited to the contrary, all heterocyclylalkyl groups described or claimed herein may be substituted or unsubstituted.

The term "heteroaryl" unless otherwise specified refers to substituted or unsubstituted 5 to 14 membered aromatic heterocyclic ring radical with one or more heteroatom(s) independently selected from N, O or S (i.e. 5 to 14 membered heteroaryl). The heteroaryl may be a mono-, bi- or tricyclic ring system. The heteroaryl ring radical may be attached to the main structure at any heteroatom or carbon atom that results in the creation of a stable structure. Examples of such heteroaryl ring radicals include, but are not limited to oxazolyl, isoxazolyl, imidazolyl, furyl, indolyl, isoindolyl, pyrrolyl, triazolyl, triazinyl, tetrazoyl, thienyl, thiazolyl, isothiazolyl, pyridyl, pyrimidinyl, pyrazinyl, pyridazinyl, pyrazolyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl and phthalazinyl. Unless set forth or recited to the contrary, all heteroaryl groups described or claimed herein may be substituted or unsubstituted.

The term "heteroarylalkyl" refers to a heteroaryl ring radical directly bonded to an alkyl group (i.e. 5 to 14 membered heterary$C_{1-8}$alkyl). The heteroarylalkyl radical may be attached to the main structure at any carbon atom in the alkyl group that results in the creation of a stable structure. Unless set forth or recited to the contrary, all heteroarylalkyl groups described or claimed herein may be substituted or unsubstituted.

Unless otherwise specified, the term "substituted" as used herein refers to substitution with any one or any combination of the following substituents: hydroxy, halogen, carboxyl, cyano, nitro, oxo (=O), thio (=S), substituted or unsubstituted alkyl, substituted or unsubstituted haloalkyl, substituted or unsubstituted hydroxyl alkyl, substituted or unsubstituted alkoxy, substituted or unsubstituted haloalkoxy, substituted or unsubstituted alkenyl, substituted or unsubstituted alkynyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted arylalkyl, substituted or unsubstituted heteroaryl, substituted or unsubstituted heteroarylalkyl, substituted or unsubstituted heterocyclylalkyl ring, substituted or unsubstituted heteroarylalkyl, substituted or unsubstituted heterocyclic ring, substituted or unsubstituted guanidine, —COOR$^{x'}$, —C(O)R$^{x'}$, —C(S)R$^{x'}$, —C(O)NR$^{x'}$R$^{y'}$, —C(O)ONR$^{x'}$R$^{y'}$, —NR$^{x'}$CONR$^{y'}$R$^{z'}$, —N(R$^{x'}$)SOR$^{y'}$, —N(R$^{x'}$)SO$_2$R$^{y'}$, —(=N—N(R$^{x'}$)R$^{y'}$), —NR$^{x'}$C(O)OR$^{y'}$, —NR$^{x'}$R$^{y'}$, —NR$^{x'}$C(O)R$^{y'}$, —NR$^{x'}$C(S) R$^{y'}$, —NR$^{x'}$—C(S)NR$^{y'}$R$^{z'}$, —SONR$^{x'}$R$^{y'}$, —SO$_2$NR$^{x'}$R$^{y'}$, —OR$^{x'}$, —OC(O)NR$^{y'}$R$^{z'}$, —OC(O)OR$^{y'}$, —OC(O)R$^{x'}$, —OC(O)NR$^{x'}$R$^{y'}$, —SR$^{x'}$, —SOR$^{x'}$, —SO$_2$R$^{x'}$, and —ONO$_2$, wherein each occurrence of R$^{x'}$, R$^{y'}$ and R$^{z'}$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, and substituted or unsubstituted heterocyclic ring. The substituents in the aforementioned "substituted" groups cannot be further substituted. For example, when the substituent on "substituted alkyl" is "substituted aryl", the substituent on "substituted aryl" can be unsubstituted alkenyl but cannot be "substituted alkenyl".

The term "pharmaceutically acceptable salt" includes salts prepared from pharmaceutically acceptable bases or acids including inorganic or organic bases and inorganic or organic acids. Examples of such salts include, but are not limited to, acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate, diphosphate, polygalacturonate, salicylate, stearate, sulfate, subacetate, succinate, tannate, tartrate, teoclate, tosylate, triethiodide and valerate. Examples of salts derived from inorganic bases include, but are not limited to, aluminum, ammonium, calcium, copper, ferric, ferrous, lithium, magnesium, manganic, mangamous, potassium, sodium, and zinc.

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

The sensation of pain can be triggered by any number of physical or chemical stimuli and the sensory neurons which mediate the response to this harmful stimulus are termed as "nociceptors". Nociceptors are primary sensory afferent (C and A6 fibers) neurons that are activated by a wide variety of noxious stimuli including chemical, mechanical, thermal, and proton (pH<6) modalities. Nociceptors are the nerves which sense and respond to parts of the body which suffer from damage. They signal tissue irritation, impending injury, or actual injury. When activated, they transmit pain signals (via the peripheral nerves as well as the spinal cord) to the brain.

The term "chronic pain" usually refers to pain which persists for 3 months or longer and can lead to significant changes in a patient's personality, lifestyle, functional ability and overall quality of life. Chronic pain can be classified as either nociceptive or neuropathic. Nociceptive pain includes tissue injury-induced pain and inflammatory pain such as that associated with arthritis. Neuropathic pain is caused by damage to the sensory nerves of the peripheral or central nervous system and is maintained by aberrant somatosensory processing. The pain is typically well localized, constant, and often with an aching or throbbing quality. Visceral pain is the subtype of nociceptive pain that involves the internal organs. It tends to be episodic and poorly localized. Nociceptive pain is usually time limited, meaning when the tissue damage heals, the pain typically resolves (arthritis is a notable exception in that it is not time limited).

Certain compounds of present patent application are capable of existing in stereoisomeric forms (e.g. diastereomers and enantiomers). With respect to the overall compounds described by the general formula (I), the present invention extends to all these stereoisomeric forms and to mixtures thereof. The different stereoisomeric forms of the compounds described herein may be separated from one another by the methods known in the art, or a given isomer may be obtained by stereospecific or asymmetric synthesis. Tautomeric forms and mixtures of compounds described herein are also contemplated. It is also to be understood that compounds described herein may exist in solvated forms (such as hydrates) as well as unsolvated forms, and that the invention encompasses all such forms.

Pharmaceutical Compositions

The compounds of the invention are typically administered in the form of a pharmaceutical composition. Such compositions can be prepared using procedures known in the pharmaceutical art and comprise at least one compound of the invention. The pharmaceutical composition of the present patent application comprises one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifying agents, and solvents.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters, and polyoxyethylene.

The pharmaceutical composition may also include one or more pharmaceutically acceptable auxiliary agents, wetting agents, suspending agents, preserving agents, buffers, sweetening agents, flavoring agents, colorants or any combination of the foregoing.

The pharmaceutical compositions may be in conventional forms, for example, capsules, tablets, solutions, suspensions, injectables or products for topical application. Further, the pharmaceutical composition of the present invention may be formulated so as to provide desired release profile.

Administration of the compounds of the invention, in pure form or in an appropriate pharmaceutical composition, can be carried out using any of the accepted routes of administration of pharmaceutical compositions. The route of administration may be any route which effectively transports the active compound of the patent application to the appropriate or desired site of action. Suitable routes of administration include, but are not limited to, oral, nasal, buccal, dermal, intradermal, transdermal, parenteral, rectal, subcutaneous, intravenous, intraurethral, intramuscular, or topical.

Solid oral formulations include, but are not limited to, tablets, capsules (soft or hard gelatin), dragees (containing the active ingredient in powder or pellet form), troches and lozenges.

Liquid formulations include, but are not limited to, syrups, emulsions, and sterile injectable liquids, such as suspensions or solutions.

Topical dosage forms of the compounds include ointments, pastes, creams, lotions, powders, solutions, eye or ear drops, impregnated dressings, and may contain appropriate conventional additives such as preservatives, solvents to assist drug penetration.

The pharmaceutical compositions of the present patent application may be prepared by conventional techniques, e.g., as described in *Remington: The Science and Practice of Pharmacy*, 20$^{th}$ Ed., 2003 (Lippincott Williams & Wilkins).

Suitable doses of the compounds for use in treating the diseases and disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. Mode of administration, dosage forms, and suitable pharmaceutical excipients can also be well used and adjusted by those skilled in the art. All changes and modifications are envisioned within the scope of the present patent application.

In another embodiment, the present invention relates to a pharmaceutical composition comprising a compound as described herein, a second therapeutic agent, and optionally a pharmaceutically-acceptable excipient. In one embodiment, the pharmaceutical composition includes a compound as described herein and a second therapeutic agent, wherein each of the compound described herein and the second therapeutic agent is formulated in admixture with a pharmaceutically-acceptable excipient.

Methods of Treatment

Compounds of the present invention are particularly useful because they may inhibit the activity of prostaglandin E synthases {and particularly microsomal prostaglandin E synthase-1 (mPGES-1)}, i.e., they prevent, inhibit, or suppress the action of mPGES-1 or a complex of which the mPGES-1 enzyme forms a part, and/or may elicit mPGES-1 modulating effect. Compounds of the invention are thus useful in the treatment of those conditions in which inhibition of a PGES, and particularly mPGES-1, is required.

Compounds of the invention are thus expected to be useful in the treatment of inflammation. The term "inflammation" will be understood by those skilled in the art to include any condition characterized by a localized or a systemic protective response, which may be elicited by physical trauma, infection, chronic diseases, such as those mentioned hereinbefore, and/or chemical and/or physiological reactions to external stimuli (e.g. as part of an allergic response). Any such response, which may serve to destroy, dilute or sequester both the injurious agent and the injured tissue, may be manifest by, for example, heat, swelling, pain, redness, dilation of blood vessels and/or increased blood flow.

The term "inflammation" is also understood to include any inflammatory disease, disorder or condition per se, any condition that has an inflammatory component associated with it, and/or any condition characterized by inflammation as a symptom, including inter alia acute, chronic, ulcerative, specific, allergic, infection by pathogens, immune reactions due to hypersensitivity, entering foreign bodies, physical injury, and necrotic inflammation, and other forms of inflammation known to those skilled in the art. The term thus also includes, for the purposes of this invention, inflammatory pain, pain generally and/or fever.

The compounds of the present invention may also be useful in the treatment of asthma, chronic obstructive pulmonary disease, pulmonary fibrosis, inflammatory bowel disease, irritable bowel syndrome, inflammatory pain, chronic pain, acute pain, fever, migraine, headache, low back pain, fibromyalgia, myofascial disorders, viral infections (e.g. influenza, common cold, herpes zoster, hepatitis C and AIDS), bacterial infections, fungal infections, dysmenorrhea, burns, surgical or dental procedures, malignancies (e.g. breast cancer, colon cancer, and prostate cancer), hyperprostaglandin E syndrome, classic Bartter syndrome, atherosclerosis, gout, arthritis, osteoarthritis, juvenile arthritis, rheumatoid arthritis, juvenile onset rheumatoid arthritis, rheumatic fever, ankylosing spondylitis, Hodgkin's disease, systemic lupus erythematosus, vasculitis, pancreatitis, nephritis, bursitis, conjunctivitis, iritis, scleritis, uveitis, wound healing, dermatitis, eczema, psoriasis, stroke, diabetes mellitus, neurodegenerative disorders such as Alzheimer's disease and multiple sclerosis, autoimmune diseases, allergic disorders, rhinitis, ulcers, mild to moderately active ulcerative colitis, familial adenomatous polyposis, coronary heart disease, sarcoidosis and any other disease with an inflammatory component.

Compounds of the invention may also have effects that are not linked to inflammatory mechanisms, such as in the reduction of bone loss in a subject. Conditions that may be mentioned in this regard include osteoporosis, osteoarthritis, Paget's disease and/or periodontal diseases.

By virtue of the mPGES-1 inhibitory activity of compounds of the present invention, the compounds are useful for the relief of pain, fever and inflammation of a variety of conditions including rheumatic fever, symptoms associated with influenza or other viral infections, common cold, low back and neck pain, dysmenorrhea, headache, migraine (acute and prophylactic treatment), toothache, sprains and strains, myositis, neuralgia, synovitis, arthritis, including rheumatoid arthritis, juvenile rheumatoid arthritis, degenerative joint diseases (osteoarthritis), acute gout and ankylosing spondylitis, acute, subacute and chronic musculoskeletal pain syndromes such as bursitis, burns, injuries, and pain following surgical (post-operative pain) and dental procedures as well as the preemptive treatment of surgical pain. The pain may be mild pain, moderate pain, severe pain, musculoskeletal pain, complex regional pain syndrome, neuropathic pain, back pain such as acute visceral pain, neuropathies, acute trauma, chemotherapy-induced mononeuropathy pain states, polyneuropathy pain states (such as diabetic peripheral neuropathy & chemotherapy induced neuropathy), autonomic neuropathy pain states, pheriphaeral nervous system (PNS) lesion or central nervous system (CNS) lesion or disease related pain states, polyradiculopathies of cervical, lumbar or sciatica type, cauda equina syndrome, piriformis syndrome, paraplegia, quadriplegia, pain states related to various Polyneuritis conditions underlying various infections, chemical injuries, radiation exposure, underlying disease or deficiency conditions (such as beriberi, vitamin deficiencies, hypothyroidism, porphyria, cancer, HIV, autoimmune disease such as multiple sclerosis and spinal-cord injury, fibromyalgia, nerve injury, ischaemia, neurodegeneration, stroke, post stroke pain, inflammatory disorders, oesophagitis, gastroeosophagal reflux disorder (GERD), irritable bowel syndrome, inflammatory bowel disease, pelvic hypersensitivity, urinary incontinence, cystitis, stomach duodenal ulcer, muscle pain, pain due to colicky and referred pain. Compounds of the present invention may also be useful for the treatment or prevention of endometriosis, hemophilic arthropathy and Parkinson's disease.

Compounds of the present invention will also inhibit prostanoid-induced smooth muscle contraction by preventing the synthesis of contractile prostanoids and hence may be of use in the treatment of dysmenorrhea, premature labor and asthma.

In addition, the compounds of the present invention may inhibit cellular neoplastic transformations and metastic tumor growth and hence can be used in the treatment of cancer, and pain associated with cancer. Furthermore, the present invention provides preferred embodiments of the methods and uses as described herein, in which cancer includes Acute Lymphoblastic Leukemia, Acute Myeloid Leukemia, Adolescents Cancer, Adrenocortical Carcinoma, Anal Cancer, Appendix Cancer, Astrocytomas, Atypical Teratoid, Basal Cell Carcinoma, Bile Duct Cancer, Extrahepatic, Bladder Cancer, Bone Cancer, Brain Stem Glioma, Brain Tumor, Breast Cancer, Bronchial Tumors, Burkitt Lymphoma, Carcinoid Tumor, Carcinoma of Unknown Primary, Cardiac (Heart) Tumors, Central Nervous System tumors, Cervical Cancer, Childhood Cancers, Chordoma, Chronic Lymphocytic Leukemia, Chronic Myelogenous Leukemia, Chronic Myeloproliferative Disorders, Colon Cancer, Colorectal Cancer, Craniopharyngioma, Cutaneous T-Cell Lymphoma, Duct Bile Extrahepatic cancer, Ductal Carcinoma In Situ, Embryonal Tumors, Central Nervous System cancer, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Fibrous Histiocytoma of Bone, Malignant, and Osteosarcoma, Gall bladder Cancer, Gastric (Stomach) Cancer, Gastrointestinal Carcinoid Tumor, Gastrointestinal Stromal Tumors, Germ Cell Tumor, Gestational Trophoblastic Tumor, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors, Pancreatic Neuroendocrine Tumors, Kaposi Sarcoma, Kidney cancer, Langerhans Cell Histiocytosis, Laryngeal Cancer, Acute Lymphoblastic Leukemia, Acute Myeloid Leukemia, Chronic Lymphocytic Leukemia, Chronic Myelogenous Leukemia, Hairy Cell Leukemia, Lip and Oral Cavity Cancer, Liver Cancer, Lobular Carcinoma In Situ, Lung Cancer, AIDS-Related Lymphoma, Cutaneous T-Cell Lymphoma, Hodgkin Lymphoma, Non-Hodgkin Lymphoma, Primary Central Nervous System (CNS) Lymphoma, Macroglobulinemia, Waldenstrom, Male Breast Cancer, Malignant Fibrous Histiocytoma of Bone and Osteosarcoma, Melanoma, Merkel Cell Carcinoma, Mesothelioma, Malignant, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic, Myeloid Leukemia Acute, Multiple Myeloma, Chronic Myeloproliferative Disorders, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and, Oropharyngeal Cancer, Osteosarcoma and Malignant Fibrous Histiocytoma of Bone, Ovarian Cancer, Pancreatic Cancer, Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Ewing Sarcoma, Kaposi Sarcoma, Osteosarcoma, Rhadomyosarcoma, Soft Tissue Sarcoma, Uterine Sarcoma, Sezary Syndrome, Skin Cancer, Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, T-Cell Lymphoma, Cutaneous, Testicular Cancer, Throat Cancer, Thymoma and Thymic Carcinoma, Thyroid Cancer, Transitional Cell Cancer of the Renal Pelvis and Ureter, Trophoblastic Tumor, Gestational, Unknown Primary, Carcinoma of, Ureter and Renal Pelvis, Transitional Cell Cancer, Urethral Cancer, Uterine Cancer, Endometrial, Uterine Sarcoma, Vaginal Cancer, Vulvar Cancer, Waldenstrim, Macroglobulinemia, Wilms Tumor and Women's Cancers.

Compounds of the present invention are indicated both in the therapeutic and/or prophylactic treatment of the above-mentioned conditions. For the above-mentioned therapeutic uses the dosage administered will, of course, vary with the compound employed, the mode of administration, the treatment desired and the disorder indicated. The daily dosage of the compound of the invention may be in the range from 0.05 mg/kg to 100 mg/kg.

General Methods of Preparation

The compounds described herein, including compounds of formula (I), (II) and (III), may be prepared using techniques known to one skilled in the art through the reaction sequences depicted in schemes provided below, as well as by other methods. Furthermore, in the following schemes, where specific acids, bases, reagents, coupling agents, solvents, etc. are mentioned, it is understood that other suitable acids, bases, reagents, coupling agents etc. may be used and are included within the scope of the present invention. Modifications to reaction conditions, for example, temperature, duration of the reaction or combinations thereof, are envisioned as part of the present invention. The compounds obtained by using the general reaction sequences may be of insufficient purity. These compounds can be purified by using any of the methods for purification of organic compounds known in the art, for example, crystallization or silica gel or alumina column chromatography using different solvents in suitable ratios. All possible geometrical isomers and stereoisomers are envisioned within the scope of this invention.

The starting materials for the below reaction schemes are commercially available or can be prepared according to methods known to one skilled in the art or by methods disclosed herein. In general, intermediates and compounds of the present application may be prepared using the reaction scheme as follows, wherein all symbols are as defined above.

Synthetic Scheme 1

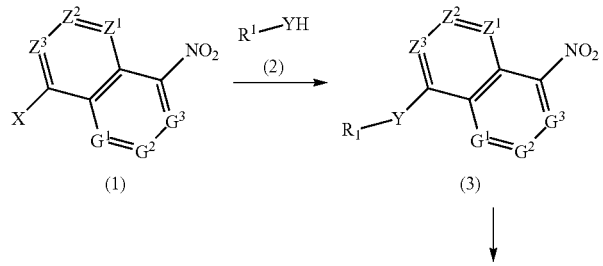

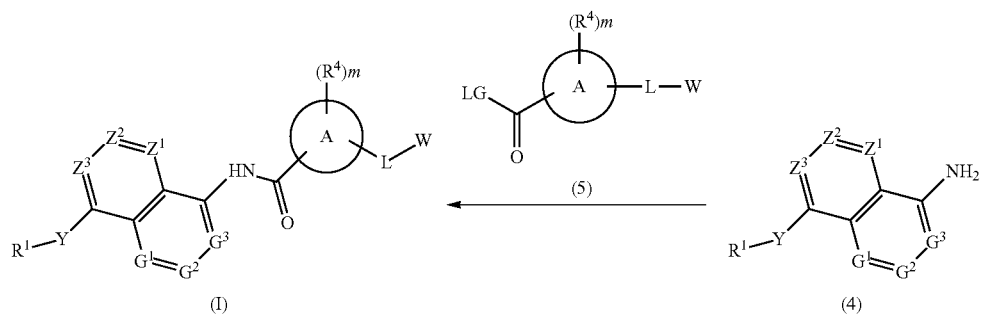

The synthesis of the compounds of formula (I) (wherein $Z^1, Z^2, Z^3, G^1, G^2, G^3, R^1, R^4, m, A, L, W$ are as defined with respect to the compounds of formula (I) and Y is $NR^c$ or O) can be performed as described in Synthetic scheme 1. The reaction of a compound of formula (I) (wherein X represents an appropriate leaving group, such as Br, Cl, I, OLG, SR', S(O)R', or S(O)$_2$R'; where LG or R' is an alkyl group, for example CH$_3$) with a compound of formula (2) under suitable conditions known in the art, for example, in a suitable solvent such as acetonitrile (CH$_3$CN), N,N-dimethylformamide (DMF), isopropanol ($^i$PrOH), tetrahydrofuran (THF), or N-methylpyrrolidinone (NMP) in the temperature range of 0-250° C. or at reflux temperature, optionally in the presence of a suitable base such NaH or potassium carbonate, can provide a compound of formula (3). Alternatively, when X represents OH, the conversion of a compound of formula (I) to a compound of formula (3) can be performed with a suitable coupling reagent such as Benzotriazole-1-yl-oxy-tris-(dimethylamino)-phosphonium hexafluorophosphate (BOP) or (Benzotriazol-1-yloxy)tripyrrolidinophosphonium hexafluorophosphate (PyBOP) in the presence of a suitable base such as 1,8-Diazabicyclo[5.4.0]undec-7-ene (DBU) or N,N-diisoporpylethylamine (DIPEA) in a suitable solvent such as DMF or CH$_3$CN in the temperature range 0-150° C.

The nitro group of the compound of formula (3) can be reduced with a suitable reducing agent, such as iron and ammonium chloride or Pd on carbon under H$_2$ gas in an appropriate solvent such as ethanol and/or water, ethyl acetate in the temperature range 0-150° C., to provide the amine of formula (4).

The treatment of amine (4) with an appropriate acyl compound of formula (5), wherein LG represent a suitable leaving group (e.g., OH or Cl or Br or O-alkyl or O-aryl or O(C=O)-alkyl) under suitable reaction conditions can provide a compound of formula (I). When LG represents OH, the reaction can be performed with a suitable coupling reagent known in the art, for example, 1-ethyl-3-(3-dimethylaminopropyl)carbodiimide (EDCI) in a suitable solvent such as DMF or tetrahydrofuran (THF) in the temperature range of 0-120° C., optionally in the presence of a suitable base such as DIPEA (diisopropylethyl amine) or Et$_3$N. Alternatively, the reaction can be performed using a suitable reagent such as isobutyl chloroformate, oxalyl chloride or thionyl chloride in a suitable solvent such as DMF, DCM or THF, in the presence of a suitable base such as DIPEA or Et$_3$N. When LG represents Cl the reaction can be performed in a suitable solvent such as DMF, DCM or THF in the temperature range of 0-120° C., optionally in the presence of a suitable base such as DIPEA. Furthermore, when LG represents O-alkyl or O-aryl or O(C=O)-alkyl the reaction can be performed with a suitable reagent such as trimethylaluminium or a strong base such as sodium hydride (NaH) in a suitable solvent such as toluene or DMF.

Synthesis of the compounds of formula (II) (wherein $Z^1, Z^3, G^1, R^1, R^2, R^3, Q^1, Q^2, Q, Q^4, R^x, R^y, n$ and W are as defined above with respect to a compound of formula (II)) and Y is O, NH or $NR^c$ can be performed as described in Synthetic scheme 2.

Synthetic Scheme 2

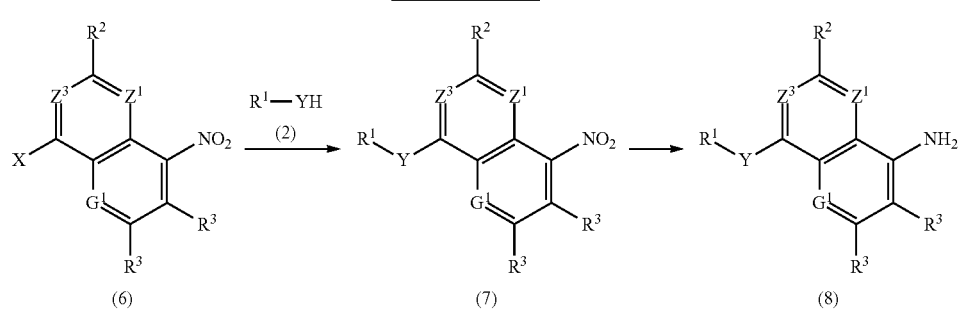

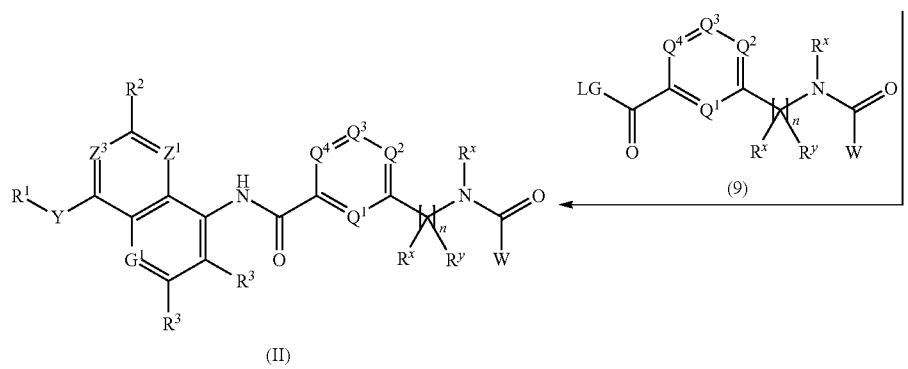

(II)

The reaction of a compound of formula (6) (wherein X represents an appropriate leaving group such as Br, Cl, I, OLG, SR', S(O)R', or S(O)₂R'; where LG or R' is an alkyl group, for example CH₃) with a compound of formula (2) under suitable conditions in the art, for example, in a suitable solvent such as acetonitrile (CH₃CN), N,N-dimethylformamide (DMF), isopropanol ($^i$PrOH), tetrahydrofuran (THF), or N-methylpyrrolidinone (NMP) in the temperature range of 0-250° C. or at reflux temperature, optionally in the presence of a suitable base such as NaH or potassium carbonate, can provide a compound of formula (7). Alternatively, when X represents OH, the conversion of a compound of formula (6) to a compound of formula (7) can be performed with a suitable coupling reagent such as Benzotriazole-1-yl-oxy-tris-(dimethylamino)-phosphonium hexafluorophosphate (BOP) or (Benzotriazol-1-yloxy)tripyrrolidinophosphonium hexafluorophosphate (PyBOP) in presence of a suitable base such as 1,8-Diazabicyclo[5.4.0]undec-7-ene (DBU) or N,N-diisoporpylethylamine (DIPEA) in a suitable solvent such as DMF or CH₃CN in the temperature range 0-150° C.

The nitro group of a compound of formula (7) can be reduced with a suitable reducing agent such as iron and ammonium chloride or Pd on carbon under H₂ gas in an appropriate solvent such as ethanol and/or water, ethyl acetate in the temperature range 0-150° C., to provide the amine of formula (8). The treatment of amine (8) with an appropriate acyl compound of formula (9), wherein LG represents OH or Cl or Br or O-alkyl or O-aryl or O(C=O)-alkyl under suitable reaction condition can provide a compound of formula (II). When LG represents OH the reaction can be performed with a suitable coupling reagent known in the art, for example, 1-ethyl-3-(3-dimethylaminopropyl)carbodiimide (EDCI) in a suitable solvent such as DMF or tetrahydrofuran (THF) in the temperature range of 0-120° C., optionally in the presence of a suitable base such as DIPEA or Et₃N. Alternatively, the reaction can be performed using a suitable reagent such as isobutyl chloroformate, oxalyl chloride or thionyl chloride in a suitable solvent such as DMF, DCM or THF, in the presence of a suitable base such as DIPEA or Et₃N. When LG represents Cl the reaction can be performed in a suitable solvent such as DMF, DCM or THF in the temperature range of 0-120° C., optionally in the presence of a suitable base such as DIPEA. Furthermore, when LG represents O-alkyl or O-aryl or O(C=O)-alkyl the reaction can be performed with a suitable reagent such as trimethylaluminium or a strong base such as sodium hydride (NaH) in a suitable solvent such as toluene or DMF.

Synthesis of the compounds of formula (III) (wherein Y, Z¹, Z³, R¹, R², R³, Q¹, Q², Q³, Q⁴, and W are as defined above with respect to a compound of formula (III)) can be performed as described in Synthetic scheme 3.

Synthetic Scheme 3

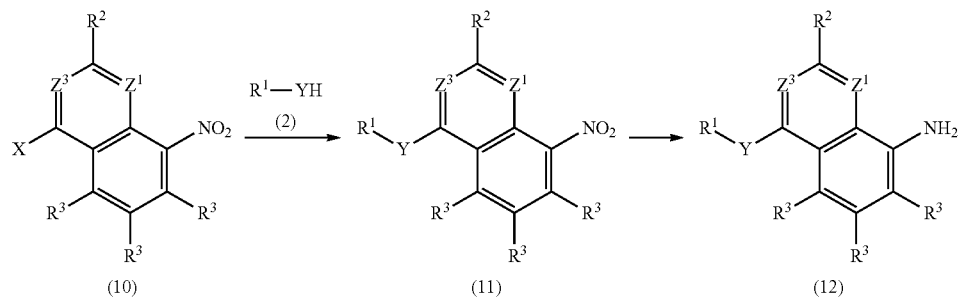

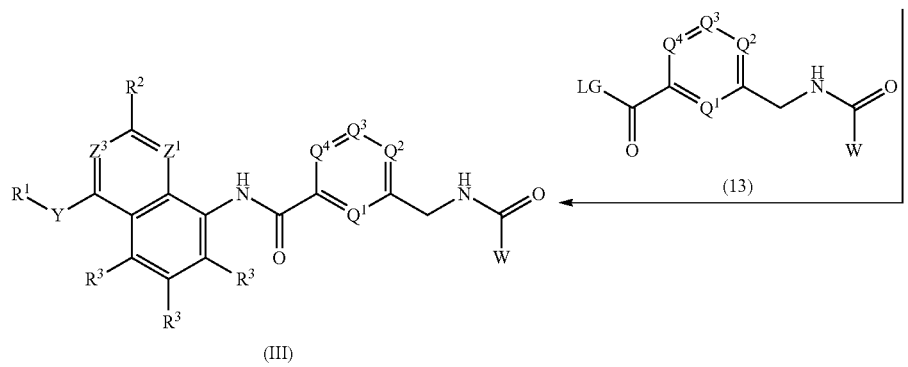

(III)

The reaction of a compound of formula (10) (wherein X represents an appropriate leaving group such as Br, Cl, I, OLG, SR', S(O)R', or S(O)₂R'; where LG or R' is an alkyl group, for example CH₃) with a compound of formula (2) under suitable conditions known in the art, for example, in a suitable solvent such as acetonitrile (CH₃CN), N,N-dimethylformamide (DMF), isopropanol (ⁱPrOH), tetrahydrofuran (THF), or N-methylpyrrolidinone (NMP) in the temperature range of 0-250° C. or at reflux temperature, optionally in the presence of a suitable base such NaH or potassium carbonate, can provide a compound of formula (11). Alternatively, when X represents OH, the conversion of a compound of formula (10) to a compound of formula (11) can be performed with a suitable coupling reagent such as Benzotriazole-1-yl-oxy-tris-(dimethylamino)-phosphonium hexafluorophosphate (BOP) or (Benzotriazol-1-yloxy)tripyrrolidinophosphonium hexafluorophosphate (PyBOP) in the presence of a suitable base such as 1,8-Diazabicyclo[5.4.0]undec-7-ene (DBU) or N,N-diisoporpylethylamine (DIPEA) in a suitable solvent such as DMF or CH₃CN in the temperature range 0-150° C.

The nitro group of a compound of formula (11) can be reduced with a suitable reducing agent such as iron and ammonium chloride or Pd on carbon under H₂ gas in an appropriate solvent such as ethanol and/or water, or ethyl acetate in the temperature range 0-150° C., to provide the amine of formula (12). The treatment of amine (12) with an appropriate acyl compound of formula (13), wherein LG represent OH or Cl or Br or O-alkyl or O-aryl or O(C=O)-alkyl under suitable reaction condition can provide a compound of formula (III). When LG represents OH the reaction can be performed with a suitable coupling reagent known in the art, for example, 1-ethyl-3-(3-dimethylaminopropyl)carbodiimide (EDCI) in a suitable solvent such as DMF or tetrahydrofuran (THF) in the temperature range of 0-120° C., optionally in the presence of a suitable base such as DIPEA or Et₃N. Alternatively, the reaction can be performed using a suitable reagent such as isobutyl chloroformate, oxalyl chloride or thionyl chloride in a suitable solvent such as DMF, DCM or THF, in the presence of a suitable base such as DIPEA or Et₃N. When LG represents Cl the reaction can be performed in a suitable solvent such as DMF, DCM or THF in the temperature range of 0-120° C., optionally in the presence of a suitable base such as DIPEA. Furthermore, when LG represents O-alkyl or O-aryl or O(C=O)-alkyl the reaction can be performed with a suitable reagent such as trimethylaluminium or a strong base such as sodium hydride (NaH) in a suitable solvent such as toluene or DMF.

Synthesis of the compounds of formula (III) (wherein Y, $Z^1, Z^3, R^1, R^2, R^3, Q^1, Q^2, Q^3, Q^4$, and W are as defined above with respect to a compound of formula (III)) can be performed as described in Synthetic scheme 4.

Synthetic Scheme 4

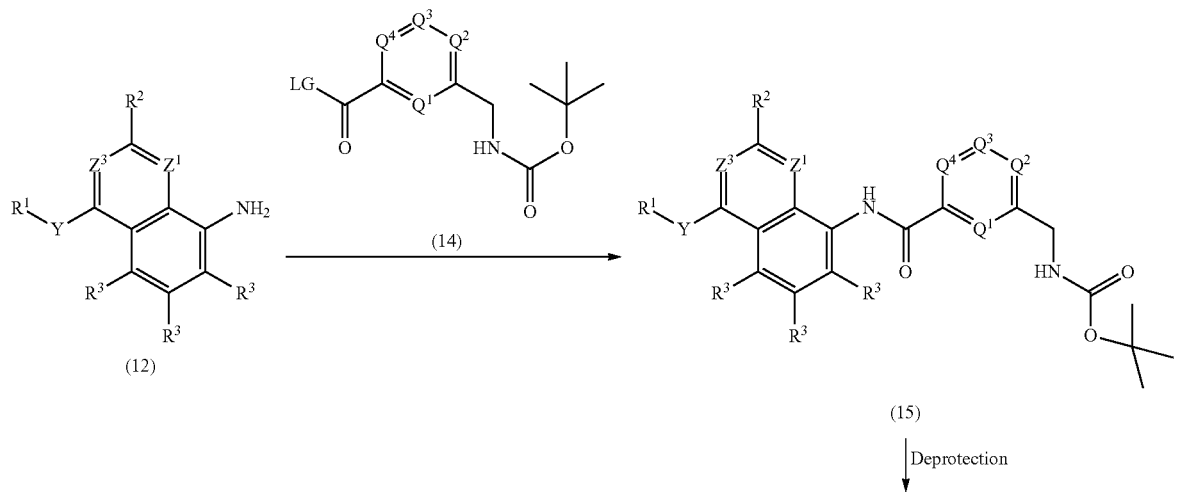

Deprotection

-continued

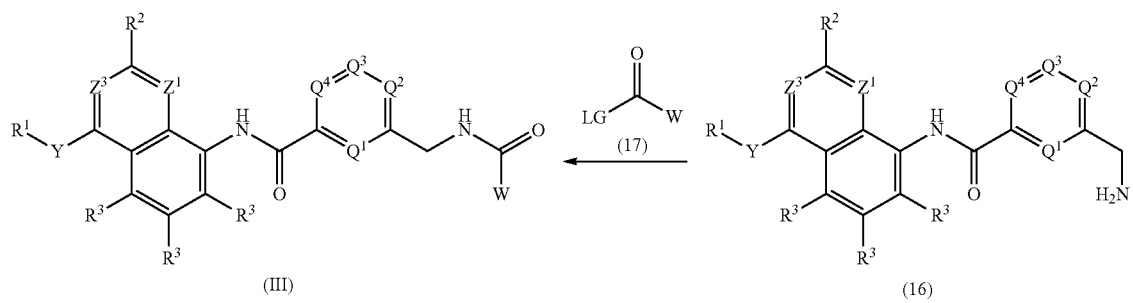

The coupling of a compound of formula (12) with a compound of formula (14) (wherein LG represents OH or Cl or O-alkyl or O-aryl or O(C=O)-alkyl) under the suitable conditions (as described in step-1 of Synthetic scheme 3) can provides a compound of formula (15). Further deprotection of a compound of formula (15) using a suitable deprotecting agent (e.g. HCl) provides a compound of formula (16).

Coupling of a compound of (16) with a compound of formula (17) (wherein LG represents OH or Cl or O-alkyl or O-aryl or O(C=O)-alkyl) can provide a compound of formula (III) under the suitable conditions (as described in step-3 of Synthetic scheme 3).

EXPERIMENTAL

Unless otherwise stated, work-up includes distribution of the reaction mixture between the organic and aqueous phase indicated within parentheses, separation of layers and drying the organic layer over sodium sulphate (Na$_2$SO$_4$), filtration and evaporation of the solvent under reduced pressure. Purification, unless otherwise mentioned, includes purification by silica gel chromatographic techniques, in suitable solvents of a suitable polarity as the mobile phase. Abbreviations used in the description of the chemistry and in the examples that follow are: AcOH: acetic acid; DMSO-d$_6$: Hexadeuterodimethyl sulfoxide; CDCl$_3$: deuterated chloroform; CHCl$_3$: chloroform; EtOAc or EA: ethyl acetate; DCM: dichloromethane; DMSO: dimethyl sulfoxide; DMF: N,N-dimethylformamide; DMA: dimethylacetamide; DIPEA: N,N-diisopropylethylamine; EDCI: 1-ethyl-3-(3-dimethylaminopropyl)carbodiimide); HOBt: hydroxybenzotriazole; K$_2$CO$_3$: potassium carbonate; LDA: lithium diisopropylamide; MeOH: methanol; EtOH: ethanol; NaHCO$_3$: sodium bicarbonate; Na$_2$CO$_3$: sodium carbonate; NaOtBu: sodiumtertiarybutoxide; NMP: N-methylpyrrolidinone; PCl$_5$: phosphorous pentachloride; POCl$_3$: phosphorous oxychloride; THF: tetrahydrofuran; TEA: triethylamine; TBAF: tetra-n-butylammonium fluoride; J: Coupling constant in units of Hz; RT or rt: room temperature (22-26° C.); aq.: aqueous; equiv. or eq.: equivalents; conc.: concentrated; i.e.: that is; h: hours; J: coupling constant in units of Hz.

Preparation of Intermediates

Intermediate-1

N'-(3-(Trifluoromethyl)phenyl)isoquinoline-1,5-diamine

Step 1: Preparation of 1-chloro-5-nitroisoquinoline

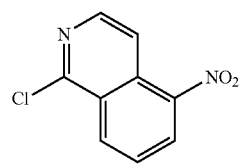 [SMILES: O=[N+]([O-])c1cccc2c(Cl)nccc12]

To a solution of 1-chloroisoquinoline (3.6 g, 22.09 mmol) in conc. H$_2$SO$_4$ (24 mL) was added conc. HNO$_3$ (8 mL) drop wise at 0-5° C. Then KNO$_3$ (2.90 g, 28.71 mmol) was added to the reaction mixture portion wise at 0-5° C. The reaction mass was stirred at rt for 2 h and diluted with water then the reaction mixture was filtered. The filter cake was dissolved in 5% methanol in chloroform and was dried over Na$_2$SO$_4$. The organic layer was filtered and concentrated to afford 4.0 g of the title product. $^1$H NMR (300 MHz, DMSO-d$_6$): δ 8.74 (t, J=6.9 Hz, 2H), 8.55 (d, J=6.3 Hz, 1H), 8.32 (d, J=6.0 Hz, 1H), 8.02 (t, J=8.1 Hz, 1H).

Step 2: Preparation of 5-nitro-N-(3-(trifluoromethyl)phenyl)isoquinolin-1-amine

To a solution of 1-chloro-5-nitroisoquinoline (1.0 g, 4.8 mmol) in N-methylpyrrolidinone (2 mL) was added 3-(trifluoromethyl)aniline (917 mg, 5.7 mmol). The reaction mass was heated at 110° C. for 2 h. The reaction mass was diluted with water and was extracted with chloroform. The organic layer was dried, filtered, concentrated and purified by column chromatography to afford 1.2 g of the title product. $^1$H NMR (300 MHz, DMSO-$d_6$): δ 8.44 (d, J=7.8 Hz, 1H), 8.33-8.29 (m, 2H), 7.96-7.89 (m, 3H), 7.68 (t, J=8.1 Hz, 1H), 7.51 (t, J=7.8 Hz, 1H), 7.36 (d, J=7.8 Hz, 1H), 7.26 (m, 1H).

Step 3: Preparation of N'-(3-(trifluoromethyl)phenyl) isoquinoline-1,5-diamine

To a solution of 5-nitro-N-(3-(trifluoromethyl)phenyl)isoquinolin-1-amine (1.0 g, 3.0 mmol) in a mixture of EtOH:H$_2$O (8:2, 10 mL) were added iron powder (1.26 g, 4.8 mmol), and NH$_4$Cl (1.6 g, 30.0 mmol). The reaction mass was heated at reflux for 2 h and filtered. The filtrate was concentrated and the residue was purified by column chromatography to afford 0.800 g of the title product. $^1$H NMR (300 MHz, DMSO-$d_6$): δ 9.18 (s, 1H), 8.35 (s, 1H), 8.20 (d, J=7.8 Hz, 1H), 7.93 (d, J=8.7 Hz, 1H), 7.65 (d, J=8.4 Hz, 1H), 7.52 (t, J=7.8 Hz, 1H), 7.42-7.24 (m, 3H), 6.86 (d, J=7.5 Hz, 1H), 5.84 (s, 2H).

Intermediate-2

6-Chloro-2-fluoro-3-(pivalamidomethyl)benzoic acid

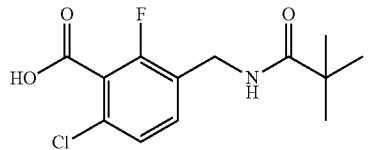 [SMILES: CC(C)(C)C(=O)NCc1ccc(Cl)c(C(=O)O)c1F]

Step 1: Preparation of ethyl 3-(aminomethyl)-6-chloro-2-fluorobenzoate

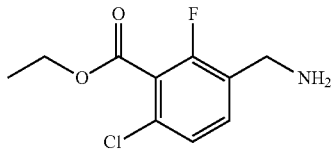

To a solution DIPEA (6.6 mL, 46.0 mmol) in THF (15 mL) was added $^n$BuLi (27 mL, 43.0 mmol, 1.6 M in hexane) at −78° C. and the reaction mixture was warmed to 0° C. over a period of 1 h. Then the reaction mixture was cooled to −78° C. and a solution of ethyl 2-chloro-6-fluorobenzoate (3.50 g, 19.0 mmol) in THF (56 mL) was added to the reaction mixture dropwise over 30 mins. The resulting mixture was stirred at −78° C. for 2 h before DMF (14 mL, 186 mmol) was added to the reaction mixture. The resulting mixture was stirred at −78° C. for 1 h and then gradually warmed to 0° C. over 1 h. The reaction mass was quenched with 10% aq. AcOH and was extracted with EtOAc. The organic layer was washed with water and brine, separated, dried, filtered and concentrated to provide ethyl 6-chloro-2-fluoro-3-formylbenzoate. $^1$H NMR (300 MHz, DMSO-$d_6$): δ 10.27 (s, 1H), 8.05-8.00 (t, J=7.8 Hz, 1H), 7.72-7.69 (d, J=8.4 Hz, 1H), 4.53-4.46 (q, J=6.9, 14.4 Hz, 2H), 1.41-1.37 (t, J=6.6 Hz, 3H). A mixture of ethyl 6-chloro-2-fluoro-3-formylbenzoate (4.04 g, 17.52 mmol) and hydroxylamine (50% aq, solution, 4.29 mL, 70 mmol) in MeOH (60 mL) was stirred at 55° C. for 1.5 h. Then the mixture was concentrated and the residue was diluted with EtOAc and was washed with water and brine. The organic layer was separated, dried, filtered and concentrated to provide ethyl 6-chloro-2-fluoro-3-((hydroxyimino)methyl)benzoate. $^1$H NMR (300 MHz, DMSO-$d_6$): δ 11.89 (s, 1H), 8.20 (s, 1H), 7.88-7.83 (t, J=8.1 Hz, 1H), 7.49-7.46 (d, J=8.4 Hz, 1H), 4.44-4.37 (q, J=7.5, 14.1 Hz, 2H), 1.34-1.29 (t, J=7.2 Hz, 3H). A mixture of ethyl 6-chloro-2-fluoro-3-((hydroxyimino) methyl)benzoate (4.21 g, 17.14 mmol), Zn (4.48 g, 68.56 mmol), and 10N HCl in EtOH (51.42 mL, 514.2 mmol) in MeOH (200 mL) was heated at reflux for 3 h. Additional Zn (2.24 g, 34.25 mmol) was added to the reaction mixture and it was heated at reflux for 2 h and then stirred at rt for 16 h. Then the reaction mixture was concentrated. The residue was diluted with EtOAc and was treated with a saturated solution of NaHCO$_3$. The mixture was filtered and the organic layer was separated, dried, filtered and concentrated to provide 3.5 g of the title product. $^1$H NMR (300 MHz, CDCl$_3$): δ 7.54 (t, J=7.8 Hz, 1H), 7.28 (d, J=7.8 Hz, 1H), 4.45 (q, J=7.5, 14.1 Hz, 2H), 4.11 (d, J=3.6 Hz, 2H), 3.37 (br s, 2H), 1.40 (t, J=7.2 Hz, 3H).

Step 2: Preparation of ethyl 6-chloro-2-fluoro-3-(pivalamidomethyl)benzoate

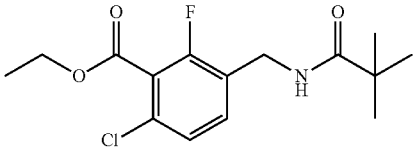 [SMILES: CCOC(=O)c1c(Cl)ccc(CNC(=O)C(C)(C)C)c1F]

To a solution of ethyl 3-(aminomethyl)-6-chloro-2-fluorobenzoate (70 mg, 0.3 mmol) in THF (3 mL) were added Et$_3$N (0.105 mL, 0.76 mmol) and pivaloyl chloride (38 μL, 0.31 mmol). The reaction mass was stirred at rt for 2 h, diluted with EtOAc and was washed with water, and brine. The organic layer was separated, dried, filtered and concentrated to afford 70 mg of the title product. $^1$H NMR (300 MHz, DMSO-$d_6$): δ 8.15 (br t, 1H), 7.43-7.35 (m, 2H), 4.38 (q, J=7.2 Hz, 2H), 4.26 (d, J=5.7 Hz, 2H), 1.30 (t, J=6.9 Hz, 3H), 1.11 (s, 9H).

Step 3: Preparation of 6-chloro-2-fluoro-3-(pivalamidomethyl)benzoic acid

To a solution of ethyl 6-chloro-2-fluoro-3-(pivalamidomethyl)benzoate (100 mg, 0.317 mmol) in THF:MeOH:H$_2$O (3:2:1; 6 mL) was added NaOH (25 mg, 0.634 mmol). The reaction mass was stirred at rt for 3 h. The reaction mass was neutralized with citric acid and concentrated. The residue was diluted with EtOAc and was washed with water and brine. The organic layer was separated, dried, filtered and concentrated to afford 70 mg of the title product. $^1$H NMR (300 MHz, DMSO-$d_6$): δ 14.10 (s, 1H), 8.14 (br t, 1H), 7.38-7.26 (m, 2H), 4.25 (d, J=5.4 Hz, 2H), 1.11 (s, 9H).

Intermediate-3

3-Chloro-6-(pivalamidomethyl)picolinic acid

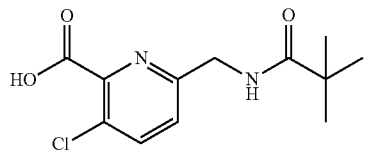 [SMILES: CC(C)(C)C(=O)NCc1ccc(Cl)c(C(=O)O)n1]

Step 1: Preparation of ethyl 3-chloro-6-iodopicolinate

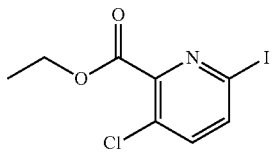

To a solution of 3,6-dichloropicolinic acid ethyl ester (5.0 g, 24 mmol) in CH$_3$CN (45 mL) was added NaI (10 g, 66.7 mmol) and acetyl chloride (2.5 mL). The reaction mass was heated in a sealed tube at 100° C. for 48 h. The reaction mass was diluted with EtOAc and was washed with saturated solutions of Na$_2$S$_2$O$_3$ and NaHCO$_3$. The organic layer was separated, dried, filtered and concentrated to afford 2 g of the title product. $^1$H NMR (300 MHz, DMSO-d$_6$): δ 8.04 (d, J=8.4 Hz, 1H), 7.82 (d, J=8.7 Hz, 1H), 4.38 (q, J=7.5 Hz, 2H), 1.32 (t, J=6.9 Hz, 3H).

Step 2: Preparation of ethyl 3-chloro-6-cyanopicolinate

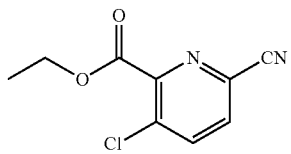

To a solution of ethyl 3-chloro-6-iodopicolinate (1.6 g, 5.38 mmol) in pyridine (40 mL) was added CuCN (480 mg, 5.36 mmol). The reaction mass was heated at 80° C. for 6 h. Then water was added to the reaction mass and it was extracted with EtOAc. The organic layer was separated, dried, filtered and concentrated to afford 850 mg of the title product. $^1$H NMR (300 MHz, DMSO-d$_6$): δ 8.44 (d, J=8.1 Hz, 1H), 8.28 (d, J=8.4 Hz, 1H), 4.42 (q, J=7.2 Hz, 2H), 1.33 (t, J=7.2 Hz, 3H).

Step 3: Preparation of ethyl 6-(((tert-butoxycarbonyl)amino)methyl)-3-chloropicolinate

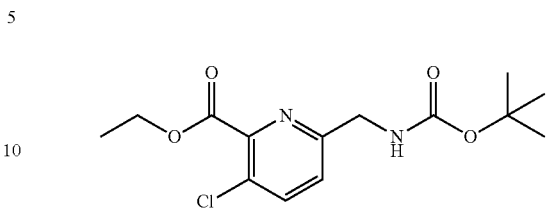

To a solution of ethyl 3-chloro-6-cyanopicolinate (1.0 g, 4.76 mmol) in ethanol (25 mL) were added Pt/C (1 g) and di-tert-butyl dicarbonate (1.037 g, 4.76 mmol). The reaction mass was hydrogenated at 60 psi for 18 h. The reaction mass was filtered through celite and the filtrate was concentrated to afford 800 mg of the title product. $^1$H NMR (300 MHz, DMSO-d$_6$): δ 8.06 (d, J=8.4 Hz, 1H), 7.56 (br t, 1H), 7.43 (d, J=8.4 Hz, 1H), 4.36 (q, J=6.9 Hz, 2H), 4.21 (d, J=6.0 Hz, 2H), 1.39-1.17 (m, 12H).

Step 4: Preparation of ethyl 3-chloro-6-(pivalamidomethyl)picolinate

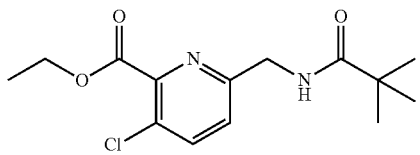 [SMILES: CCOC(=O)c1nc(CNC(=O)C(C)(C)C)ccc1Cl]

A solution of ethyl 6-(((tert-butoxycarbonyl)amino)methyl)-3-chloropicolinate (100 mg, 0.318 mmol) in EtOAc saturated with HCl (1 mL) was stirred at rt for 1 h. The reaction mixture was concentrated and the concentrate was dissolved in CH$_2$Cl$_2$ (2 mL). The solution was treated with DIPEA (0.5 mL) followed by pivaloyl chloride (38 mg, 0.318 mmol) at 0° C. The reaction mixture was stirred at rt for 2 h. The reaction mixture was diluted with EtOAc and was washed with H$_2$O and brine. The organic layer was separated, dried, filtered and concentrated to afford 85 mg of the title product. $^1$H NMR (300 MHz, DMSO-d$_6$): δ 8.26 (br t, 1H), 8.04 (d, J=8.4 Hz, 1H), 7.35 (d, J=8.1 Hz, 1H), 4.40-4.31 (m, 4H), 1.33-1.10 (m, 12H).

Step 5: Preparation of 3-chloro-6-(pivalamidomethyl)picolinic acid

The title compound was prepared following the procedure described in Step 3 of Intermediate-2 using ethyl 3-chloro-6-(pivalamidomethyl)picolinate (1.00 g, 3.35 mmol) in THF:MeOH:H$_2$O (3:2:1; 6 mL) and NaOH (268 mg, 6.71 mmol) to afford 750 mg of the title product. $^1$H NMR (300 MHz, DMSO-d$_6$): δ 13.85 (br s, 1H), 8.25 (br t, 1H), 7.99 (d, J=8.4 Hz, 1H), 7.29 (d, J=8.1 Hz, 1H), 4.32 (d, J=6.0 Hz, 2H), 1.19 (s, 9H).

Intermediate-4

2,6-Dimethyl-3-(pivalamidomethyl)benzoic acid

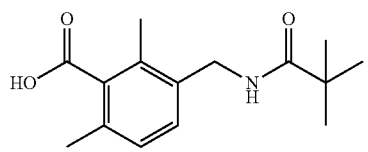 [SMILES: Cc1ccc(CNC(=O)C(C)(C)C)c(C)c1C(=O)O]

Step 1: Preparation of 2,6-dimethyl-3-((2,2,2-trifluoroacetamido)methyl)benzoic acid

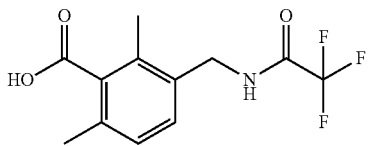 [SMILES: Cc1ccc(CNC(=O)C(F)(F)F)c(C)c1C(=O)O]

To a solution of 2,6-dimethyl benzoic acid (2.0 g, 13.33 mmol) in conc. $H_2SO_4$ (4 mL) was added 2,2,2-trifluoro-N-(hydroxymethyl)acetamide (2.1 g, 13.33 mmol). The mixture was stirred at rt for 16 h. The reaction mixture was poured into ice-water and stirred for 2 h. The precipitate was collected by filtration and dried to afford 3.2 g of the title product. $^1$H NMR (300 MHz, DMSO-$d_6$): δ 9.92 (m, 2H), 7.15-7.04 (m, 2H), 4.36 (s, 2H), 2.18 (m, 6H).

Step 2: Preparation of 2,6-dimethyl-3-(pivalamidomethyl)benzoic acid

To a solution of 2,6-dimethyl-3-((2,2,2-trifluoroacetamido)methyl)benzoic acid (3.2 g) in THF (15 mL) was added 1N HCl (15 mL) and the reaction mass was heated at reflux for 3 h. The reaction mixture was concentrated and the crude was co-distilled with toluene to afford 2.0 g of the 3-(aminomethyl)-2,6-dimethylbenzoic acid which was used in the next step without further purification. To a solution of 3-(aminomethyl)-2,6-dimethylbenzoic acid (500 mg, 2.46 mmol) in THF was added N,O-bis(trimethylsilyl)trifluoroacetamide (948 mg, 3.69 mmol) and the reaction mass was heated at reflux for 20 minutes. The reaction mass was cooled to 0° C. and Et$_3$N (1.77 mL, 9.85 mmol) was added, followed by pivaloyl chloride (0.44 mL, 3.69 mmol). The reaction mixture was stirred at rt for 18 h before it was quenched with water and was extracted with chloroform. The organic layer was separated, dried, filtered and concentrated to afford 450 mg of the title product. $^1$H NMR (300 MHz, DMSO-$d_6$): δ 13.15 (br s, 1H), 7.93 (br t, 1H), 7.08-7.01 (m, 2H), 4.19 (d, J=5.7 Hz, 2H), 2.21 (s, 3H), 2.17 (s, 3H), 1.12 (s, 9H).

Intermediate-5

2-Chloro-5-(pivalamidomethyl)benzoic acid

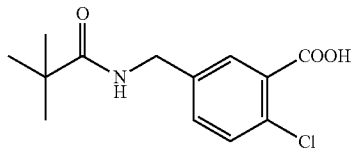 [SMILES: CC(C)(C)C(=O)NCc1ccc(Cl)c(C(=O)O)c1]

Step 1: Preparation of 2-chloro-5-{[(trifluoroacetyl)amino]methyl}benzoic acid

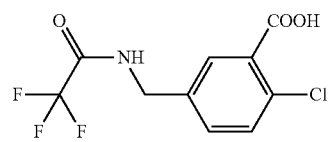

To a solution of 2-chlorobenzoic acid (500 mg, 3.49 mmol) in conc. $H_2SO_4$ was added 2,2,2-trifluoro-N-(hydroxymethyl)acetamide (547 mg, 3.49 mmol). The mixture was stirred at rt for 16 h. The reaction mixture was poured into ice-water and the precipitate obtained, was collected by filtration, dried and the re-crystallized from toluene/butan-2-one (7:1) to afford 800 mg of the title product. $^1$H NMR (300 MHz, DMSO $d_6$): δ 13.47 (br s, 1H), 10.06 (br s, 1H), 7.71 (s, 1H), 7.54 (d, J=8.4 Hz, 1H), 7.43 (d, J=9.9 Hz, 1H), 4.42 (d, J=6.0 Hz, 2H); MS (m/z): 280.18 (M-H)$^-$.

Step 2: Preparation of 5-{[(tert-butoxycarbonyl)amino]methyl}-2-chlorobenzoic acid

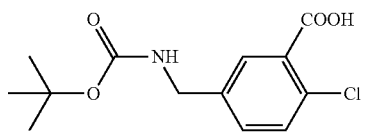 [SMILES: CC(C)(C)OC(=O)NCc1ccc(Cl)c(C(=O)O)c1]

A solution of 2-chloro-5-{[(trifluoroacetyl)amino]methyl}benzoic acid (800 mg, 2.84 mmol) in conc. HCl (5 mL) and dioxane (1 mL) was heated at reflux for 12 h. The reaction mixture was concentrated and the concentrate was dissolved in THF (10 mL). The solution was treated with NaOH (284 mg, 7.10 mmol) in H$_2$O (1 mL) at 0° C. followed by di-tert-butyl dicarbonate (840 mg, 3.00 mmol). The reaction mixture was stirred at rt for 16 h. The reaction mixture was acidified with 1N HCl and the pH was adjusted to 2-3. The reaction mixture was extracted with 5% MeOH in CHCl$_3$. The organic layer was separated, dried, filtered and concentrated. The concentrate was re-crystallized from toluene/butan-2-one (7:1) to afford 800 mg of the title product. $^1$H NMR (300 MHz, DMSO d$_6$): δ 13.1 (br s, 1H), 7.64 (s, 1H), 7.49 (d, J=8.1 Hz, 1H), 7.37 (d, J=7.8 Hz, 1H), 4.13 (d, J=5.7 Hz, 2H), 1.38 (s, 9H); MS (m/z): 283.94 (M−H)⁻.

Step 3: Preparation of methyl 5-(((tert-butoxycarbonyl)amino)methyl)-2-chlorobenzoate

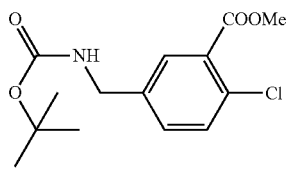 [SMILES: COC(=O)c1cc(CNC(=O)OC(C)(C)C)ccc1Cl]

To a solution of 5-{[(tert-butoxycarbonyl)amino]methyl}-2-chlorobenzoic acid (1.0 g, 3.50 mmol) in DMF (5.0 mL) were added methyl iodide (496 mg, 3.50 mmol) and K₂CO₃ (966 mg, 7.00 mmol). The reaction mass was stirred at rt for 18 h. The reaction mass was diluted with EtOAc and the organic layer was washed with water and brine. The organic layer was separated, dried, filtered and concentrated. The concentrate was purified by column chromatography to afford 440 mg of the title product. ¹H NMR (300 MHz, DMSO d₆): δ 7.66 (s, 1H), 7.49-7.52 (m, 2H), 7.42 (d, J=6.3 Hz, 1H), 4.13 (d, J=5.7 Hz, 2H), 3.85 (s, 3H), 1.38 (s, 9H).

Step 4: Preparation of methyl 5-(aminomethyl)-2-chlorobenzoate hydrochloride

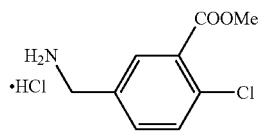 [SMILES: Cl ; COC(=O)c1cc(CN)ccc1Cl]

A solution of methyl 5-(((tert-butoxycarbonyl)amino)methyl)-2-chlorobenzoate (100 mg, 0.334 mmol) in EtOAc saturated with HCl (1 mL) was stirred at rt for 2 h. The reaction mixture was concentrated and was triturated with pentane to afford 80 mg of the title product. ¹H NMR (300 MHz, DMSO d₆): δ 8.20 (br s, 3H), 7.95 (s, 1H), 7.67 (s, 2H), 4.00 (s, 2H), 3.88 (s, 3H).

Step 5: Preparation of methyl 2-chloro-5-(pivalamidomethyl)benzoate

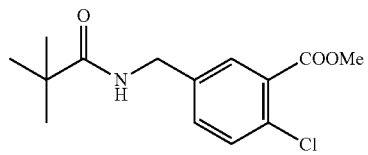 [SMILES: COC(=O)c1cc(CNC(=O)C(C)(C)C)ccc1Cl]

The title compound was prepared following the procedure described in step-2 of Intermediate-2 using methyl 5-(aminomethyl)-2-chlorobenzoate hydrochloride (1.80 g, 6.00 mmol), DIPEA (3.096 g, 2.4 mmol) and pivaloyl chloride (1.2 mL, 9.0 mmol) in THF (20 mL) to afford 2.0 g of the title product. ¹H NMR (300 MHz, DMSO d₆): 8.16 (m, 1H), 7.65 (s, 1H), 7.53 (d, J=8.4 Hz, 1H), 7.41 (d, J=8.4 Hz, 1H), 4.25 (d, J=5.7 Hz, 2H), 3.85 (s, 3H), 1.15 (s, 9H).

Step 6: Preparation of 2-chloro-5-(pivalamidomethyl)benzoic acid

The title compound was prepared following the procedure described in step-3 of Intermediate-2 using methyl 2-chloro-5-(pivalamidomethyl)benzoate (2.00 g, 7.05 mmol) in THF:MeOH:H₂O (3:2:1; 6 mL) and NaOH (564 mg, 14.1 mmol) to afford 1.8 g of the title product. ¹H NMR (300 MHz, DMSO d₆): 12.3 (br s, 1H), 8.14 (br t, 1H), 7.61 (s, 1H), 7.47-7.44 (d, J=8.1 Hz, 1H), 7.34-7.32 (d, J=7.8 Hz, 1H), 4.22 (d, J=6.0 Hz, 2H), 1.18 (s, 9H).

Intermediate-6

1-(3-(Trifluoromethyl)phenoxy)isoquinolin-5-amine

Step 1: Preparation of 5-nitro-1-(3-(trifluoromethyl)phenoxy)isoquinoline

To a solution of 1-chloro-5-nitroisoquinoline (Step-1, Intermediate-1, 200 mg, 0.96 mmol) in CH₃CN (2 mL) were added 3-(trifluoromethyl)phenol (233 mg, 1.4 mmol) and K₂CO₃ (265 mg, 1.92 mmol). The reaction mass was heated at reflux for 5 h and it was diluted with water and extracted with chloroform. The organic layer was separated, dried, filtered and concentrated. The residue was purified by column chromatography to afford 1.2 g of the title product. ¹H NMR (300 MHz, DMSO d₆): δ 8.82 (d, J=8.4 Hz, 1H), 8.58 (d, J=7.8 Hz, 1H), 8.17 (s, 2H), 7.76 (t, J=8.4 Hz, 1H), 7.61-7.47 (m, 4H); MS (m/z): 335.12 (M+H)⁺.

Step 2: Preparation of 1-(3-(trifluoromethyl)phenoxy)isoquinolin-5-amine

The title compound was prepared following the procedure described in Step 3 of Intermediate-1 using 5-nitro-1-(3-(trifluoromethyl)phenoxy)isoquinoline (200 mg, 0.59 mmol), iron powder (267 mg, 4.7 mmol), and NH₄Cl (312 mg, 5.9 mmol) in EtOH (4 mL) and water (1 mL) to afford 170 mg of the title product. ¹H NMR (300 MHz, DMSO d₆): δ 7.79 (d, J=5.7 Hz, 1H), 7.70-7.50 (m, 6H), 7.40 (t, J=7.8 Hz, 1H), 6.93 (d, J=7.2 Hz, 1H), 6.02 (br s, 2H).

Intermediate-7

N⁴-(3-(Trifluoromethyl)phenyl)quinazoline-4,8-diamine

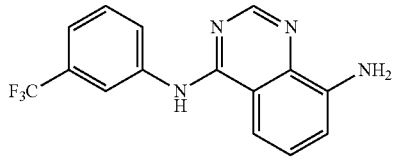

Step 1: Preparation of 8-Nitroquinazolin-4(3H)-one

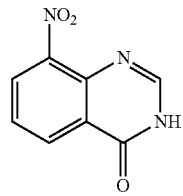 [SMILES: O=c1[nH]cnc2c([N+](=O)[O-])cccc12]

A suspension of 2-amino-3-nitrobenzoic acid (3.0 g, 16.48 mmol) and NH₄OAc (5.2 g, 83.87 mmol) in CH(OEt)₃ (20 mL) was heated in a sealed tube at 150° C. for 24 h. Then the reaction was quenched with aq. NaHCO₃ solution at rt and the precipitate obtained was filtered and dried. The solid mass was purified by column chromatography using 2-3% MeOH in CHCl₃ to afford 1.8 g of the title product. ¹H NMR (300 MHz, DMSO d₆): δ 12.72 (br s, 1H), 8.34 (d, J=7.8 Hz, 1H), 8.29 (d, J=7.8 Hz, 1H), 8.24 (s, 1H), 7.69-7.64 (t, J=7.8 Hz, 1H); MS (m/z): 192.19 (M+H)⁺.

Step 2: Preparation of 4-chloro-8-nitroquinazoline

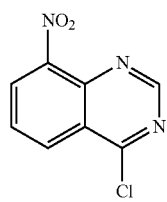 [SMILES: O=[N+]([O-])c1cccc2c(Cl)ncnc12]

A suspension of 8-nitroquinazolin-4(3H)-one (1.0 g, 5.23 mmol) and PCl₅ (1.3 g, 6.24 mmol) in POCl₃ (5 mL) was heated at reflux for 4 h. Then the reaction mixture was concentrated and the concentrate was diluted with Et₂O. The precipitated solid was filtered and dried to afford 1.0 g of the title product. ¹H NMR (300 MHz, DMSO d₆): δ 9.25 (s, 1H), 8.71 (d, J=7.8 Hz, 1H), 8.59 (d, J=7.8 Hz, 1H), 8.07-8.02 (t, J=7.8 Hz, 1H).

Step 3: Preparation of 8-nitro-N-(3-(trifluoromethyl)phenyl)quinazolin-4-amine

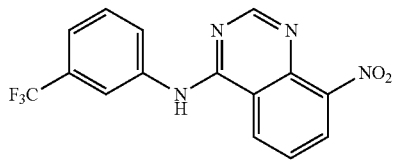 [SMILES: O=[N+]([O-])c1cccc2c(Nc3cccc(C(F)(F)F)c3)ncnc12]

A solution of 4-chloro-8-nitroquinazoline (300 mg, 1.43 mmol) and 3-(trifluoromethyl)aniline (461 mg, 2.86 mmol) in ⁱPrOH (1.5 mL) was heated in a sealed tube at 120° C. for 2 h. Then the reaction mixture was concentrated and purified by triturating in Et₂O to afford 425 mg of the title product. ¹H NMR (300 MHz, DMSO d₆): δ 10.52 (br s, 1H), 8.88 (d, J=7.8 Hz, 1H), 8.75 (s, 1H), 8.42 (d, J=7.2 Hz, 1H), 8.31 (s, 1H), 8.22 (d, J=6.9 Hz, 1H), 7.87-7.81 (t, J=8.4 Hz, 1H), 7.71-7.65 (t, J=7.8 Hz, 1H), 7.56-7.30 (d, J=7.8 Hz, 1H); MS (m/z): 335.19 (M+H)⁺.

Step 4: Preparation of N⁴-(3-(trifluoromethyl)phenyl)quinazoline-4,8-diamine

To a suspension of 8-nitro-N-(3-(trifluoromethyl)phenyl) quinazolin-4-amine (500 mg, 1.49 mmol) and iron powder (834 mg, 14.9 mmol) in EtOH (10 mL) was added a solution of NH₄Cl (649 mg, 11.92 mmol) in water (3 mL) and the reaction mixture was heated at reflux for 2 h. Then the reaction mixture was cooled to rt and filtered. The filtrate was concentrated and the concentrate was dissolved in CHCl₃. The organic layer was washed with an aq. saturated solution of NaHCO₃ and brine. The organic layer was dried, filtered and concentrated to afford 350 mg of the title product. ¹H NMR (300 MHz, DMSO d₆): δ 9.74 (br s, 1H), 8.59 (s, 1H), 8.38 (s, 1H), 8.26 (d, J=7.8 Hz, 1H), 7.64-7.59 (m, 2H), 7.45-7.42 (d, J=7.5 Hz, 1H), 7.37-7.32 (t, J=8.0 Hz, 1H), 7.00-6.98 (d, J=7.8 Hz, 1H), 5.91 (br s, 2H); MS (m/z): 305.27 (M+H)⁺.

Intermediate-8

4-(3-(Trifluoromethyl)phenoxy)quinazolin-8-amine

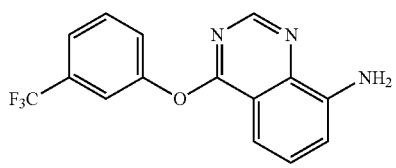 [SMILES: O=[N+]([O-])c1cccc2c(Oc3cccc(C(F)(F)F)c3)ncnc12]

Step 1: Preparation of 8-nitro-4-(3-(trifluoromethyl)phenoxy)quinazoline

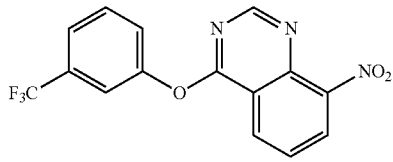

To a solution of 3-(trifluoromethyl)phenol (726 mg, 4.48 mmol) in THF (2 mL) was added NaH (179 mg, 4.48 mmol, 60% in mineral oil) at 0° C. and the reaction mixture was stirred for 15 min. Then a solution of 4-chloro-8-nitroquinazoline (Intermediate-7, step 2, 470 mg, 2.24 mmol) in THF (3 mL) was added to the reaction mixture at the same temperature and the reaction mixture was stirred at rt for 4 h. Then the reaction mixture was quenched with 1N HCl at 0° C. and the precipitate obtained was filtered and purified by column chromatography using 5-10% EtOAc in petroleum ether to afford 430 mg of the title product. $^1$H NMR (300 MHz, DMSO $d_6$): δ 8.88 (s, 1H), 8.68 (d, J=7.8 Hz, 1H), 8.60 (d, J=7.2 Hz, 1H), 7.99-7.94 (t, J=8.4 Hz, 1H), 7.89 (s, 1H), 7.77 (s, 3H); MS (m/z): 336.12 (M+H)$^+$.

Step 2: Preparation of 4-(3-(trifluoromethyl)phenoxy)quinazolin-8-amine

To a solution of 8-nitro-4-(3-(trifluoromethyl)phenoxy) quinazoline (400 mg, 1.19 mmol) in EtOAc (5 mL) was added 10% Pd on C (200 mg) and the suspension was hydrogenated in a Parr apparatus for 1 h at 20 psi. Then the reaction mixture was filtered through celite and the filtrate was concentrated. The residue was purified by column chromatography using 5% EtOAc in CHCl$_3$ to afford 300 mg of the title product. $^1$H NMR (300 MHz, DMSO $d_6$): δ 8.60 (s, 1H), 7.79 (s, 1H), 7.75-7.71 (m, 3H), 7.47-7.44 (m, 2H), 7.11 (d, J=6.3 Hz, 1H), 6.07 (s, 2H); MS (m/z): 305.19 (M+H)$^+$.

Intermediate-9

N$^4$-(4,4-Difluorocyclohexyl)quinazoline-4,8-diamine

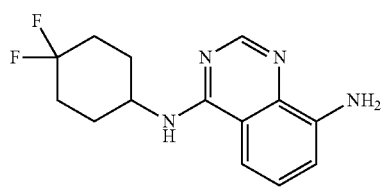 [SMILES: Nc1cccc2c(NC3CCC(F)(F)CC3)ncnc12]

Step 1: Preparation of N-(4,4-difluorocyclohexyl)-8-nitroquinazolin-4-amine

A solution of 4-chloro-8-nitroquinazoline (Intermediate-7, step 2, 200 mg, 0.954 mmol), 4,4-difluorocyclohexanamine (491 mg, 2.86 mmol) and DIPEA (367 mg, 2.86 mmol) in $^i$PrOH (2 mL) was heated in a sealed tube at 80° C. for 2 h. Then the reaction mixture was quenched with water at rt and was extracted with CHCl$_3$. The organic layer was separated, dried, filtered and concentrated. The concentrate was purified by column chromatography using 3-5% EtOAc in CHCl$_3$ to afford 180 mg of the title product. $^1$H NMR (300 MHz, DMSO $d_6$): δ 8.59-8.55 (m, 2H), 8.43-8.40 (d, J=7.2 Hz, 1H), 8.27-8.25 (d, J=7.8 Hz, 1H), 7.69-7.63 (t, J=7.8 Hz, 1H), 4.41 (m, 1H), 2.26-2.00 (m, 6H), 1.75-1.71 (m, 2H); MS (m/z): 309.18 (M+H)$^+$.

Step 2: Preparation of N$^4$-(4,4-difluorocyclohexyl) quinazoline-4,8-diamine To a solution of N-(4,4-difluorocyclohexyl)-8-nitroquinazolin-4-amine (90 mg, 0.292 mmol) in EtOH (2 mL) were added iron powder (163 mg, 2.92 mmol) and NH$_4$Cl (127 mg, 2.33 mmol) and the reaction mixture was heated at reflux for 2 h. Then the reaction mixture was filtered through celite. The celite bed was washed with 10% MeOH in CHCl$_3$. The filtrate was washed with a saturated aq. NaHCO$_3$ solution and water. The organic layer was separated, dried, filtered and concentrated to afford 70 mg of the title product. $^1$H NMR (300 MHz, DMSO $d_6$): δ 8.38 (s, 1H), 7.64 (d, J=7.2 Hz, 1H), 7.35 (d, J=7.8 Hz, 1H), 7.19-7.14 (t, J=7.8 Hz, 1H), 6.87 (d, J=7.8 Hz, 1H), 5.71 (s, 2H), 4.38 (m, 1H), 2.09-1.97 (m, 6H), 1.73-1.69 (m, 2H); MS (m/z): 279.12 (M+H)$^+$.

Intermediate-10

4-((4,4-Dimethylcyclohexyl)oxy)quinazolin-8-amine

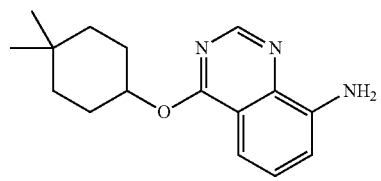

Step 1: Preparation of 4-((4,4-dimethylcyclohexyl)oxy)-8-nitroquinazoline

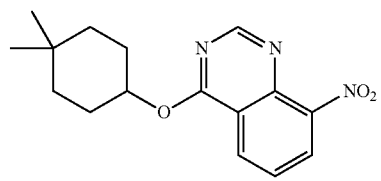 [SMILES: CC1(C)CCC(Oc2ncnc3c([N+](=O)[O-])cccc23)CC1]

To a solution of 4,4-dimethylcyclohexanol (140 mg, 1.097 mmol) in THF (2 mL) was added NaH (43 mg, 1.097 mmol, 60% in mineral oil) at 0° C. Then the reaction mixture was stirred at that temperature for 20 min and 4-chloro-8-nitroquinazoline (Intermediate-7, step 2, 115 mg, 0.549 mmol) was added to the reaction mixture. Then the reaction mixture was stirred at 0-5° C. for 4 h and then at rt for 12 h. Then the reaction mixture was quenched with water and was extracted with chloroform. The organic layer was washed with brine, separated, dried, filtered and concentrated. The residue was purified by column chromatography using chloroform to afford 80 mg of the title product. $^1$H NMR (300 MHz, DMSO $d_6$): δ 8.89 (s, 1H), 8.49-8.46 (d, J=7.8 Hz, 1H), 8.45-8.42 (d, J=7.8 Hz, 1H), 7.86-7.80 (t, J=8.4 Hz, 1H), 5.41 (m, 1H), 1.94

(m, 2H), 1.82-1.79 (m, 2H), 1.54 (m, 2H), 1.37-1.34 (m, 2H), 0.99 (s, 3H), 0.67 (s, 3H); MS (m/z): 301.93 (M+H)$^+$.

Step 2: Preparation of 4-((4,4-dimethylcyclohexyl)oxy)quinazolin-8-amine

The title compound was prepared following the procedure described in step-2, Intermediate-9 using 4-((4,4-dimethylcyclohexyl)oxy)-8-nitroquinazoline (80 mg, 0.265 mmol), NH$_4$Cl (114 mg, 2.216 mmol) and iron powder (148 mg, 2.65 mmol) in EtOH (2 mL) and water (0.5 mL) to afford 53 mg of the title product. $^1$H NMR (300 MHz, DMSO d$_6$): δ 8.63 (s, 1H), 7.34-7.30 (t, J=7.8 Hz, 1H), 7.23-7.20 (d, J=7.8 Hz, 1H), 7.01-6.99 (d, J=8.4 Hz, 1H), 5.92 (s, 2H), 5.32 (m, 1H), 1.92 (m, 2H), 1.77-1.74 (m, 2H), 1.49 (m, 2H), 1.36 (m, 2H), 0.98 (s, 3H), 0.96 (s, 3H); MS (m/z): 271.99 (M+H)$^+$.

Intermediate-11

4-(3-(Trifluoromethyl)phenoxy)quinolin-8-amine

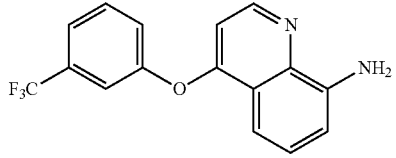

Step 1: Preparation of 4-chloroquinoline

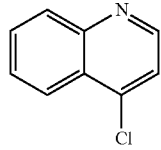

A solution of 4-quinolinol (1.0 g, 6.88 mmol) in POCl$_3$ (3 mL) was heated at reflux for 2 h. Then the reaction mixture was concentrated and the concentrate was dissolved in EtOAc. The organic layer was washed with a saturated solution of NaHCO$_3$ and water. The organic layer was separated, dried, filtered and concentrated to afford 1.1 g of the title product. $^1$H NMR (300 MHz, DMSO d$_6$): δ 8.87 (d, J=4.5 Hz, 1H), 8.23 (d, J=7.8 Hz, 1H), 8.14-8.11 (d, J=8.7 Hz, 1H), 7.93-7.88 (t, J=7.5 Hz, 1H), 7.82-7.77 (m, 2H).

Step 2. Preparation of 4-chloro-8-nitroquinoline

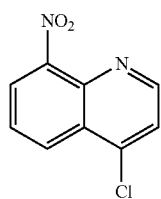 [SMILES: O=[N+]([O-])c1cccc2c(Cl)ccnc12]

To a solution of 4-chloroquinoline (1.0 g, 6.13 mmol) in conc. H$_2$SO$_4$ (4.5 mL) was drop wise added conc. HNO$_3$ (1.8 mL) at 0° C. and the reaction mixture was stirred at 0-15° C. for 3 h. Then the reaction mixture was quenched by addition of aq. NH$_4$OH at 0° C. and the pH of the reaction mixture was adjusted to 8. The solid precipitate was filtered and the filter cake was further purified by column chromatography to afford 900 mg of the title product. $^1$H NMR (300 MHz, DMSO d$_6$): δ 8.98 (d, J=5.1 Hz, 1H), 8.50-8.47 (d, J=9.0 Hz, 1H), 8.41 (d, J=7.8 Hz, 1H), 8.02-7.99 (d, J=4.8 Hz, 1H), 7.96-7.90 (t, J=7.8 Hz, 1H).

Step 3: Preparation of 8-nitro-4-(3-(trifluoromethyl)phenoxy)quinoline

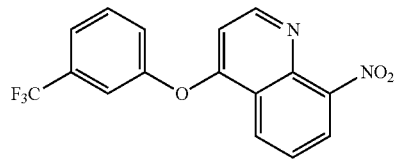 [SMILES: O=[N+]([O-])c1cccc2c(Oc3cccc(C(F)(F)F)c3)ccnc12]

A suspension of 4-chloro-8-nitroquinoline (200 mg, 0.96 mmol), 3-(trifluoromethyl)phenol (250 mg, 1.54 mmol), K$_2$CO$_3$ (414 mg, 2.99 mmol) in CH$_3$CN (2 mL) was heated in a sealed tube at 100° C. for 8 h. Then the reaction mixture was quenched with water and was extracted with EtOAc. The organic layer was washed with brine, separated, dried, filtered and concentrated. The residue was purified by column chromatography to afford 120 mg of the title product. $^1$H NMR (300 MHz, DMSO d$_6$): δ 8.83 (d, J=5.4 Hz, 1H), 8.60-8.57 (d, J=8.4 Hz, 1H), 8.36 (d, J=6.9 Hz, 1H), 7.85-7.73 (m, 5H), 6.87 (d, J=5.4 Hz, 1H).

Step 4: Preparation of 4-(3-(trifluoromethyl)phenoxy)quinolin-8-amine

To a suspension of 8-nitro-4-(3-(trifluoromethyl)phenoxy) quinoline (200 mg, 0.60 mmol) and iron powder (267 mg, 4.77 mmol) in EtOH (3 mL) was added a solution of NH$_4$Cl (312 mg, 5.89 mmol) in water (2 mL) and the reaction mixture was heated at reflux for 2 h. Then the reaction mixture was cooled to rt and filtered. The filtrate was concentrated and the concentrate was dissolved in CHCl$_3$. The organic layer was washed with an aq. saturated solution of NaHCO$_3$ and brine. The organic layer was separated, dried, filtered and concentrated to afford 150 mg of the title product. $^1$H NMR (300 MHz, DMSO d$_6$): δ 8.58 (d, J=4.8 Hz, 1H), 7.77-7.65 (m, 3H), 7.55 (d, J=7.8 Hz, 1H), 7.32 (m, 2H), 6.64 (m, 1H), 6.71 (d, J=4.8 Hz, 1H), 6.00 (br s, 2H); MS (m/z): 305.22 (M+H)$^+$.

Intermediate-12

N$^8$-(3-(Trifluoromethyl)phenyl)quinoline-4,8-diamine

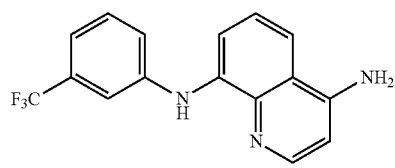 [SMILES: Nc1ccnc2c(Nc3cccc(C(F)(F)F)c3)cccc12]

Step 1: Preparation of ethyl 8-bromo-4-hydroxyquinoline-3-carboxylate

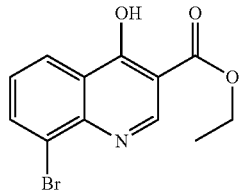 [SMILES: CCOC(=O)c1cnc2c(Br)cccc2c1O]

A solution of 2-bromoaniline (2.5 g, 14.62 mmol) and ethyl ethoxymethylenemalonate (3.16 g, 14.62 mmol) was heated at 100° C. for 3 h. Then the volatiles were removed by passing a stream of nitrogen and the molten mass was added slowly onto boiling diphenyl ether (10 mL) and the mixture was heated at reflux for 2 h. Then petroleum ether was added to the reaction mixture at rt and the precipitated solid was collected by filtration and dried to afford 3.5 g of the title product. $^1$H NMR (300 MHz, DMSO d$_6$): δ 11.65 (br s, 1H), 8.45 (s, 1H), 8.17 (d, J=7.8 Hz, 1H), 8.05 (d, J=7.8 Hz, 1H), 7.39-7.34 (t, J=7.8 Hz, 1H), 4.26-4.19 (q, J=7.2, 14.1 Hz, 2H), 1.30-1.26 (t, J=6.9 Hz, 3H).

Step 2: Preparation of ethyl 8-bromo-4-chloroquinoline-3-carboxylate

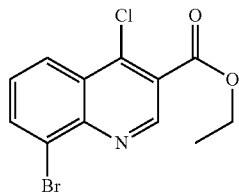

A solution of ethyl 8-bromo-4-hydroxyquinoline-3-carboxylate (2.0 g, 6.75 mmol) in POCl$_3$ (10 mL) was heated at 80° C. for 3 h. Then the volatiles were removed and ice-water was added to the residue. The precipitated solid was filtered and dried to afford 1.8 g of the title product. $^1$H NMR (300 MHz, DMSO d$_6$): δ 9.26 (s, 1H), 8.44-8.37 (m, 2H), 7.79-7.64 (t, J=7.8 Hz, 1H), 4.48-4.43 (q, J=7.2, 14.1 Hz, 2H), 1.41-1.36 (t, J=6.9 Hz, 3H); MS (m/z): 314.01 (M+H)$^+$.

Step 3: Preparation of ethyl 8-bromo-4-((4-methoxybenzyl)amino)quinoline-3-carboxylate

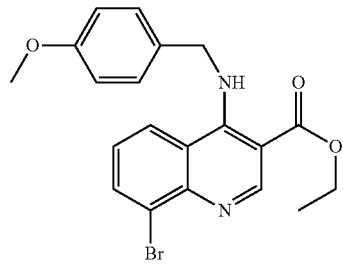 [SMILES: CCOC(=O)c1cnc2c(Br)cccc2c1NCc1ccc(OC)cc1]

To a solution of ethyl 8-bromo-4-chloroquinoline-3-carboxylate (1.8 g, 5.72 mmol) in DMF (10 mL) were added p-methoxybenzyl amine (860 mg, 6.27 mmol) and DIPEA (2.22 g, 17.21 mmol) and the reaction mixture was heated at 120° C. for 4 h. Then the reaction mixture was quenched with water and was extracted with EtOAc. The organic layer was washed with brine, separated, dried, filtered and concentrated. The residue was purified by column chromatography to afford 1.2 g of the title product. $^1$H NMR (300 MHz, DMSO d$_6$): δ 9.11 (br s, 1H), 8.89 (s, 1H), 8.46-8.43 (d, J=8.7 Hz, 1H), 8.12-8.09 (d, J=7.8 Hz, 1H), 7.38-7.33 (t, J=8.4 Hz, 1H), 7.27-7.24 (d, J=8.4 Hz, 2H), 6.91-6.89 (d, J=8.1 Hz, 2H), 8.17 (d, 2H), 4.26-4.24 (q, J=7.2, 14.1 Hz, 2H), 3.72 (s, 3H), 1.29-1.24 (t, J=6.9 Hz, 3H).

Step 4: Preparation of 8-bromo-4-((4-methoxybenzyl)amino)quinoline-3-carboxylic acid

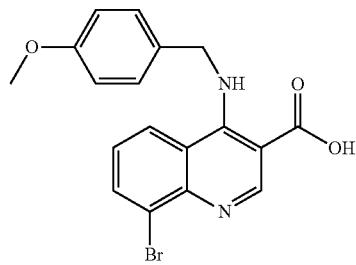 [SMILES: COc1ccc(CNc2c(C(=O)O)cnc3c(Br)cccc23)cc1]

To a solution of ethyl 8-bromo-4-((4-methoxybenzyl)amino)quinoline-3-carboxylate (1.2 g, 2.89 mmol) in THF-MeOH—H$_2$O (10:7:3, 20 mL) was added LiOH—H$_2$O (452 mg, 10.77 mmol) and the reaction mixture was stirred at rt for 12 h. Then the reaction mixture was acidified with citric acid and the organic volatiles were removed. The residue was extracted with EtOAc. The organic layer was washed with brine, separated, dried, filtered and concentrated to afford 1.0 g of the title product. $^1$H NMR (300 MHz, DMSO d$_6$): δ 8.96 (s, 1H), 8.42-8.39 (d, J=8.7 Hz, 1H), 8.11-8.09 (d, J=7.2 Hz, 1H), 7.35-7.30 (m, 3H), 6.95-6.92 (d, J=8.7 Hz, 2H), 4.91 (s, 2H), 3.74 (s, 3H).

Step 5: Preparation of 8-bromo-N-(4-methoxybenzyl)quinolin-4-amine

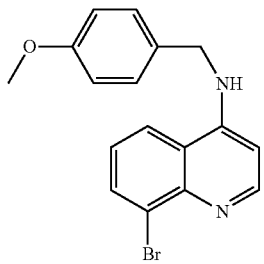 [SMILES: COc1ccc(CNc2ccnc3c(Br)cccc23)cc1]

A solution of 8-bromo-4-((4-methoxybenzyl)amino)quinoline-3-carboxylic acid (1.0 g, 2.58 mmol) in diphenyl ether (5 mL) was heated at 240° C. for 30 min. Then petroleum ether was added to the reaction mixture at rt and the precipitated solid was filtered and dried to afford 900 mg of the title product. $^1$H NMR (300 MHz, DMSO d$_6$): δ 8.38 (d, J=5.4 Hz, 1H), 8.34-8.31 (d, J=9.0 Hz, 1H), 8.06 (t, 1H), 8.02-7.99 (d, J=7.5 Hz, 1H), 7.37-7.29 (m, 3H), 6.90-6.87 (d, J=8.4 Hz, 2H), 6.44 (d, J=5.1 Hz, 1H), 4.49 (d, J=6.0 Hz, 2H), 3.71 (s, 3H).

Step 6: Preparation of $N^4$-(4-methoxybenzyl)-N-(3-(trifluoromethyl)phenyl)quinoline-4,8-diamine

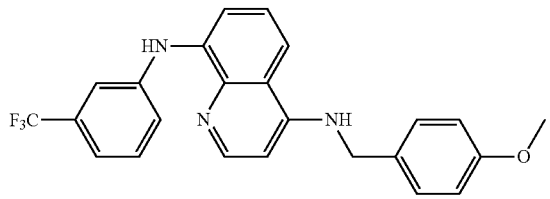 [SMILES: COc1ccc(CNc2ccnc3c(Nc4cccc(C(F)(F)F)c4)cccc23)cc1]

A solution of 8-bromo-N-(4-methoxybenzyl)quinolin-4-amine (300 mg, 0.874 mmol), m-trifluoroaniline (1.55 g, 9.63 mmol), tris(dibenzylideneacetone)palladium (0) (16 mg, 0.017 mmol), 2,2'-bis(diphenylphosphino)-1,1'-binaphthyl (32 mg, 0.051 mmol) and NaOtBu (109 mg, 1.14 mmol) in toluene (3 mL) was heated in a microwave vial at 100° C. for 30 min. Then water was added to the reaction mixture and it was extracted with EtOAc. The organic layer was washed with brine, separated, dried, filtered and concentrated. The residue was purified by column chromatography to afford 180 mg of the title product. $^1$H NMR (300 MHz, DMSO $d_6$): δ 8.87 (s, 1H), 8.30 (d, J=5.4 Hz, 1H), 7.86 (br t, 1H), 7.76-7.73 (d, J=9.0 Hz, 1H), 7.67 (m, 2H), 7.45 (m, 2H), 7.37-7.30 (m, 3H), 7.20 (d, J=6.6 Hz, 1H), 6.91-6.88 (d, J=8.1 Hz, 2H), 6.42 (d, J=5.4 Hz, 1H), 4.48 (d, 2H), 3.71 (s, 3H).

Step 7: Preparation of $N^8$-(3-(trifluoromethyl)phenyl)quinoline-4,8-diamine

A solution of $N^4$-(4-methoxybenzyl)-$N^8$-(3-(trifluoromethyl)phenyl)quinoline-4,8-diamine (180 mg, 0.425 mmol) in TFA (2 mL) was stirred at 80° C. for 2 h. Then the reaction mixture was quenched with a saturated solution of NaHCO$_3$ and was extracted with EtOAc. The organic layer was washed with water and brine, separated, dried, filtered and concentrated. The residue was triturated with Et$_2$O to afford 120 mg of the title product. $^1$H NMR (300 MHz, DMSO $d_6$): δ 8.86 (s, 1H), 8.30 (d, J=4.5 Hz, 1H), 7.66-7.43 (m, 4H), 7.38 (t, J=7.8 Hz, 1H), 7.21-7.18 (d, J=7.8 Hz, 1H), 6.83 (m, 3H), 6.60 (d, J=5.1 Hz, 1H).

Intermediate-13

4-Nitrophenyl 2-chloro-5-(pivalamidomethyl)benzoate

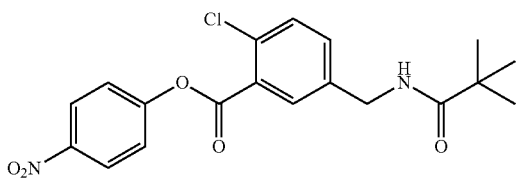 [SMILES: CC(C)(C)C(=O)NCc1ccc(Cl)c(C(=O)Oc2ccc([N+](=O)[O-])cc2)c1]

To a solution of 2-chloro-5-(pivalamidomethyl)benzoic acid (Intermediate-5, 300 mg, 1.12 mmol) in THF (5 mL) were added EDCI (210 mg, 1.09 mmol), p-nitrophenol (154 mg, 1.10 mmol) and DIPEA (558 mg, 4.39 mmol) and the reaction mixture was stirred at rt for 4 h. Then water was added to the reaction mixture and it was extracted with EtOAc. The organic layer was washed with brine, separated, dried, filtered and concentrated. The residue was purified by column chromatography to afford 222 mg of the title product. $^1$H NMR (300 MHz, DMSO $d_6$): δ 8.36 (d, J=9.0 Hz, 2H), 8.20 (t, 1H), 7.97 (s, 1H), 7.62-7.59 (m, 3H), 7.51 (d, J=8.1 Hz, 1H), 4.30 (d, J=6.0 Hz, 2H), 1.11 (s, 9H).

Intermediate-14

$N^4$-(2-Fluoro-5-(trifluoromethyl)phenyl)quinazoline-4,8-diamine

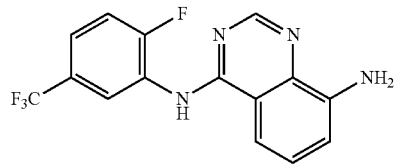 [SMILES: Nc1cccc2c(Nc3cc(C(F)(F)F)ccc3F)ncnc12]

Step 1: Preparation of N-(2-fluoro-5-(trifluoromethyl)phenyl)-8-nitroquinazolin-4-amine

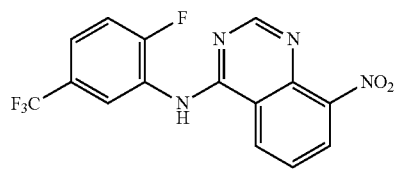 [SMILES: O=[N+]([O-])c1cccc2c(Nc3cc(C(F)(F)F)ccc3F)ncnc12]

A solution of 4-chloro-8-nitroquinazoline (Intermediate-7, step-2, 150 mg, 0.72 mmol) and 2-fluoro-5-(trifluoromethyl)aniline (387 mg, 2.16 mmol) in THF (4 mL) was heated at 50° C. for 2 h. Then water was added to the reaction mixture and it was extracted with EtOAc. The organic layer was washed with brine, separated, dried, filtered and concentrated. The residue was purified by column chromatography to afford 250 mg of the title product. $^1$H NMR (300 MHz, DMSO $d_6$): δ 10.46 (s, 1H), 8.74-8.71 (d, J=8.7 Hz, 1H), 8.63 (s, 1H), 8.43-8.40 (d, J=7.2 Hz, 1H), 8.01 (d, 1H), 7.86-7.81 (m, 2H), 7.66-7.63 (t, J=9.3 Hz, 1H); MS [M+H]$^+$: 353.14.

Step 2: Preparation of $N^4$-(2-fluoro-5-(trifluoromethyl)phenyl)quinazoline-4,8-diamine The title compound was prepared following the procedure described in step-2, Intermediate-9 using N-(2-fluoro-5-(trifluoromethyl)phenyl)-8-nitroquinazolin-4-amine (250 mg, 0.71 mmol), NH$_4$Cl (304 mg, 5.68 mmol) and iron powder (398 mg, 7.10 mmol) in EtOH (3 mL) and water (2 mL) to afford 100 mg of the title product. $^1$H NMR (300 MHz, DMSO $d_6$): δ 9.71 (s, 1H), 8.44 (s, 1H), 7.98 (d, 1H), 7.70 (m, 1H), 7.60-7.57 (t, J=9.6 Hz, 1H), 7.50-7.47 (d, J=8.4 Hz, 1H), 7.36-7.30 (t, J=7.8 Hz, 1H), 6.99-6.97 (d, J=7.8 Hz, 1H), 5.89 (s, 2H); MS [M+H]⁺: 323.29.

Intermediate-15

N⁴-(4,4-Dimethylcyclohexyl)quinazoline-4,8-diamine

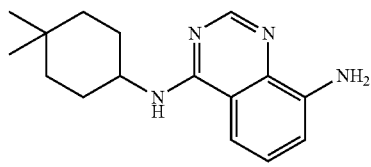 [SMILES: CC1(C)CCC(Nc2ncnc3c(N)cccc23)CC1]

Step 1: Preparation of N-(4,4-dimethylcyclohexyl)-8-nitroquinazolin-4-amine

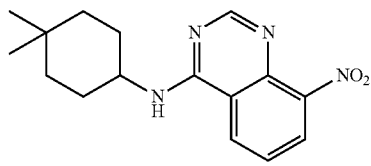 [SMILES: CC1(C)CCC(Nc2ncnc3c([N+](=O)[O-])cccc23)CC1]

To a solution of 4-chloro-8-nitroquinazoline (Intermediate-7, step-2, 150 mg, 0.72 mmol) in CH₃CN (3 mL) were added K₂CO₃ (300 mg, 2.15 mmol) and 4,4-dimethylcyclohexanamine hydrochloride (352 mg, 2.15 mmol) and the reaction mixture was heated at reflux for 3 h. Then water was added to the reaction mixture and it was extracted with EtOAc. The organic layer was washed with brine, separated, dried, filtered and concentrated. The residue was purified by column chromatography to afford 150 mg of the title product. ¹H NMR (300 MHz, DMSO d₆): δ 8.58-8.55 (d, J=8.4 Hz, 1H), 8.50 (s, 1H), 8.38-8.35 (d, J=7.2 Hz, 1H), 8.25-8.22 (d, J=7.8 Hz, 1H), 7.67-7.61 (t, J=7.8 Hz, 1H), 4.17 (m, 1H), 1.75-1.56 (m, 4H), 1.46-1.18 (m, 4H), 0.98 (s, 3H), 0.95 (s, 3H); MS [M+H]⁺: 301.20.

Step 2: Preparation of N⁴-(4,4-dimethylcyclohexyl)quinazoline-4,8-diamine

The title compound was prepared following the procedure described in step-2, Intermediate-9 using N-(4,4-dimethylcyclohexyl)-8-nitroquinazolin-4-amine (210 mg, 0.69 mmol), NH₄Cl (295 mg, 5.52 mmol) and iron powder (386 mg, 6.90 mmol) in EtOH (5 mL) and water (1.5 mL) to afford 200 mg of the title product. ¹H NMR (300 MHz, DMSO d₆): δ 8.32 (s, 1H), 7.57-7.55 (d, J=6.6 Hz, 1H), 7.33-7.29 (d, J=8.4 Hz, 1H), 7.13-7.11 (t, J=7.8 Hz, 1H), 6.84-6.82 (d, J=7.2 Hz, 1H), 5.66 (s, 2H), 4.08 (m, 1H), 1.69-1.60 (m, 4H), 1.38-1.28 (m, 4H), 0.95 (s, 3H), 0.92 (s, 3H).

Intermediate-16 tert-Butyl 4-chloro-2-fluoro-3-((4-((3-(trifluoromethyl)phenyl)amino)quinazolin-8-yl)carbamoyl)benzylcarbamate

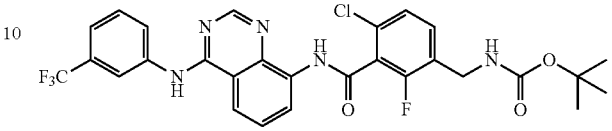

The title compound was prepared following the procedure described in Example-1 using N⁴-(3-(trifluoromethyl)phenyl)quinazoline-4,8-diamine (Intermediate-7, 87 mg, 0.285 mmol), 3-(((tert-butoxycarbonyl)amino)methyl)-6-chloro-2-fluorobenzoic acid (130 mg, 0.428 mmol), oxalyl chloride (81 mg, 0.64 mmol), DMF (1 drop) and DIPEA (111 mg, 0.86 mmol) in CH₂Cl₂ (4 mL) to afford 80 mg of the title product. ¹H NMR (300 MHz, DMSO-d₆): δ 10.66 (s, 1H), 10.14 (s, 1H), 8.82 (d, 1H), 8.71 (s, 1H), 8.36 (m, 2H), 8.23 (d, 1H), 7.73 (t, 1H), 7.66 (t, 1H), 7.51 (m, 2H), 7.42 (m, 2H), 4.18 (d, 2H), 1.40 (s, 9H); MS [M+H]⁺: 590.08.

Intermediate-17

N⁴-(4-Fluoro-3-(trifluoromethyl)phenyl)quinazoline-4,8-diamine

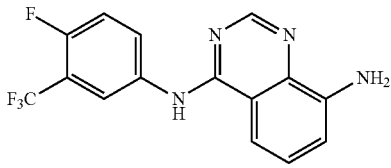 [SMILES: Nc1cccc2c(Nc3ccc(F)c(C(F)(F)F)c3)ncnc12]

Step 1: Preparation of N-(4-fluoro-3-(trifluoromethyl)phenyl)-8-nitroquinazolin-4-amine

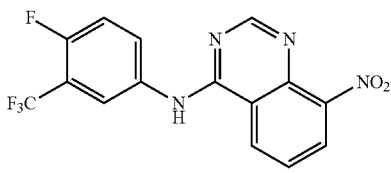 [SMILES: O=[N+]([O-])c1cccc2c(Nc3ccc(F)c(C(F)(F)F)c3)ncnc12]

A solution of 4-chloro-8-nitroquinazoline (Intermediate-7, step-2, 200 mg, 0.95 mmol) and 4-fluoro-3-(trifluoromethyl)aniline (510 mg, 2.85 mmol) in THF (4 mL) was stirred at rt for 2 h. Then water was added to the reaction mixture and it was extracted with EtOAc. The organic layer was washed with brine, separated, dried, filtered and concentrated. The residue was purified by column chromatography to afford 250 mg of the title product. ¹H NMR (300 MHz, DMSO d₆): δ 10.47 (s, 1H), 8.83-8.80 (d, J=8.4 Hz, 1H), 8.72 (s, 1H), 8.42-8.39 (d, J=7.8 Hz, 1H), 8.31-8.25 (m, 2H), 7.86-7.81 (t, J=7.8 Hz, 1H), 7.64-7.58 (t, J=9.6 Hz, 1H).

Step 2: Preparation of N⁴-(4-fluoro-3-(trifluoromethyl)phenyl)quinazoline-4,8-diamine The title compound was prepared following the procedure described in step-2, Intermediate-9 using N-(4-fluoro-3-(trifluoromethyl)phenyl)-8-nitroquinazolin-4-amine (250 mg, 0.71 mmol), NH₄Cl (304 mg, 5.68 mmol) and iron powder (398 mg, 7.10 mmol) in EtOH (3 mL) and water (2 mL) to afford 200 mg of the title product. ¹H NMR (300 MHz, DMSO d₆): δ 9.75 (s, 1H), 8.56 (s, 1H), 8.35 (m, 1H), 8.27 (m, 1H), 7.60-7.51 (m, 2H), 7.37-7.32 (t, J=7.5 Hz, 1H), 7.00-6.98 (d, J=7.5 Hz, 1H), 5.91 (s, 2H).

Intermediate-18

8-Nitro-4-(((1s,4s)-4-(trifluoromethyl)cyclohexyl)oxy)quinazoline

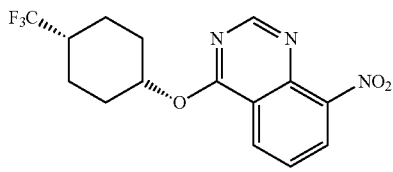

Intermediate-19

8-Nitro-4-(((1r,4r)-4-(trifluoromethyl)cyclohexyl)oxy)quinazoline

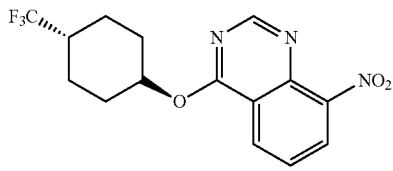

The title compounds were prepared following the procedure described in step-1, Intermediate-10 using 4-chloro-8-nitroquinazoline (Intermediate-7, step-2, 500 mg, 2.39 mmol) and 4-(trifluoromethyl)cyclohexanol (cis and trans mixture) (803 mg, 4.78 mmol) and NaH (191 mg, 4.78 mmol, 60% in mineral oil) in THF (10 mL) to afford 70 mg of Intermediate-18 and 301 mg of Intermediate-19. Intermediate-18: ¹H NMR (300 MHz, DMSO-d₆): δ 8.91 (s, 1H), 8.51-8.45 (t, J=8.4 Hz, 2H), 7.89-7.84 (t, J=7.8 Hz, 1H), 5.66 (m, 1H), 3.83 (m, 1H), 2.22-2.18 (m, 2H), 1.81-1.61 (m, 6H); Intermediate-19: ¹H NMR (300 MHz, DMSO-d₆): δ 8.92 (s, 1H), 8.50-8.48 (d, J=7.8 Hz, 1H), 8.41-8.38 (d, J=7.8 Hz, 1H), 7.85-7.80 (t, J=8.4 Hz, 1H), 5.38-5.31 (m, 1H), 2.28 (m, 2H), 2.02-1.98 (m, 3H), 1.68-1.57 (m, 4H); MS [M+H]⁺: 341.98.

Intermediate-20

4-(((1s,4s)-4-(Trifluoromethyl)cyclohexyl)oxy)quinazolin-8-amine

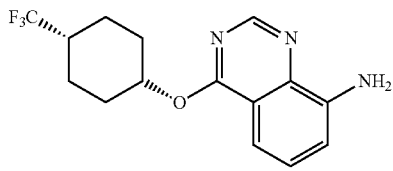

The title compound was prepared following the procedure described in step-2, Intermediate-9 using 8-nitro-4-(((1s,4s)-4-(trifluoromethyl)cyclohexyl)oxy)quinazoline (Intermediate-18, 150 mg, 0.44 mmol), NH₄Cl (188 mg, 3.52 mmol) and iron powder (246 mg, 4.40 mmol) in EtOH (2 mL) and water (1 mL) to afford 94 mg of the title product. ¹H NMR (300 MHz, DMSO-d₆): δ 8.63 (s, 1H), 7.37-7.32 (t, J=7.8 Hz, 1H), 7.22-7.19 (d, J=7.8 Hz, 1H), 7.01-6.98 (d, J=7.5 Hz, 1H), 5.93 (s, 2H), 5.57 (m, 1H), 2.15-2.11 (m, 3H), 1.79-1.75 (m, 6H); MS [M+H]⁺: 312.07.

Intermediate-21

4-(((1r,4r)-4-(Trifluoromethyl)cyclohexyl)oxy)quinazolin-8-amine

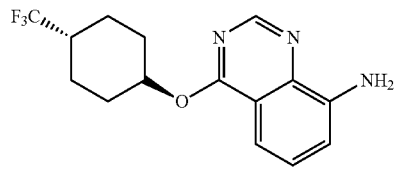

The title compound was prepared following the procedure described in step-2, Intermediate-9 using 8-nitro-4-(((1r,4r)-4-(trifluoromethyl)cyclohexyl)oxy)quinazoline (Intermediate-19, 250 mg, 0.733 mmol), NH₄Cl (313 mg, 5.865 mmol) and iron powder (410 mg, 7.33 mmol) in EtOH (5 mL) and water (2 mL) to afford 160 mg of the title product. ¹H NMR (300 MHz, DMSO-d₆): δ 8.65 (s, 1H), 7.34-7.29 (t, J=7.8 Hz, 1H), 7.18-7.16 (d, J=7.8 Hz, 1H), 7.01-6.99 (d, J=7.5 Hz, 1H), 5.94 (s, 2H), 5.25 (m, 1H), 2.49 (m, 1H), 2.25 (m, 2H), 2.00-1.97 (m, 2H), 1.62-1.55 (m, 4H); MS [M+H]⁺: 312.10.

Intermediate-22

4-(2-Fluoro-5-(trifluoromethyl)phenoxy)quinazolin-8-amine

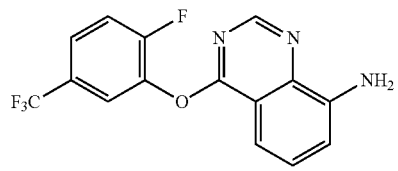 [SMILES: O=[N+]([O-])c1cccc2c(Oc3cc(C(F)(F)F)ccc3F)ncnc12]

Step 1: Preparation of 4-(2-fluoro-5-(trifluoromethyl)phenoxy)-8-nitroquinazoline The title compound was prepared following the procedure described in step-1, Intermediate-8 using 4-chloro-8-nitroquinazoline (Intermediate-7, step 2, 300 mg, 1.43 mmol), 2-fluoro-5-(trifluoromethyl)phenol (309 mg, 1.72 mmol) and NaH (69 mg, 1.72 mmol, 60% in mineral oil) in THF (5 mL) to afford 290 mg of the title product. ¹H NMR (300 MHz, DMSO d₆): δ 8.93 (s, 1H), 8.72-8.69 (d, J=8.1 Hz, 1H), 8.66-8.64 (d, J=7.8 Hz, 1H), 8.15-8.13 (d, J=4.8 Hz, 1H), 8.03-7.98 (t, J=8.1 Hz, 1H), 7.86 (m, 1H), 7.80-7.74 (t, J=9.6 Hz, 1H).

Step 2: Preparation of 4-(2-fluoro-5-(trifluoromethyl)phenoxy)quinazolin-8-amine The title compound was prepared following the procedure described in step-2, Intermediate-9 using 4-(2-fluoro-5-(trifluoromethyl)phenoxy)-8-nitroquinazoline (500 mg, 1.42 mmol), NH₄Cl (760 mg, 14.2 mmol) and iron powder (239 mg, 4.26 mmol) in EtOH (10 mL) and water (2 mL) to afford 300 mg of the title product. ¹H NMR (300 MHz, DMSO-d₆): δ 8.60 (s, 1H), 8.06-8.04 (d, J=5.1 Hz, 1H), 7.79 (m, 1H), 7.69-7.67 (t, J=9.0 Hz, 1H), 7.50-7.40 (m, 2H), 7.13-7.10 (d, J=7.2 Hz, 1H), 6.12 (br s, 2H).

Intermediate-23

N⁴-(2-Fluoro-4-(trifluoromethyl)phenyl)quinazoline-4,8-diamine

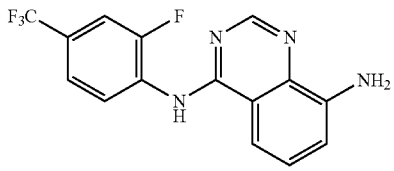

Step 1: Preparation of N-(2-fluoro-4-(trifluoromethyl)phenyl)-8-nitroquinazolin-4-amine

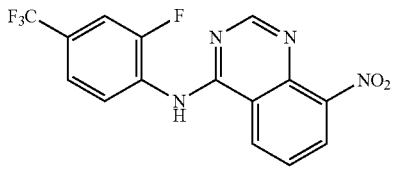 [SMILES: O=[N+]([O-])c1cccc2c(Nc3ccc(C(F)(F)F)cc3F)ncnc12]

The title compound was prepared following the procedure described in step-1, Intermediate-17 using 4-chloro-8-nitroquinazoline (Intermediate-7, step-2, 300 mg, 1.43 mmol) and 2-fluoro-4-(trifluoromethyl)aniline (512 mg, 2.86 mmol) in THF (10 mL) to afford 275 mg of the title product. ¹H NMR (300 MHz, DMSO d₆): δ 8.84-8.81 (d, J=9.0 Hz, 1H), 8.59 (s, 1H), 8.44-8.42 (d, J=7.8 Hz, 1H), 7.84-7.82 (m, 4H), 7.69-7.66 (d, J=7.8 Hz, 1H).

Step 2: Preparation of N⁴-(2-fluoro-4-(trifluoromethyl)phenyl)quinazoline-4,8-diamine The title compound was prepared following the procedure described in step-2, Intermediate-9 using N-(2-fluoro-4-(trifluoromethyl)phenyl)-8-nitroquinazolin-4-amine (275 mg, 0.78 mmol), NH₄Cl (418 mg, 7.80 mmol) and iron powder (131 mg, 2.34 mmol) in EtOH (10 mL) and water (3 mL) to afford 220 mg of the title product. ¹H NMR (300 MHz, DMSO-d₆): δ 9.74 (s, 1H), 8.43 (s, 1H), 7.84-7.76 (m, 2H), 7.64-7.62 (d, J=7.8 Hz, 1H), 7.52-7.49 (d, J=8.1 Hz, 1H), 7.32 (t, 1H), 6.99-6.96 (d, J=7.2 Hz, 1H), 5.88 (br s, 2H).

Intermediate-24

N⁴-(6-(Trifluoromethyl)pyridin-3-yl)quinazoline-4,8-diamine

Step 1: Preparation of 8-nitro-N-(6-(trifluoromethyl)pyridin-3-yl)quinazolin-4-amine

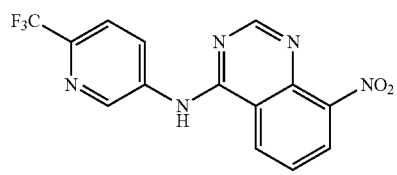 [SMILES: O=[N+]([O-])c1cccc2c(Nc3ccc(C(F)(F)F)nc3)ncnc12]

The title compound was prepared following the procedure described in step-1, Intermediate-17 using 4-chloro-8-nitroquinazoline (Intermediate-7, step-2, 250 mg, 1.19 mmol) and 6-(trifluoromethyl)pyridin-3-amine (386 mg, 2.38 mmol) in THF (5 mL) to afford 400 mg of the title product. ¹H NMR (300 MHz, DMSO d₆): δ 10.60 (s, 1H), 9.21 (s, 1H), 8.85-8.82 (d, J=8.7 Hz, 1H), 8.79 (s, 1H), 8.65-8.63 (d, J=8.7 Hz, 1H), 8.44-8.42 (d, J=7.2 Hz, 1H), 7.99-7.96 (d, J=9.0 Hz, 1H), 7.89-7.87 (t, J=7.8 Hz, 1H).

Step 2: Preparation of N⁴-(6-(trifluoromethyl)pyridin-3-yl)quinazoline-4,8-diamine The title compound was prepared following the procedure described in step-2, Intermediate-9 using 8-nitro-N-(6-(trifluoromethyl)pyridin-3-yl)quinazolin-4-amine (400 mg, 1.19 mmol), NH₄Cl (637 mg, 11.90 mmol) and iron powder (200 mg, 3.57 mmol) in EtOH (5 mL) and water (2 mL) to afford 94 mg of the title product. ¹H NMR (300 MHz, DMSO-d₆): δ 9.97 (s, 1H), 9.22 (s, 1H), 8.69-8.67 (d, J=7.2 Hz, 1H), 8.61 (s, 1H), 7.93-7.89 (d, J=8.1 Hz, 1H), 7.63-7.60 (d, J=7.8 Hz, 1H), 7.37 (t, 1H), 7.01-6.99 (d, J=7.2 Hz, 1H), 5.95 (br s, 2H).

Intermediate-25

N⁴-(3-(Trifluoromethyl)phenyl)quinoline-4,8-diamine

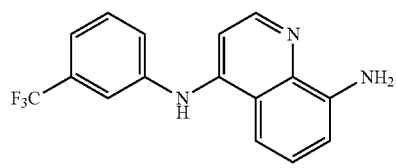

Step 1: Preparation of 8-nitro-N-(3-(trifluoromethyl) phenyl)quinolin-4-amine

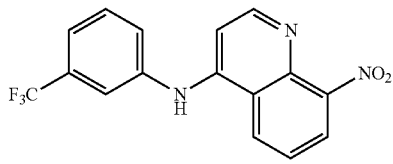 [SMILES: Nc1cccc2c(Nc3cccc(C(F)(F)F)c3)ccnc12]

A mixture of 4-chloro-8-nitroquinoline (step-2, Intermediate-11, 100 mg, 0.48 mmol) and 3-(trifluoromethyl)aniline (309 mg, 1.92 mmol) was heated at 150° C. for 20 minutes in microwave. Then water was added to the reaction mixture and it was extracted with $CHCl_3$. The organic layer was washed with brine, separated, dried, filtered and concentrated. The residue was purified by column chromatography to afford 250 mg of the title product.

Step 2: Preparation of $N^4$-(3-(trifluoromethyl)phenyl)quinoline-4,8-diamine The title compound was prepared following the procedure described in step-2, Intermediate-9 using 8-nitro-N-(3-(trifluoromethyl)phenyl)quinolin-4-amine (250 mg, 0.75 mmol), $NH_4Cl$ (321 mg, 6.00 mmol) and iron powder (420 mg, 7.50 mmol) in EtOH (3 mL) and water (2 mL) to afford 100 mg of the title product.

Intermediate-26

$N^4$-(4,4-Dimethylcyclohexyl)-2-(trifluoromethyl) quinazoline-4,8-diamine

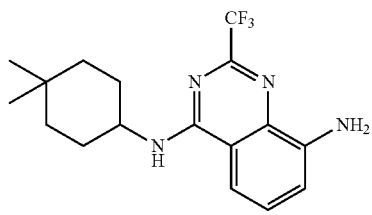 [SMILES: CC1(C)CCC(Nc2nc(C(F)(F)F)nc3c(N)cccc23)CC1]

Step 1: Preparation of 2-amino-3-nitrobenzamide

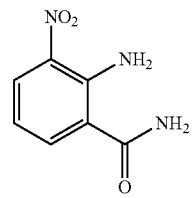 [SMILES: NC(=O)c1cccc([N+](=O)[O-])c1N]

To a solution of 2-amino-3-nitrobenzoic acid (5.00 g, 27.47 mmol) in DMSO (30 mL) were added BOP (18.21 g, 41.21 mmol), $NH_4Cl$ (4.41 g, 82.41 mmol) and DIPEA (10.63 g, 82.41 mmol) and the reaction mixture was stirred at rt for 14 h and it was quenched with ice-water and the precipitate obtained was filtered, washed with $Et_2O$ and dried to afford 4.90 g of the title product. $^1H$ NMR (300 MHz, DMSO $d_6$): δ 8.48 (br s, 2H), 8.19-8.17 (m, 2H), 7.96-7.94 (d, J=7.2 Hz, 1H), 7.62 (br s, 1H), 6.71-6.65 (t, J=7.8 Hz, 1H).

Step 2: Preparation of 8-nitro-2-(trifluoromethyl)quinazolin-4(3H)-one

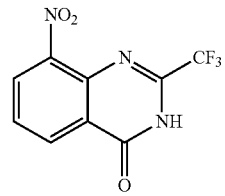 [SMILES: O=c1[nH]c(C(F)(F)F)nc2c([N+](=O)[O-])cccc12]

A solution of 2-amino-3-nitrobenzamide (1.0 g, 5.52 mmol) in trifluoroacetic anhydride (5 mL) was heated at 100° C. for 4 h in a sealed tube. Then the reaction mixture was quenched with water and the precipitate obtained was filtered and dried to afford 1.0 g of the title product. $^1H$ NMR (300 MHz, DMSO $d_6$): δ 8.43-8.40 (d, J=7.8 Hz, 2H), 7.85-7.80 (t, J=7.8 Hz, 1H); MS (m/z): 258.26 (M−H)$^+$.

Step 3: Preparation of 4-chloro-8-nitro-2-(trifluoromethyl)quinazoline

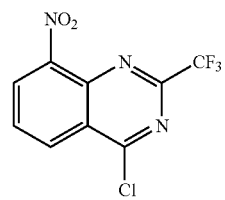 [SMILES: O=[N+]([O-])c1cccc2c(Cl)nc(C(F)(F)F)nc12]

The title compound was prepared following the procedure described in Intermediate-7, step-2 using 8-nitro-2-(trifluoromethyl)quinazolin-4(3H)-one (500 mg, 1.93 mmol) and $PCl_5$ (477 mg, 2.32 mmol) in $POCl_3$ (2.5 mL) to afford 1.0 g of the title product.

Step 4: Preparation of N-(4,4-dimethylcyclohexyl)-8-nitro-2-(trifluoromethyl)quinazolin-4-amine

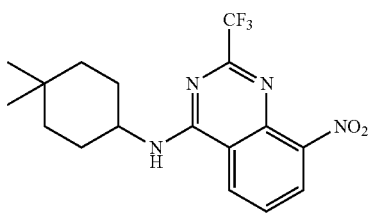

A suspension of 4-chloro-8-nitro-2-(trifluoromethyl) quinazoline (200 mg, 0.72 mmol), 4,4-dimethylcyclohexanamine (109 mg, 0.86 mmol), $K_2CO_3$ (398 mg, 2.89 mmol) in $CH_3CN$ (2 mL) was heated at reflux for 8 h. Then the reaction mixture was quenched with water and was extracted with EtOAc. The organic layer was washed with brine, separated, dried, filtered and concentrated. The residue was purified by column chromatography to afford 120 mg of the title product. $^1$H NMR (300 MHz, DMSO $d_6$): δ 8.91-8.89 (d, J=7.2 Hz, 1H), 8.69-8.66 (d, J=7.8 Hz, 1H), 8.39-8.37 (d, J=7.8 Hz, 1H), 7.84-7.79 (t, J=8.1 Hz, 1H), 4.12 (m, 1H), 1.76-1.64 (m, 4H), 1.46-1.28 (m, 4H), 0.98 (s, 3H), 0.95 (s, 3H).

Step 5: Preparation of N$^4$-(4,4-dimethylcyclohexyl)-2-(trifluoromethyl)quinazoline-4,8-diamine The title compound was prepared following the procedure described in step-2, Intermediate-9 using N-(4,4-dimethylcyclohexyl)-8-nitro-2-(trifluoromethyl)quinazolin-4-amine (200 mg, 0.54 mmol), NH$_4$Cl (115 mg, 2.17 mmol) and iron powder (121 mg, 2.17 mmol) in EtOH (3 mL) and water (2 mL) to afford 120 mg of the title product. $^1$H NMR (300 MHz, DMSO-d$_6$): δ 8.11-8.08 (d, J=8.1 Hz, 1H), 7.45-7.42 (d, J=8.4 Hz, 1H), 7.34-7.29 (t, J=7.8 Hz, 1H), 6.99-6.69 (d, J=7.2 Hz, 1H), 5.81 (br s, 2H), 4.07 (m, 1H), 1.76-1.62 (m, 4H), 1.44-1.22 (m, 4H), 0.97 (s, 3H), 0.94 (s, 3H).

Intermediate-27

2-Methyl-N$^4$-(3-(trifluoromethyl)phenyl)quinazoline-4,8-diamine

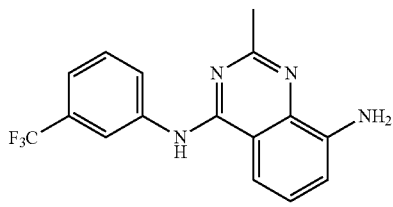

Step 1: Preparation of 2-methyl-8-nitroquinazolin-4(3H)-one

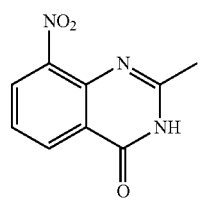

A solution of 2-amino-3-nitrobenzoic acid (500 mg, 2.75 mmol) in Ac$_2$O (3.5 mL) was heated at reflux for 1 h. Then the reaction mixture was concentrated and the residue was triturated with Et$_2$O. The precipitate obtained was filtered and dried. Then the solid mass was dissolved in aq. NH$_3$ (10 mL) and the solution was heated at reflux for 2 h. Then the reaction mixture was concentrated and the residue was triturated with Et$_2$O. The precipitate obtained was filtered and dried to afford 250 mg of the title product. $^1$H NMR (300 MHz, DMSO-d$_6$): δ 12.62 (br s, 1H), 8.31-8.28 (d, J=8.4 Hz, 1H), 8.24-8.21 (d, J=7.8 Hz, 1H), 7.61-7.56 (t, J=7.8 Hz, 1H), 2.36 (s, 3H).

Step 2: Preparation of 4-chloro-2-methyl-8-nitroquinazoline

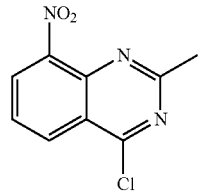

To a solution of 2-methyl-8-nitroquinazolin-4(3H)-one (250 mg, 1.22 mmol) in toluene (1 mL) was added POCl$_3$ (374 mg, 2.44 mmol) and the reaction mixture was heated at reflux for 10 h. Then the reaction mixture was concentrated and triturated with Et$_2$O. The precipitate obtained was filtered and dried to afford 150 mg of the title product. $^1$H NMR (300 MHz, DMSO-d$_6$): δ 8.60-8.58 (d, J=7.8 Hz, 1H), 8.52-8.49 (d, J=9.0 Hz, 1H), 7.95-7.89 (t, J=7.8 Hz, 1H), 2.75 (s, 3H).

Step 3: Preparation of 2-methyl-8-nitro-N-(3-(trifluoromethyl)phenyl)quinazolin-4-amine

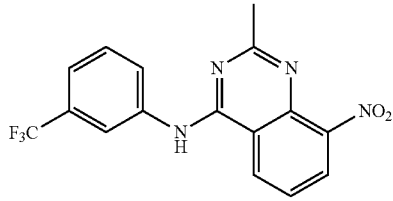 [SMILES: Cc1nc(Nc2cccc(C(F)(F)F)c2)c2cccc([N+](=O)[O-])c2n1]

The title compound was prepared following the procedure described in step-1, Intermediate-17 using 4-chloro-2-methyl-8-nitroquinazoline (150 mg, 0.671 mmol) and 3-(trifluoromethyl)aniline (324 mg, 2.01 mmol) in THF (5 mL) to afford 150 mg of the title product. $^1$H NMR (300 MHz, DMSO-d$_6$): δ 10.24 (s, 1H), 8.78-8.75 (d, J=8.7 Hz, 1H), 8.36 (s, 1H), 8.32-8.29 (d, J=7.5 Hz, 1H), 8.27-8.24 (d, J=9.3 Hz, 1H), 7.74-7.62 (m, 2H), 7.50-7.48 (d, J=8.7 Hz, 1H), 2.52 (s, 3H).

Step 4: Preparation of 2-Methyl-N$^4$-(3-(trifluoromethyl)phenyl)quinazoline-4,8-diamine The title compound was prepared following the procedure described in step-2, Intermediate-9 using 2-methyl-8-nitro-N-(3-(trifluoromethyl)phenyl)quinazolin-4-amine (150 mg, 0.43 mmol), NH$_4$Cl (184 mg, 3.44 mmol) and iron powder (241 mg, 4.31 mmol) in EtOH (5 mL) and water (1 mL) to afford 100 mg of the title product. $^1$H NMR (300 MHz, DMSO-d$_6$): δ 9.66 (s, 1H), 8.47 (s, 1H), 8.32-8.29 (d, J=7.8 Hz, 1H), 7.61 (m, 2H), 7.42-7.40 (d, J=7.2 Hz, 1H), 7.29-7.24 (t, J=7.2 Hz, 1H), 6.96-6.94 (d, J=7.5 Hz, 1H), 5.79 (br s, 2H), 2.55 (s, 3H).

Intermediate-28

1-((4,4-Dimethylcyclohexyl)oxy)isoquinolin-5-amine

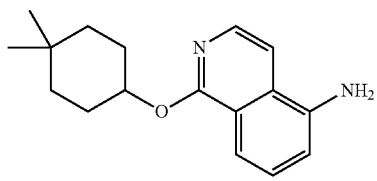 [SMILES: CC1(C)CCC(Oc2nccc3c([N+](=O)[O-])cccc23)CC1]

Step 1: Preparation of 1-((4,4-dimethylcyclohexyl)oxy)-5-nitroisoquinoline

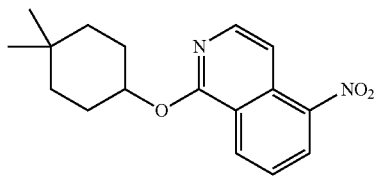

The title compounds were prepared following the procedure described in step-1, Intermediate-10 using 1-chloro-5-nitroisoquinoline (Intermediate-1, step-1, 200 mg, 0.96 mmol) and 4,4-dimethylcyclohexanol (135 mg, 1.05 mmol) and NaH (42 mg, 1.05 mmol, 60% in mineral oil) in THF (10 mL) to afford 180 mg of the title product. $^1$H NMR (300 MHz, DMSO-d$_6$): δ 8.65 (d, J=7.8 Hz, 1H), 8.47 (d, J=7.8 Hz, 1H), 8.18 (d, J=6.6 Hz, 1H), 7.94 (d, J=6.3 Hz, 1H), 7.06 (d, J=7.8 Hz, 1H), 5.33 (m, 1H), 2.04-1.96 (m, 2H), 1.87-1.80 (m, 2H), 1.43-1.39 (m, 4H), 1.02 (s, 3H), 0.99 (s, 3H).

Step 2: Preparation of 1-((4,4-dimethylcyclohexyl)oxy)isoquinolin-5-amine

The title compound was prepared following the procedure described in step-2, Intermediate-9 using 1-((4,4-dimethylcyclohexyl)oxy)-5-nitroisoquinoline (95 mg, 0.32 mmol), NH$_4$Cl (170 mg, 3.16 mmol) and iron powder (48 mg, 0.95 mmol) in EtOH (10 mL) and water (2 mL) to afford 70 mg of the title product. $^1$H NMR (300 MHz, DMSO-d$_6$): δ 7.95 (d, J=6.0 Hz, 1H), 7.73 (d, J=7.8 Hz, 1H), 7.32 (t, J=7.8 Hz, 1H), 7.08 (d, J=5.7 Hz, 1H), 6.92 (d, J=7.8 Hz, 1H), 5.28 (m, 1H), 2.04-1.94 (m, 2H), 1.82 (m, 2H), 1.41-1.37 (m, 4H), 1.01 (s, 3H), 0.97 (s, 3H).

Intermediate-29

N'-((1r,4r)-4-(Trifluoromethyl)cyclohexyl)isoquinoline-1,5-diamine

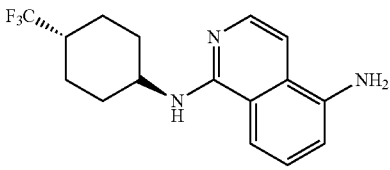

Step 1: Preparation of 5-nitro-N-((1r,4r)-4-(trifluoromethyl)cyclohexyl)isoquinolin-1-amine

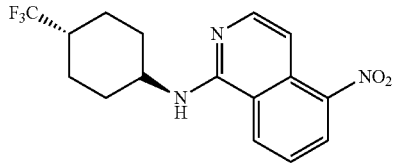

The title compound was prepared following the procedure described in step-1, Intermediate-15 using 1-chloro-5-nitroisoquinoline (Intermediate-1, step-1, 250 mg, 1.20 mmol), K$_2$CO$_3$ (105 mg, 1.44 mmol) and (1r,4r)-4-(trifluoromethyl)cyclohexanamine (200 mg, 1.20 mmol) to afford 150 mg of the title product. $^1$H NMR (300 MHz, DMSO-d$_6$): δ 8.74 (d, J=8.7 Hz, 1H), 8.46 (d, J=7.2 Hz, 1H), 8.08 (d, J=6.3 Hz, 1H), 7.64 (t, J=8.1 Hz, 1H), 7.57 (d, J=7.2 Hz, 1H), 7.26 (d, J=5.7 Hz, 1H), 4.12 (m, 1H), 2.31 (m, 1H), 2.10 (m, 2H), 1.98 (m, 2H), 1.44 (m, 4H).

Step 2: Preparation of N-((1r,4r)-4-(trifluoromethyl)cyclohexyl)isoquinoline-1,5-diamine The title compound was prepared following the procedure described in step-2, Intermediate-9 using 5-nitro-N-((1r,4r)-4-(trifluoromethyl)cyclohexyl)isoquinolin-1-amine (150 mg, 0.44 mmol), NH$_4$Cl (239 mg, 4.43 mmol) and iron powder (75 mg, 1.33 mmol) in EtOH (5 mL) and water (2 mL) to afford 60 mg of the title product.

Intermediate-30

N$^4$-((1r,4r)-4-(Trifluoromethyl)cyclohexyl)quinazoline-4,8-diamine

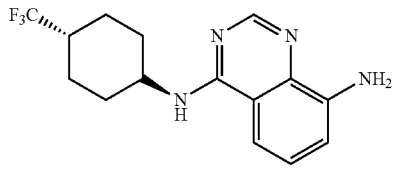

Step 1: Preparation of 8-nitro-N-((1r,4r)-4-(trifluoromethyl)cyclohexyl)quinazolin-4-amine

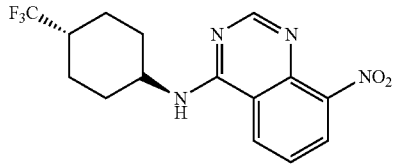

The title compound was prepared following the procedure described in step-1, Intermediate-15 using 4-chloro-8-nitroquinazoline (Intermediate-7, step-2, 150 mg, 0.72 mmol), K$_2$CO$_3$ (198 mg, 1.43 mmol) and (1r,4r)-4-(trifluoromethyl)cyclohexanamine (239 mg, 1.43 mmol) to afford 200 mg of the title product. $^1$H NMR (300 MHz, DMSO d$_6$): δ 8.60 (d, J=8.4 Hz, 1H), 8.52 (s, 1H), 8.44 (d, J=7.5 Hz, 1H), 8.24 (d, J=7.2 Hz, 1H), 7.64 (t, J=8.1 Hz, 1H), 4.16 (m, 1H), 2.34 (m, 1H), 2.06 (m, 2H), 1.98-1.94 (m, 2H), 1.52-1.40 (m, 4H).

Step 2: Preparation of N⁴-((1r,4r)-4-(trifluoromethyl)cyclohexyl)quinazoline-4,8-diamine The title compound was prepared following the procedure described in step-2, Intermediate-9 using 8-nitro-N-((1r,4r)-4-(trifluoromethyl)cyclohexyl)quinazolin-4-amine (200 mg, 0.59 mmol), NH₄Cl (249 mg, 4.70 mmol) and iron powder (329 mg, 5.88 mmol) in EtOH (4 mL) and water (1 mL) to afford 150 mg of the title product. ¹H NMR (300 MHz, DMSO d₆): δ 8.36 (s, 1H), 7.66 (d, J=7.5 Hz, 1H), 7.36 (d, J=7.8 Hz, 1H), 7.15 (d, J=7.2 Hz, 1H), 6.86 (d, J=7.8 Hz, 1H), 5.69 (s, 2H), 4.16 (m, 1H), 2.28 (m, 1H), 2.03 (m, 2H), 1.96-1.93 (m, 2H), 1.50-1.23 (m, 4H).

Intermediate-31

5-Nitro-1-(((1r,4r)-4-(trifluoromethyl)cyclohexyl)oxy)isoquinoline

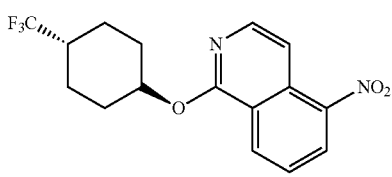

Intermediate-32

5-Nitro-1-(((1s,4s)-4-(trifluoromethyl)cyclohexyl)oxy)isoquinoline

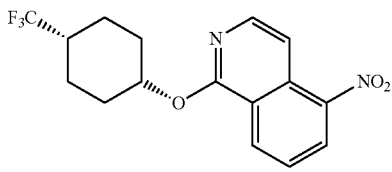

The title compounds were prepared following the procedure described in step-1, Intermediate-10 using 1-chloro-5-nitroisoquinoline (Intermediate-1, step-1, 250 mg, 1.28 mmol) and 4-(trifluoromethyl)cyclohexanol (cis and trans mixture) (324 mg, 1.93 mmol) and NaH (61 mg, 2.56 mmol, 60% in mineral oil) in THF (4 mL) to afford 150 mg of Intermediate-31 and 83 mg of Intermediate-32. Intermediate-31: ¹H NMR (300 MHz, DMSO-d₆): δ 8.61 (d, J=8.4 Hz, 1H), 8.47 (d, J=7.8 Hz, 1H), 8.17 (d, J=6.3 Hz, 1H), 7.97 (d, J=6.3 Hz, 1H), 7.61 (t, J=7.8 Hz, 1H), 5.30-5.27 (m, 1H), 2.41 (m, 2H), 2.11-2.09 (m, 3H), 1.68-1.56 (m, 4H).

Intermediate-32: ¹H NMR (300 MHz, DMSO-d₆): δ 8.63 (d, J=8.4 Hz, 1H), 8.49 (d, J=7.2 Hz, 1H), 8.18 (d, J=6.3 Hz, 1H), 7.98 (d, J=6.3 Hz, 1H), 7.66 (t, J=8.4 Hz, 1H), 5.65 (m, 1H), 2.34-2.29 (m, 2H), 1.86-1.82 (m, 3H), 1.75-1.70 (m, 4H).

Intermediate-33

1-(((1r,4r)-4-(Trifluoromethyl)cyclohexyl)oxy)isoquinolin-5-amine

The title compound was prepared following the procedure described in step-2, Intermediate-9 using 5-Nitro-1-(((1r,4r)-4-(trifluoromethyl)cyclohexyl)oxy)isoquinoline (150 mg, 0.44 mmol), NH₄Cl (187 mg, 3.52 mmol) and iron powder (246 mg, 4.40 mmol) in EtOH (4 mL) and water (2 mL) to afford 130 mg of the title product. ¹H NMR (300 MHz, DMSO-d₆): δ 7.81 (d, J=6.3 Hz, 1H), 7.45 (d, J=5.7 Hz, 1H), 7.29-7.20 (m, 2H), 6.82 (d, J=6.9 Hz, 1H), 5.82 (br s, 2H), 5.12 (m, 1H), 2.35 (m, 1H), 2.25-2.22 (m, 2H), 1.96-1.92 (m, 2H), 1.55-1.43 (m, 4H).

Intermediate-34

1-(((1s,4s)-4-(Trifluoromethyl)cyclohexyl)oxy)isoquinolin-5-amine

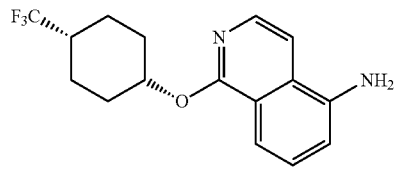

The title compound was prepared following the procedure described in step-2, Intermediate-9 using 5-nitro-1-(((1s,4s)-4-(trifluoromethyl)cyclohexyl)oxy)isoquinoline (100 mg, 0.29 mmol), NH₄Cl (122 mg, 2.35 mmol) and iron powder (164 mg, 2.94 mmol) in EtOH (3 mL) and water (2 mL) to afford 70 mg of the title product. ¹H NMR (300 MHz, DMSO-d₆): δ 7.82 (d, J=6.6 Hz, 1H), 7.45 (d, J=5.7 Hz, 1H), 7.35 (d, J=7.8 Hz, 1H), 7.28 (t, J=7.8 Hz, 1H), 6.84 (d, J=6.6 Hz, 1H), 5.83 (br s, 2H), 5.46 (s, 1H), 2.37 (m, 1H), 2.24 (m, 2H), 2.09 (m, 2H), 1.70-1.67 (m, 4H).

Intermediate-35

4-(2-Fluoro-5-(trifluoromethyl)phenoxy)quinolin-8-amine

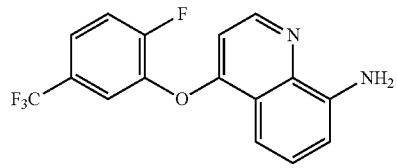 [SMILES: Nc1cccc2c(Oc3cc(C(F)(F)F)ccc3F)ccnc12]

Step 1: Preparation of 4-(2-fluoro-5-(trifluoromethyl)phenoxy)-8-nitroquinoline

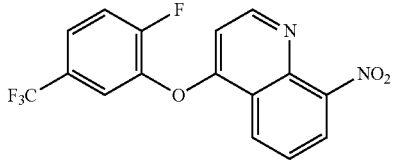 [SMILES: O=[N+]([O-])c1cccc2c(Oc3cc(C(F)(F)F)ccc3F)ccnc12]

The title compound was prepared following the procedure described in Intermediate-11, step-3 using 4-chloro-8-nitroquinoline (Intermediate-11, step-2, 300 mg, 1.44 mmol), 2-fluoro-5-(trifluoromethyl)phenol (389 mg, 2.16 mmol), $K_2CO_3$ (596 mg, 4.32 mmol) in $CH_3CN$ (4 mL) to afford 432 mg of the title product. $^1$H NMR (300 MHz, DMSO $d_6$): δ 8.82 (d, J=4.8 Hz, 1H), 8.60 (d, J=8.4 Hz, 1H), 8.36 (d, J=7.5 Hz, 1H), 8.11 (d, J=5.7 Hz, 1H), 7.86-7.75 (m, 3H), 6.93 (d, J=4.8 Hz, 1H); MS (m/z): 353.21 (M+H)$^+$.

Step 2: Preparation of 4-(2-fluoro-5-(trifluoromethyl)phenoxy)quinolin-8-amine The title compound was prepared following the procedure described in Intermediate-11, step-4 using 4-(2-fluoro-5-(trifluoromethyl)phenoxy)-8-nitroquinoline (432 mg, 1.22 mmol), iron powder (683 mg, 12.2 mmol), and $NH_4Cl$ (517 mg, 9.76 mmol) in EtOH (5 mL) and water (2 mL) to afford 330 mg of the title product. $^1$H NMR (300 MHz, DMSO $d_6$): δ 8.52 (d, J=5.1 Hz, 1H), 7.94 (d, J=6.6 Hz, 1H), 7.79-7.70 (m, 2H), 7.35 (d, J=6.0 Hz, 2H), 6.91 (d, J=3.6 Hz, 1H), 6.63 (d, J=4.2 Hz, 1H), 5.98 (br s, 2H).

Intermediate-36

1-(2-Fluoro-5-(trifluoromethyl)phenoxy)isoquinolin-5-amine

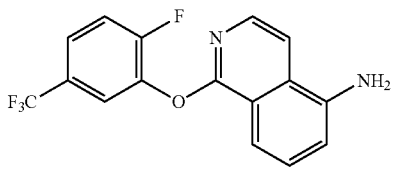 [SMILES: Nc1cccc2c(Oc3cc(C(F)(F)F)ccc3F)nccc12]

Step 1: Preparation of 1-(2-fluoro-5-(trifluoromethyl)phenoxy)-5-nitroisoquinoline

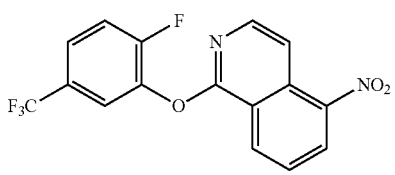 [SMILES: O=[N+]([O-])c1cccc2c(Oc3cc(C(F)(F)F)ccc3F)nccc12]

The title compound was prepared following the procedure described in step-1, Intermediate-6 using 1-chloro-5-nitroisoquinoline (Step-1, Intermediate-1, 250 mg, 1.19 mmol), 2-fluoro-5-(trifluoromethyl)phenol (323 mg, 1.79 mmol), and $K_2CO_3$ (331 mg, 2.39 mmol) in $CH_3CN$ (4 mL) to afford 330 mg of the title product. $^1$H NMR (300 MHz, DMSO $d_6$): δ 8.86 (d, J=8.4 Hz, 1H), 8.73 (d, J=7.8 Hz, 1H), 8.19 (d, J=5.7 Hz, 1H), 8.05 (d, J=6.0 Hz, 2H), 7.95 (d, J=8.4 Hz, 1H), 7.81-7.68 (m, 2H).

Step 2: Preparation of 1-(2-fluoro-5-(trifluoromethyl)phenoxy)isoquinolin-5-amine The title compound was prepared following the procedure described in Step 3 of Intermediate-1 using 1-(2-fluoro-5-(trifluoromethyl)phenoxy)-5-nitroisoquinoline (320 mg, 0.90 mmol), iron powder (500 mg, 9.09 mmol), and $NH_4Cl$ (389 mg, 7.2 mmol) in EtOH (8 mL) and water (2 mL) to afford 230 mg of the title product. $^1$H NMR (300 MHz, DMSO $d_6$): δ 7.89 (d, J=5.7 Hz, 1H), 7.75-7.59 (m, 4H), 7.50 (d, J=7.8 Hz, 1H), 7.40 (t, J=8.1 Hz, 1H), 6.93 (d, J=7.5 Hz, 1H), 6.03 (s, 2H); MS (m/z): 323.28 (M+H)$^+$.

Intermediate-37

7-Methyl-$N^4$-(3-(trifluoromethyl)phenyl)quinazoline-4,8-diamine

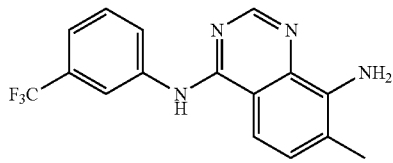 [SMILES: Cc1ccc2c(Nc3cccc(C(F)(F)F)c3)ncnc2c1N]

Step 1: Preparation of 4-methyl-2-nitrobenzamide

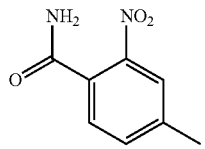

To a solution of 4-methyl-2-nitrobenzoic acid (1.0 g, 5.52 mmol) in toluene (5 mL) was added oxalyl chloride (1.04 g, 8.28 mmol) at 0° C. and the reaction mixture was stirred at rt for 2 h. Then the reaction mixture was concentrated and the concentrate was dissolved in THF (5 mL). Then $NH_4OH$ (1.93 g, 55.20 mmol) was added to the solution at 0-5° C. and the reaction mixture was stirred at rt for 4 h before it was quenched with water and was extracted with EtOAc. The organic layer was washed with brine, separated, dried, filtered and concentrated to afford 1.6 g of the desired product. $^1$H NMR (300 MHz, DMSO-$d_6$): δ 8.08 (br s, 1H), 7.79 (s, 1H), 7.62 (br s, 1H), 7.57-7.50 (m, 2H), 2.41 (s, 3H).

Step 2: Preparation of 2-amino-4-methylbenzamide

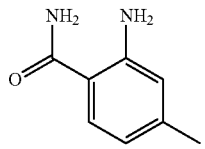

The title compound was prepared following the procedure described in Step 3 of Intermediate-1 using 4-methyl-2-nitrobenzamide (1.60 g, 8.88 mmol), iron powder (2.97 g, 53.33 mmol), and NH$_4$Cl (2.85 g, 53.33 mmol) in EtOH (8 mL) and water (2 mL) to afford 1.2 g of the title product. $^1$H NMR (300 MHz, DMSO-d$_6$): δ 7.62 (br s, 1H), 7.42 (d, J=7.8 Hz, 1H), 6.93 (br s, 1H), 6.53 (s, 2H), 6.46 (s, 1H), 6.29 (d, J=7.8 Hz, 1H), 2.15 (s, 3H).

Step 3: Preparation of 7-methylquinazolin-4(3H)-one

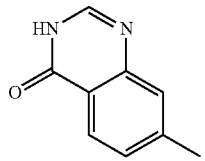

A suspension of 2-amino-4-methylbenzamide (1.2 g, 8.0 mmol) in CH(OEt)$_3$ (10 mL) was heated in a sealed tube at 110° C. for 4 h. Then the reaction was quenched with aq. NaHCO$_3$ solution at rt and the precipitate obtained was filtered and dried. The solid mass was purified by column chromatography to afford 1.1 g of the title product. $^1$H NMR (300 MHz, DMSO-d$_6$): δ 12.14 (br s, 1H), 8.05 (s, 1H), 8.00 (d, J=7.8 Hz, 1H), 7.47 (s, 1H), 7.34 (d, J=7.8 Hz, 1H), 2.45 (s, 3H).

Step 4: Preparation of 5-bromo-7-methylquinazolin-4(3H)-one

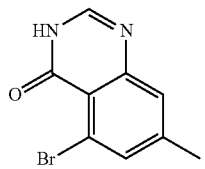

To a solution of 7-methylquinazolin-4(3H)-one (900 mg, 5.63 mmol) in MeOH (180 mg, 5.63 mmol) and AcOH (5.07 g, 84.45 mmol) was added bromine (300 µL, 5.63 mmol) and the reaction mixture was stirred at rt for 4 h. Then the reaction mixture was quenched with an aq. solution of sodium thiosulphate. The precipitate obtained was filtered and dried to afford 900 mg of the title product. $^1$H NMR (300 MHz, DMSO-d$_6$): δ 12.24 (br s, 1H), 8.18 (s, 1H), 8.08 (s, 1H), 7.66 (s, 1H), 2.48 (s, 3H).

Step 5: Preparation of 5-bromo-7-methyl-8-nitroquinazolin-4(3H)-one

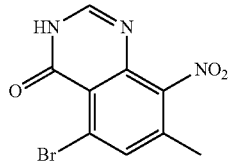 [SMILES: Cc1cc(Br)c2c(=O)[nH]cnc2c1[N+](=O)[O-]]

To a solution of 5-bromo-7-methylquinazolin-4(3H)-one (700 mg, 2.94 mmol) in conc. H$_2$SO$_4$ (10 mL) was added fuming HNO$_3$ (185 µL, 2.94 mmol) at 0° C. and then the reaction mixture was stirred at rt for 12 h. Then the reaction mixture was quenched with water and the precipitate obtained was filtered and dried to afford 500 mg of the title product. $^1$H NMR (300 MHz, DMSO-d$_6$): δ 12.80 (br s, 1H), 8.40 (s, 1H), 8.24 (s, 1H), 2.41 (s, 3H).

Step 6: Preparation of 5-bromo-7-methyl-8-nitro-N-(3-(trifluoromethyl)phenyl)quinazolin-4-amine

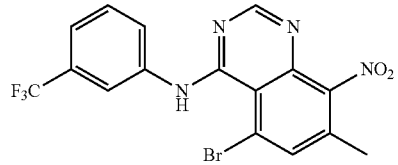 [SMILES: Cc1cc(Br)c2c(Nc3cccc(C(F)(F)F)c3)ncnc2c1[N+](=O)[O-]]

A solution of 5-bromo-7-methyl-8-nitroquinazolin-4(3H)-one (200 mg, 0.71 mmol) in POCl$_3$ (4 mL) was heated at reflux for 4 h. Then the reaction mixture was concentrated and the residue was co-evaporated with toluene and dried to afford 5-bromo-4-chloro-7-methyl-8-nitroquinazoline which was dissolved in THF (5 mL). Then the solution was treated with 3-(trifluoromethyl)aniline (457 mg, 2.84 mmol) and DIPEA (458 mg, 3.55 mmol) at 0° C. and the reaction mixture was stirred at rt for 12 h before it was quenched with water and was extracted with EtOAc. The organic layer was washed with brine, separated, dried, filtered, concentrated and purified by column chromatography to afford 215 mg of the title product. $^1$H NMR (300 MHz, DMSO-d$_6$): δ 10.36 (s, 1H), 9.15 (s, 1H), 8.72 (s, 1H), 8.29 (s, 1H), 8.23 (d, J=8.4 Hz, 1H), 7.67 (t, J=7.8 Hz, 1H), 7.53 (d, J=7.8 Hz, 1H), 2.47 (s, 3H); MS (m/z): 427.17 (M)$^+$.

Step 7: Preparation of 7-methyl-N$^4$-(3-(trifluoromethyl)phenyl)quinazoline-4,8-diamine To a solution of 5-bromo-7-methyl-8-nitro-N-(3-(trifluoromethyl)phenyl)quinazolin-4-amine (400 mg, 0.94 mmol) in EtOH (10 mL) was added 10% Pd/C (420 mg) and the suspension was stirred under H$_2$ (1 atm) for 5 h. Then the reaction mixture was filtered through celite and concentrated. The residue was purified by column chromatography to afford 200 mg of the title product. $^1$H NMR (300 MHz, DMSO-d$_6$): δ 9.73 (s, 1H), 8.59 (s, 1H), 8.38 (s, 1H), 8.26 (d, J=7.2 Hz, 1H), 7.65-7.58 (m, 2H), 7.42 (d, J=7.2 Hz, 1H), 7.30 (d, J=8.7 Hz, 1H), 5.63 (br s, 2H), 2.80 (s, 3H).

Intermediate-38

4-Ethoxyquinazolin-8-amine

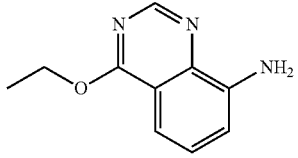

Step 1: Preparation of 4-ethoxy-8-nitroquinazoline

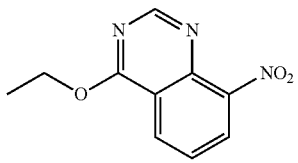 [SMILES: CCOc1ncnc2c([N+](=O)[O-])cccc12]

A solution of 8-nitroquinazolin-4(3H)-one (Intermediate-7, step-1, 300 mg, 1.57 mmol) in POCl$_3$ (3 mL) was heated at reflux for 2 h. Then the reaction mixture was concentrated and dried to afford 4-chloro-8-nitroquinazoline which was used for the next step without further purification. Then NaH (263 mg, 11.54 mmol, 95%) was added to EtOH (2 mL) at 0° C. and stirred at that temperature for 15 minutes before it was added to a solution of 4-chloro-8-nitroquinazoline in THF (2 mL) at 0° C. Then the reaction mixture was stirred at rt for 4 h. Then the reaction mixture was quenched with water and was extracted with EtOAc. The organic layer was washed with brine, separated, dried, filtered and concentrated. The residue was purified by column chromatography to afford 200 mg of the title product. MS (m/z): 220.23 (M+H)$^+$.

Step 2: Preparation of 4-ethoxyquinazolin-8-amine

The title compound was prepared following the procedure described in step-2, Intermediate-9 using 4-ethoxy-8-nitroquinazoline (200 mg, 0.91 mmol), NH$_4$Cl (146 mg, 2.74 mmol) and iron powder (153 mg, 2.74 mmol) in EtOH (2 mL) and water (0.5 mL) to afford 140 mg of the title product. MS (m/z): 190.14 (M+H)$^+$.

Intermediate-39

N'-(2-Fluoro-4-(trifluoromethyl)phenyl)isoquinoline-1,5-diamine

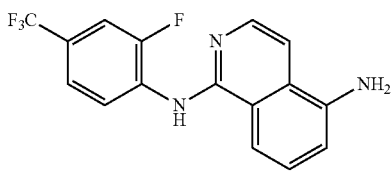 [SMILES: Nc1cccc2c(Nc3ccc(C(F)(F)F)cc3F)nccc12]

Step 1: Preparation of N-(2-fluoro-4-(trifluoromethyl)phenyl)-5-nitroisoquinolin-1-amine

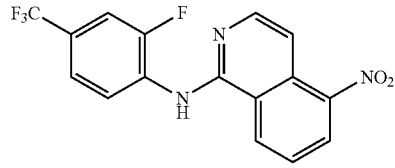 [SMILES: O=[N+]([O-])c1cccc2c(Nc3ccc(C(F)(F)F)cc3F)nccc12]

The title compound was prepared following the procedure described in Intermediate-1, step-2 using 1-chloro-5-nitroisoquinoline (Intermediate-1, step-1, 250 mg, 1.19 mmol), and 2-fluoro-4-(trifluoromethyl)aniline (330 mg, 1.84 mmol) in N-methylpyrrolidinone (2 mL) to afford 195 mg of the title product. $^1$H NMR (300 MHz, DMSO-d$_6$): δ 9.69 (s, 1H), 8.84 (d, J=7.8 Hz, 1H), 8.55 (d, J=7.8 Hz, 1H), 8.15 (d, J=5.7 Hz, 1H), 7.86-7.57 (m, 5H); MS (m/z): 352.18 (M+H)$^+$.

Step 2: Preparation of N'-(2-fluoro-4-(trifluoromethyl)phenyl)isoquinoline-1,5-diamine The title compound was prepared following the procedure described in Intermediate-1, step-2 using N-(2-fluoro-4-(trifluoromethyl)phenyl)-5-nitroisoquinolin-1-amine (190 mg, 0.54 mmol), iron powder (303 mg, 5.41 mmol), and NH$_4$Cl (232 mg, 4.32 mmol) in EtOH:H$_2$O (3:1, 4 mL) to afford 120 mg of the title product. $^1$H NMR (300 MHz, DMSO-d$_6$): δ 8.93 (s, 1H), 7.89 (t, J=8.4 Hz, 1H), 7.82 (d, J=6.0 Hz, 1H), 7.64 (d, J=10.8 Hz, 1H), 7.51 (t, 8.4 Hz, 2H), 7.40 (d, J=6.0 Hz, 1H), 7.30 (t, J=7.8 Hz, 1H0, 6.84 (d, J=7.2 Hz, 1H), 5.83 (s, 2H); MS (m/z): 322.33 (M+H)$^+$.

Intermediate-40

N'-(4-(Trifluoromethyl)phenyl)isoquinoline-1,5-diamine

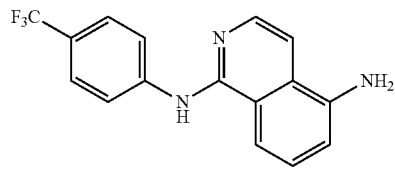 [SMILES: Nc1cccc2c(Nc3ccc(C(F)(F)F)cc3)nccc12]

Step 1: Preparation of 5-nitro-N-(4-(trifluoromethyl)phenyl)isoquinolin-1-amine

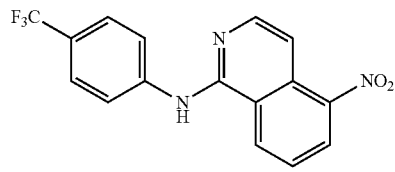 [SMILES: O=[N+]([O-])c1cccc2c(Nc3ccc(C(F)(F)F)cc3)nccc12]

The title compound was prepared following the procedure described in Intermediate-1, step-2 using 1-chloro-5-nitroisoquinoline (Intermediate-1, step-1, 500 mg, 2.30 mmol), and 4-(trifluoromethyl)aniline (772 mg, 4.70 mmol) in N-methylpyrrolidinone (3 mL) to afford 750 mg of the title product. $^1$H NMR (300 MHz, DMSO-d$_6$): δ 9.83 (s, 1H), 8.94 (d, J=8.4

Hz, 1H), 8.53 (d, J=7.2 Hz, 1H), 8.26 (d, J=6.3 Hz, 1H), 8.06 (d, J=9.0 Hz, 2H), 8.33 (t, J=7.8 Hz, 1H), 7.66 (m, 3H); MS (m/z): 334.19 (M+H)⁺.

Step 2: Preparation of N-(4-(trifluoromethyl)phenyl) isoquinoline-1,5-diamine The title compound was prepared following the procedure described in Intermediate-1, step-3 using 5-nitro-N-(4-(trifluoromethyl)phenyl)isoquinolin-1-amine (750 mg, 2.25 mmol), iron powder (1.26 g, 22.5 mmol), and NH₄Cl (963 mg, 18.0 mmol) in EtOH—H₂O (5:2, 7 mL) to afford 260 mg of the title product. ¹H NMR (300 MHz, DMSO-d₆): δ 9.27 (s, 1H), 8.09 (d, J=9.0 Hz, 2H), 7.94 (d, J=6.0 Hz, 1H), 7.64 (m, 3H), 7.44 (d, J=5.7 Hz, 1H), 7.33 (t, J=7.8 Hz, 1H), 6.87 (d, J=7.8 Hz, 1H), 5.87 (br s, 2H); MS (m/z): 304.28 (M+H)⁺.

Intermediate-41

1-(4-(Trifluoromethyl)phenoxy)isoquinolin-5-amine

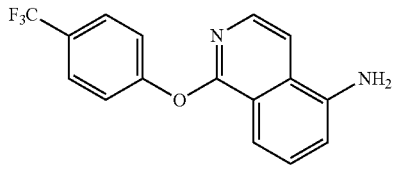 [SMILES: Nc1cccc2c(Oc3ccc(C(F)(F)F)cc3)nccc12]

Step 1: Preparation of 5-nitro-1-(4-(trifluoromethyl)phenoxy)isoquinoline

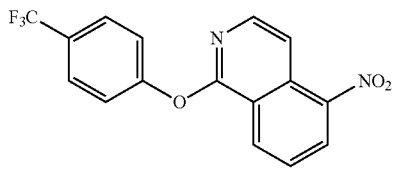 [SMILES: O=[N+]([O-])c1cccc2c(Oc3ccc(C(F)(F)F)cc3)nccc12]

The title compound was prepared following the procedure described in Intermediate-6, step-1 using 1-chloro-5-nitroisoquinoline (Step-1, Intermediate-1, 500 mg, 2.39 mmol), 4-(trifluoromethyl)phenol (776 mg, 4.79 mmol) and K₂CO₃ (989 mg, 7.17 mmol) in CH₃CN (5 mL) to afford 800 mg of the title product. MS (m/z): 335.09 (M+H)⁺.

Step 2: Preparation of 1-(4-(trifluoromethyl)phenoxy)isoquinolin-5-amine

The title compound was prepared following the procedure described in Step 3 of Intermediate-1 using 5-nitro-1-(4-(trifluoromethyl)phenoxy)isoquinoline (800 mg, 2.39 mmol), iron powder (1.34 g, 23.9 mmol), and NH₄Cl (1.02 g, 19.1 mmol) in EtOH (5 mL) and water (1 mL) to afford 140 mg of the title product. ¹H NMR (300 MHz, DMSO d₆): δ 7.81 (m, 3H), 7.72 (d, 1H), 7.46-7.40 (m, 4H), 6.94 (d, J=6.9 Hz, 1H), 6.03 (s, 2H); MS (m/z): 305.17 (M+H)⁺.

Intermediate-42

1-(4-Fluoro-3-(trifluoromethyl)phenoxy)isoquinolin-5-amine

Step 1: Preparation of 1-(4-fluoro-3-(trifluoromethyl)phenoxy)-5-nitroisoquinoline

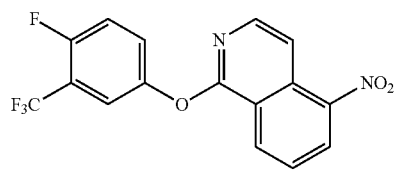 [SMILES: O=[N+]([O-])c1cccc2c(Oc3ccc(F)c(C(F)(F)F)c3)nccc12]

The title compound was prepared following the procedure described in Intermediate-6, step-1 using 1-chloro-5-nitroisoquinoline (Step-1, Intermediate-1, 500 mg, 2.38 mmol), 4-fluoro-3-(trifluoromethyl)phenol (859 mg, 4.77 mmol) and K₂CO₃ (821 mg, 5.95 mmol) in CH₃CN (5 mL) to afford 850 mg of the title product. ¹H NMR (300 MHz, DMSO d₆): δ 8.84 (d, J=8.4 Hz, 1H), 8.71 (d, J=7.8 Hz, 1H), 8.19 (d, J=6.3 Hz, 1H), 8.01-7.92 (m, 2H), 7.87 (m, 1H), 7.76 (m, 1H), 7.66 (t, J=9.6 Hz, 1H); MS (m/z): 353.20 (M+H)⁺.

Step 2: Preparation of 1-(4-fluoro-3-(trifluoromethyl)phenoxy)isoquinolin-5-amine The title compound was prepared following the procedure described in Step 3 of Intermediate-1 using 1-(4-fluoro-3-(trifluoromethyl)phenoxy)-5-nitroisoquinoline (830 mg, 2.35 mmol), iron powder (1.31 mg, 23.5 mmol), and NH₄Cl (1.09 g, 18.8 mmol) in EtOH (8 mL) and water (2 mL) to afford 660 mg of the title product. ¹H NMR (300 MHz, DMSO d₆): δ 7.79 (d, J=6.0 Hz, 1H), 7.71-7.56 (m, 4H), 7.51 (d, J=8.1 Hz, 1H), 7.40 (t, J=8.1 Hz, 1H), 6.94 (d, J=7.2 Hz, 1H), 6.01 (s, 2H).

Intermediate-43

6-Chloro-2-methoxy-3-(pivalamidomethyl)benzoic acid

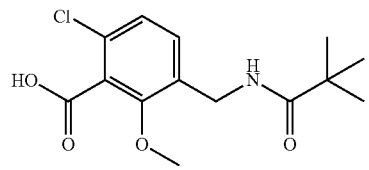 [SMILES: COc1c(CNC(=O)C(C)(C)C)ccc(Cl)c1C(=O)O]

To a solution of ethyl 6-chloro-2-fluoro-3-(pivalamidomethyl)benzoate (Intermediate-2; step-2, 1.00 g, 3.31 mmol) in THF:MeOH:H$_2$O (2:2:1; 5 mL) was added KOH (930 mg, 16.57 mmol). The reaction mass was heated in a sealed tube at 100° C. for 3 h. The reaction mass was neutralized with citric acid and concentrated. The residue was diluted with EtOAc and was washed with water and brine. The organic layer was separated, dried, filtered and concentrated to afford 700 mg of the title product. $^1$H NMR (300 MHz, DMSO-d$_6$): δ 13.65 (br s, 1H), 8.08 (t, 1H), 7.29-7.26 (d, J=8.4 Hz, 1H), 7.22-7.19 (d, J=8.7 Hz, 1H), 4.25 (d, J=5.7 Hz, 2H), 3.79 (s, 3H), 1.13 (s, 9H); MS (m/z): 300.05 (M+H)$^+$.

Intermediate-44

4-(4-Fluoro-3-(trifluoromethyl)phenoxy)quinolin-8-amine

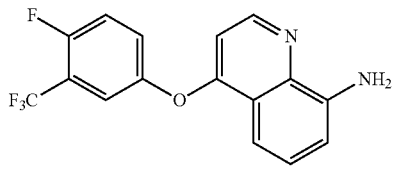 [SMILES: Nc1cccc2c(Oc3ccc(F)c(C(F)(F)F)c3)ccnc12]

Step 1: Preparation of 4-(4-fluoro-3-(trifluoromethyl)phenoxy)-8-nitroquinoline

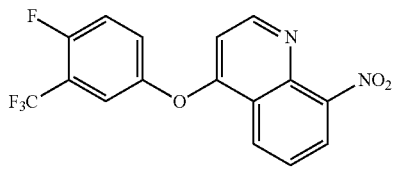 [SMILES: O=[N+]([O-])c1cccc2c(Oc3ccc(F)c(C(F)(F)F)c3)ccnc12]

The title compound was prepared following the procedure described in Intermediate-11, step-3 using 4-chloro-8-nitroquinoline (Intermediate-11, step-2, 250 mg, 1.20 mmol), 4-fluoro-3-(trifluoromethyl)phenol (430 mg, 2.40 mmol), K$_2$CO$_3$ (479 mg, 3.60 mmol) in CH$_3$CN (5 mL) to afford 380 mg of the title product. $^1$H NMR (300 MHz, DMSO d$_6$): δ 10.75 (s, 1H), 8.82 (d, J=5.4 Hz, 1H), 7.92 (m, 1H), 7.86-7.81 (m, 3H), 7.31 (t, J=9.6 Hz, 1H), 6.90 (d, J=5.1 Hz, 1H); MS (m/z): 353.14 (M+H)$^+$.

Step 2: Preparation of 4-(4-fluoro-3-(trifluoromethyl)phenoxy)quinolin-8-amine

The title compound was prepared following the procedure described in Intermediate-11, step-4 using 4-(4-fluoro-3-(trifluoromethyl)phenoxy)-8-nitroquinoline (380 mg, 1.07 mmol), iron powder (604 mg, 10.79 mmol), and NH$_4$Cl (461 mg, 8.63 mmol) in EtOH (10 mL) and water (3 mL) to afford 223 mg of the title product. $^1$H NMR (300 MHz, DMSO d$_6$): δ 8.55 (d, J=4.8 Hz, 1H), 7.75 (d, 1H), 7.67 (d, J=7.5 Hz, 2H), 7.34 (d, J=4.5 Hz, 2H), 6.92 (t, 1H), 6.68 (d, J=4.8 Hz, 1H), 5.98 (s, 2H); MS (m/z): 323.28 (M+H)$^+$.

Intermediate-45

4-(4-Fluoro-3-(trifluoromethyl)phenoxy)quinazolin-8-amine

Step 1: Preparation of 4-(4-fluoro-3-(trifluoromethyl)phenoxy)-8-nitroquinazoline

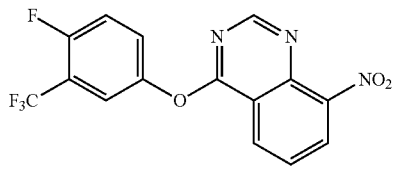 [SMILES: O=[N+]([O-])c1cccc2c(Oc3ccc(F)c(C(F)(F)F)c3)ncnc12]

The title compound was prepared following the procedure described in step-1, Intermediate-8 using 4-chloro-8-nitroquinazoline (Intermediate-7, step 2, 500 mg, 2.38 mmol), 4-fluoro-3-(trifluoromethyl)phenol (859 mg, 4.77 mmol) and NaH (150 mg, 5.95 mmol, 60% in mineral oil) in THF (10 mL) to afford 830 mg of the title product. $^1$H NMR (300 MHz, DMSO d$_6$): δ 8.89 (s, 1H), 8.67 (d, J=8.4 Hz, 1H), 8.60 (d, J=6.9 Hz, 1H), 7.99-7.94 (m, 2H), 7.86-7.84 (m, 1H), 7.71 (t, J=9.6 Hz, 1H); MS (m/z): 354.13 (M+H)$^+$.

Step 2: Preparation of 4-(4-fluoro-3-(trifluoromethyl)phenoxy)quinazolin-8-amine The title compound was prepared following the procedure described in step-2, Intermediate-9 using 4-(4-fluoro-3-(trifluoromethyl)phenoxy)-8-nitroquinazoline (830 mg, 2.35 mmol), NH$_4$Cl (1.00 g, 18.8 mmol) and iron powder (1.31 g, 23.5 mmol) in EtOH (10 mL) and water (5 mL) to afford 650 mg of the title product. $^1$H NMR (300 MHz, DMSO-d$_6$): δ 8.60 (s, 1H), 7.88 (m, 1H), 7.76 (m, 1H), 7.66 (t, J=9.6 Hz, 1H), 7.45 (d, J=9.3 Hz, 2H), 7.10 (d, J=5.7 Hz, 1H), 6.08 (s, 2H); MS (m/z): 324.23 (M+H)$^+$.

Intermediate-46

4-(4-(Trifluoromethyl)phenoxy)quinolin-8-amine

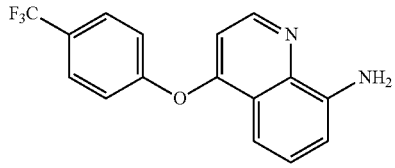

Step 1: Preparation of 8-nitro-4-(4-(trifluoromethyl)phenoxy)quinoline

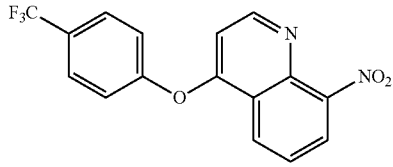 [SMILES: O=[N+]([O-])c1cccc2c(Oc3ccc(C(F)(F)F)cc3)ccnc12]

The title compound was prepared following the procedure described in Intermediate-11, step-3 using 4-chloro-8-nitroquinoline (Intermediate-11, step-2, 200 mg, 0.96 mmol), 4-(trifluoromethyl)phenol (233 mg, 1.43 mmol), K$_2$CO$_3$ (264 mg, 1.91 mmol) in CH$_3$CN (5 mL) to afford 200 mg of the title product. $^1$H NMR (300 MHz, DMSO d$_6$): δ 8.85 (d, J=4.8 Hz, 1H), 8.56 (d, J=8.4 Hz, 1H), 8.36 (d, J=7.2 Hz, 1H), 7.93 (d, J=8.7 Hz, 2H), 7.82 (t, J=8.1 Hz, 1H), 7.58 (d, J=8.4 Hz, 2H), 6.98 (d, J=5.4 Hz, 1H).

Step 2: Preparation of 4-(4-(trifluoromethyl)phenoxy)quinolin-8-amine

The title compound was prepared following the procedure described in Intermediate-11, step-4 using 8-nitro-4-(4-(trifluoromethyl)phenoxy)quinoline (200 mg, 0.59 mmol), iron powder (335 mg, 5.98 mmol), and NH$_4$Cl (260 mg, 4.70 mmol) in EtOH (5 mL) and water (1 mL) to afford 126 mg of the title product. $^1$H NMR (300 MHz, DMSO d$_6$): δ 8.60 (d, J=4.8 Hz, 1H), 7.85 (d, J=8.7 Hz, 2H), 7.40 (d, J=8.4 Hz, 2H), 7.31 (d, J=7.8 Hz, 1H), 7.25 (d, J=7.8 Hz, 1H), 6.92 (d, J=7.2 Hz, 1H), 6.85 (d, J=5.4 Hz, 1H), 6.01 (s, 2H).

Intermediate-47

N$^4$-(4-Dimethylcyclohexyl)-2-methylquinazoline-4,8-diamine

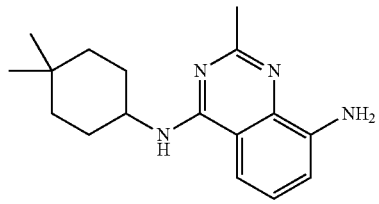 [SMILES: Cc1nc(NC2CCC(C)(C)CC2)c2cccc([N+](=O)[O-])c2n1]

Step 1: Preparation of N-(4,4-dimethylcyclohexyl)-2-methyl-8-nitroquinazolin-4-amine

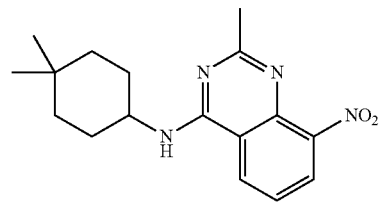

The title compound was prepared following the procedure described in Intermediate-15, step-1 using 4-chloro-2-methyl-8-nitroquinazoline (Intermediate-27, step-2, 217 mg, 0.97 mmol), 4,4-dimethylcyclohexanamine hydrochloride (477 mg, 2.9 mmol),) and K$_2$CO$_3$ (402 mg, 2.9 mmol) in CH$_3$CN (5 mL) to afford 265 mg of the title product. $^1$H NMR (300 MHz, DMSO d$_6$): δ 8.50 (d, J=8.1 Hz, 1H), 8.20-8.13 (m, 2H), 7.53 (t, J=8.4 Hz, 1H), 4.15 (m, 1H), 2.42 (s, 3H), 1.73 (m, 2H), 1.67-1.55 (m, 2H), 1.45-1.28 (m, 4H), 0.97 (s, 3H), 0.94 (s, 3H); MS [M+H]$^+$: 315.23.

Step 2: Preparation of N$^4$-(4,4-dimethylcyclohexyl)-2-methylquinazoline-4,8-diamine The title compound was prepared following the procedure described in step-2, Intermediate-9 using N-(4,4-dimethylcyclohexyl)-2-methyl-8-nitroquinazolin-4-amine (265 mg, 0.84 mmol), NH$_4$Cl (368 mg, 6.74 mmol) and iron powder (472 mg, 8.43 mmol) in EtOH (5 mL) and water (2 mL) to afford 200 mg of the title product. $^1$H NMR (300 MHz, DMSO d$_6$): 6.7.42 (d, 1H), 7.30 (d, J=8.4 Hz, 1H), 7.07 (t, J=8.1 Hz, 1H), 6.81 (d, J=7.5 Hz, 1H), 5.56 (s, 2H), 4.11 (m, 1H), 2.42 (s, 3H), 1.69 (m, 2H), 1.62-1.58 (m, 2H), 1.39-1.23 (m, 4H), 0.97 (s, 3H), 0.94 (s, 3H).

Intermediate-48

Quinolin-8-amine

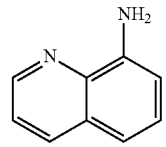 [SMILES: Nc1cccc2cccnc12]

To a solution of 4-chloro-8-nitroquinoline (Intermediate-11, step-2, 150 mg, 0.71 mmol) in EtOAc (3 mL) was added 10% Pd on C (75 mg) and the suspension was hydrogenated in a Parr apparatus for 4 h at 20 psi. Then the reaction mixture was filtered through celite and the filtrate was concentrated. The residue was purified by column chromatography using 10% EtOAc in CHCl$_3$ to afford 50 mg of the title product. $^1$H NMR (300 MHz, DMSO d$_6$): δ 8.71 (d, 1H), 8.17 (d, J=8.4 Hz, 1H), 7.47-7.43 (m, 1H), 7.28 (t, J=7.8 Hz, 1H), 7.05 (d, J=8.4 Hz, 1H), 6.86 (d, J=7.2 Hz, 1H), 5.90 (s, 2H).

Intermediate-49

2-Methyl-4-(3-(trifluoromethyl)phenoxy)quinazolin-8-amine

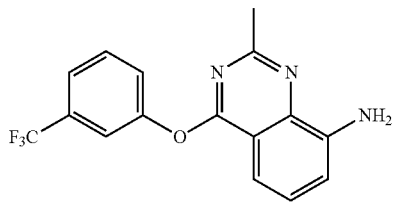 [SMILES: Cc1nc(Oc2cccc(C(F)(F)F)c2)c2cccc(N)c2n1]

Step 1: Preparation of 2-methyl-8-nitro-4-(3-(trifluoromethyl)phenoxy)quinazoline

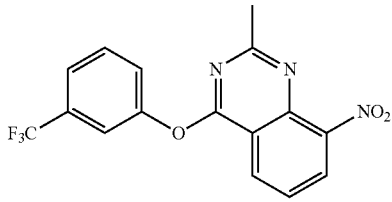 [SMILES: Cc1nc(Oc2cccc(C(F)(F)F)c2)c2cccc([N+](=O)[O-])c2n1]

The title compound was prepared following the procedure described in step-1, Intermediate-8 using 4-chloro-2-methyl-8-nitroquinazoline (Intermediate-27, step-2, 500 mg, 2.24 mmol), 4-fluoro-3-(trifluoromethyl)phenol (545 mg, 3.36 mmol) and NaH (107 mg, 4.48 mmol, 60% in mineral oil) in THF (5 mL) to afford 386 mg of the title product. $^1$H NMR (300 MHz, DMSO d$_6$): δ8.63-8.60 (d, J=8.7 Hz, 1H), 8.53-8.51 (d, J=7.8 Hz, 1H), 7.87 (m, 2H), 7.76 (m, 3H), 2.50 (s, 3H); MS (m/z): 350.19 (M+H)$^+$.

Step 2: Preparation of 2-methyl-4-(3-(trifluoromethyl)phenoxy)quinazolin-8-amine The title compound was prepared following the procedure described in step-2, Intermediate-9 using 2-methyl-8-nitro-4-(3-(trifluoromethyl)phenoxy)quinazoline (386 mg, 1.10 mmol), NH$_4$Cl (619 mg, 11.0 mmol) and iron powder (479 mg, 8.80 mmol) in EtOH (3 mL) and water (1 mL) to afford 120 mg of the title product. $^1$H NMR (300 MHz, DMSO-d$_6$): δ 7.76-7.69 (m, 2H), 7.40-7.36 (m, 2H), 7.12-7.03 (m, 3H), 5.93 (s, 2H), 2.50 (s, 3H).

Intermediate-50

N$^4$-isopropyl-2-methylquinazoline-4,8-diamine

Step 1: Preparation of N-isopropyl-2-methyl-8-nitroquinazolin-4-amine

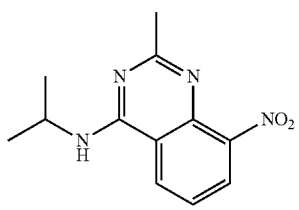 [SMILES: Cc1nc(NC(C)C)c2cccc([N+](=O)[O-])c2n1]

A solution of 4-chloro-2-methyl-8-nitroquinazoline (Intermediate-27, step-2, 100 mg, 0.45 mmol) in isopropylamine (1 mL) was heated at reflux for 30 mins. Then the reaction mixture was diluted with water and was extracted with ethyl acetate. The organic layer was washed with brine, separated, dried, filtered and concentrated. The residue was purified by column chromatography to afford 60 mg of the title product. $^1$H NMR (300 MHz, DMSO-d$_6$): δ 8.54-8.51 (d, J=8.4 Hz, 1H), 8.23-8.21 (d, J=7.5 Hz, 1H), 8.17-8.14 (d, J=7.8 Hz, 1H), 7.56-7.51 (t, J=7.8 Hz, 1H), 4.58-4.51 (m, 1H), 2.44 (s, 3H), 1.27 (s, 3H), 1.25 (s, 3H).

Step 2: Preparation of N$^4$-isopropyl-2-methylquinazoline-4,8-diamine

The title compound was prepared following the procedure described in step-2, Intermediate-9 using N-isopropyl-2-methyl-8-nitroquinazolin-4-amine (60 mg, 0.24 mmol), NH$_4$Cl (103 mg, 1.95 mmol) and iron powder (136 mg, 2.43 mmol) in EtOH (2 mL) and water (1 mL) to afford 30 mg of the title product. $^1$H NMR (300 MHz, CDCl$_3$): δ 7.17-7.14 (t, J=7.8 Hz, 1H), 6.91-6.88 (d, J=7.2 Hz, 2H), 4.82 (br s, 2H), 4.62-4.53 (m, 1H), 2.61 (s, 3H), 1.32 (s, 3H), 1.31 (s, 3H).

Intermediate-51

2-Methyl-4-morpholinoquinazolin-8-amine

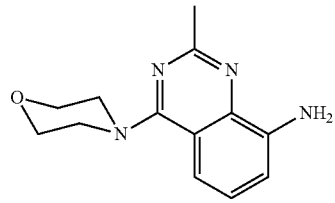 [SMILES: Cc1nc(N2CCOCC2)c2cccc(N)c2n1]

Step 1: Preparation of 4-(2-methyl-8-nitroquinazolin-4-yl)morpholine

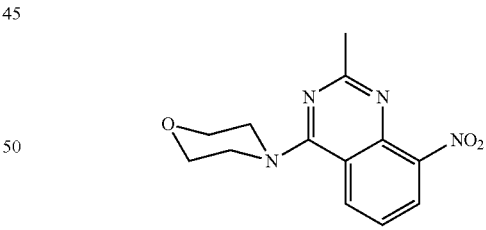

The title compound was prepared following the procedure described in Intermediate-15, step-1 using 4-chloro-2-methyl-8-nitroquinazoline (Intermediate-27, step-2, 280 mg, 1.26 mmol), morpholine (219 mg, 2.52 mmol), and K$_2$CO$_3$ (521 mg, 3.78 mmol) in CH$_3$CN (5 mL) to afford 270 mg of the title product. MS [M+H]$^+$: 275.22.

Step 2: Preparation of 2-methyl-4-morpholinoquinazolin-8-amine

The title compound was prepared following the procedure described in step-2, Intermediate-9 using 4-(2-methyl-8-nitroquinazolin-4-yl)morpholine (250 mg, 0.91 mmol), NH$_4$Cl (386 mg, 7.29 mmol) and iron powder (510 mg, 9.12 mmol) in EtOH (5 mL) and water (2 mL) to afford 100 mg of the title product. MS [M+H]⁺: 245.30.

Intermediate-52

4-Isopropoxyquinazolin-8-amine

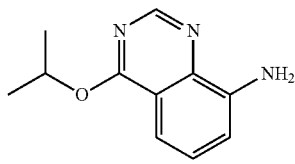

Step 1: Preparation of 4-isopropoxy-8-nitroquinazoline

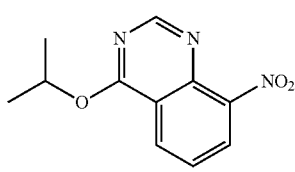 [SMILES: CC(C)Oc1ncnc2c([N+](=O)[O-])cccc12]

The title compound was prepared following the procedure described in step-1, intermediate-38 using 8-nitroquinazolin-4(3H)-one (Intermediate-7, step-1, 300 mg, 1.57 mmol), POCl₃ (3 mL), NaH (277 mg, 10.99 mmol, 95%), ⁱPrOH (2 mL) and THF (5 mL) to afford 180 mg of the title product. MS [M+H]⁺: 234.02.

Step 2: Preparation of 4-isopropoxyquinazolin-8-amine

The title compound was prepared following the procedure described in step-2, Intermediate-9 using 4-isopropoxy-8-nitroquinazoline (150 mg, 0.641 mmol), NH₄Cl (216 mg, 3.85 mmol) and iron powder (205 mg, 3.85 mmol) in EtOH (5 mL) and water (1 mL) to afford 100 mg of the title product. MS [M+H]⁺: 204.06.

Intermediate-53

N⁴-(4,4-Difluorocyclohexyl)-2-methylquinazoline-4,8-diamine

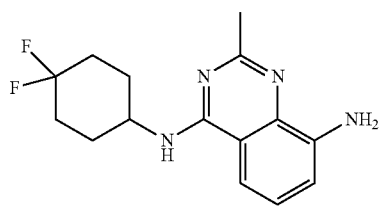

Step 1: Preparation of N-(4,4-difluorocyclohexyl)-2-methyl-8-nitroquinazolin-4-amine

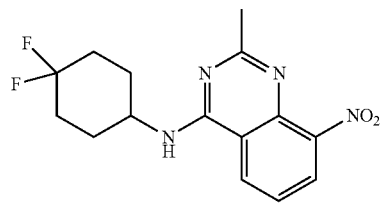 [SMILES: Cc1nc(NC2CCC(F)(F)CC2)c2cccc([N+](=O)[O-])c2n1]

The title compound was prepared following the procedure described in Intermediate-15, step-1 using 4-chloro-2-methyl-8-nitroquinazoline (Intermediate-27, step-2, 200 mg, 0.896 mmol), 4,4-difluorocyclohexanamine hydrochloride (228 mg, 1.345 mmol), and K₂CO₃ (370 mg, 2.68 mmol) in CH₃CN (4 mL) to afford 200 mg of the title product. MS [M+H]⁺: 323.23.

Step 2: Preparation of N⁴-(4,4-difluorocyclohexyl)-2-methylquinazoline-4,8-diamine The title compound was prepared following the procedure described in step-2, Intermediate-9 using N-(4,4-difluorocyclohexyl)-2-methyl-8-nitroquinazolin-4-amine (200 mg, 0.621 mmol), NH₄Cl (263 mg, 4.96 mmol) and iron powder (347 mg, 6.21 mmol) in EtOH (4 mL) and water (1 mL) to afford 100 mg of the title product. MS [M+H]⁺: 293.27.

Intermediate-54

N⁴,N⁴-Dimethylquinazoline-4,8-diamine

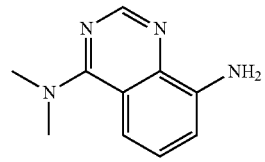

Step 1: Preparation of N,N-dimethyl-8-nitroquinazolin-4-amine

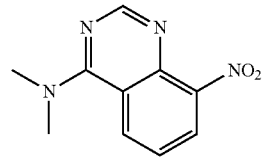 [SMILES: CN(C)c1ncnc2c([N+](=O)[O-])cccc12]

A solution of 8-nitroquinazolin-4(3H)-one (Intermediate-7, step-1, 280 mg, 1.46 mmol) in POCl₃ (3 mL) was heated at reflux for 3 h. Then the reaction mixture was concentrated and the residue was dissolved in THF (2 mL). Then the solution was treated with a solution of 10% dimethylamine in THF (6 mL) at 0-5° C. and the reaction mixture was stirred at 10-15° C. for 2 h before it was quenched with water and was extracted with chloroform. The organic layer was washed with brine, separated, dried, filtered and concentrated. The residue was purified by column chromatography to afford 170 mg of the title product. $^1$H NMR (400 MHz, DMSO $d_6$): δ 8.51 (s, 1H), 8.42-8.39 (d, J=8.8 Hz, 1H), 8.23-8.21 (d, J=7.6 Hz, 1H), 7.57-7.53 (t, J=8.0 Hz, 1H), 3.31 (s, 6H); MS [M+H]$^+$: 219.12.

Step 2: Preparation of N$^4$,N$^4$-dimethylquinazoline-4,8-diamine

The title compound was prepared following the procedure described in step-2, Intermediate-9 using N,N-dimethyl-8-nitroquinazolin-4-amine (170 mg, 0.78 mmol), NH$_4$Cl (333 mg, 6.24 mmol) and iron powder (436 mg, 7.80 mmol) in EtOH (4 mL) and water (1 mL) to afford 140 mg of the title product. $^1$H NMR (400 MHz, DMSO $d_6$): δ 8.42 (s, 1H), 7.23-7.14 (m, 2H), 6.90-6.88 (dd, J=1.2, 7.2 Hz, 1H), 5.74 (br s, 2H), 3.29 (s, 6H); MS [M+H]$^+$: 189.27.

Intermediate-55

N$^4$-(tert-Butyl)quinazoline-4,8-diamine

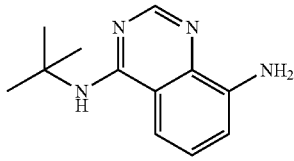 [SMILES: CC(C)(C)Nc1ncnc2c([N+](=O)[O-])cccc12]

Step 1: Preparation of N-(tert-butyl)-8-nitroquinazolin-4-amine

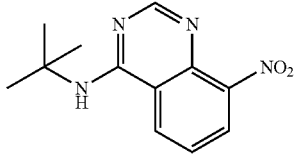

A solution of 4-chloro-8-nitroquinazoline (Intermediate-7, step-2, 500 mg, 2.39 mmol), and tert-butylamine (350 mg, 4.78 mmol) in pyridine (5 mL) was stirred at rt for 3 h. Then the reaction mixture was concentrated and the residue was dissolved in EtOAc. Then the solution was washed with water and brine, separated, dried, filtered, concentrated and purified by column chromatography to afford 300 mg of the title product. $^1$H NMR (300 MHz, DMSO $d_6$): δ 8.67 (d, J=8.4 Hz, 1H), 8.53 (s, 1H), 8.22 (d, J=7.8 Hz, 1H), 7.74 (s, 1H), 7.63-7.58 (t, J=8.0 Hz, 1H), 1.54 (s, 9H); MS [M+H]$^+$: 247.18.

Step 2: Preparation of N$^4$-(tert-butyl)quinazoline-4,8-diamine

The title compound was prepared following the procedure described in step-2, Intermediate-9 using N-(tert-butyl)-8-nitroquinazolin-4-amine (300 mg, 1.22 mmol), NH$_4$Cl (653 mg, 12.2 mmol) and iron powder (194 mg, 3.66 mmol) in EtOH (4 mL) and water (1 mL) to afford 150 mg of the title product. $^1$H NMR (300 MHz, DMSO $d_6$): δ 8.38 (s, 1H), 7.38 (d, J=7.8 Hz, 1H), 7.17-7.11 (t, J=7.8 Hz, 1H), 6.93 (s, 1H), 6.85 (d, J=7.8 Hz, 1H), 5.69 (s, 2H), 1.53 (s, 9H); MS [M+H]$^+$: 217.11.

Intermediate-56

4-Ethoxyquinolin-8-amine

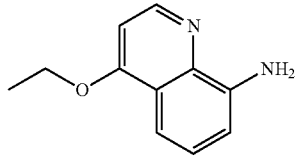

Step 1: Preparation of 4-chloroquinolin-8-amine

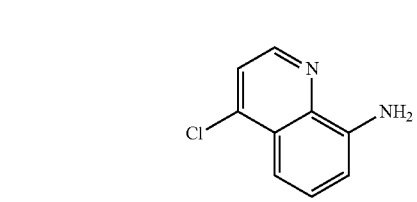 [SMILES: Nc1cccc2c(Cl)ccnc12]

The title compound was prepared following the procedure described in step-2, Intermediate-9 using 4-chloro-8-nitroquinoline (Intermediate-11, step-2, 250 mg, 1.20 mmol), NH$_4$Cl (513 mg, 9.60 mmol) and iron powder (671 mg, 12.0 mmol) in EtOH (6 mL) and water (3 mL) to afford 200 mg of the title product. $^1$H NMR (400 MHz, CDCl$_3$): δ 8.69 ((d, J=4.6 Hz, 1H), 7.55-7.53 (d, J=8.4 Hz, 1H), 7.48 (d, J=4.6 Hz, 1H), 7.46-7.42 (t, J=7.6 Hz, 1H), 7.00-6.98 (d, J=7.6 Hz, 1H), 5.06 (br s, 2H); MS [M+H]$^+$: 179.25.

Step 2: Preparation of 4-ethoxyquinolin-8-amine

To a solution of ethanol (5 mL) was added NaH (141 mg, 5.6 mmol, 95%) at 0° C. and the reaction mixture was stirred at rt for 30 min. before 4-chloroquinolin-8-amine (200 mg, 1.12 mmol) was added to the reaction mixture. Then the reaction mixture was heated in a sealed tube at 110° C. for 12 h before it was quenched with 1N HCl. Then the reaction mixture was extracted with chloroform and the organic layer was washed with brine, separated, dried, filtered and concentrated. The residue was purified by column chromatography to afford 140 mg of the title product. MS [M+H]$^+$: 189.15.

Intermediate-57

N$^4$-Isopropylquinazoline-4,8-diamine

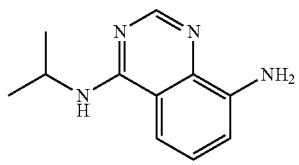

Step 1: Preparation of N-isopropyl-8-nitroquinazolin-4-amine

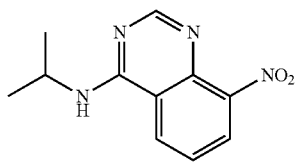 [SMILES: CC(C)Nc1ncnc2c([N+](=O)[O-])cccc12]

The title compound was prepared following the procedure described in step-1, Intermediate-55 using 4-chloro-8-nitroquinazoline (Intermediate-7, step-2, 300 mg, 1.43 mmol), and isopropylamine (169 mg, 2.86 mmol) in pyridine (5 mL) to afford 250 mg of the title product. $^1$H NMR (400 MHz, DMSO $d_6$): δ 8.58-8.56 (d, J=8.4 Hz, 1H), 8.51 (s, 1H), 8.35 (d, J=7.6 Hz, 1H), 8.23-8.20 (d, J=7.6 Hz, 1H), 7.63-7.59 (t, J=8.0 Hz, 1H), 4.55-4.50 (m, 1H), 1.27 (s, 3H), 1.26 (s, 3H); MS [M+H]$^+$: 233.14.

Step 2: Preparation of N$^4$-isopropylquinazoline-4,8-diamine

The title compound was prepared following the procedure described in step-2, Intermediate-9 using N-isopropyl-8-nitroquinazolin-4-amine (250 mg, 1.08 mmol), NH$_4$Cl (576 mg, 10.76 mmol) and iron powder (172 mg, 3.24 mmol) in EtOH (4 mL) and water (1 mL) to afford 200 mg of the title product. $^1$H NMR (400 MHz, DMSO $d_6$): δ 8.35 (s, 1H), 7.55 (d, J=7.6 Hz, 1H), 7.35-7.33 (d, J=8.0 Hz, 1H), 7.16-7.12 (t, J=8.0 Hz, 1H), 6.86-6.84 (d, J=8.0 Hz, 1H), 5.66 (br s, 2H), 4.51-4.45 (m, 1H), 1.24 (s, 3H), 1.22 (s, 3H); MS [M+H]$^+$: 203.17.

Intermediate-58

N$^4$-(tert-Butyl)-2-methylquinazoline-4,8-diamine

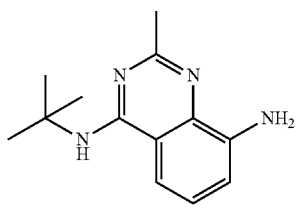 [SMILES: Cc1nc(NC(C)(C)C)c2cccc(N)c2n1]

Step 1: Preparation of N-(tert-butyl)-2-methyl-8-nitroquinazolin-4-amine

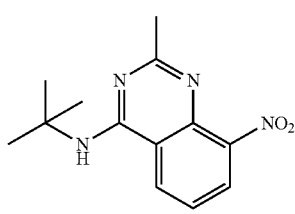 [SMILES: Cc1nc(NC(C)(C)C)c2cccc([N+](=O)[O-])c2n1]

The title compound was prepared following the procedure described in Intermediate-55, step-1 using 4-chloro-2-methyl-8-nitroquinazoline (Intermediate-27, step-2, 300 mg, 1.34 mmol), and tert-butylamine (196 mg, 2.68 mmol) in pyridine (5 mL) to afford 200 mg of the title product. $^1$H NMR (300 MHz, DMSO d$_6$): δ 8.62-8.59 (d, J=8.1 Hz, 1H), 8.16-8.13 (d, J=7.5 Hz, 1H), 7.61 (s, 1H), 7.51 (t, J=7.8 Hz, 1H), 2.45 (s, 3H), 1.55 (s, 9H); MS (m/z): 261.20 (M+H)$^+$.

Step 2: Preparation of N$^4$-(tert-butyl)-2-methylquinazoline-4,8-diamine

The title compound was prepared following the procedure described in step-2, Intermediate-9 using N-(tert-butyl)-2-methyl-8-nitroquinazolin-4-amine (200 mg, 0.77 mmol), NH$_4$Cl (411 mg, 7.68 mmol) and iron powder (83 mg, 1.54 mmol) in EtOH (4 mL) and water (1 mL) to afford 150 mg of the title product. $^1$H NMR (300 MHz, DMSO d$_6$): δ 7.35-7.33 (d, J=7.8 Hz, 1H), 7.09-7.03 (t, J=7.8 Hz, 1H), 6.82-6.79 (m, 2H), 5.57 (s, 2H), 2.46 (s, 3H), 1.53 (s, 9H); MS (m/z): 231.26 (M+H)$^+$.

Intermediate-59

6-Chloro-2-fluoro-3-((3-hydroxy-2,2-dimethylpropanamido)methyl)benzoic acid

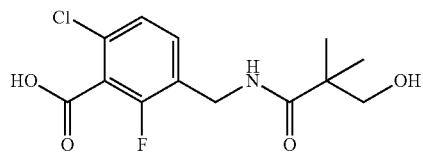 [SMILES: CC(C)(CO)C(=O)NCc1ccc(Cl)c(C(=O)O)c1F]

Step 1: Preparation of ethyl 6-chloro-2-fluoro-3-((3-hydroxy-2,2-dimethylpropanamido)methyl)benzoate

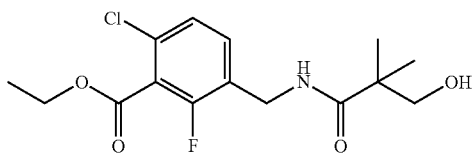 [SMILES: CCOC(=O)c1c(Cl)ccc(CNC(=O)C(C)(C)CO)c1F]

To a solution of ethyl 3-(aminomethyl)-6-chloro-2-fluorobenzoate (Intermediate-2, step-1, 800 mg, 3.45 mmol) and 3-hydroxy-2,2-dimethylpropanoic acid (591 mg, 5.00 mmol) in DMF (5 mL) were added (benzotriazol-1-yloxy)tris(dimethylamino)phosphonium hexafluorophosphate (2.29 g, 5.18 mmol) and DIPEA (1.29 g, 10.0 mmol). Then reaction mixture was stirred at rt for 12 h and it was diluted with EtOAc, washed with H$_2$O and brine. The organic layer was separated, dried, filtered and concentrated. The residue was purified by column chromatography to afford 700 mg of the title product. $^1$H NMR (400 MHz, DMSO d$_6$): δ 8.09-8.06 (t, J=8.0 Hz, 1H), 7.45-7.38 (m, 2H), 4.91-4.88 (t, J=5.2 Hz, 1H), 4.42-4.37 (q, J=8.0 Hz, 2H), 4.29-4.28 (d, J=5.6 Hz, 2H), 3.48 (m, 2H), 1.33-1.29 (t, J=8.0 Hz, 3H), 1.05 (s, 6H).

Step 2: Preparation of 6-chloro-2-fluoro-3-((3-hydroxy-2,2-dimethylpropanamido)methyl)benzoic acid The title compound was prepared following the procedure described in Step 3 of Intermediate-2 using ethyl 6-chloro-2-fluoro-3-((3-hydroxy-2,2-dimethylpropanamido)methyl) benzoate (712 mg, 2.15 mmol) in THF:MeOH:H$_2$O (2:1:1; 8 mL) and NaOH (344 mg, 8.60 mmol) to afford 510 mg of the title product. $^1$H NMR (400 MHz, DMSO-d$_6$): δ 8.08-8.05 (t, J=8.0 Hz, 1H), 7.36-7.33 (m, 2H), 4.90 (t, 1H), 4.29-4.28 (d, J=6.0 Hz, 2H), 3.38 (m, 2H), 1.06 (s, 6H).

Intermediate-60

6-Chloro-2-fluoro-3-(isobutyramidomethyl)benzoic acid

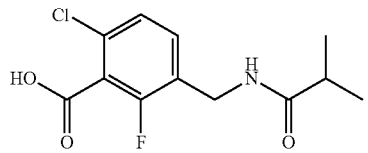 [SMILES: CC(C)C(=O)NCc1ccc(Cl)c(C(=O)O)c1F]

Step 1: Preparation of ethyl 6-chloro-2-fluoro-3-(isobutyramidomethyl)benzoate

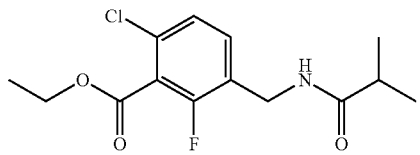 [SMILES: CCOC(=O)c1c(Cl)ccc(CNC(=O)C(C)C)c1F]

The title compound was prepared following the procedure described in Intermediate-2, step-2 using ethyl 3-(aminomethyl)-6-chloro-2-fluorobenzoate (Intermediate-2, step-1, 1.00 g, 4.32 mmol), isobutyryl chloride (690 mg, 6.48 mmol) and DIPEA (1.67 g, 12.96 mmol) in THF (30 mL) to afford 1.0 g of the title product.

Step 2: Preparation of 6-chloro-2-fluoro-3-(isobutyramidomethyl)benzoic acid

The title compound was prepared following the procedure described in Intermediate-2, step-3 using ethyl 6-chloro-2-fluoro-3-(isobutyramidomethyl)benzoate (1.00 g, 3.31 mmol) and NaOH (530 mg, 13.26 mmol) in THF:MeOH:H$_2$O (3:2:1; 12 mL) to afford 800 mg of the title product. $^1$H NMR (300 MHz, DMSO-d$_6$): δ 14.10 (s, 1H), 8.32 (br t, 1H), 7.38-7.29 (m, 2H), 4.25 (d, J=5.1 Hz, 2H), 2.40 (m, 1H), 1.00 (d, J=6.9 Hz, 6H).

Intermediate-61

Methyl 5-(aminomethyl)-2-chloro-4-fluorobenzoate

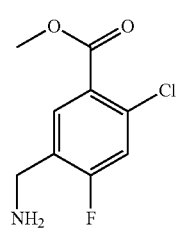

Intermediate-62

Methyl 3-(aminomethyl)-2-chloro-4-fluorobenzoate

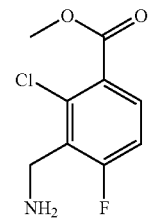

Step 1: Preparation of 2-chloro-4-fluoro-5-((2,2,2-trifluoroacetamido)methyl)benzoic acid and 2-chloro-4-fluoro-3-((2,2,2-trifluoroacetamido)methyl)benzoic acid

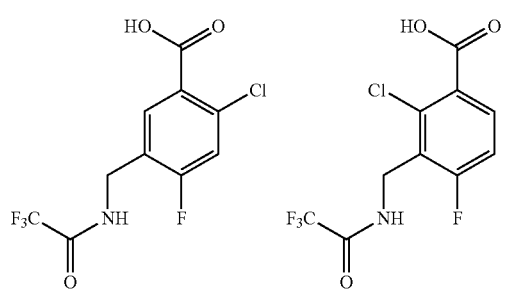 [SMILES: O=C(O)c1cc(CNC(=O)C(F)(F)F)c(F)cc1Cl ; O=C(O)c1ccc(F)c(CNC(=O)C(F)(F)F)c1Cl]

The title compound was prepared following the procedure described in Intermediate-5, step-1 using 2-chloro-4-fluorobenzoic acid (10.0 g, 57.29 mmol), and 2,2,2-trifluoro-N-(hydroxymethyl)acetamide (9.02 g, 63.02 mmol) in conc. H$_2$SO$_4$ (100 mL) to afford 12 g of the title products as a mixture of regioisomers which was taken to the next step without further purification.

Step 2: Preparation of 5-(((tert-butoxycarbonyl)amino)methyl)-2-chloro-4-fluorobenzoic acid and 3-(((tert-butoxycarbonyl)amino)methyl)-2-chloro-4-fluorobenzoic acid

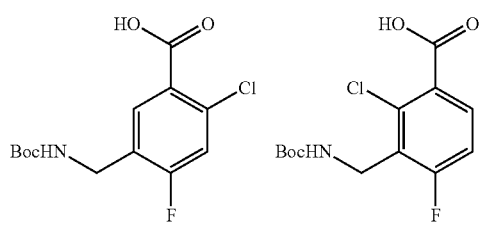 [SMILES: CC(C)(C)OC(=O)NCc1cc(C(=O)O)c(Cl)cc1F ; CC(C)(C)OC(=O)NCc1c(F)ccc(C(=O)O)c1Cl]

The title compound was prepared following the procedure described in Intermediate-5, step-2 using the regioisomeric mixture obtained from step-1 (12.0 g, 40.05 mmol), conc. HCl (30 mL), dioxane (50 mL), di-tert-butyl dicarbonate (10.48 g, 48.06 mmol), NaOH (2.4 g, 60.08 mmol), THF (40 mL), and H₂O (5 mL) to afford 4.5 g of the title products as mixture of regioisomers which was taken to the next step without further purification.

Step 3: Preparation of methyl 5-(((tert-butoxycarbonyl)amino)methyl)-2-chloro-4-fluorobenzoate and methyl 3-(((tert-butoxycarbonyl)amino)methyl)-2-chloro-4-fluorobenzoate

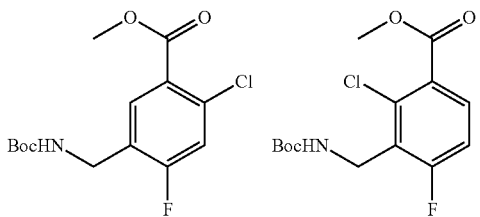 [SMILES: COC(=O)c1cc(CNC(=O)OC(C)(C)C)c(F)cc1Cl ; COC(=O)c1ccc(F)c(CNC(=O)OC(C)(C)C)c1Cl]

The title compound was prepared following the procedure described in Intermediate-5, step-3 using the regioisomeric mixture obtained from step-2 (4.50 g, 14.82 mmol), methyl iodide (3.11 g, 22.23 mmol) and K₂CO₃ (6.14 g, 44.46 mmol) in DMF (25 mL) to afford 3.2 g of the title products as mixture of regioisomers.

Step 4. Preparation of methyl 5-(aminomethyl)-2-chloro-4-fluorobenzoate and methyl 3-(aminomethyl)-2-chloro-4-fluorobenzoate A solution of the regioisomeric mixture obtained from step-3 (3.00 g, 9.44 mmol) in EtOAc saturated with HCl (10 mL) was stirred at rt for 2 h. The reaction mixture was neutralized with 1N NaOH solution at 0° C. and was extracted with 5% MeOH in CHCl₃. The organic layer was separated, dried, filtered and concentrated. The residue was purified by column chromatography to afford 400 mg of intermediate-61 and 200 mg of intermediate-62. Intermediate-61: ¹H NMR (300 MHz, DMSO-d₆): δ 8.03-8.01 (d, J=8.1 Hz, 1H), 7.53-7.50 (d, J=9.9 Hz, 1H), 3.85 (s, 3H), 3.74 (s, 2H). Intermediate-62: ¹H NMR (300 MHz, DMSO-d₆): δ 7.75-7.69 (dd, J=6.9, 14.7 Hz, 1H), 7.36-7.29 (t, J=9.3 Hz, 1H), 3.85-3.83 (m, 5H).

Intermediate-63

2-Chloro-4-fluoro-5-(pivalamidomethyl)benzoic acid

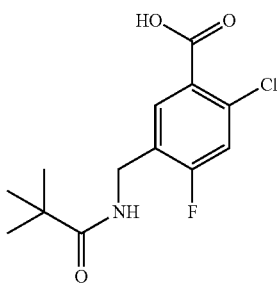 [SMILES: CC(C)(C)C(=O)NCc1cc(C(=O)O)c(Cl)cc1F]

Step 1: Preparation of methyl 2-chloro-4-fluoro-5-(pivalamidomethyl)benzoate

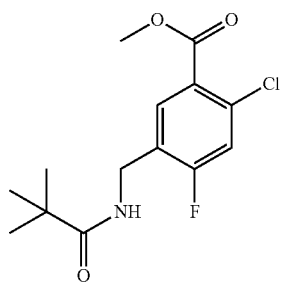 [SMILES: COC(=O)c1cc(CNC(=O)C(C)(C)C)c(F)cc1Cl]

The title compound was prepared following the procedure described in step-2 of Intermediate-2 using methyl 5-(aminomethyl)-2-chloro-4-fluorobenzoate (180 mg, 0.83 mmol), DIPEA (321 mg, 2.49 mmol) and pivaloyl chloride (120 mg, 1.0 mmol) in CH₂Cl₂ (5 mL) to afford 250 mg of the title product. ¹H NMR (300 MHz, DMSO-d₆): δ 8.16 (t, 1H), 7.73 (d, J=6.9 Hz, 1H), 7.58-7.54 (d, J=10.2 Hz, 1H), 4.26-4.24 (d, J=5.7 Hz, 2H), 3.83 (s, 3H), 1.11 (s, 9H).

Step 2: Preparation of 2-chloro-4-fluoro-5-(pivalamidomethyl)benzoic acid

The title compound was prepared following the procedure described in step-3 of Intermediate-2 using methyl 2-chloro-4-fluoro-5-(pivalamidomethyl)benzoate (250 mg, 0.83 mmol) in THF:MeOH:H₂O (3:2:1; 6 mL) and NaOH (66 mg, 1.66 mmol) to afford 200 mg of the title product. ¹H NMR (300 MHz, DMSO-d₆): δ 8.17-8.14 (t, J=6.0 Hz, 1H), 7.76-7.73 (d, J=8.4 Hz, 1H), 7.53-7.50 (d, J=9.9 Hz, 1H), 4.26 (d, J=5.7 Hz, 2H), 1.12 (s, 9H).

Intermediate-64

2-Chloro-4-fluoro-3-(pivalamidomethyl)benzoic acid

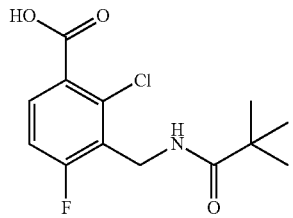 [SMILES: CC(C)(C)C(=O)NCc1c(F)ccc(C(=O)O)c1Cl]

Step 1: Preparation of methyl 2-chloro-4-fluoro-3-(pivalamidomethyl)benzoate

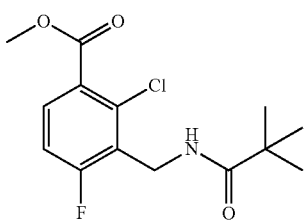 [SMILES: COC(=O)c1ccc(F)c(CNC(=O)C(C)(C)C)c1Cl]

The title compound was prepared following the procedure described in step-2 of Intermediate-2 using methyl 3-(aminomethyl)-2-chloro-4-fluorobenzoate (340 mg, 1.42 mmol), DIPEA (550 mg, 4.27 mmol) and pivaloyl chloride (204 mg, 1.7 mmol) in CH$_2$Cl$_2$ (5 mL) to afford 350 mg of the title product. $^1$H NMR (300 MHz, DMSO-d$_6$): δ 7.81-7.74 (m, 2H), 7.36-7.30 (t, J=9.0 Hz, 1H), 4.39-4.37 (d, J=4.5 Hz, 2H), 3.85 (s, 3H), 1.06 (s, 9H).

Step 2: Preparation of 2-chloro-4-fluoro-3-(pivalamidomethyl)benzoic acid

The title compound was prepared following the procedure described in step-3 of Intermediate-2 using methyl 2-chloro-4-fluoro-3-(pivalamidomethyl)benzoate (350 mg, 1.16 mmol) in THF:MeOH:H$_2$O (3:2:1; 6 mL) and NaOH (93 mg, 2.32 mmol) to afford 250 mg of the title product. $^1$H NMR (300 MHz, DMSO-d$_6$): δ 12.55 (br s, 1H), 7.78 (m, 2H), 7.32-7.26 (t, J=8.7 Hz, 1H), 4.38 (d, J=4.5 Hz, 2H), 1.07 (s, 9H).

Intermediate-65

N$^4$-(2,2,2-trifluoroethyl)quinazoline-4,8-diamine

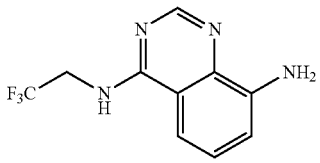 [SMILES: O=[N+]([O-])c1cccc2c(NCC(F)(F)F)ncnc12]

Step 1: Preparation of 8-nitro-N-(2,2,2-trifluoroethyl)quinazolin-4-amine

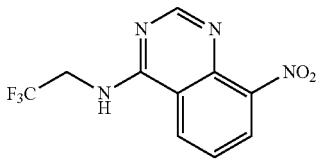

The title compound was prepared following the procedure described in step-1, Intermediate-55 using 4-chloro-8-nitro-quinazoline (Intermediate-7, step-2, 400 mg, 1.91 mmol), and 2,2,2-trifluoroethanamine (189 mg, 1.91 mmol) in pyridine (2 mL) to afford 85 mg of the title product. $^1$H NMR (300 MHz, DMSO-d$_6$): δ 9.22 (t, 1H), 8.66 (s, 1H), 8.61-8.59 (d, J=8.4 Hz, 1H), 8.36-8.34 (d, J=7.8 Hz, 1H), 7.77-7.72 (t, J=8.1 Hz, 1H), 4.52-4.44 (m, 2H); MS [M+H]$^+$: 273.41.

Step 2: Preparation of N$^4$-(2,2,2-trifluoroethyl)quinazoline-4,8-diamine

The title compound was prepared following the procedure described in step-2, Intermediate-9 using 8-nitro-N-(2,2,2-trifluoroethyl)quinazolin-4-amine (80 mg, 0.29 mmol), NH$_4$Cl (63 mg, 1.17 mmol) and iron powder (65 mg, 1.17 mmol) in EtOH (2 mL) and water (0.5 mL) to afford 50 mg of the title product. $^1$H NMR (300 MHz, DMSO d$_6$): δ 8.47 (m, 2H), 7.36-7.33 (d, J=8.4 Hz, 1H), 7.27-7.22 (t, J=7.8 Hz, 1H), 6.94-6.91 (d, J=7.8 Hz, 1H), 5.84 (br s, 2H), 4.44-4.39 (m, 2H); MS [M+H]$^+$: 243.45.

Intermediate-66

2-(Difluoromethyl)-5-(isobutyramidomethyl)nicotinic acid

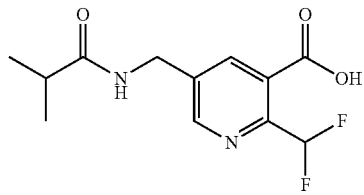 [SMILES: CC(C)C(=O)NCc1cnc(C(F)F)c(C(=O)O)c1]

Step 1: Preparation of (Z)-ethyl 2-(ethoxymethylene)-4,4-difluoro-3-oxobutanoate

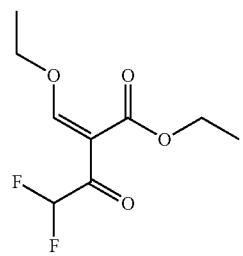

To a freshly prepared solution of sodium ethoxide (prepared by addition of 1.11 g, 48.35 mmol Na metal in 8 mL EtOH) in EtOH was added a solution of ethyl difluoroacetate (5.0 g, 40.29 mmol) in EtOAc (9 mL) at rt and the reaction mixture was heated at 65° C. for 2 h. Then the reaction mixture was quenched with 1N HCl at rt and the pH was adjusted to 6-7. Then the reaction mixture was extracted with EtOAc and the organic layer was washed with water and brine, separated, dried, filtered and concentrated to afford 5.5 g of ethyl 4,4-difluoro-3-oxobutanoate which was taken to the next step without further purification. To a mixture of ethyl 4,4-difluoro-3-oxobutanoate (5.5 g, 33.11 mmol) and triethyl orthoformate (12 mL, 66.26 mmol) was added acetic anhydride (27.0 g, 265.0 mmol) and the reaction mixture was heated at 100° C. for 12 h. Then the reaction mixture was concentrated to afford 5.5 g of the title product which was taken to the next step without further purification.

Step 2: Preparation of ethyl 5-cyano-2-(difluoromethyl)nicotinate

To a solution of cyanoacetic acid (2.0 g, 23.53 mmol) in 1,4-dioxane (10 mL) was added N,N-dimethylformamide dimethylacetal (3.35 g, 28.23 mmol) and the reaction mixture was heated at 80° C. for 4 h. Then the reaction mixture was concentrated, diluted with Et$_2$O and filtered through a pad of silica. The filtrate was concentrated to afford 2.37 g of (E)-3-(dimethylamino)acrylonitrile which was taken to the next step without further purification. To a solution of (Z)-ethyl 2-(ethoxymethylene)-4,4-difluoro-3-oxobutanoate (5.5 g, 24.77 mmol) in DMF (15 mL) at 65° C. was added (E)-3-(dimethylamino)acrylonitrile (2.37 g, 24.77 mmol) dropwise and the reaction mixture was heated at the same temperature for 5 h. Then NH$_4$OAc (2.86 g, 37.15 mmol) was added to the reaction mixture and heating was continued for 12 h. Then the reaction mixture was quenched with water at rt and was extracted with Et$_2$O. The organic layer was separated, dried, filtered and concentrated. The residue was purified by column chromatography to afford 1.3 g of the title product. $^1$H NMR (300 MHz, DMSO-d$_6$): δ 9.09 (s, 1H), 8.60 (s, 1H), 7.62-7.26 (t, J=54 Hz, 1H), 4.51-4.44 (q, J=7.2 Hz, 2H), 1.46-1.42 (t, J=7.2 Hz, 3H); MS [M+H]$^+$: 227.38.

Step 3: Preparation of ethyl 5-(((tert-butoxycarbonyl)amino)methyl)-2-(difluoromethyl)nicotinate

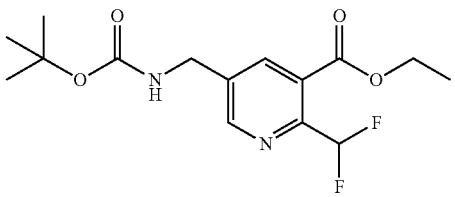 [SMILES: CCOC(=O)c1cc(CNC(=O)OC(C)(C)C)cnc1C(F)F]

To a solution of ethyl 5-cyano-2-(difluoromethyl)nicotinate (500 mg, 2.21 mmol), Et$_3$N (0.4 mL, 2.87 mmol) and (Boc)$_2$O (963 mg, 4.42 mmol) in EtOH (2 mL) was added 10% Pd/C (300 mg) and the reaction mixture was hydrogenated at 40 psi for 2 h. Then the reaction mixture was filtered through celite and the filtrate was concentrated. The residue was purified by column chromatography to afford 500 mg of the title product. $^1$H NMR (300 MHz, DMSO-d$_6$): δ 8.77 (s, 1H), 8.24 (s, 1H), 7.60-7.27 (t, J=54 Hz, 1H), 4.48-4.41 (m, 4H), 1.47-1.40 (m, 12H); MS [M+H]$^+$: 331.31.

Step 4: Preparation of ethyl 2-(difluoromethyl)-5-(isobutyramidomethyl)nicotinate

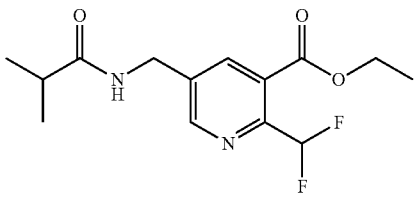 [SMILES: CCOC(=O)c1cc(CNC(=O)C(C)C)cnc1C(F)F]

A solution of ethyl 5-(((tert-butoxycarbonyl)amino)methyl)-2-(difluoromethyl)nicotinate (500 mg, 1.51 mmol) in HCl in EtOH (2 mL) was stirred at rt for 2 h. The reaction mixture was concentrated and the concentrate was dissolved in DMF (2 mL). The solution was treated with DIPEA (464 mg, 3.60 mmol) and isobutyryl chloride (115 mg, 1.08 mmol) at rt. The reaction mixture was stirred for 2 h before it was diluted with EtOAc and was washed with H$_2$O and brine. The organic layer was separated, dried, filtered and concentrated. The residue was purified by column chromatography to afford 200 mg of the title product. $^1$H NMR (300 MHz, DMSO d$_6$): δ 8.75 (s, 1H), 8.48 (t, 1H), 8.14 (s, 1H), 7.59-7.24 (t, J=54 Hz, 1H), 4.39-4.32 (m, 4H), 2.44 (m, 1H), 1.35-1.29 (t, J=6.9 Hz, 3H), 1.04-1.02 (d, J=6.9 Hz, 6H); MS [M+H]$^+$: 301.36.

Step 5: Preparation of 2-(difluoromethyl)-5-(isobutyramidomethyl)nicotinic acid

To a solution of ethyl 2-(difluoromethyl)-5-(isobutyramidomethyl)nicotinate (200 mg, 0.66 mmol) in 1,4-Dioxane was added a solution of LiOH (70 mg, 1.66 mmol) in H$_2$O (1 mL) and the reaction mixture was stirred at rt for 1 h. Then the reaction mixture was quenched with 1N HCl and the precipitated solid was filtered and dried to afford 150 mg of the title product. $^1$H NMR (300 MHz, DMSO d$_6$): δ 13.98 (br s, 1H), 8.72 (s, 1H), 8.45 (t, 1H), 8.17 (s, 1H), 7.67-7.32 (t, J=54 Hz, 1H), 4.39-4.37 (d, J=5.7 Hz, 2H), 2.43 (m, 1H), 1.04-1.02 (d, J=6.6 Hz, 6H).

Intermediate-67

6-Chloro-2-fluoro-3-((3-fluoro-2,2-dimethylpropanamido)methyl)benzoic acid

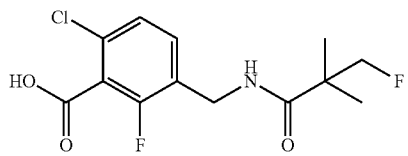 [SMILES: CC(C)(CF)C(=O)NCc1ccc(Cl)c(C(=O)O)c1F]

Step 1: Preparation of ethyl 6-chloro-2-fluoro-3-((3-fluoro-2,2-dimethylpropanamido)methyl)benzoate

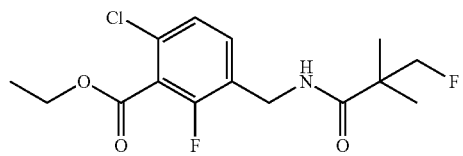 [SMILES: CCOC(=O)c1c(Cl)ccc(CNC(=O)C(C)(C)CF)c1F]

To a solution of ethyl 6-chloro-2-fluoro-3-((3-hydroxy-2,2-dimethylpropanamido)methyl)benzoate (Intermediate-59, step 1, 200 mg, 0.60 mmol) in THF (2 mL) was added diethylaminosulfur trifluoride (146 mg, 0.90 mmol) and the reaction mixture was stirred at rt for 12 h. Then the reaction mixture was quenched with water and was extracted with CHCl$_3$. The organic layer was washed with brine, separated, dried, filtered and concentrated. The residue was purified by column chromatography to afford 0.104 g of the title product. $^1$H NMR (300 MHz, DMSO d$_6$): δ 8.32 (t, 1H), 7.44-7.36 (m, 2H), 4.47-4.29 (m, 6H), 1.33-1.29 (t, J=6.9 Hz, 3H), 1.14 (s, 6H).

Step 2: Preparation of 6-Chloro-2-fluoro-3-((3-fluoro-2,2-dimethylpropanamido)methyl)benzoic acid The title compound was prepared following the procedure described in step-3 of Intermediate-2 using ethyl 6-chloro-2-fluoro-3-((3-fluoro-2,2-dimethylpropanamido)methyl)benzoate (100 mg, 0.30 mmol) in THF:MeOH:H$_2$O (3:2:1; 6 mL) and NaOH (24 mg, 0.60 mmol) to afford 84 mg of the title product. $^1$H NMR (300 MHz, DMSO d$_6$): δ 8.30 (t, 1H), 7.39-7.29 (m, 2H), 4.47-4.28 (m, 4H), 1.14 (s, 6H).

EXAMPLES

Example-1

6-Chloro-2-fluoro-3-(pivalamidomethyl)-N-(1-((3-(trifluoromethyl)phenyl)amino)isoquinolin-5-yl)benzamide

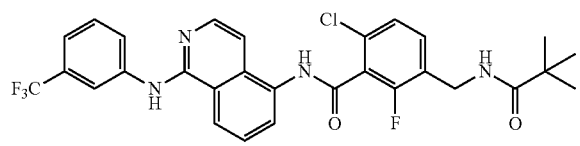

To a solution of 6-chloro-2-fluoro-3-(pivalamidomethyl)benzoic acid (Intermediate-2, 190 mg, 0.66 mmol) in $CH_2Cl_2$ (4.0 mL) was added oxalyl chloride (153 mg, 1.22 mmol) and DMF (1 drop). The reaction mass was stirred at rt for 2 h before it was concentrated. The concentrate was dissolved in $CH_2Cl_2$ (1 mL) and was added to a solution of N'-(3-(trifluoromethyl)phenyl)isoquinoline-1,5-diamine (Intermediate-1, 100 mg, 0.33 mmol) in $CH_2Cl_2$ (2 mL) and DIPEA (1.0 mL) at 0° C. The reaction mass was stirred at rt for 2 h before it was quenched with water and was extracted with chloroform. The organic layer was separated, dried, filtered, and concentrated. The residue was purified by column chromatography to afford 25 mg of the title product. $^1$H NMR (300 MHz, DMSO-$d_6$): δ 10.90 (s, 1H), 9.56 (s, 1H), 8.49 (d, J=8.4 Hz, 1H), 8.35 (s, 1H), 8.23-8.21 (m, 2H), 8.12 (d, J=6.3 Hz, 1H), 7.95 (d, J=7.5 Hz, 1H), 7.72 (t, J=7.8 Hz, 1H), 7.56 (t, J=7.8 Hz, 1H), 7.47-7.31 (m, 4H), 4.35 (d, J=5.4 Hz, 2H), 1.15 (s, 9H); MS (m/z): 573.13 (M+H)$^+$.

Example-2

3-Chloro-6-(pivalamidomethyl)-N-(1-((3-(trifluoromethyl)phenyl)amino)isoquinolin-5-yl)picolinamide

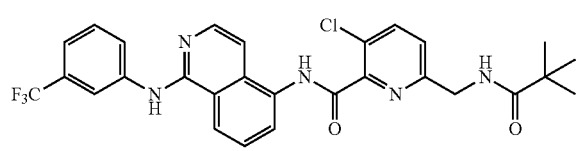 [SMILES: CC(C)(C)C(=O)NCc1ccc(Cl)c(C(=O)Nc2cccc3c(Nc4cccc(C(F)(F)F)c4)nccc23)n1]

The title compound was prepared following the procedure described in Example-1 using N'-(3-(trifluoromethyl)phenyl)isoquinoline-1,5-diamine (Intermediate-1, 70 mg, 0.23 mmol), 3-chloro-6-(pivalamidomethyl)picolinic acid (Intermediate-3, 121 mg, 0.45 mmol), oxalyl chloride (85 mg, 0.68 mmol), DMF (1 drop) and DIPEA (89 mg, 0.69 mmol) in $CH_2Cl_2$ (3 mL) to afford 15 mg of the title product. $^1$H NMR (300 MHz, DMSO-$d_6$): δ 10.78 (s, 1H), 9.56 (s, 1H), 8.48 (d, J=8.1 Hz, 1H), 8.36-8.22 (m, 3H), 8.12-8.03 (m, 3H), 7.71 (t, J=8.4 Hz, 1H), 7.56 (t, J=7.8 Hz, 1H), 7.44-7.38 (m, 2H), 7.31 (d, J=7.8 Hz, 1H), 4.44 (d, J=5.7 Hz, 2H), 1.17 (s, 9H); MS (m/z): 556.12 (M+H)$^+$.

Example-3

2,6-Dimethyl-3-(pivalamidomethyl)-N-(1-((3-(trifluoromethyl)phenyl)amino)isoquinolin-5-yl)benzamide

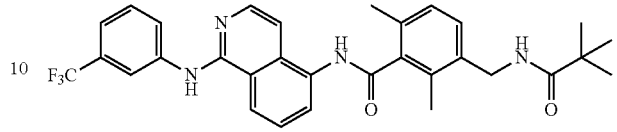

The title compound was prepared following the procedure described in Example-1 using N'-(3-(trifluoromethyl)phenyl)isoquinoline-1,5-diamine (Intermediate-1, 70 mg, 0.23 mmol), 2,6-dimethyl-3-(pivalamidomethyl)benzoic acid (Intermediate-4, 120 mg, 0.45 mmol), oxalyl chloride (85 mg, 0.68 mmol), DMF (1 drop) and DIPEA (89 mg, 0.69 mmol) in $CH_2Cl_2$ (3 mL) to afford 10 mg of the title product. $^1$H NMR (300 MHz, DMSO-$d_6$): δ 10.51 (s, 1H), 9.51 (s, 1H), 8.44 (d, 1H), 8.31 (s, 1H), 8.22 (d, 1H), 8.08 (d, 1H), 7.97 (m, 1H), 7.69 (m, 1H), 7.53 (m, 2H), 7.37 (d, 1H), 7.30 (d, 1H), 7.11 (s, 2H), 4.24 (d, 2H), 2.36 (s, 3H), 2.32 (s, 3H), 1.14 (s, 9H); MS [M+H]$^+$: 549.15.

Example-4

2-Chloro-5-(pivalamidomethyl)-N-(1-((3-(trifluoromethyl)phenyl)amino)isoquinolin-5-yl)benzamide

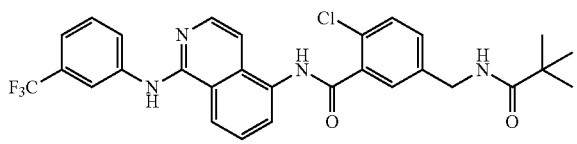 [SMILES: CC(C)(C)C(=O)NCc1ccc(Cl)c(C(=O)Nc2cccc3c(Nc4cccc(C(F)(F)F)c4)nccc23)c1]

The title compound was prepared following the procedure described in Example-1 using N'-(3-(trifluoromethyl)phenyl)isoquinoline-1,5-diamine (Intermediate-1, 70 mg, 0.23 mmol), 2-chloro-5-(pivalamidomethyl)benzoic acid (Intermediate-5, 128 mg, 0.45 mmol), oxalyl chloride (85 mg, 0.68 mmol), DMF (1 drop) and DIPEA (89 mg, 0.69 mmol) in $CH_2Cl_2$ (3 mL) to afford 15 mg of the title product. $^1$H NMR (300 MHz, DMSO-$d_6$): δ 10.62 (s, 1H), 9.54 (s, 1H), 8.45 (m, 1H), 8.35 (s, 1H), 8.22 (m, 2H), 8.07 (s, 1H), 7.94 (s, 1H), 7.70 (s, 1H), 7.53 (m, 3H), 7.44 (s, 1H), 7.33 (m, 2H), 4.32 (m, 2H), 1.15 (s, 9H); MS [M+H]$^+$: 555.19.

Example-5

6-Chloro-2-fluoro-3-(pivalamidomethyl)-N-(1-(3-(trifluoromethyl)phenoxy)isoquinolin-5-yl)benzamide

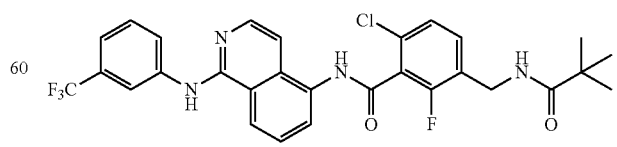

The title compound was prepared following the procedure described in Example-1 using 1-(3-(trifluoromethyl)phenoxy)isoquinolin-5-amine (Intermediate-6, 70 mg, 0.23 mmol), 6-chloro-2-fluoro-3-(pivalamidomethyl)benzoic acid (Intermediate-2, 129 mg, 0.45 mmol), oxalyl chloride (85 mg, 0.68 mmol), DMF (1 drop) and DIPEA (89 mg, 0.69 mmol) in CH$_2$Cl$_2$ (3 mL) to afford 17 mg of the title product. $^1$H NMR (300 MHz, DMSO-d$_6$): δ 11.02 (s, 1H), 8.34 (d, J=8.4 Hz, 1H), 8.21 (br t, 1H), 8.10-8.01 (m, 2H), 7.81-7.67 (m, 6H), 7.47-7.36 (m, 2H), 4.34 (m, 2H), 1.15 (s, 9H); MS [M+H]$^+$: 574.09.

Example-6

3-Chloro-6-(pivalamidomethyl)-N-(1-(3-(trifluoromethyl)phenoxy)isoquinolin-5-yl)picolinamide

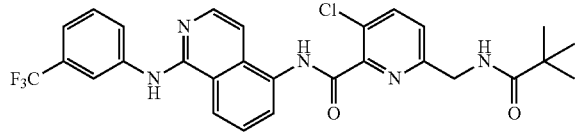

The title compound was prepared following the procedure described in Example-1 using 1-(3-(trifluoromethyl)phenoxy)isoquinolin-5-amine (Intermediate-6, 100 mg, 0.329 mmol), 3-chloro-6-(pivalamidomethyl)picolinic acid (Intermediate-3, 126 mg, 0.46 mmol), oxalyl chloride (87 mg, 0.69 mmol), DMF (1 drop) and DIPEA (129 mg, 1.00 mmol) in CH$_2$Cl$_2$ (5 mL) to afford 20 mg of the title product. $^1$H NMR (300 MHz, DMSO-d$_6$): δ 10.89 (s, 1H), 8.34-8.30 (m, 2H), 8.17 (d, J=7.5 Hz, 1H), 8.09 (d, J=8.4 Hz, 1H), 8.00 (d, J=6.3 Hz, 1H), 7.83-7.78 (t, J=7.8 Hz, 1H), 7.73-7.67 (m, 5H), 7.40 (d, J=8.7 Hz, 1H), 4.45 (d, J=6.0 Hz, 2H), 1.17 (s, 9H); MS [M+H]$^+$: 557.18.

Example-7

2-Chloro-5-(pivalamidomethyl)-N-(1-(3-(trifluoromethyl)phenoxy)isoquinolin-5-yl)benzamide

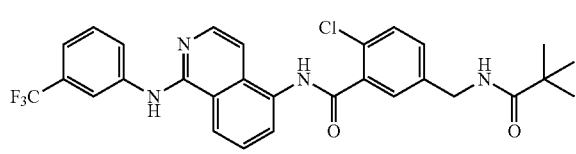

The title compound was prepared following the procedure described in Example-1 using 1-(3-(trifluoromethyl)phenoxy)isoquinolin-5-amine (Intermediate-6, 100 mg, 0.329 mmol), 2-chloro-5-(pivalamidomethyl)benzoic acid (Intermediate-5, 133 mg, 0.493 mmol), oxalyl chloride (87 mg, 0.69 mmol), DMF (1 drop) and DIPEA (129 mg, 1.00 mmol) in CH$_2$Cl$_2$ (5 mL) to afford 31 mg of the title product. $^1$H NMR (300 MHz, DMSO-d$_6$): δ 10.76 (s, 1H), 8.32 (d, J=8.4 Hz, 1H), 8.22 (br t, 1H), 8.08 (d, J=7.2 Hz, 1H), 7.98 (d, J=5.7 Hz, 1H), 7.82-7.67 (m, 6H), 7.55 (m, 2H), 7.39 (d, 1H), 4.34-4.32 (d, J=5.7 Hz, 2H), 1.14 (s, 9H); MS [M+H]$^+$: 556.16.

Example-8

3-Chloro-6-(pivalamidomethyl)-N-(4-((3-(trifluoromethyl)phenyl)amino)quinazolin-8-yl)picolinamide

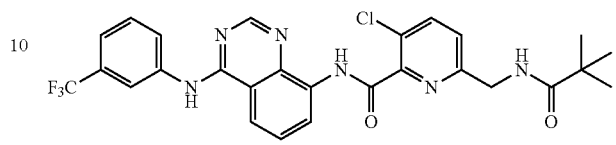

The title compound was prepared following the procedure described in Example-1 using N$^4$-(3-(trifluoromethyl)phenyl)quinazoline-4,8-diamine (Intermediate-7, 50 mg, 0.164 mmol), 3-chloro-6-(pivalamidomethyl)picolinic acid (Intermediate-3, 85 mg, 0.314 mmol), oxalyl chloride (59 mg, 0.47 mmol), DMF (1 drop) and DIPEA (63 mg, 0.49 mmol) in CH$_2$Cl$_2$ (2 mL) to afford 40 mg of the title product. $^1$H NMR (300 MHz, DMSO-d$_6$): δ 11.62 (s, 1H), 10.14 (s, 1H), 8.94 (d, J=7.8 Hz, 1H), 8.77 (s, 1H), 8.32-8.27 (m, 4H), 8.11 (d, J=8.7 Hz, 1H), 7.75-7.64 (m, 2H), 7.51-7.46 (m, 2H), 4.49 (d, J=5.7 Hz, 2H), 1.17 (s, 9H); MS [M+H]$^+$: 557.16.

Example-9

3-Chloro-6-(pivalamidomethyl)-N-(4-(3-(trifluoromethyl)phenoxy)quinazolin-8-yl)picolinamide

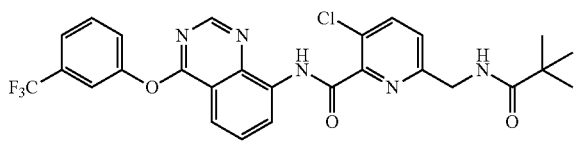 [SMILES: CC(C)(C)C(=O)NCc1ccc(Cl)c(C(=O)Nc2cccc3c(Oc4cccc(C(F)(F)F)c4)ncnc23)n1]

The title compound was prepared following the procedure described in Example-1 using 4-(3-(trifluoromethyl)phenoxy)quinazolin-8-amine (Intermediate-8, 50 mg, 0.164 mmol), 3-chloro-6-(pivalamidomethyl)picolinic acid (Intermediate-3, 88 mg, 0.326 mmol), oxalyl chloride (59 mg, 0.47 mmol), DMF (1 drop) and DIPEA (63 mg, 0.49 mmol) in CH$_2$Cl$_2$ (2 mL) to afford 48 mg of the title product. $^1$H NMR (300 MHz, DMSO-d$_6$): δ 11.63 (s, 1H), 9.06 (d, J=7.8 Hz, 1H), 8.86 (s, 1H), 8.33 (br t, 1H), 8.12 (d, J=8.1 Hz, 2H), 7.88-7.82 (m, 2H), 7.76 (m, 3H), 7.48 (d, J=8.4 Hz, 1H), 4.48 (d, J=5.4 Hz, 2H), 1.16 (s, 9H); MS [M+H]$^+$: 558.11.

Example-10

2-Chloro-5-(pivalamidomethyl)-N-(4-(3-(trifluoromethyl)phenoxy)quinazolin-8-yl)benzamide

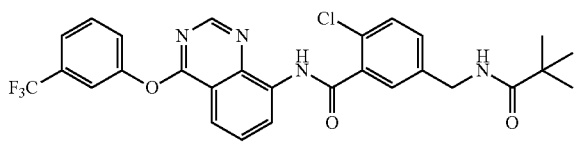

The title compound was prepared following the procedure described in Example-1 using 4-(3-(trifluoromethyl)phenoxy)quinazolin-8-amine (Intermediate-8, 50 mg, 0.164 mmol), 2-chloro-5-(pivalamidomethyl)benzoic acid (Intermediate-5, 88 mg, 0.326 mmol), oxalyl chloride (59 mg, 0.47 mmol), DMF (1 drop) and DIPEA (63 mg, 0.49 mmol) in CH$_2$Cl$_2$ (2 mL) to afford 30 mg of the title product. $^1$H NMR (300 MHz, DMSO-d$_6$): δ 10.35 (s, 1H), 8.92 (d, 1H), 8.77 (s, 1H), 8.13 (d, J=7.8 Hz, 1H), 7.85 (m, 2H), 7.73 (s, 3H), 7.59-7.53 (m, 2H), 7.39 (d, J=7.2 Hz, 1H), 4.29 (d, J=5.4 Hz, 2H), 1.11 (s, 9H); MS [M+H]$^+$: 557.14.

Example-11

6-Chloro-2-fluoro-3-(pivalamidomethyl)-N-(4-(3-(trifluoromethyl)phenoxy)quinazolin-8-yl)benzamide

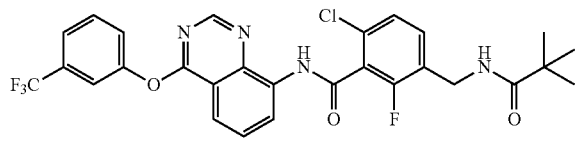

The title compound was prepared following the procedure described in Example-1 using 4-(3-(trifluoromethyl)phenoxy)quinazolin-8-amine (Intermediate-8, 80 mg, 0.262 mmol), 6-chloro-2-fluoro-3-(pivalamidomethyl)benzoic acid (Intermediate-2, 150 mg, 0.521 mmol), oxalyl chloride (98 mg, 0.78 mmol), DMF (1 drop) and DIPEA (101 mg, 0.79 mmol) in CH$_2$Cl$_2$ (3 mL) to afford 30 mg of the title product. $^1$H NMR (300 MHz, DMSO-d$_6$): δ 10.95 (s, 1H), 8.90 (d, J=8.1 Hz, 1H), 8.79 (s, 1H), 8.18 (d, J=6.9 Hz, 2H), 7.85 (m, 2H), 7.75 (s, 3H), 7.41-7.33 (m, 2H), 4.31 (d, J=5.4 Hz, 2H), 1.14 (s, 9H); MS [M+H]$^+$: 575.16.

Example-12

6-Chloro-2-fluoro-3-(pivalamidomethyl)-N-(4-((3-(trifluoromethyl)phenyl)amino)quinazolin-8-yl)benzamide

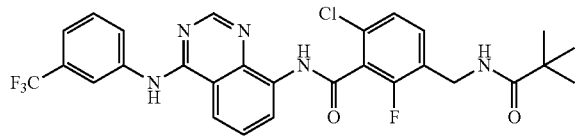

The title compound was prepared following the procedure described in Example-1 using N$^4$-(3-(trifluoromethyl)phenyl)quinazoline-4,8-diamine (Intermediate-7, 80 mg, 0.263 mmol), 6-chloro-2-fluoro-3-(pivalamidomethyl)benzoic acid (Intermediate-2, 150 mg, 0.521 mmol), oxalyl chloride (98 mg, 0.78 mmol), DMF (1 drop) and DIPEA (101 mg, 0.79 mmol) in CH$_2$Cl$_2$ (3 mL) to afford 30 mg of the title product. $^1$H NMR (300 MHz, DMSO-d$_6$): δ 10.64 (s, 1H), 10.14 (s, 1H), 8.80 (d, J=7.5 Hz, 1H), 8.71 (s, 1H), 8.37 (s, 2H), 8.23-8.17 (m, 2H), 7.72-7.65 (m, 2H), 7.50-7.39 (3H), 4.30 (d, 2H), 1.14 (s, 9H); MS [M+H]$^+$: 574.14.

Example-13

2-Chloro-5-(pivalamidomethyl)-N-(4-((3-(trifluoromethyl)phenyl)amino)quinazolin-8-yl)benzamide

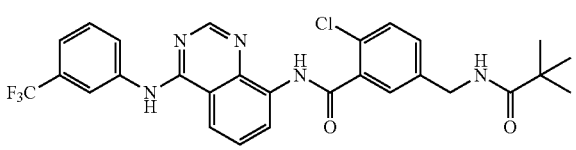

The title compound was prepared following the procedure described in Example-1 using N$^4$-(3-(trifluoromethyl)phenyl)quinazoline-4,8-diamine (Intermediate-7, 50 mg, 0.164 mmol), 2-chloro-5-(pivalamidomethyl)benzoic acid (Intermediate-5, 88 mg, 0.326 mmol), oxalyl chloride (59 mg, 0.47 mmol), DMF (1 drop) and DIPEA (63 mg, 0.49 mmol) in CH$_2$Cl$_2$ (2 mL) to afford 25 mg of the title product. $^1$H NMR (300 MHz, DMSO-d$_6$): δ 10.24 (s, 1H), 10.16 (s, 1H), 8.83 (d, J=6.6 Hz, 1H), 8.69 (s, 1H), 8.33 (m, 2H), 8.23 (m, 2H), 7.75-7.55 (m, 4H), 7.50 (d, J=6.9 Hz, 1H), 7.40 (d, J=8.4 Hz, 1H), 4.31 (d, J=5.4 Hz, 2H), 1.13 (s, 9H); MS [M+H]$^+$: 556.23.

Example-14

2-Chloro-N-(4-((4,4-difluorocyclohexyl)amino)quinazolin-8-yl)-5-(pivalamidomethyl)benzamide

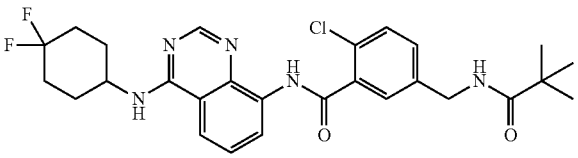 [SMILES: CC(C)(C)C(=O)NCc1ccc(Cl)c(C(=O)Nc2cccc3c(NC4CCC(F)(F)CC4)ncnc23)c1]

The title compound was prepared following the procedure described in Example-1 using N$^4$-(4,4-difluorocyclohexyl)quinazoline-4,8-diamine (Intermediate-9, 60 mg, 0.215 mmol), 2-chloro-5-(pivalamidomethyl)benzoic acid (Intermediate-5, 116 mg, 0.431 mmol), oxalyl chloride (81 mg, 0.65 mmol), DMF (1 drop) and DIPEA (84 mg, 0.65 mmol) in CH$_2$Cl$_2$ (3 mL) to afford 25 mg of the title product. $^1$H NMR (300 MHz, DMSO-d$_6$): δ 10.13 (s, 1H), 8.71 (d, 1H), 8.49 (s, 1H), 8.19 (m, 2H), 8.05 (d, 1H), 7.57-7.54 (m, 3H), 7.41 (d, 1H), 4.41 (m, 1H), 4.31 (d, 2H), 2.00 (m, 6H), 1.75 (m, 2H), 1.12 (s, 9H); MS (m/z): 530.20 (M+H)$^+$.

Example-15

2-Chloro-N-(4-((4,4-dimethylcyclohexyl)oxy)quinazolin-8-yl)-5-(pivalamidomethyl)benzamide

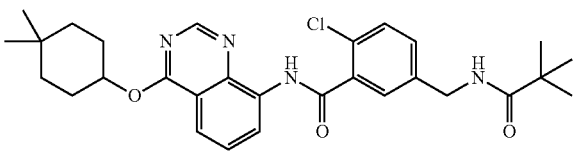 [SMILES: CC1(C)CCC(Oc2ncnc3c(NC(=O)c4cc(CNC(=O)C(C)(C)C)ccc4Cl)cccc23)CC1]

The title compound was prepared following the procedure described in Example-1 using 4-((4,4-dimethylcyclohexyl)oxy)quinazolin-8-amine (Intermediate-10, 50 mg, 0.185 mmol), 2-chloro-5-(pivalamidomethyl)benzoic acid (Intermediate-5, 99 mg, 0.369 mmol), oxalyl chloride (70 mg, 0.55 mmol), DMF (1 drop) and DIPEA (72 mg, 0.56 mmol) in CH$_2$Cl$_2$ (3 mL) to afford 50 mg of the title product. $^1$H NMR (300 MHz, DMSO-d$_6$): δ 10.24 (s, 1H), 8.80 (s, 2H), 8.18 (m, 1H), 7.90 (d, J=7.2 Hz, 1H), 7.73-7.71 (m, 1H), 7.59-7.54 (m, 2H), 7.39 (d, J=7.8 Hz, 1H), 5.38 (m, 1H), 4.30 (d, J=6.0 Hz, 2H), 1.95 (m, 2H), 1.81 (m, 2H), 1.51 (m, 2H), 1.34 (m, 2H), 1.12 (s, 9H), 1.00 (s, 3H), 0.97 (s, 3H); MS (m/z): 523.07 (M+H)$^+$.

Example-16

2-Chloro-5-(pivalamidomethyl)-N-(4-(3-(trifluoromethyl)phenoxy)quinolin-8-yl)benzamide

The title compound was prepared following the procedure described in Example-1 using 4-(3-(trifluoromethyl)phenoxy)quinolin-8-amine (Intermediate-11, 40 mg, 0.132 mmol), 2-chloro-5-(pivalamidomethyl)benzoic acid (Intermediate-5, 200 mg, 0.743 mmol), oxalyl chloride (140 mg, 1.11 mmol), DMF (1 drop) and DIPEA (52 mg, 0.40 mmol) in CH$_2$Cl$_2$ (5 mL) to afford 15 mg of the title product. $^1$H NMR (300 MHz, DMSO-d$_6$): δ 10.5 (s, 1H), 9.01 (d, J=7.8 Hz, 1H), 8.60 (d, J=4.8 Hz, 1H), 8.05 (d, J=8.7 Hz, 1H), 7.71-7.60 (m, 4H), 7.48-7.38 (m, 4H), 6.64 (d, J=5.1 Hz, 1H), 6.05 (br s, 1H), 4.49 (d, J=6.0 Hz, 2H), 1.23 (s, 9H); MS [M+H]$^+$: 556.19.

Example-17

3-Chloro-6-(pivalamidomethyl)-N-(4-(3-(trifluoromethyl)phenoxy)quinolin-8-yl)picolinamide

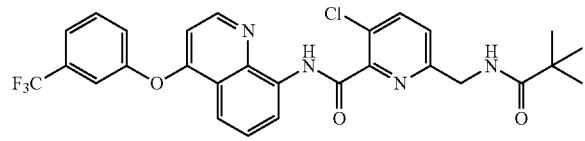 [SMILES: CC(C)(C)C(=O)NCc1ccc(Cl)c(C(=O)Nc2cccc3c(Oc4cccc(C(F)(F)F)c4)ccnc23)n1]

The title compound was prepared following the procedure described in Example-1 using 4-(3-(trifluoromethyl)phenoxy)quinolin-8-amine (Intermediate-11, 100 mg, 0.327 mmol), 3-chloro-6-(pivalamidomethyl)picolinic acid (Intermediate-3, 180 mg, 0.66 mmol), oxalyl chloride (125 mg, 0.99 mmol), DMF (1 drop) and DIPEA (126 mg, 0.98 mmol) in CH$_2$Cl$_2$ (5 mL) to afford 70 mg of the title product. $^1$H NMR (300 MHz, DMSO-d$_6$): δ 11.86 (s, 1H), 8.91 (d, J=6.9 Hz, 1H), 8.81 (d, 1H), 8.35 (br t, 1H), 8.12 (d, J=7.8 Hz, 1H), 8.06 (d, J=9.1 Hz, 1H), 7.80-7.70 (m, 5H), 7.47 (d, J=7.8 Hz, 1H), 6.83 (d, J=4.8 Hz, 1H), 4.50 (d, J=6.0 Hz, 2H), 1.16 (s, 9H); MS [M+H]$^+$: 557.26.

Example-18

6-Chloro-2-fluoro-3-(pivalamidomethyl)-N-(4-(3-(trifluoromethyl)phenoxy)quinolin-8-yl)benzamide

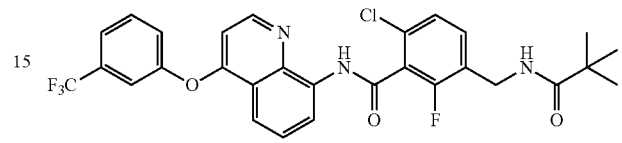

The title compound was prepared following the procedure described in Example-1 using 4-(3-(trifluoromethyl)phenoxy)quinolin-8-amine (Intermediate-11, 100 mg, 0.327 mmol), 6-chloro-2-fluoro-3-(pivalamidomethyl)benzoic acid (Intermediate-2, 200 mg, 0.699 mmol), oxalyl chloride (125 mg, 0.99 mmol), DMF (1 drop) and DIPEA (126 mg, 0.98 mmol) in CH$_2$Cl$_2$ (5 mL) to afford 40 mg of the title product. $^1$H NMR (300 MHz, DMSO-d$_6$): δ 10.77 (s, 1H), 8.79 (d, J=8.7 Hz, 1H), 8.73 (d, 1H), 8.17 (br t, 1H), 8.08 (d, J=8.7 Hz, 1H), 7.78-7.67 (m, 5H), 7.41-7.35 (m, 2H), 6.83 (d, 1H), 4.32 (d, 2H), 1.14 (s, 9H); MS [M+H]$^+$: 574.31.

Example-19

2-Chloro-5-(pivalamidomethyl)-N-(8-((3-(trifluoromethyl)phenyl)amino)quinolin-4-yl)benzamide

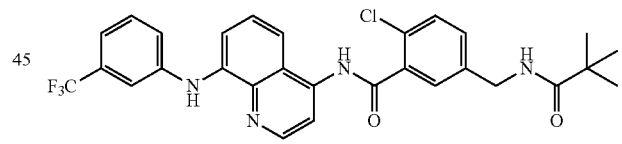

To a solution of N-(3-(trifluoromethyl)phenyl)quinoline-4,8-diamine (Intermediate-12, 80 mg, 0.264 mmol) in DMF (2 mL) was added NaH (26 mg, 0.65 mmol, 60% in mineral oil) at 0° C. and the reaction mixture was stirred at 0-5° C. for 30 minutes. Then a solution of 4-nitrophenyl 2-chloro-5-(pivalamidomethyl)benzoate (Intermediate-13, 123 mg, 0.314 mmol) in DMF (1 mL) was added to the reaction mixture at 0° C. and the reaction mixture was stirred at 0° C.—rt for 2 h. Then the reaction mixture was quenched with water and was extracted with EtOAc. The organic layer was washed with brine, separated, dried, filtered and concentrated. The residue was purified by column chromatography to afford 15 mg of the title product. $^1$H NMR (300 MHz, DMSO-d$_6$): δ 10.92 (s, 1H), 9.07 (s, 1H), 8.86 (d, J=4.8 Hz, 1H), 8.21-8.18 (m, 2H), 7.80-7.57 (m, 3H), 7.59-7.54 (m, 5H), 7.39 (d, J=8.4 Hz, 1H), 7.25 (d, J=7.2 Hz, 1H), 4.32 (d, J=6.0 Hz, 2H), 1.19 (s, 9H); MS [M+H]$^+$: 555.25.

Example-20

6-Chloro-N-(4-((4,4-difluorocyclohexyl)amino) quinazolin-8-yl)-2-fluoro-3-(pivalamidomethyl)benzamide

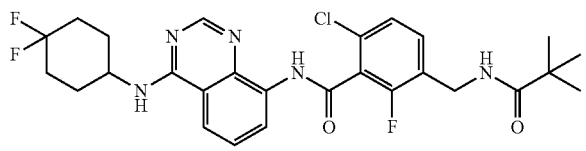 [SMILES: CC(C)(C)C(=O)NCc1ccc(Cl)c(C(=O)Nc2cccc3c(NC4CCC(F)(F)CC4)ncnc23)c1F]

The title compound was prepared following the procedure described in Example-1 using $N^4$-(4,4-difluorocyclohexyl) quinazoline-4,8-diamine (Intermediate-9, 75 mg, 0.27 mmol), 6-chloro-2-fluoro-3-(pivalamidomethyl)benzoic acid (Intermediate-2, 116 mg, 0.41 mmol), oxalyl chloride (78 mg, 0.62 mmol), DMF (1 drop) and DIPEA (105 mg, 0.81 mmol) in $CH_2Cl_2$ (5 mL) to afford 42 mg of the title product. $^1$H NMR (300 MHz, DMSO-$d_6$): δ 10.40 (s, 1H), 8.69-8.66 (d, J=7.8 Hz, 1H), 8.49 (s, 1H), 8.12-8.09 (m, 2H), 7.53 (t, 1H), 7.40-7.32 (m, 2H), 4.28 (m, 3H), 2.09-1.98 (m, 6H), 1.73 (m, 2H), 1.12 (s, 9H); MS [M]$^+$: 548.33.

Example-21

6-Chloro-2-fluoro-N-(4-((2-fluoro-5-(trifluoromethyl)phenyl)amino)quinazolin-8-yl)-3-(pivalamidomethyl)benzamide

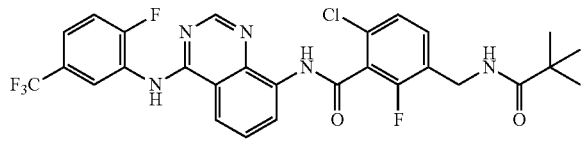 [SMILES: CC(C)(C)C(=O)NCc1ccc(Cl)c(C(=O)Nc2cccc3c(Nc4cc(C(F)(F)F)ccc4F)ncnc23)c1F]

The title compound was prepared following the procedure described in Example-1 using $N^4$-(2-fluoro-5-(trifluoromethyl)phenyl)quinazoline-4,8-diamine (Intermediate-14, 100 mg, 0.31 mmol), 6-chloro-2-fluoro-3-(pivalamidomethyl) benzoic acid (Intermediate-2, 178 mg, 0.62 mmol), oxalyl chloride (117 mg, 0.93 mmol), DMF (1 drop) and DIPEA (120 mg, 0.93 mmol) in $CH_2Cl_2$ (5 mL) to afford 12 mg of the title product. $^1$H NMR (300 MHz, CDCl$_3$): δ 9.92 (s, 1H), 9.15 (d, 1H), 9.08 (d, 1H), 8.79 (s, 1H), 7.83 (s, 1H), 7.66 (m, 2H), 7.40 (m, 2H), 4.50 (d, 2H), 1.23 (s, 9H); MS (m/z): 592.20 (M+H)$^+$.

Example-22

6-Chloro-N-(4-((4,4-dimethylcyclohexyl)amino) quinazolin-8-yl)-2-fluoro-3-(pivalamidomethyl)benzamide

The title compound was prepared following the procedure described in Example-1 using $N^4$-(4,4-dimethylcyclohexyl) quinazoline-4,8-diamine (Intermediate-15, 100 mg, 0.37 mmol), 6-chloro-2-fluoro-3-(pivalamidomethyl)benzoic acid (Intermediate-2, 212 mg, 0.99 mmol), oxalyl chloride (188 mg, 1.49 mmol), DMF (1 drop) and DIPEA (143 mg, 1.11 mmol) in $CH_2Cl_2$ (5 mL) to afford 10 mg of the title product. $^1$H NMR (300 MHz, CDCl$_3$): δ 9.91 (s, 1H), 8.96 (d, 1H), 8.55 (s, 1H), 7.51-7.44 (m, 3H), 6.11 (br s, 1H), 5.67 (br s, 1H), 4.50 (d, 1H), 4.19 (m, 1H), 1.69-1.60 (m, 4H), 1.38-1.28 (m, 4H), 1.12 (s, 9H), 0.95 (s, 3H), 0.92 (s, 3H); MS (m/z): 540.36 (M)$^+$.

Example-23

(S)—N-(4-Chloro-2-fluoro-3-((4-((3-(trifluoromethyl)phenyl)amino)quinazolin-8-yl)carbamoyl)benzyl)tetrahydrofuran-2-carboxamide

A solution of tert-butyl 4-chloro-2-fluoro-3-((4-((3-(trifluoromethyl)phenyl)amino)quinazolin-8-yl)carbamoyl)benzylcarbamate (Intermediate-16, 80 mg, 0.135 mmol) in HCl in MeOH (2 mL) was stirred at rt for 2 h. The reaction mixture was concentrated and the concentrate was dissolved in DMF (1 mL). The solution was treated with DIPEA (87 mg, 0.675 mmol) and benzotriazole-1-yl-oxy-tris-(dimethylamino)-phosphonium hexafluorophosphate (119 mg, 0.27 mmol) followed by (S)-(−)-tetrahydro-2-furoic acid (24 mg, 0.203 mmol) at rt. The reaction mixture was stirred for 2 h before it was diluted with EtOAc and was washed with H$_2$O and brine. The organic layer was separated, dried, filtered and concentrated. The residue was purified by column chromatography to afford 35 mg of the title product. $^1$H NMR (300 MHz, DMSO d$_6$): δ 10.67 (s, 1H), 10.14 (s, 1H), 8.79 (d, 1H), 8.71 (s, 1H), 8.47 (br t, 1H), 8.37 (m, 2H), 8.25 (d, 1H), 7.73-7.65 (m, 2H), 7.50 (d, 1H), 7.39 (m, 2H), 4.33 (m, 3H), 3.94 (m, 1H), 3.80 (m, 1H), 2.14 (m, 1H), 1.84 (m, 3H); MS (m/z): 588.34 (M+H)$^+$.

Example-24

6-Chloro-N-(4-((4,4-dimethylcyclohexyl)oxy) quinazolin-8-yl)-2-fluoro-3-(pivalamidomethyl)benzamide

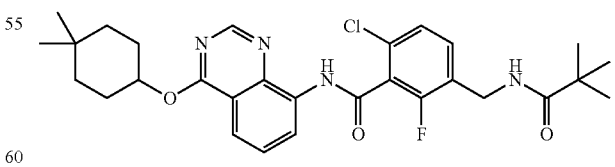

The title compound was prepared following the procedure described in Example-1 using 4-((4,4-dimethylcyclohexyl) oxy)quinazolin-8-amine (Intermediate-10, 100 mg, 0.369 mmol), 6-chloro-2-fluoro-3-(pivalamidomethyl)benzoic acid (Intermediate-2, 211 mg, 0.738 mmol), oxalyl chloride (139 mg, 1.11 mmol), DMF (1 drop) and DIPEA (143 mg, 1.11 mmol) in CH$_2$Cl$_2$ (5 mL) to afford 8 mg of the title product. $^1$H NMR (300 MHz, DMSO-d$_6$): δ 10.76 (s, 1H), 8.81-8.62 (m, 2H), 8.16 (br t, 1H), 7.95-7.92 (d, J=8.4 Hz, 1H), 7.74-7.69 (t, J=8.4 Hz, 1H), 7.41-7.30 (m, 2H), 5.37 (m, 1H), 4.31-4.30 (d, J=5.4 Hz, 2H), 1.94 (m, 2H), 1.82-1.78 (m, 2H), 1.52 (m, 2H), 1.34 (m, 2H), 1.14 (s, 9H), 1.00 (s, 3H), 0.67 (s, 3H); MS (m/z): 541.14 (M+H)$^+$.

Example-25

6-Chloro-2-fluoro-N-(4-((4-fluoro-3-(trifluoromethyl)phenyl)amino)quinazolin-8-yl)-3-(pivalamidomethyl)benzamide

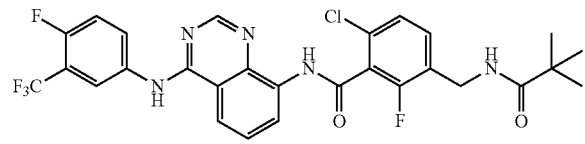 [SMILES: CC(C)(C)C(=O)NCc1ccc(Cl)c(C(=O)Nc2cccc3c(Nc4ccc(F)c(C(F)(F)F)c4)ncnc23)c1F]

The title compound was prepared following the procedure described in Example-1 using N$^4$-(4-fluoro-3-(trifluoromethyl)phenyl)quinazoline-4,8-diamine (Intermediate-17, 100 mg, 0.31 mmol), 6-chloro-2-fluoro-3-(pivalamidomethyl)benzoic acid (Intermediate-2, 178 mg, 0.62 mmol), oxalyl chloride (118 mg, 0.93 mmol), DMF (1 drop) and DIPEA (120 mg, 0.93 mmol) in CH$_2$Cl$_2$ (5 mL) to afford 16 mg of the title product. $^1$H NMR (300 MHz, DMSO-d$_6$): δ 10.62 (s, 1H), 10.15 (s, 1H), 8.82-8.79 (d, J=8.1 Hz, 1H), 8.69 (s, 1H), 8.33-8.30 (m, 3H), 8.16 (br t, 1H), 7.75-7.69 (t, J=8.4 Hz, 1H), 7.62-7.55 (d, J=10.2 Hz, 1H), 7.42-7.34 (m, 2H), 4.32-4.30 (d, J=5.4 Hz, 2H), 1.14 (s, 9H); MS (m/z): 592.28 (M+H)$^+$.

Example-26

6-Chloro-2-fluoro-3-(pivalamidomethyl)-N-(4-(((1s,4s)-4-(trifluoromethyl)cyclohexyl)oxy)quinazolin-8-yl)benzamide

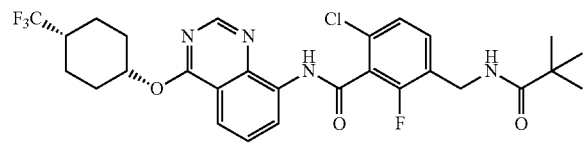

The title compound was prepared following the procedure described in Example-1 using 4-(((1s,4s)-4-(trifluoromethyl)cyclohexyl)oxy)quinazolin-8-amine (Intermediate-20, 94 mg, 0.302 mmol), 6-chloro-2-fluoro-3-(pivalamidomethyl)benzoic acid (Intermediate-2, 174 mg, 0.604 mmol), oxalyl chloride (115 mg, 0.91 mmol), DMF (1 drop) and DIPEA (117 mg, 0.91 mmol) in CH$_2$Cl$_2$ (5 mL) to afford 43 mg of the title product. $^1$H NMR (300 MHz, DMSO-d$_6$): δ 1077 (s, 1H), 8.81 (s, 1H), 8.79 (d, 1H), 8.15 (br t, 1H), 7.96-7.93 (d, J=8.4 Hz, 1H), 7.73 (t, 1H), 7.40-7.32 (m, 2H), 5.63 (m, 1H), 4.31-4.29 (d, J=5.4 Hz, 2H), 2.17 (m, 2H), 1.78 (m, 6H), 1.13 (s, 9H); MS (m/z): 581.19 (M)$^+$.

Example-27

6-Chloro-2-fluoro-3-(pivalamidomethyl)-N-(4-(((1r,4r)-4-(trifluoromethyl)cyclohexyl)oxy)quinazolin-8-yl)benzamide

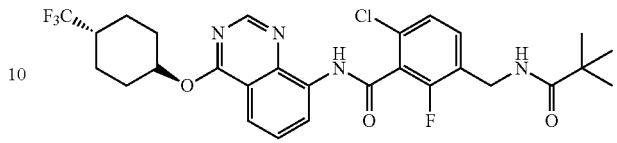

The title compound was prepared following the procedure described in Example-1 using 4-(((1r,4r)-4-(trifluoromethyl)cyclohexyl)oxy)quinazolin-8-amine (Intermediate-21, 130 mg, 0.452 mmol), 6-chloro-2-fluoro-3-(pivalamidomethyl)benzoic acid (Intermediate-2, 85 mg, 0.678 mmol), oxalyl chloride (129 mg, 1.02 mmol), DMF (1 drop) and DIPEA (175 mg, 1.36 mmol) in CH$_2$Cl$_2$ (8 mL) to afford 75 mg of the title product. $^1$H NMR (300 MHz, DMSO-d$_6$): δ 10.78 (s, 1H), 8.83 (s, 1H), 8.79 (s, 1H), 8.16 (m, 1H), 7.91-7.89 (d, J=8.4 Hz, 1H), 7.71 (t, 1H), 7.38-7.33 (m, 2H), 5.33 (m, 1H), 4.32-4.30 (d, J=5.1 Hz, 2H), 2.28 (m, 3H), 1.99 (m, 2H), 1.64-1.53 (m, 4H), 1.15 (s, 9H); MS (m/z): 581.45 (M)$^+$.

Example-28

6-Chloro-2-fluoro-N-(4-(2-fluoro-5-(trifluoromethyl)phenoxy)quinazolin-8-yl)-3-(pivalamidomethyl)benzamide

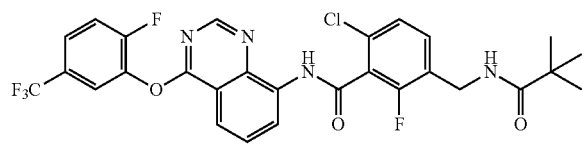 [SMILES: CC(C)(C)C(=O)NCc1ccc(Cl)c(C(=O)Nc2cccc3c(Oc4cc(C(F)(F)F)ccc4F)ncnc23)c1F]

The title compound was prepared following the procedure described in Example-1 using 4-(2-fluoro-5-(trifluoromethyl)phenoxy)quinazolin-8-amine (Intermediate-22, 300 mg, 0.93 mmol), 6-chloro-2-fluoro-3-(pivalamidomethyl)benzoic acid (Intermediate-2, 322 mg, 1.12 mmol), oxalyl chloride (212 mg, 1.68 mmol), DMF (1 drop) and DIPEA (360 mg, 2.79 mmol) in CH$_2$Cl$_2$ (10 mL) to afford 75 mg of the title product. $^1$H NMR (300 MHz, DMSO-d$_6$): δ 10.97 (s, 1H), 8.92-8.90 (d, J=7.2 Hz, 1H), 8.81 (s, 1H), 8.19-8.10 (m, 3H), 7.89-7.84 (m, 2H), 7.77-7.71 (t, J=9.9 Hz, 1H), 7.40-7.32 (m, 2H), 4.31-4.29 (d, J=6.0 Hz, 2H), 1.13 (s, 9H); MS (m/z): 593.31 (M+H)$^+$.

Example-29

6-Chloro-2-fluoro-N-(4-((2-fluoro-4-(trifluoromethyl)phenyl)amino)quinazolin-8-yl)-3-(pivalamidomethyl)benzamide

The title compound was prepared following the procedure described in Example-1 using N$^4$-(2-fluoro-4-(trifluoromethyl)phenyl)quinazoline-4,8-diamine (Intermediate-23, 230 mg, 0.71 mmol), 6-chloro-2-fluoro-3-(pivalamidomethyl)benzoic acid (Intermediate-2, 245 mg, 0.85 mmol), oxalyl chloride (161 mg, 1.28 mmol), DMF (1 drop) and DIPEA (275 mg, 2.13 mmol) in CH$_2$Cl$_2$ (8 mL) to afford 70 mg of the title product. $^1$H NMR (300 MHz, DMSO-d$_6$): δ 10.63 (s, 1H), 10.22 (s, 1H), 8.82-8.79 (d, J=8.1 Hz, 1H), 8.59 (s, 1H), 8.28-8.25 (d, J=9.0 Hz, 1H), 8.16 (m, 1H), 7.89-7.83 (m, 2H), 7.75-7.67 (m, 2H), 7.42-7.34 (m, 2H), 4.32-4.30 (d, J=5.4 Hz, 2H), 1.14 (s, 9H); MS (m/z): 592.33 (M+H)$^+$.

Example-30

6-Chloro-2-fluoro-3-(pivalamidomethyl)-N-(4-((6-(trifluoromethyl)pyridin-3-yl)amino)quinazolin-8-yl)benzamide

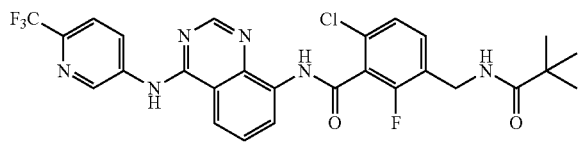 [SMILES: CC(C)(C)C(=O)NCc1ccc(Cl)c(C(=O)Nc2cccc3c(Nc4ccc(C(F)(F)F)nc4)ncnc23)c1F]

The title compound was prepared following the procedure described in Example-1 using N$^4$-(6-(trifluoromethyl)pyridin-3-yl)quinazoline-4,8-diamine (Intermediate-24, 150 mg, 0.49 mmol), 6-chloro-2-fluoro-3-(pivalamidomethyl)benzoic acid (Intermediate-2, 170 mg, 0.59 mmol), oxalyl chloride (112 mg, 0.89 mmol), DMF (1 drop) and DIPEA (190 mg, 1.47 mmol) in CH$_2$Cl$_2$ (5 mL) to afford 25 mg of the title product. $^1$H NMR (300 MHz, DMSO-d$_6$): δ 10.68 (s, 1H), 10.36 (s, 1H), 9.23 (s, 1H), 8.83-8.80 (d, J=7.8 Hz, 1H), 8.75 (s, 1H), 8.69-8.65 (d, J=9.6 Hz, 1H), 8.37-8.34 (d, J=8.7 Hz, 1H), 8.16 (br t, 1H), 7.97-7.94 (d, J=8.7 Hz, 1H), 7.79 (t, 1H), 7.41-7.33 (m, 2H), 4.31-4.29 (d, J=5.4 Hz, 2H), 1.13 (s, 9H); MS (m/z): 575.18 (M+H)$^+$.

Example-31

6-Chloro-2-fluoro-3-(pivalamidomethyl)-N-(4-((3-(trifluoromethyl)phenyl)amino)quinolin-8-yl)benzamide

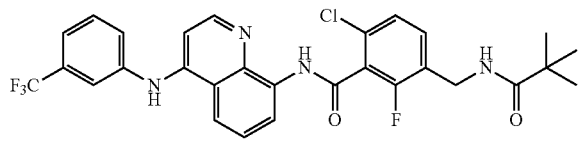

The title compound was prepared following the procedure described in Example-1 using N$^4$-(3-(trifluoromethyl)phenyl)quinoline-4,8-diamine (Intermediate-25, 100 mg, 0.33 mmol), 6-chloro-2-fluoro-3-(pivalamidomethyl)benzoic acid (Intermediate-2, 190 mg, 0.66 mmol), oxalyl chloride (125 mg, 0.99 mmol), DMF (1 drop) and DIPEA (128 mg, 0.99 mmol) in CH$_2$Cl$_2$ (6 mL) to afford 20 mg of the title product. $^1$H NMR (300 MHz, DMSO-d$_6$): δ 10.62 (s, 1H), 9.35 (s, 1H), 8.73-8.71 (d, J=7.2 Hz, 1H), 8.52 (d, 1H), 8.17 (m, 2H), 7.71-7.62 (m, 4H), 7.48-7.36 (m, 3H), 7.14 (m, 1H), 4.31 (d, 2H), 1.14 (s, 9H); MS (m/z): 573.36 (M+H)$^+$.

Example-32

6-Chloro-N-(4-((4,4-dimethylcyclohexyl)amino)-2-(trifluoromethyl)quinazolin-8-yl)-2-fluoro-3-(pivalamidomethyl)benzamide

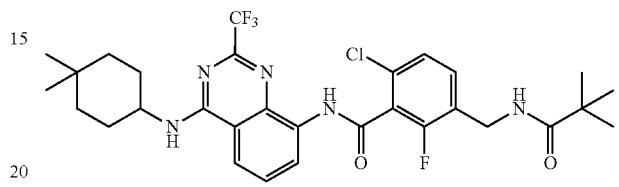

The title compound was prepared following the procedure described in Example-1 using N$^4$-(4,4-dimethylcyclohexyl)-2-(trifluoromethyl)quinazoline-4,8-diamine (Intermediate-26, 100 mg, 0.295 mmol), 6-chloro-2-fluoro-3-(pivalamidomethyl)benzoic acid (Intermediate-2, 127 mg, 0.443 mmol), oxalyl chloride (84 mg, 0.66 mmol), DMF (1 drop) and DIPEA (115 mg, 0.89 mmol) in CH$_2$Cl$_2$ (3 mL) to afford 35 mg of the title product. $^1$H NMR (300 MHz, DMSO-d$_6$): δ 10.30 (s, 1H), 8.67-8.65 (d, J=7.2 Hz, 1H), 8.59-8.56 (d, J=8.1 Hz, 1H), 8.22-8.16 (m, 2H), 7.74-7.68 (t, J=8.4 Hz, 1H), 7.45-7.33 (m, 2H), 4.32-4.30 (d, J=5.4 Hz, 2H), 4.14 (m, 1H), 1.76-1.66 (m, 4H), 1.43-1.24 (m, 4H), 1.14 (s, 9H), 0.99 (s, 3H), 0.95 (s, 3H); MS (m/z): 608.38 (M+H)$^+$.

Example-33

6-Chloro-2-fluoro-N-(2-methyl-4-((3-(trifluoromethyl)phenyl)amino)quinazolin-8-yl)-3-(pivalamidomethyl)benzamide

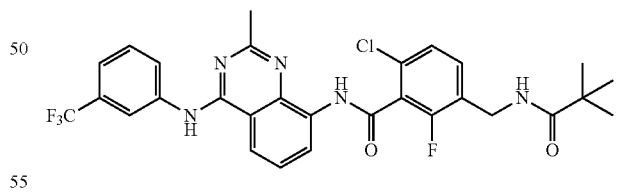

The title compound was prepared following the procedure described in Example-1 using 2-methyl-N$^4$-(3-(trifluoromethyl)phenyl)quinazoline-4,8-diamine (Intermediate-27, 100 mg, 0.314 mmol), 6-chloro-2-fluoro-3-(pivalamidomethyl)benzoic acid (Intermediate-2, 181 mg, 0.629 mmol), oxalyl chloride (119 mg, 0.94 mmol), DMF (1 drop) and DIPEA (122 mg, 0.94 mmol) in CH$_2$Cl$_2$ (4 mL) to afford 17 mg of the title product. $^1$H NMR (300 MHz, DMSO-d$_6$): δ 10.42 (s, 1H), 10.04 (s, 1H), 8.77 (d, 1H), 8.43 (s, 1H), 8.31 (m 2H), 8.16 (m, 1H), 7.64 (m, 2H), 7.48-7.36 (m, 3H), 4.31 (d, 2H), 2.58 (s, 3H), 1.14 (s, 9H); MS (m/z): 588.31 (M+H)$^+$.

Example-34

2-Chloro-6-fluoro-N-(4-((2-fluoro-5-(trifluoromethyl)phenyl)amino)quinazolin-8-yl)benzamide

The title compound was prepared following the procedure described in Example-1 using $N^4$-(2-fluoro-5-(trifluoromethyl)phenyl)quinazoline-4,8-diamine (Intermediate-14, 60 mg, 0.18 mmol), 6-chloro-2-fluorobenzoic acid (48 mg, 0.27 mmol), oxalyl chloride (52 mg, 0.41 mmol), DMF (1 drop) and DIPEA (70 mg, 0.54 mmol) in $CH_2Cl_2$ (2 mL) to afford 45 mg of the title product. $^1$H NMR (300 MHz, DMSO-$d_6$): δ 10.69 (s, 1H), 10.16 (s, 1H), 8.80 (d, J=7.5 Hz, 1H), 8.57 (s, 1H), 8.23 (d, J=8.4 Hz, 1H), 8.02 (d, J=5.7 Hz, 1H), 7.74-7.68 (m, 2H), 7.63-7.51 (m, 2H), 7.44-7.36 (m, 2H); MS (m/z): 479.30 (M+H)$^+$.

Example-35

6-Chloro-N-(1-((4,4-dimethylcyclohexyl)oxy)isoquinolin-5-yl)-2-fluoro-3-(pivalamidomethyl)benzamide

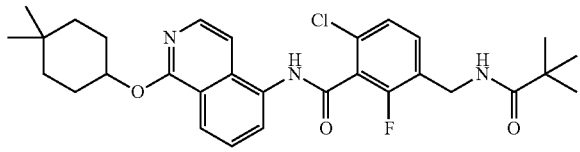 [SMILES: CC1(C)CCC(Oc2nccc3c(NC(=O)c4c(Cl)ccc(CNC(=O)C(C)(C)C)c4F)cccc23)CC1]

The title compound was prepared following the procedure described in Example-1 using 1-((4,4-dimethylcyclohexyl)oxy)isoquinolin-5-amine (Intermediate-28, 70 mg, 0.25 mmol), 6-chloro-2-fluoro-3-(pivalamidomethyl)benzoic acid (Intermediate-2, 89 mg, 0.31 mmol), oxalyl chloride (59 mg, 0.47 mmol), DMF (1 drop) and DIPEA (97 mg, 0.75 mmol) in $CH_2Cl_2$ (3 mL) to afford 45 mg of the title product. $^1$H NMR (300 MHz, DMSO-$d_6$): δ 10.89 (s, 1H), 8.19 (t, 1H), 8.14 (d, J=8.4 Hz, 1H), 8.04 (d, J=5.7 Hz, 1H), 7.95 (d, J=7.8 Hz, 1H), 7.67 (t, J=7.8 Hz, 1H), 7.48 (d, J=6.0 Hz, 1H), 7.43 (s, 1H), 7.37 (d, J=7.8 Hz, 1H), 5.28 (m, 1H), 4.34 (d, J=5.4 Hz, 2H), 1.90 (m, 2H), 1.78 (m, 2H), 1.53 (m, 2H), 1.34 (m, 2H), 1.15 (s, 9H), 1.00 (s, 3H), 0.97 (s, 3H); MS (m/z): 540.10 (M+H)$^+$.

Example-36

6-Chloro-2-fluoro-3-(pivalamidomethyl)-N-(1-(((1r,4r)-4-(trifluoromethyl)cyclohexyl)amino)isoquinolin-5-yl)benzamide

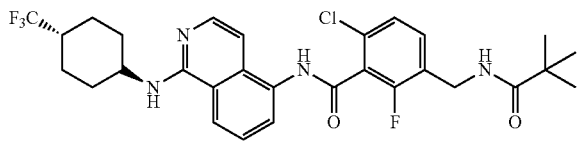

The title compound was prepared following the procedure described in Example-1 using N-((1r,4r)-4-(trifluoromethyl)cyclohexyl)isoquinoline-1,5-diamine (Intermediate-29, 63 mg, 0.20 mmol), 6-chloro-2-fluoro-3-(pivalamidomethyl)benzoic acid (Intermediate-2, 70 mg, 0.24 mmol), oxalyl chloride (45 mg, 0.36 mmol), DMF (1 drop) and DIPEA (77 mg, 0.60 mmol) in $CH_2Cl_2$ (2 mL) to afford 30 mg of the title product. $^1$H NMR (300 MHz, DMSO-$d_6$): δ 10.72 (s, 1H), 8.25-8.22 (m, 2H), 7.90 (d, J=6.0 Hz, 1H), 7.80 (d, J=7.5 Hz, 1H), 7.51 (t, J=7.2 Hz, 1H), 7.43 (d, J=8.1 Hz, 1H), 7.36 (t, J=7.2 Hz, 1H), 7.18 (d, J=7.5 Hz, 1H), 7.05 (d, J=6.0 Hz, 1H), 4.33 (d, J=5.4 Hz, 2H), 4.11 (m, 1H), 2.28 (m, 1H), 2.11 (m, 2H), 1.96 (m, 2H), 1.44 (m, 4H), 1.14 (s, 9H); MS (m/z): 579.40 (M)$^+$.

Example-37

6-Chloro-2-fluoro-3-(pivalamidomethyl)-N-(4-(((1r,4r)-4-(trifluoromethyl)cyclohexyl)amino)quinazolin-8-yl)benzamide

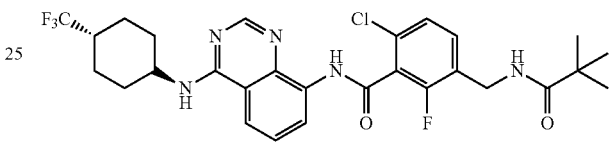

The title compound was prepared following the procedure described in Example-1 using $N^4$-((1r,4r)-4-(trifluoromethyl)cyclohexyl)quinazoline-4,8-diamine (Intermediate-30, 188 mg, 0.60 mmol), 6-chloro-2-fluoro-3-(pivalamidomethyl)benzoic acid (Intermediate-2, 311 mg, 1.09 mmol), oxalyl chloride (207 mg, 1.64 mmol), DMF (1 drop) and DIPEA (232 mg, 1.80 mmol) in $CH_2Cl_2$ (7 mL) to afford 30 mg of the title product. $^1$H NMR (300 MHz, DMSO-$d_6$): δ 10.38 (s, 1H), 8.66 (d, 1H), 8.46 (s, 1H), 8.13-8.06 (m, 3H), 7.52 (t, 1H), 7.37 (m, 2H), 4.28 (d, J=6.0 Hz, 2H), 4.17 (m, 1H), 2.31 (m, 1H), 2.18 (m, 2H), 1.82 (m, 2H), 1.42 (m, 4H), 1.12 (s, 9H); MS (m/z): 580.42 (M+H)$^+$.

Example-38

2-Chloro-5-(pivalamidomethyl)-N-(1-(((1r,4r)-4-(trifluoromethyl)cyclohexyl)oxy)isoquinolin-5-yl)benzamide

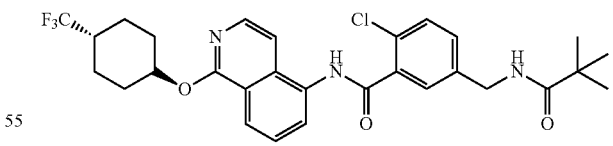

The title compound was prepared following the procedure described in Example-1 using 1-(((1r,4r)-4-(trifluoromethyl)cyclohexyl)oxy)isoquinolin-5-amine (Intermediate-33, 130 mg, 0.41 mmol), 2-chloro-5-(pivalamidomethyl)benzoic acid (Intermediate-5, 169 mg, 0.62 mmol), oxalyl chloride (117 mg, 0.93 mmol), DMF (1 drop) and DIPEA (159 mg, 1.23 mmol) in $CH_2Cl_2$ (5 mL) to afford 120 mg of the title product. $^1$H NMR (300 MHz, DMSO-$d_6$): δ 10.61 (s, 1H), 8.17 (m, 1H), 8.05 (d, J=7.5 Hz, 1H), 8.00 (d, J=6.3 Hz, 1H), 7.92 (d, 1H), 7.63 (m, 1H), 7.50 (m, 3H), 7.34 (d, J=7.8 Hz, 1H), 5.19 (m, 1H), 4.29 (d, 1H), 2.38 (m, 1H), 2.25 (m, 2H), 1.95 (m, 2H), 1.61-1.46 (m, 4H), 1.12 (s, 9H); MS (m/z): 562.10 (M+H)⁺.

Example-39

2-Chloro-5-(pivalamidomethyl)-N-(4-(((1r,4r)-4-(trifluoromethyl)cyclohexyl)oxy)quinazolin-8-yl)benzamide

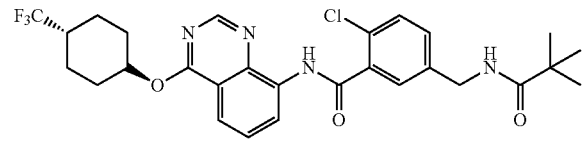

The title compound was prepared following the procedure described in Example-1 using 4-(((1r,4r)-4-(trifluoromethyl)cyclohexyl)oxy)quinazolin-8-amine (Intermediate-21, 60 mg, 0.19 mmol), 2-chloro-5-(pivalamidomethyl)benzoic acid (Intermediate-5, 100 mg, 0.38 mmol), oxalyl chloride (72 mg, 0.57 mmol), DMF (1 drop) and DIPEA (74 mg, 0.57 mmol) in CH$_2$Cl$_2$ (2 mL) to afford 20 mg of the title product. $^1$H NMR (300 MHz, DMSO-d$_6$): δ 10.23 (s, 1H), 8.80 (m, 2H), 8.16 (t, 1H), 7.83 (d, 1H), 7.69 (t, 1H), 7.58-7.52 (m, 2H), 7.38 (d, 1H), 5.30 (m, 1H), 4.27 (d, 2H), 2.38 (m, 1H), 2.26 (m, 2H), 1.96 (m, 2H), 1.62-1.50 (m, 4H), 1.11 (s, 9H); MS (m/z): 563.09 (M+H)⁺.

Example-40

6-Chloro-2-fluoro-N-(4-(2-fluoro-5-(trifluoromethyl)phenoxy)quinolin-8-yl)-3-(pivalamidomethyl)benzamide

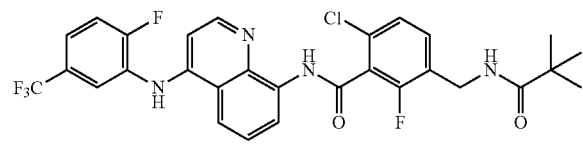

The title compound was prepared following the procedure described in Example-1 using 4-(2-fluoro-5-(trifluoromethyl)phenoxy)quinolin-8-amine (Intermediate-35, 100 mg, 0.31 mmol), 6-chloro-2-fluoro-3-(pivalamidomethyl)benzoic acid (Intermediate-2, 133 mg, 0.46 mmol), oxalyl chloride (187 mg, 0.69 mmol), DMF (1 drop) and DIPEA (120 mg, 0.93 mmol) in CH$_2$Cl$_2$ (4 mL) to afford 80 mg of the title product. $^1$H NMR (300 MHz, DMSO-d$_6$): δ 10.74 (s, 1H), 8.78 (d, J=7.8 Hz, 1H), 8.70 (d, J=5.4 Hz, 1H), 8.11-8.05 (m, 3H), 7.83-7.71 (m, 3H), 7.41-7.30 (m, 2H), 6.83 (d, J=4.8 Hz, 1H), 4.29 (d, J=5.4 Hz, 2H), 1.12 (s, 9H); MS (m/z): 592.33 (M+H)⁺.

Example-41

2-Chloro-N-(1-(2-fluoro-5-(trifluoromethyl)phenoxy)isoquinolin-5-yl)-5-(pivalamidomethyl)benzamide

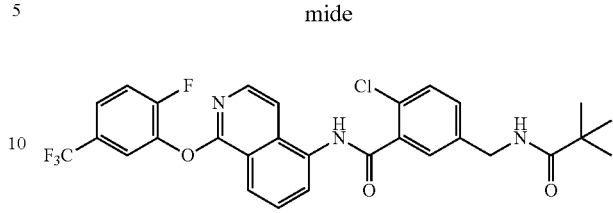

The title compound was prepared following the procedure described in Example-1 using 1-(2-fluoro-5-(trifluoromethyl)phenoxy)isoquinolin-5-amine (Intermediate-36, 80 mg, 0.24 mmol), 2-chloro-5-(pivalamidomethyl)benzoic acid (Intermediate-5, 134 mg, 0.49 mmol), oxalyl chloride (93 mg, 0.74 mmol), DMF (1 drop) and DIPEA (93 mg, 0.72 mmol) in CH$_2$Cl$_2$ (5 mL) to afford 35 mg of the title product. $^1$H NMR (300 MHz, DMSO-d$_6$): δ 10.77 (s, 1H), 8.32 (d, 1H), 8.11 (t, 1H), 8.09 (d, 1H), 8.00-7.96 (m, 2H), 7.75-7.69 (m, 4H), 7.55 (m, 2H), 7.38 (d, 1H), 4.32 (d, J=5.4 Hz, 2H), 1.14 (s, 9H).

Example-42

6-Chloro-2-fluoro-N-(7-methyl-4-((3-(trifluoromethyl)phenyl)amino)quinazolin-8-yl)-3-(pivalamidomethyl)benzamide

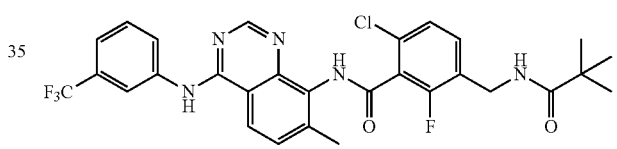

The title compound was prepared following the procedure described in Example-1 using 7-methyl-N⁴-(3-(trifluoromethyl)phenyl)quinazoline-4,8-diamine (Intermediate-37, 140 mg, 0.44 mmol), 6-chloro-2-fluoro-3-(pivalamidomethyl)benzoic acid (Intermediate-2, 163 mg, 0.57 mmol), oxalyl chloride (108 mg, 0.86 mmol), DMF (1 drop) and DIPEA (170 mg, 1.32 mmol) in CH$_2$Cl$_2$ (5 mL) to afford 25 mg of the title product. $^1$H NMR (300 MHz, DMSO-d$_6$): δ 10.71 (s, 1H), 10.03 (s, 1H), 8.72 (s, 1H), 8.46 (d, J=8.4 Hz, 1H), 8.35 (s, 1H), 8.27 (d, J=9.3 Hz, 1H), 8.19 (t, 1H), 7.66-7.63 (m, 2H), 7.46 (d, J=6.9 Hz, 1H), 7.40 (d, J=8.7 Hz, 1H), 7.31 (t, J=8.1 Hz, 1H), 4.33 (d, J=5.4 Hz, 2H), 2.50 (s, 3H), 1.15 (s, 9H); MS (m/z): 588.23 (M)⁺.

Example-43

6-Chloro-N-(4-ethoxyquinazolin-8-yl)-2-fluoro-3-(pivalamidomethyl)benzamide

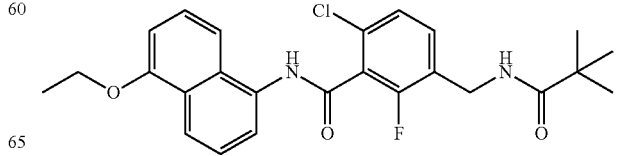

The title compound was prepared following the procedure described in Example-1 using 4-ethoxyquinazolin-8-amine (Intermediate-38, 140 mg, 0.80 mmol), 6-chloro-2-fluoro-3-(pivalamidomethyl)benzoic acid (Intermediate-2, 323 mg, 1.12 mmol), oxalyl chloride (141 mg, 1.12 mmol), DMF (1 drop) and DIPEA (310 mg, 2.40 mmol) in CH$_2$Cl$_2$ (4 mL) to afford 65 mg of the title product. $^1$H NMR (300 MHz, DMSO-d$_6$): δ 10.75 (s, 1H), 8.79 (m, 2H), 8.13 (t, 1H), 7.91 (d, J=8.4 Hz, 1H), 7.69 (t, 1H), 7.36-7.31 (m, 2H), 4.62 (m, 2H), 4.29 (d, J=6.0 Hz, 2H), 1.44 (t, J=7.5 Hz, 3H), 1.12 (s, 9H); MS (m/z): 459.20 (M+H)$^+$.

Example-44

2-Chloro-N-(1-((2-fluoro-4-(trifluoromethyl)phenyl)amino)isoquinolin-5-yl)-5-(pivalamidomethyl)benzamide

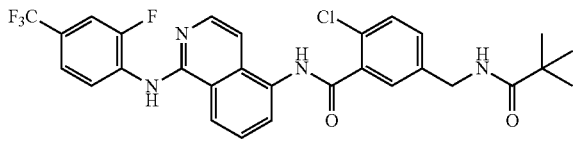 [SMILES: CC(C)(C)C(=O)NCc1ccc(Cl)c(C(=O)Nc2cccc3c(Nc4ccc(C(F)(F)F)cc4F)nccc23)c1]

The title compound was prepared following the procedure described in Example-1 using N$^1$-(2-fluoro-4-(trifluoromethyl)phenyl)isoquinoline-1,5-diamine (Intermediate-39, 80 mg, 0.24 mmol), 2-chloro-5-(pivalamidomethyl)benzoic acid (Intermediate-5, 134 mg, 0.49 mmol), oxalyl chloride (93 mg, 0.74 mmol), DMF (1 drop) and DIPEA (93 mg, 0.72 mmol) in CH$_2$Cl$_2$ (5 mL) to afford 25 mg of the title product. $^1$H NMR (300 MHz, DMSO-d$_6$): δ 10.62 (s, 1H), 9.38 (s, 1H), 8.35 (d, J=8.4 Hz, 1H), 8.21 (t, 1H), 8.00-7.93 (m, 2H), 7.88 (t, J=7.5 Hz, 1H), 7.71 (d, J=9.3 Hz, 2H), 7.60-7.53 (m, 3H), 7.44 (d, J=5.7 Hz, 1H), 7.36 (d, J=9.0 Hz, 1H), 4.32 (d, J=5.4 Hz, 2H), 1.14 (s, 9H); MS (m/z): 573.29 (M+H)$^+$.

Example-45

2-Chloro-5-(pivalamidomethyl)-N-(1-((4-(trifluoromethyl)phenyl)amino)isoquinolin-5-yl)benzamide

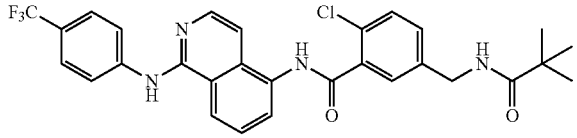 [SMILES: CC(C)(C)C(=O)NCc1ccc(Cl)c(C(=O)Nc2cccc3c(Nc4ccc(C(F)(F)F)cc4)nccc23)c1]

The title compound was prepared following the procedure described in Example-1 using N'-(4-(trifluoromethyl)phenyl)isoquinoline-1,5-diamine (Intermediate-40, 100 mg, 0.33 mmol), 2-chloro-5-(pivalamidomethyl)benzoic acid (Intermediate-5, 177 mg, 0.66 mmol), oxalyl chloride (125 mg, 0.99 mmol), DMF (1 drop) and DIPEA (128 mg, 0.99 mmol) in CH$_2$Cl$_2$ (5 mL) to afford 40 mg of the title product. $^1$H NMR (300 MHz, DMSO-d$_6$): δ 10.62 (s, 1H), 9.59 (s, 1H), 8.47 (d, J=8.4 Hz, 1H), 8.21 (t, 1H), 8.12 (m, 3H), 7.94 (d, 1H), 7.68-7.65 (m, 3H), 7.53 (m, 2H), 7.47 (d, J=6.0 Hz, 1H), 7.38 (d, 1H), 4.32 (d, 2H), 1.15 (s, 9H); MS (m/z): 555.30 (M+H)$^+$.

Example-46

2-Chloro-5-(pivalamidomethyl)-N-(1-(4-(trifluoromethyl)phenoxy)isoquinolin-5-yl)benzamide

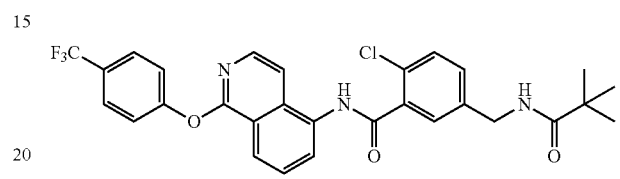

The title compound was prepared following the procedure described in Example-1 using 1-(4-(trifluoromethyl)phenoxy)isoquinolin-5-amine (Intermediate-41, 100 mg, 0.32 mmol), 2-chloro-5-(pivalamidomethyl)benzoic acid (Intermediate-5, 177 mg, 0.65 mmol), oxalyl chloride (123 mg, 0.98 mmol), DMF (1 drop) and DIPEA (124 mg, 0.96 mmol) in CH$_2$Cl$_2$ (5 mL) to afford 33 mg of the title product. $^1$H NMR (300 MHz, DMSO-d$_6$): δ 10.76 (s, 1H), 8.30 (d, J=7.8 Hz, 1H), 8.21 (t, 1H), 8.08 (d, J=6.9 Hz, 1H), 7.99 (d, J=6.0 Hz, 1H), 7.86 (d, J=8.1 Hz, 2H), 7.73 (d, J=6.3 Hz, 1H), 7.54 (m, 4H), 7.37 (d, J=8.4 Hz, 2H), 4.32 (d, J=5.7 Hz, 2H), 1.14 (s, 9H); MS (m/z): 556.29 (M+H)$^+$.

Example-47

2-Chloro-5-(pivalamidomethyl)-N-(1-(((1s,4s)-4-(trifluoromethyl)cyclohexyl)oxy)isoquinolin-5-yl)benzamide

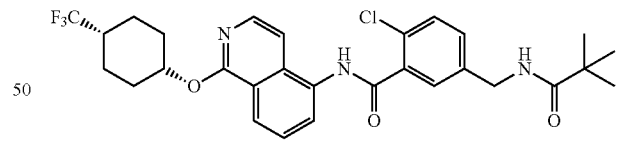

The title compound was prepared following the procedure described in Example-1 using 1-(((1s,4s)-4-(trifluoromethyl)cyclohexyl)oxy)isoquinolin-5-amine (Intermediate-34, 40 mg, 0.12 mmol), 2-chloro-5-(pivalamidomethyl)benzoic acid (Intermediate-5, 52 mg, 0.19 mmol), oxalyl chloride (37 mg, 0.29 mmol), DMF (1 drop) and DIPEA (46 mg, 0.36 mmol) in CH$_2$Cl$_2$ (2 mL) to afford 17 mg of the title product. $^1$H NMR (300 MHz, DMSO-d$_6$): δ 10.64 (s, 1H), 8.20 (t, 1H), 8.13 (d, J=8.1 Hz, 1H), 8.02 (d, J=6.3 Hz, 1H), 7.96 (d, J=7.2 Hz, 1H), 7.69 (t, J=7.8 Hz, 1H), 7.56-7.51 (m, 3H), 7.36 (d, J=7.8 Hz, 1H), 5.55 (m, 1H), 4.32 (d, J=5.4 Hz, 2H), 2.42 (m, 1H), 2.26 (m, 2H), 2.17 (m, 2H), 1.76-1.73 (m, 4H), 1.14 (s, 9H); MS (m/z): 562.11 (M)$^+$.

Example-48

2-Chloro-N-(1-(4-fluoro-3-(trifluoromethyl)phenoxy)isoquinolin-5-yl)-5-(pivalamidomethyl)benzamide

The title compound was prepared following the procedure described in Example-1 using 1-(4-fluoro-3-(trifluoromethyl)phenoxy)isoquinolin-5-amine (Intermediate-42, 80 mg, 0.24 mmol), 2-chloro-5-(pivalamidomethyl)benzoic acid (Intermediate-5, 134 mg, 0.49 mmol), oxalyl chloride (93 mg, 0.74 mmol), DMF (1 drop) and DIPEA (93 mg, 0.72 mmol) in $CH_2Cl_2$ (5 mL) to afford 26 mg of the title product. $^1$H NMR (300 MHz, DMSO-$d_6$): δ 10.75 (s, 1H), 8.30 (d, 1H), 8.21 (t, 1H), 8.08 (d, J=7.5 Hz, 1H), 7.98 (d, J=6.3 Hz, 1H), 7.82-7.55 (m, 7H), 7.37 (d, J=8.4 Hz, 1H), 4.32 (J=5.4 Hz, 2H), 1.14 (s, 9H); MS (m/z): 574.22 (M+H)$^+$.

Example-49

6-Chloro-2-methoxy-3-(pivalamidomethyl)-N-(4-(3-(trifluoromethyl)phenoxy)quinazolin-8-yl)benzamide

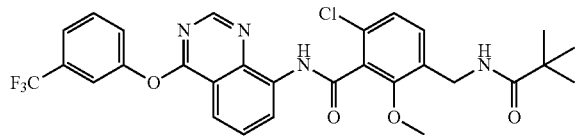

The title compound was prepared following the procedure described in Example-1 using 4-(3-(trifluoromethyl)phenoxy)quinazolin-8-amine (Intermediate-8, 60 mg, 0.19 mmol), 6-chloro-2-methoxy-3-(pivalamidomethyl)benzoic acid (Intermediate-43, 88 mg, 0.29 mmol), oxalyl chloride (55 mg, 0.44 mmol), DMF (1 drop) and DIPEA (74 mg, 0.57 mmol) in $CH_2Cl_2$ (2 mL) to afford 36 mg of the title product. $^1$H NMR (300 MHz, DMSO-$d_6$): δ 10.49 (s, 1H), 8.92 (d, J=7.8 Hz, 1H), 8.77 (s, 1H), 8.17-8.11 (m, 2H), 7.86 (m, 2H), 7.74 (m, 3H), 7.30 (m, 2H), 4.29 (d, 2H), 3.84 (s, 3H), 1.15 (s, 9H); MS (m/z): 587.17 (M+H)$^+$.

Example-50

6-Chloro-2-fluoro-3-(pivalamidomethyl)-N-(1-(((1r,4r)-4-(trifluoromethyl)cyclohexyl)oxy)isoquinolin-5-yl)benzamide

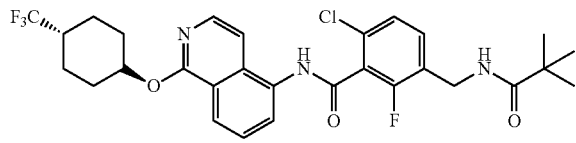

The title compound was prepared following the procedure described in Example-1 using 1-(((1r,4r)-4-(trifluoromethyl)cyclohexyl)oxy)isoquinolin-5-amine (Intermediate-33, 80 mg, 0.25 mmol), 6-chloro-2-fluoro-3-(pivalamidomethyl)benzoic acid (Intermediate-2, 111 mg, 0.38 mmol), oxalyl chloride (72 mg, 0.57 mmol), DMF (1 drop) and DIPEA (97 mg, 0.75 mmol) in $CH_2Cl_2$ (5 mL) to afford 35 mg of the title product. $^1$H NMR (300 MHz, DMSO-$d_6$): δ 10.90 (s, 1H), 8.19 (t, J=6.0 Hz, 1H), 8.10 (d, J=8.1 Hz, 1H), 8.06 (d, J=6.6 Hz, 1H), 7.96 (d, J=6.9 Hz, 1H), 7.66 (t, J=8.1 Hz, 1H), 7.51 (d, J=6.0 Hz, 1H), 7.45 (d, J=8.7 Hz, 1H), 7.35 (t, J=8.1 Hz, 1H), 5.22 (m, 1H), 4.34 (d, J=5.1 Hz, 2H), 2.41 (m, 1H), 2.27 (m, 2H), 2.01-1.97 (m, 2H), 1.64-1.44 (m, 4H), 1.15 (s, 9H); MS (m/z): 580.12 (M+H)$^+$.

Example-51

6-Chloro-2-fluoro-N-(4-(4-fluoro-3-(trifluoromethyl)phenoxy)quinolin-8-yl)-3-(pivalamidomethyl)benzamide

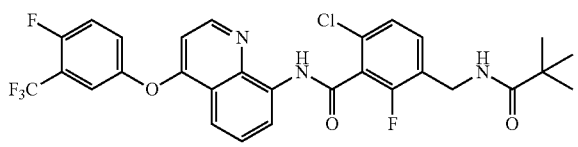 [SMILES: CC(C)(C)C(=O)NCc1ccc(Cl)c(C(=O)Nc2cccc3c(Oc4ccc(F)c(C(F)(F)F)c4)ccnc23)c1F]

The title compound was prepared following the procedure described in Example-1 using 4-(4-fluoro-3-(trifluoromethyl)phenoxy)quinolin-8-amine (Intermediate-44, 60 mg, 0.18 mmol), 6-chloro-2-fluoro-3-(pivalamidomethyl)benzoic acid (Intermediate-2, 80 mg, 0.27 mmol), oxalyl chloride (52 mg, 0.41 mmol), DMF (1 drop) and DIPEA (70 mg, 0.54 mmol) in $CH_2Cl_2$ (2 mL) to afford 35 mg of the title product. $^1$H NMR (300 MHz, DMSO-$d_6$): δ 10.75 (s, 1H), 8.79 (d, J=7.5 Hz, 1H), 8.71 (d, J=5.1 Hz, 1H), 8.16 (t, 1H), 8.09 (d, J=8.7 Hz, 1H), 7.88 (m, 1H), 7.75-7.70 (m, 3H), 7.38 (m, 2H), 6.83 (d, J=5.4 Hz, 1H), 4.32 (d, J=5.1 Hz, 2H), 1.14 (s, 9H); MS (m/z): 592.29 (M+H)$^+$.

Example-52

6-Chloro-2-fluoro-N-(4-(4-fluoro-3-(trifluoromethyl)phenoxy)quinazolin-8-yl)-3-(pivalamidomethyl)benzamide

The title compound was prepared following the procedure described in Example-1 using 4-(4-fluoro-3-(trifluoromethyl)phenoxy)quinazolin-8-amine (Intermediate-45, 60 mg, 0.18 mmol), 6-chloro-2-fluoro-3-(pivalamidomethyl)benzoic acid (Intermediate-2, 80 mg, 0.27 mmol), oxalyl chloride (52 mg, 0.41 mmol), DMF (1 drop) and DIPEA (70 mg, 0.54 mmol) in $CH_2Cl_2$ (2 mL) to afford 42 mg of the title product. $^1$H NMR (300 MHz, DMSO-$d_6$): δ 10.93 (s, 1H), 8.91 (d, J=7.8 Hz, 1H), 8.80 (s, 1H), 8.17 (d, J=7.2 Hz, 2H), 7.96 (t, 1H), 7.85 (m, 2H), 7.69 (t, J=9.6 Hz, 1H), 7.37 (m, 2H), 4.31 (d, J=5.4 Hz, 2H), 1.14 (s, 9H); MS (m/z): 593.10 (M+H)⁺.

Example-53

6-Chloro-2-fluoro-3-(pivalamidomethyl)-N-(4-(4-(trifluoromethyl)phenoxy)quinolin-8-yl)benzamide

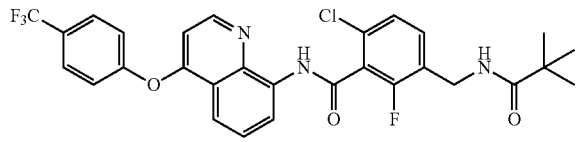 [SMILES: CC(C)(C)C(=O)NCc1ccc(Cl)c(C(=O)Nc2cccc3c(Oc4ccc(C(F)(F)F)cc4)ccnc23)c1F]

The title compound was prepared following the procedure described in Example-1 using 4-(4-(trifluoromethyl)phenoxy)quinolin-8-amine (Intermediate-46, 126 mg, 0.44 mmol), 6-chloro-2-fluoro-3-(pivalamidomethyl)benzoic acid (Intermediate-2, 142 mg, 0.49 mmol), oxalyl chloride (93 mg, 0.74 mmol), DMF (1 drop) and DIPEA (170 mg, 1.32 mmol) in CH$_2$Cl$_2$ (5 mL) to afford 30 mg of the title product. ¹H NMR (300 MHz, DMSO-d$_6$): δ10.78 (s, 1H), 8.80-8.75 (m, 2H), 8.16 (t, 1H), 8.03 (d, J=8.4 Hz, 1H), 7.90 (d, J=8.4 Hz, 2H), 7.72 (t, J=7.8 Hz, 1H), 7.52 (d, J=8.7 Hz, 2H), 7.42 (d, J=8.4 Hz, 1H), 7.36 (d, J=7.2 Hz, 1H), 6.96 (d, J=5.1 Hz, 1H), 4.31 (d, J=5.4 Hz, 2H), 1.14 (s, 9H); MS (m/z): 574.26 (M+H)⁺.

Example-54

6-Chloro-N-(4-((4,4-dimethylcyclohexyl)amino)-2-methylquinazolin-8-yl)-2-fluoro-3-(pivalamidomethyl)benzamide

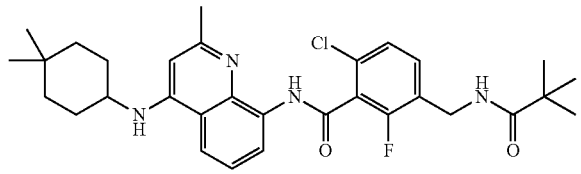 [SMILES: Cc1cc(NC2CCC(C)(C)CC2)c2cccc(NC(=O)c3c(Cl)ccc(CNC(=O)C(C)(C)C)c3F)c2n1]

The title compound was prepared following the procedure described in Example-1 using N⁴-(4,4-dimethylcyclohexyl)-2-methylquinazoline-4,8-diamine (Intermediate-47, 180 mg, 0.63 mmol), 6-chloro-2-fluoro-3-(pivalamidomethyl)benzoic acid (Intermediate-2, 271 mg, 0.95 mmol), oxalyl chloride (180 mg, 1.43 mmol), DMF (1 drop) and DIPEA (244 mg, 1.89 mmol) in CH$_2$Cl$_2$ (8 mL) to afford 25 mg of the title product. ¹H NMR (300 MHz, DMSO-d$_6$): δ 10.18 (s, 1H), 8.66 (d, J=7.8 Hz, 1H), 8.14 (t, 1H), 8.02 (d, J=8.1 Hz, 1H), 7.93 (d, 1H), 7.43 (m, 2H), 7.37 (d, J=7.8 Hz, 1H), 4.31 (d, 2H), 4.17 (m, 1H), 2.44 (s, 3H), 1.72 (m, 2H), 1.64-1.60 (m, 2H), 1.41-1.28 (m, 4H), 1.14 (s, 9H), 0.98 (s, 3H), 0.94 (s, 3H); MS (m/z): 554.35 (M+H)⁺.

Example-55

6-Chloro-2-fluoro-3-(pivalamidomethyl)-N-(quinolin-8-yl)benzamide

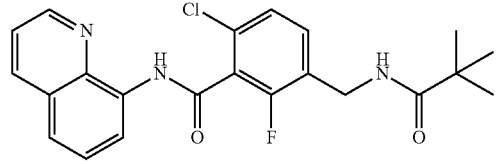 [SMILES: CC(C)(C)C(=O)NCc1ccc(Cl)c(C(=O)Nc2cccc3cccnc23)c1F]

The title compound was prepared following the procedure described in Example-1 using quinolin-8-amine (Intermediate-48, 50 mg, 0.34 mmol), 6-chloro-2-fluoro-3-(pivalamidomethyl)benzoic acid (Intermediate-2, 119 mg, 0.41 mmol), oxalyl chloride (78 mg, 0.62 mmol), DMF (1 drop) and DIPEA (132 mg, 1.02 mmol) in CH$_2$Cl$_2$ (5 mL) to afford 15 mg of the title product. ¹H NMR (300 MHz, DMSO-d$_6$): δ 10.73 (s, 1H), 8.91 (s, 1H), 8.71 (d, J=8.1 Hz, 1H), 8.48 (d, 1H), 8.16 (t, 1H), 7.78 (d, 1H), 7.67 (t, J=7.2 Hz, 2H), 7.40 (m, 2H), 4.32 (d, 2H), 1.14 (s, 9H); MS (m/z): 414.23 (M+H)⁺.

Example-56

6-Chloro-2-fluoro-N-(2-methyl-4-(3-(trifluoromethyl)phenoxy)quinazolin-8-yl)-3-(pivalamidomethyl)benzamide

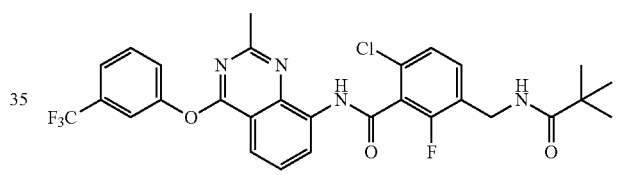

The title compound was prepared following the procedure described in Example-1 using 2-methyl-4-(3-(trifluoromethyl)phenoxy)quinazolin-8-amine (Intermediate-49, 150 mg, 0.47 mmol), 6-chloro-2-fluoro-3-(pivalamidomethyl) benzoic acid (Intermediate-2, 200 mg, 0.71 mmol), oxalyl chloride (135 mg, 1.07 mmol), DMF (1 drop) and DIPEA (182 mg, 1.41 mmol) in CH$_2$Cl$_2$ (6 mL) to afford 38 mg of the title product. ¹H NMR (300 MHz, DMSO-d$_6$): δ 10.65 (s, 1H), 8.99 (d, 1H), 8.12 (m, 2H), 7.84-7.74 (m, 4H), 7.41 (m, 2H), 4.32 (d, 2H), 2.50 (s, 3H), 1.14 (s, 9H); MS (m/z): 589.20 (M+H)⁺.

Example-57

6-Chloro-2-fluoro-N-(4-(isopropylamino)-2-methylquinazolin-8-yl)-3-(pivalamidomethyl)benzamide

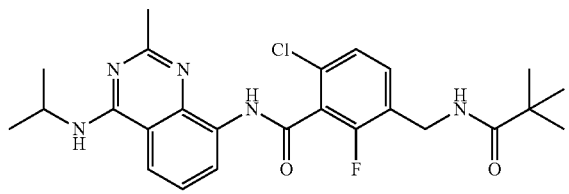 [SMILES: Cc1nc(NC(C)C)c2cccc(NC(=O)c3c(Cl)ccc(CNC(=O)C(C)(C)C)c3F)c2n1]

The title compound was prepared following the procedure described in Example-1 using N⁴-isopropyl-2-methylquinazoline-4,8-diamine (Intermediate-50, 30 mg, 0.14 mmol), 6-chloro-2-fluoro-3-(pivalamidomethyl)benzoic acid (Intermediate-2, 60 mg, 0.20 mmol), oxalyl chloride (38 mg, 0.30 mmol), DMF (1 drop) and DIPEA (77 mg, 0.60 mmol) in CH$_2$Cl$_2$ (2 mL) to afford 23 mg of the title product. $^1$H NMR (400 MHz, DMSO-d$_6$): δ 10.16 (s, 1H), 8.65 (d, J=7.6 Hz, 1H), 8.12-8.01 (t, J=8.4 Hz, 1H), 7.92 (d, J=7.6 Hz, 1H), 7.43 (d, J=7.7 Hz, 1H), 7.41-7.35 (m, 3H), 4.57-4.52 (m, 1H), 4.30 (d, J=5.6 Hz, 2H), 2.44 (s, 3H), 1.25 (s, 3H), 1.24 (s, 3H), 1.13 (s, 9H); MS (m/z): 486.27 (M+H)$^+$.

Example-58

6-Chloro-2-fluoro-N-(2-methyl-4-morpholino-quinazolin-8-yl)-3-(pivalamidomethyl)benzamide

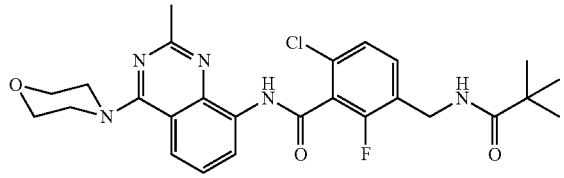 [SMILES: Cc1nc(N2CCOCC2)c2cccc(NC(=O)c3c(Cl)ccc(CNC(=O)C(C)(C)C)c3F)c2n1]

The title compound was prepared following the procedure described in Example-1 using 2-methyl-4-morpholino-quinazolin-8-amine (Intermediate-51, 100 mg, 0.41 mmol), 6-chloro-2-fluoro-3-(pivalamidomethyl)benzoic acid (Intermediate-2, 176 mg, 0.61 mmol), oxalyl chloride (115 mg, 0.92 mmol), DMF (1 drop) and DIPEA (159 mg, 1.23 mmol) in CH$_2$Cl$_2$ (5 mL) to afford 53 mg of the title product. $^1$H NMR (400 MHz, DMSO-d$_6$): δ 10.36 (s, 1H), 8.69 (d, J=7.6 Hz, 1H), 8.14-8.11 (t, J=5.7 Hz, 1H), 7.76-7.74 (d, J=8.4 Hz, 1H), 7.50-7.46 (t, J=8.1 Hz, 1H), 7.42 (d, J=8.4 Hz, 1H), 7.37-7.33 (t, J=8.0 Hz, 1H), 4.30 (d, J=5.7 Hz, 2H), 3.77 (d, J=4.7 Hz, 2H), 3.73 (d, J=4.6 Hz, 2H), 3.30 (s, 3H), 1.13 (s, 9H); MS (m/z): 514.29 (M+H)$^+$.

Example-59

6-Chloro-2-fluoro-N-(4-isopropoxyquinazolin-8-yl)-3-(pivalamidomethyl)benzamide

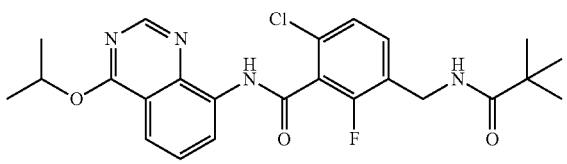 [SMILES: CC(C)Oc1ncnc2c(NC(=O)c3c(Cl)ccc(CNC(=O)C(C)(C)C)c3F)cccc12]

The title compound was prepared following the procedure described in Example-1 using 4-isopropoxyquinazolin-8-amine (Intermediate-52, 100 mg, 0.49 mmol), 6-chloro-2-fluoro-3-(pivalamidomethyl)benzoic acid (Intermediate-2, 184 mg, 0.64 mmol), oxalyl chloride (87 mg, 0.69 mmol), DMF (1 drop) and DIPEA (571 mg, 1.48 mmol) in CH$_2$Cl$_2$ (5 mL) to afford 40 mg of the title product. $^1$H NMR (400 MHz, DMSO-d$_6$): δ 10.73 (s, 1H), 8.78 (s, 1H), 8.76 (s, 1H), 8.15- 8.12 (t, J=5.2 Hz, 1H), 7.87 (d, J=8.4 Hz, 1H), 7.69-7.65 (t, J=8.0 Hz, 1H), 7.37 (d, J=8.4 Hz, 1H), 7.32-7.28 (t, J=8.0 Hz, 1H), 5.60-5.54 (m, 1H), 4.28 (d, J=6.0 Hz, 2H), 1.42 (d, J=6.0 Hz, 6H), 1.11 (s, 9H); MS (m/z): 473.11 (M+H)$^+$.

Example-60

6-Chloro-N-(4-((4,4-difluorocyclohexyl)amino)-2-methylquinazolin-8-yl)-2-fluoro-3-(pivalamidomethyl)benzamide

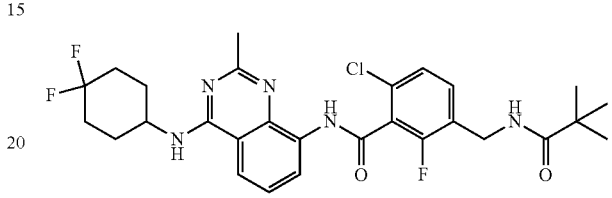

The title compound was prepared following the procedure described in Example-1 using N$^4$-(4,4-difluorocyclohexyl)-2-methylquinazoline-4,8-diamine (Intermediate-53, 100 mg, 0.342 mmol), 6-chloro-2-fluoro-3-(pivalamidomethyl)benzoic acid (Intermediate-2, 147 mg, 0.513 mmol), oxalyl chloride (97 mg, 0.77 mmol), DMF (1 drop) and DIPEA (132 mg, 1.026 mmol) in CH$_2$Cl$_2$ (3 mL) to afford 46 mg of the title product. $^1$H NMR (400 MHz, DMSO-d$_6$): δ 10.25 (s, 1H), 8.68 (d, J=7.6 Hz, 1H), 8.18-8.15 (t, J=5.8 Hz, 1H), 8.06-8.04 (d, J=8.4 Hz, 1H), 7.97-7.95 (d, J=7.6 Hz, 1H), 7.48-7.42 (m, 2H), 7.38-7.36 (d, J=8.0 Hz, 1H), 4.44 (m, 1H), 4.30 (d, J=5.6 Hz, 2H), 2.46 (s, 3H), 2.10-1.99 (m, 6H), 1.76-1.73 (m, 2H), 1.14 (s, 9H); MS (m/z): 562.32 (M+H)$^+$.

Example-61

6-Chloro-N-(4-(dimethylamino)quinazolin-8-yl)-2-fluoro-3-(pivalamidomethyl)benzamide

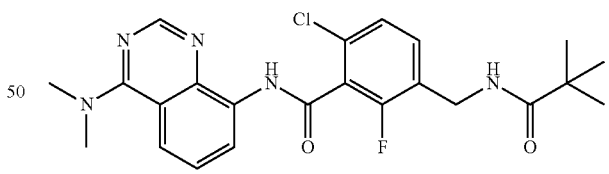

The title compound was prepared following the procedure described in Example-1 using N$^4$,N$^4$-dimethylquinazoline-4,8-diamine (Intermediate-54, 100 mg, 0.53 mmol), 6-chloro-2-fluoro-3-(pivalamidomethyl)benzoic acid (Intermediate-2, 184 mg, 0.64 mmol), oxalyl chloride (203 mg, 1.6 mmol), DMF (1 drop) and DIPEA (344 mg, 2.67 mmol) in CH$_2$Cl$_2$ (2 mL) to afford 46 mg of the title product. $^1$H NMR (400 MHz, DMSO-d$_6$): δ10.43 (s, 1H), 8.70-8.68 (d, J=7.6 Hz, 1H), 8.50 (s, 1H), 8.14-8.11 (t, J=5.6 Hz, 1H), 7.95-7.93 (d, J=8.4 Hz, 1H), 7.51-7.47 (t, J=8.0 Hz, 1H), 7.41-7.39 (d, J=8.4 Hz, 1H), 7.36-7.32 (t, J=8.0 Hz, 1H), 4.31-4.29 (d, J=5.6 Hz, 2H), 3.35 (s, 3H), 3.31 (s, 3H), 1.13 (s, 9H); MS (m/z): 458.22 (M+H)$^+$.

Example-62

N-(4-(tert-Butylamino)quinazolin-8-yl)-6-chloro-2-fluoro-3-(pivalamidomethyl)benzamide

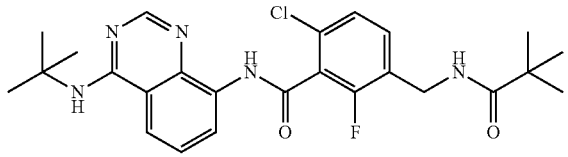 [SMILES: CC(C)(C)Nc1ncnc2c(NC(=O)c3c(Cl)ccc(CNC(=O)C(C)(C)C)c3F)cccc12]

The title compound was prepared following the procedure described in Example-1 using $N^4$-(tert-butyl)quinazoline-4,8-diamine (Intermediate-55, 100 mg, 0.46 mmol), 6-chloro-2-fluoro-3-(pivalamidomethyl)benzoic acid (Intermediate-2, 146 mg, 0.51 mmol), oxalyl chloride (126 mg, 0.99 mmol), DMF (1 drop) and DIPEA (132 mg, 1.03 mmol) in $CH_2Cl_2$ (3 mL) to afford 30 mg of the title product. $^1$H NMR (400 MHz, DMSO-$d_6$): δ 10.39 (s, 1H), 8.69-8.67 (d, J=7.4 Hz, 1H), 8.51 (s, 1H), 8.18-8.16 (m, 2H), 7.54-7.50 (t, J=8.0 Hz, 1H), 7.44-7.40 (m, 2H), 7.37-7.33 (t, J=8.0 Hz, 1H), 4.32-4.30 (d, J=6.0 Hz, 2H), 1.56 (s, 9H), 1.14 (s, 9H); MS (m/z): 486.25 (M+H)$^+$.

Example-63

6-Chloro-N-(4-ethoxyquinolin-8-yl)-2-fluoro-3-(pivalamidomethyl)benzamide

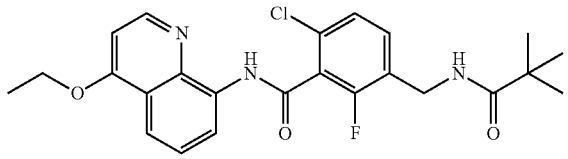 [SMILES: CCOc1ccnc2c(NC(=O)c3c(Cl)ccc(CNC(=O)C(C)(C)C)c3F)cccc12]

The title compound was prepared following the procedure described in Example-1 using 4-ethoxyquinolin-8-amine (Intermediate-56, 80 mg, 0.425 mmol), 6-chloro-2-fluoro-3-(pivalamidomethyl)benzoic acid (Intermediate-2, 159 mg, 0.553 mmol), oxalyl chloride (162 mg, 1.27 mmol), DMF (1 drop) and DIPEA (219 mg, 1.7 mmol) in $CH_2Cl_2$ (2 mL) to afford 46 mg of the title product. $^1$H NMR (400 MHz, DMSO-$d_6$): δ 10.59 (s, 1H), 8.71-8.68 (m, 2H), 8.13 (t, 1H), 7.93-7.90 (dd, J=1.2, 8.4 Hz, 1H), 7.61-7.57 (t, J=8.0 Hz, 1H), 7.42-7.40 (d, J=8.4 Hz, 1H), 7.36-7.23 (t, J=8.0 Hz, 1H), 7.12-7.11 (d, J=5.2 Hz, 1H), 4.35-4.29 (m, 4H), 1.50-1.47 (t, J=7.2 Hz, 3H), 1.14 (s, 9H); MS (m/z): 458.24 (M+H)$^+$.

Example-64

6-Chloro-2-fluoro-N-(4-(isopropylamino)quinazolin-8-yl)-3-(pivalamidomethyl)benzamide

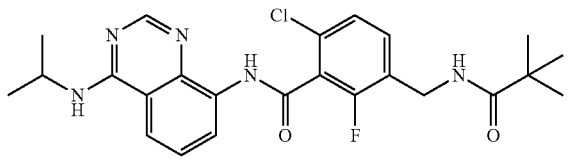 [SMILES: CC(C)Nc1ncnc2c(NC(=O)c3c(Cl)ccc(CNC(=O)C(C)(C)C)c3F)cccc12]

The title compound was prepared following the procedure described in Example-1 using $N^4$-isopropylquinazoline-4,8-diamine (Intermediate-57, 140 mg, 0.69 mmol), 6-chloro-2-fluoro-3-(pivalamidomethyl)benzoic acid (Intermediate-2, 223 mg, 0.78 mmol), oxalyl chloride (147 mg, 1.17 mmol), DMF (1 drop) and DIPEA (267 mg, 2.07 mmol) in $CH_2Cl_2$ (5 mL) to afford 40 mg of the title product. $^1$H NMR (400 MHz, DMSO-$d_6$): δ 10.38 (s, 1H), 8.69 (d, J=7.0 Hz, 1H), 8.48 (s, 1H), 8.16-8.14 (t, J=5.8 Hz, 1H), 8.10-8.07 (m, 2H), 7.55-7.51 (t, J=8.0 Hz, 1H), 7.42-7.40 (d, J=8.4 Hz, 1H), 7.36-7.33 (t, J=8.0 Hz, 1H), 4.56-4.51 (m, 1H), 4.31 (d, J=5.8 Hz, 2H), 1.28 (s, 3H), 1.25 (s, 3H), 1.14 (s, 9H); MS (m/z): 472.40 (M+H)$^+$.

Example-65

N-(4-(tert-Butylamino)-2-methylquinazolin-8-yl)-6-chloro-2-fluoro-3-(pivalamidomethyl)benzamide

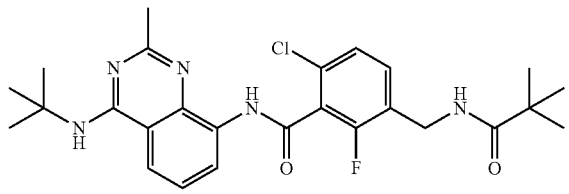 [SMILES: Cc1nc(NC(C)(C)C)c2cccc(NC(=O)c3c(Cl)ccc(CNC(=O)C(C)(C)C)c3F)c2n1]

The title compound was prepared following the procedure described in Example-1 using $N^4$-(tert-butyl)-2-methylquinazoline-4,8-diamine (Intermediate-58, 100 mg, 0.43 mmol), 6-chloro-2-fluoro-3-(pivalamidomethyl)benzoic acid (Intermediate-2, 150 mg, 0.52 mmol), oxalyl chloride (82 mg, 0.65 mmol), DMF (1 drop) and DIPEA (166 mg, 1.29 mmol) in $CH_2Cl_2$ (3 mL) to afford 46 mg of the title product. $^1$H NMR (400 MHz, DMSO-$d_6$): δ 10.21 (s, 1H), 8.66 (d, J=7.4 Hz, 1H), 8.15 (t, 1H), 8.10 (d, J=8.0 Hz, 1H), 7.44-7.33 (m, 4H), 4.31 (d, J=5.8 Hz, 2H), 2.48 (s, 3H), 1.14 (s, 9H); MS (m/z): 500.60 (M+H)$^+$.

Example-66

6-Chloro-2-fluoro-3-((3-hydroxy-2,2-dimethylpropanamido)methyl)-N-(4-(3-(trifluoromethyl)phenoxy)quinazolin-8-yl)benzamide

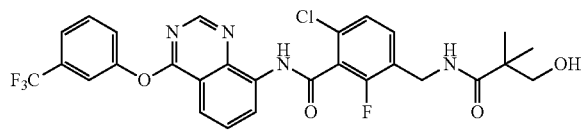 [SMILES: CC(C)(CO)C(=O)NCc1ccc(Cl)c(C(=O)Nc2cccc3c(Oc4cccc(C(F)(F)F)c4)ncnc23)c1F]

The title compound was prepared following the procedure described in Example-1 using 4-(3-(trifluoromethyl)phenoxy)quinazolin-8-amine (Intermediate-8, 200 mg, 0.655 mmol), 6-chloro-2-fluoro-3-((3-hydroxy-2,2-dimethylpropanamido)methyl)benzoic acid (Intermediate-59, 237 mg, 0.78 mmol), oxalyl chloride (166 mg, 1.32 mmol), DMF (1 drop) and DIPEA (253 mg, 1.96 mmol) in $CH_2Cl_2$ (3 mL) to afford 10 mg of the title product. $^1$H NMR (300 MHz, DMSO-$d_6$): δ 10.94 (s, 1H), 8.88 (d, 1H), 8.77 (s, 1H), 8.14 (m, 2H), 7.85 (m, 2H), 7.73 (s, 3H), 7.36 (m, 2H), 4.91 (t, 1H), 4.31 (d, 2H), 3.40 (m, 2H), 1.06 (s, 6H); MS [M+H]$^+$: 591.29.

Example-67

N-(4-(tert-Butylamino)quinazolin-8-yl)-2-chloro-5-(pivalamidomethyl)benzamide

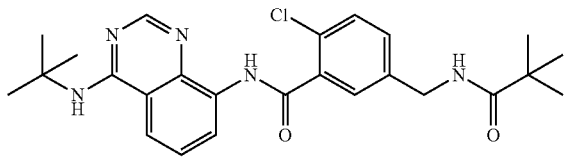 [SMILES: CC(C)(C)Nc1ncnc2c(NC(=O)c3cc(CNC(=O)C(C)(C)C)ccc3Cl)cccc12]

The title compound was prepared following the procedure described in Example-1 using $N^4$-(tert-butyl)quinazoline-4,8-diamine (Intermediate-55, 50 mg, 0.23 mmol), 2-chloro-5-(pivalamidomethyl)benzoic acid (Intermediate-5, 93 mg, 0.34 mmol), thionyl chloride (1 mL), and DIPEA (119 mg, 0.92 mmol) in THF (2 mL) to afford 85 mg of the title product. $^1$H NMR (300 MHz, DMSO-$d_6$): δ 10.11 (s, 1H), 8.69-8.67 (d, J=7.4 Hz, 1H), 8.49 (s, 1H), 8.16-8.13 (m, 2H), 7.58-7.38 (m, 5H), 4.31-4.29 (d, J=5.6 Hz, 2H), 1.55 (s, 9H), 1.12 (s, 9H); MS (m/z): 468.42 (M+H)$^+$.

Example-68

N-(4-(tert-Butylamino)quinazolin-8-yl)-2,6-dimethyl-3-(pivalamidomethyl)benzamide

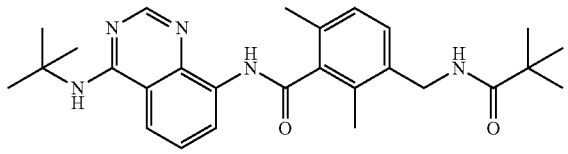 [SMILES: Cc1ccc(CNC(=O)C(C)(C)C)c(C)c1C(=O)Nc1cccc2c(NC(C)(C)C)ncnc12]

The title compound was prepared following the procedure described in Example-1 using $N^4$-(tert-butyl)quinazoline-4,8-diamine (Intermediate-55, 275 mg, 1.27 mmol), 2,6-dimethyl-3-(pivalamidomethyl)benzoic acid (Intermediate-4, 401 mg, 1.52 mmol), oxalyl chloride (230 mg, 1.82 mmol), DMF (1 drop) and DIPEA (392 mg, 3.04 mmol) in $CH_2Cl_2$ (10 mL) to afford 30 mg of the title product. $^1$H NMR (300 MHz, DMSO-$d_6$): δ 9.68 (s, 1H), 8.70-8.67 (d, J=7.8 Hz, 1H), 8.44 (s, 1H), 8.13-8.10 (d, J=8.4 Hz, 1H), 7.94 (t, 1H), 7.49-7.43 (m, 2H), 7.13-7.11 (m, 2H), 4.23 (d, 2H), 2.24 (s, 3H), 2.21 (s, 3H), 1.52 (s, 9H), 1.12 (s, 9H); MS [M+H]$^+$: 462.44.

Example-69

N-(4-(tert-Butylamino)quinazolin-8-yl)-6-chloro-2-fluoro-3-((3-hydroxy-2,2-dimethylpropanamido)methyl)benzamide

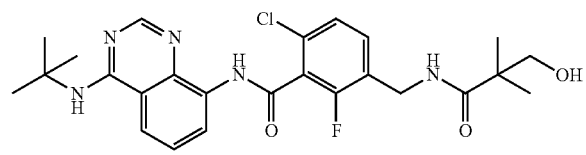 [SMILES: CC(C)(C)Nc1ncnc2c(NC(=O)c3c(Cl)ccc(CNC(=O)C(C)(C)CO)c3F)cccc12]

The title compound was prepared following the procedure described in Example-1 using $N^4$-(tert-butyl)quinazoline-4,8-diamine (Intermediate-55, 100 mg, 0.46 mmol), 6-chloro-2-fluoro-3-((3-hydroxy-2,2-dimethylpropanamido)methyl) benzoic acid (Intermediate-59, 168 mg, 0.56 mmol), oxalyl chloride (116 mg, 0.92 mmol), DMF (1 drop) and DIPEA (178 mg, 1.37 mmol) in $CH_2Cl_2$ (2 mL) to afford 25 mg of the title product. $^1$H NMR (300 MHz, DMSO-$d_6$): δ 10.41 (s, 1H), 8.68 (d, J=7.8 Hz, 1H), 8.51 (s, 1H), 8.17 (d, J=8.1 Hz, 1H), 8.11 (t, 1H), 7.52-7.38 (m, 4H), 4.91 (t, 1H), 4.33 (d, J=6.3 Hz, 2H), 3.42 (d, 2H), 1.55 (s, 9H), 1.08 (s, 6H); MS [M+H]$^+$: 502.46.

Example-70

N-(4-(tert-Butylamino)quinazolin-8-yl)-6-chloro-2-fluoro-3-(isobutyramidomethyl)benzamide

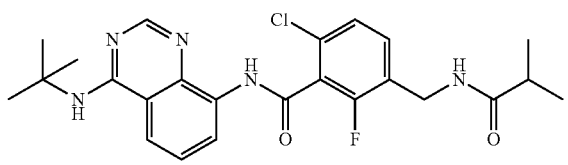 [SMILES: CC(C)C(=O)NCc1ccc(Cl)c(C(=O)Nc2cccc3c(NC(C)(C)C)ncnc23)c1F]

The title compound was prepared following the procedure described in Example-1 using $N^4$-(tert-butyl)quinazoline-4,8-diamine (Intermediate-55, 100 mg, 0.46 mmol), 6-chloro-2-fluoro-3-(isobutyramidomethyl)benzoic acid (Intermediate-60, 188 mg, 0.69 mmol), thionyl chloride (1 mL), and DIPEA (238 mg, 1.80 mmol) in THF (2 mL) to afford 13 mg of the title product. $^1$H NMR (300 MHz, DMSO-$d_6$): δ 10.42 (s, 1H), 8.69 (d, 1H), 8.50 (s, 1H), 8.37 (t, 1H), 8.15 (d, 1H), 7.52-7.40 (m, 4H), 4.32 (d, 2H), 1.55 (s, 9H), 1.03 (d, J=6.3 Hz, 6H); MS [M+H]$^+$: 474.34.

Example-71

N-(4-(tert-Butylamino)quinazolin-8-yl)-2-chloro-4-fluoro-5-(pivalamidomethyl)benzamide

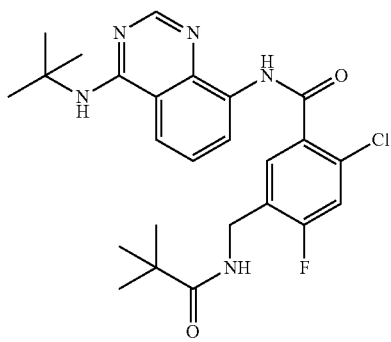 [SMILES: CC(C)(C)Nc1ncnc2c(NC(=O)c3cc(CNC(=O)C(C)(C)C)c(F)cc3Cl)cccc12]

The title compound was prepared following the procedure described in Example-1 using $N^4$-(tert-butyl)quinazoline-4,8-diamine (Intermediate-55, 100 mg, 0.46 mmol), 2-chloro-4-fluoro-5-(pivalamidomethyl)benzoic acid (Intermediate-63, 159 mg, 0.56 mmol), oxalyl chloride (117 mg, 0.93 mmol), DMF (1 drop) and DIPEA (178 mg, 1.38 mmol) in $CH_2Cl_2$ (5 mL) to afford 20 mg of the title product. $^1$H NMR (300 MHz, DMSO-$d_6$): δ 10.18 (s, 1H), 8.69-8.66 (d, J=7.2

Hz, 1H), 8.47 (s, 1H), 8.16-8.11 (m, 2H), 7.62-7.57 (m, 2H), 7.52-7.45 (m, 2H), 4.31-4.29 (d, J=5.7 Hz, 2H), 1.53 (s, 9H), 1.10 (s, 9H); MS [M+H]+: 486.45.

Example-72

N-(4-(tert-Butylamino)quinazolin-8-yl)-2-chloro-4-fluoro-3-(pivalamidomethyl)benzamide

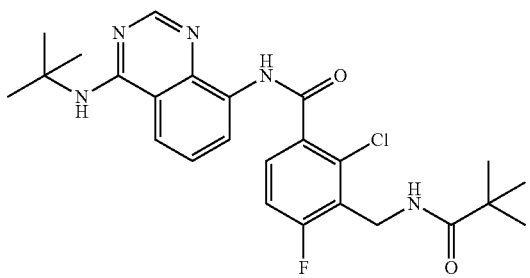 [SMILES: CC(C)(C)Nc1ncnc2c(NC(=O)c3ccc(F)c(CNC(=O)C(C)(C)C)c3Cl)cccc12]

The title compound was prepared following the procedure described in Example-1 using N4-(tert-butyl)quinazoline-4,8-diamine (Intermediate-55, 100 mg, 0.46 mmol), 2-chloro-4-fluoro-3-(pivalamidomethyl)benzoic acid (Intermediate-64, 159 mg, 0.56 mmol), oxalyl chloride (117 mg, 0.93 mmol), DMF (1 drop) and DIPEA (178 mg, 1.38 mmol) in CH$_2$Cl$_2$ (5 mL) to afford 12 mg of the title product. $^1$H NMR (300 MHz, DMSO-d$_6$): δ 10.05 (s, 1H), 8.71-8.69 (d, J=7.2 Hz, 1H), 8.49 (s, 1H), 8.15-8.13 (d, J=7.8 Hz, 1H), 7.83 (t, 1H), 7.75-7.73 (m, 1H), 7.53-7.47 (m, 2H), 7.40-7.34 (t, J=8.7 Hz, 1H), 4.43 (d, 2H), 1.54 (s, 9H), 1.08 (s, 9H); MS [M+H]+: 486.56.

Example-73

6-Chloro-2-fluoro-3-(isobutyramidomethyl)-N-(4-((2,2,2-trifluoroethyl)amino)quinazolin-8-yl)benzamide

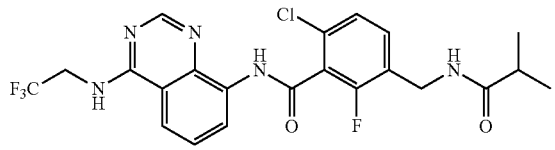 [SMILES: CC(C)C(=O)NCc1ccc(Cl)c(C(=O)Nc2cccc3c(NCC(F)(F)F)ncnc23)c1F]

The title compound was prepared following the procedure described in Example-1 using N4-(2,2,2-trifluoroethyl)quinazoline-4,8-diamine (Intermediate-65, 70 mg, 0.29 mmol), 6-chloro-2-fluoro-3-(isobutyramidomethyl)benzoic acid (Intermediate-60, 118 mg, 0.43 mmol), thionyl chloride (1 mL), and DIPEA (148 mg, 1.15 mmol) in THF (2 mL) to afford 18 mg of the title product. $^1$H NMR (300 MHz, DMSO-d$_6$): δ 10.57 (s, 1H), 8.93 (t, 1H), 8.76-8.73 (d, J=7.2 Hz, 1H), 8.61 (s, 1H), 8.38 (t, 1H), 8.12-8.09 (d, J=9.3 Hz, 1H), 7.66-7.61 (t, J=7.8 Hz, 1H), 7.40-7.38 (m, 2H), 4.47 (m, 2H), 4.32 (d, J=4.8 Hz, 2H), 2.42 (m, 1H), 1.05-1.03 (d, J=6.9 Hz, 6H); MS [M+H]+: 498.31.

Example-74

2-(Difluoromethyl)-5-(isobutyramidomethyl)-N-(4-(3-(trifluoromethyl)phenoxy)quinazolin-8-yl)nicotinamide

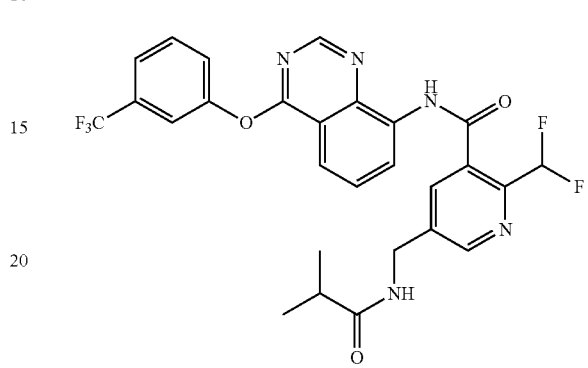

The title compound was prepared following the procedure described in Example-1 using 4-(3-(trifluoromethyl)phenoxy)quinazolin-8-amine (Intermediate-8, 50 mg, 0.18 mmol), 2-(difluoromethyl)-5-(isobutyramidomethyl)nicotinic acid (Intermediate-66, 56 mg, 0.18 mmol), oxalyl chloride (23 mg, 0.18 mmol), DMF (1 drop) and DIPEA (48 mg, 0.37 mmol) in CH$_2$Cl$_2$ (1.5 mL) to afford 10 mg of the title product. $^1$H NMR (300 MHz, DMSO-d$_6$): δ 10.67 (s, 1H), 8.84-8.82 (d, J=7.8 Hz, 1H), 8.79 (s, 1H), 8.71 (d, J=1.8 Hz, 1H), 8.48 (t, 1H), 8.21-8.19 (d, J=8.4 Hz, 1H), 8.08 (s, 1H), 7.89-7.86 (m, 2H), 7.76 (s, 3H), 7.42-7.06 (t, J=54.6 Hz, 1H), 4.44-4.42 (d, J=5.4 Hz, 2H), 2.44 (m, 1H), 1.05 (d, J=6.6 Hz, 6H); MS [M+H]+: 560.45.

Example-75

N-(4-(tert-Butylamino)quinazolin-8-yl)-2-(difluoromethyl)-5-(isobutyramidomethyl)nicotinamide

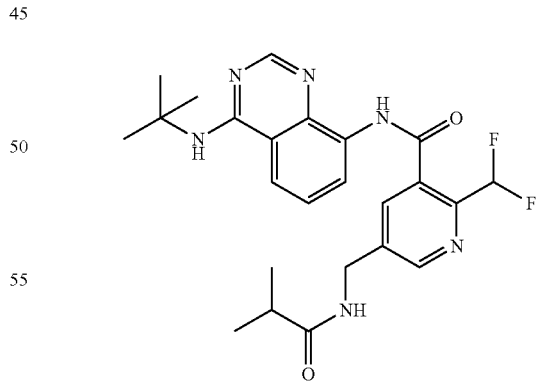

The title compound was prepared following the procedure described in Example-1 using N4-(tert-butyl)quinazoline-4,8-diamine (Intermediate-55, 100 mg, 0.46 mmol), 2-(difluoromethyl)-5-(isobutyramidomethyl)nicotinic acid (Intermediate-66, 150 mg, 0.55 mmol), oxalyl chloride (104 mg, 0.83 mmol), DMF (1 drop) and DIPEA (178 mg, 1.38 mmol) in CH$_2$Cl$_2$ (2 mL) to afford 12 mg of the title product. $^1$H NMR (300 MHz, DMSO-d$_6$): δ 10.32 (s, 1H), 8.71 (s, 1H), 8.63 (m, 1H), 8.49 (m, 2H), 8.16 (d, 1H), 8.05 (m, 1H), 7.46 (m, 2H), 7.22 (t, J=54 Hz, 1H), 4.42 (d, 2H), 1.55 (s, 9H), 1.05 (d, J=6.6 Hz, 6H); MS [M+H]$^+$: 471.49.

Example-76

2-(Difluoromethyl)-5-(isobutyramidomethyl)-N-(4-(isopropylamino)quinazolin-8-yl)nicotinamide

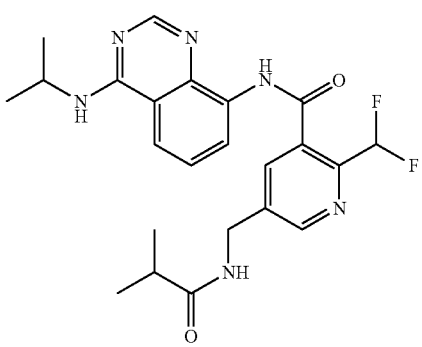 [SMILES: CC(C)Nc1ncnc2c(NC(=O)c3cc(CNC(=O)C(C)C)cnc3C(F)F)cccc12]

The title compound was prepared following the procedure described in Example-1 using N$^4$-isopropylquinazoline-4,8-diamine (Intermediate-57, 100 mg, 0.50 mmol), 2-(difluoromethyl)-5-(isobutyramidomethyl)nicotinic acid (Intermediate-66, 161 mg, 0.60 mmol), oxalyl chloride (113 mg, 0.90 mmol), DMF (1 drop) and DIPEA (192 mg, 1.49 mmol) in CH$_2$Cl$_2$ (2 mL) to afford 10 mg of the title product. $^1$H NMR (300 MHz, DMSO-d$_6$): δ 10.32 (s, 1H), 8.71 (s, 1H), 8.64 (m, 1H), 8.48 (m, 2H), 8.08 (m, 3H), 7.53 (m, 1H), 7.23 (t, J=54 Hz, 1H), 4.44 (m, 1H), 4.41 (d, 2H), 2.50 (m, 1H), 1.27 (d, J=6.9 Hz, 6H), 1.04 (d, J=7.5 Hz, 6H); MS [M+H]$^+$: 457.47.

Example-77

6-Chloro-2-fluoro-3-(isobutyramidomethyl)-N-(4-(isopropylamino)quinazolin-8-yl)benzamide

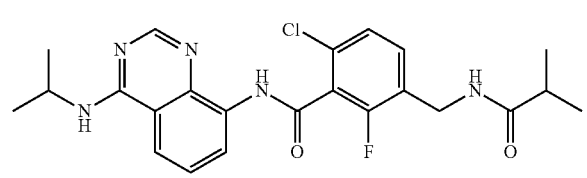 [SMILES: CC(C)Nc1ncnc2c(NC(=O)c3c(Cl)ccc(CNC(=O)C(C)C)c3F)cccc12]

The title compound was prepared following the procedure described in Example-1 using N$^4$-isopropylquinazoline-4,8-diamine (Intermediate-57, 50 mg, 0.25 mmol), 6-chloro-2-fluoro-3-(isobutyramidomethyl)benzoic acid (Intermediate-60, 100 mg, 0.37 mmol), thionyl chloride (1 mL), and DIPEA (127 mg, 0.99 mmol) in THF (2 mL) to afford 20 mg of the title product. $^1$H NMR (300 MHz, DMSO-d$_6$): δ 10.42 (s, 1H), 8.70-8.67 (d, J=7.2 Hz, 1H), 8.48 (s, 1H), 8.37 (t, 1H), 8.11-8.08 (d, J=7.8 Hz, 2H), 7.53 (t, 1H), 7.41 (m, 2H), 4.55 (m, 1H), 4.31 (d, 2H), 2.50 (m, 1H), 1.27 (d, J=6.6 Hz, 6H), 1.05-1.03 (d, J=6.9 Hz, 6H); MS [M+H]$^+$: 458.47.

Example-78

2-(Difluoromethyl)-5-(isobutyramidomethyl)-N-(4-((2,2,2-trifluoroethyl)amino)quinazolin-8-yl)nicotinamide

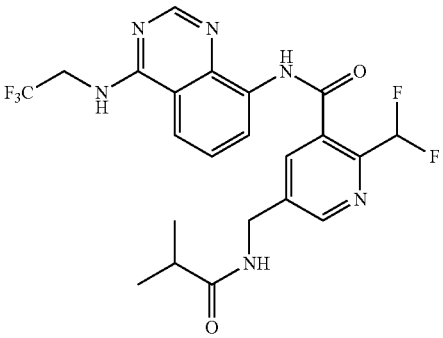 [SMILES: CC(C)C(=O)NCc1cnc(C(F)F)c(C(=O)Nc2cccc3c(NCC(F)(F)F)ncnc23)c1]

The title compound was prepared following the procedure described in Example-1 using N$^4$-(2,2,2-trifluoroethyl)quinazoline-4,8-diamine (Intermediate-65, 48 mg, 0.20 mmol), 2-(difluoromethyl)-5-(isobutyramidomethyl)nicotinic acid (Intermediate-66, 107 mg, 0.40 mmol), oxalyl chloride (50 mg, 0.40 mmol), DMF (1 drop) and DIPEA (127 mg, 0.99 mmol) in CH$_2$Cl$_2$ (2 mL) to afford 5 mg of the title product. $^1$H NMR (300 MHz, DMSO-d$_6$): δ 10.40 (s, 1H), 8.95 (t, 1H), 8.71 (d, 1H), 8.61 (s, 1H), 8.48 (t, 1H), 8.07 (m, 2H), 7.65 (t, 1H), 7.41-7.05 (t, J=54.0 Hz, 1H), 4.42 (m, 4H), 2.50 (m, 1H), 1.05 (d, J=7.2 Hz, 6H); MS [M+H]$^+$: 497.52.

Example-79

N-(4-(tert-Butylamino)quinazolin-8-yl)-6-chloro-2-fluoro-3-((3-fluoro-2,2-dimethylpropanamido)methyl)benzamide

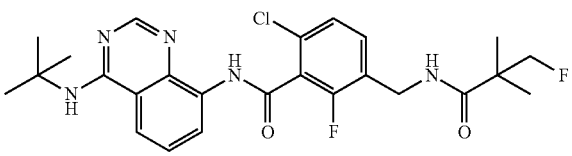 [SMILES: CC(C)(C)Nc1ncnc2c(NC(=O)c3c(Cl)ccc(CNC(=O)C(C)(C)CF)c3F)cccc12]

The title compound was prepared following the procedure described in Example-1 using N$^4$-(tert-butyl)quinazoline-4,8-diamine (Intermediate-55, 50 mg, 0.23 mmol), 6-chloro-2-fluoro-3-((3-fluoro-2,2-dimethylpropanamido)methyl)benzoic acid (Intermediate-67, 84 mg, 0.27 mmol), oxalyl chloride (52 mg, 0.41 mmol), DMF (1 drop) and DIPEA (89 mg, 0.69 mmol) in CH$_2$Cl$_2$ (2 mL) to afford 30 mg of the title product. $^1$H NMR (300 MHz, DMSO-d$_6$): δ 10.41 (s, 1H), 8.69-8.66 (d, J=8.4 Hz, 1H), 8.50 (s, 1H), 8.33 (t, 1H), 8.18-8.15 (d, J=9.3 Hz, 1H), 7.54-7.34 (m, 4H), 4.48-4.33 (m, 4H), 1.55 (s, 9H), 1.16 (s, 6H); MS (m/z): 504.64 (M+H)$^+$.

Example-80

2-(Difluoromethyl)-N-(4-(4-fluoro-3-(trifluoromethyl)phenoxy)quinolin-8-yl)-5-(isobutyramidomethyl)nicotinamide

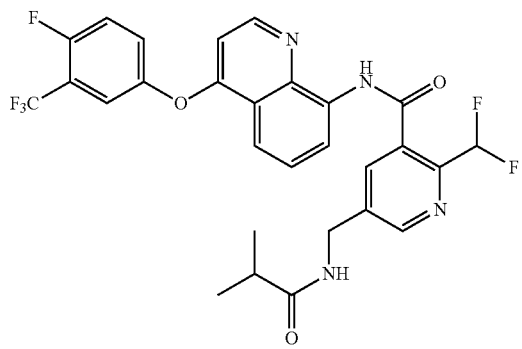 [SMILES: CC(C)C(=O)NCc1cnc(C(F)F)c(C(=O)Nc2cccc3c(Oc4ccc(F)c(C(F)(F)F)c4)ccnc23)c1]

The title compound was prepared following the procedure described in Example-1 using 4-(4-fluoro-3-(trifluoromethyl)phenoxy)quinolin-8-amine (Intermediate-44, 50 mg, 0.16 mmol), 2-(difluoromethyl)-5-(isobutyramidomethyl) nicotinic acid (Intermediate-66, 52 mg, 0.19 mmol), oxalyl chloride (37 mg, 0.29 mmol), DMF (1 drop) and DIPEA (74 mg, 0.57 mmol) in $CH_2Cl_2$ (2 mL) to afford 7 mg of the title product. $^1$H NMR (300 MHz, $CDCl_3$): δ 10.39 (s, 1H), 8.93 (d, 1H), 8.75 (s, 1H), 8.60 (d, 1H), 8.07 (m, 2H), 7.66 (t, 1H), 7.47 (m, 1H), 7.37-7.15 (m, 2H), 6.60 (d, J=5.4 Hz, 1H), 4.63-4.60 (d, J=6.9 Hz, 2H), 2.45 (m, 1H), 1.21 (d, J=6.9 Hz, 6H); MS (m/z): 577.97 (M+H)$^+$.

Pharmacological Activity

In-Vitro Protocol for Screening of mPGES-1 Inhibitors:

mPGES-1 (microsomal prostaglandin E synthase-1) is a microsomal enzyme that converts endoperoxide substrate $PGH_2$ (prostaglandin $H_2$) to product $PGE_2$ (prostaglandin $E_2$) by isomerization in the presence of reduced glutathione (GSH). mPGES-1 inhibitors were screened by assessing their ability to inhibit formation of $PGE_2$ from $PGH_2$ in presence of mPGES-1 using an anti-$PGE_2$ antibody based detection method. Recombinant human mPGES-1 was generated in-house by expression in CHO cells (Ouellet M et al. (2002), Protein Expression and Purification 26: 489-495). The assay was set up using crude microsomal fractions at protein concentration of 40-60 μg/mL. Test compounds were prepared in 100% dimethyl sulfoxide (DMSO) to obtain 20 mM stock solution and then diluted using assay buffer comprising 0.1 M Potassium phosphate buffer with 2 mM EDTA. The final concentration of DMSO in reaction was 0.5% (v/v). Negative controls were comprised of all assay reagents except the enzyme. Positive controls were comprised of the enzyme reaction in the absence of any inhibitor. Test compounds were incubated for 10 minutes in assay buffer containing 2.5 mM GSH and mPGES-1 enzyme followed by addition of $PGH_2$ at a concentration of 15 μM for 1 minute. The reaction was stopped by addition of Stannous chloride (11 mg/ml) and $PGE_2$ levels were measured (Masse F et al. (2005), Journal of Biomolecular Screening 10(6) 599-605., Goedken R E et al. (2008), Journal of Biomolecular Screening 13(7): 619-625) by HTRF kit (CisBio)).

Inhibition of mPGES-1 enzyme activity was measured using the percent of reaction occurring in the positive control. Concentration response curves were plotted using percent inhibition of maximum enzyme reaction. The $IC_{50}$ value was calculated from the concentration response curve by nonlinear regression analysis using GraphPad PRISM software.

The compounds prepared were tested using the above assay procedure and the results obtained are given in Table 1. Percentage inhibition at concentrations of 1.0 μM and 10.0 μM are given in the table along with $IC_{50}$ (nM) details for selected examples. The compounds prepared were tested using the above assay procedure and were found to have $IC_{50}$ less than 200 nM, preferably less than 100 nM, more preferably less than 50 nM or most preferably less than 20 nM.

The $IC_{50}$ (nM) values of the compounds are set forth in Table 1 wherein "A" refers to an $IC_{50}$ value of less than 50 nM, "B" refers to $IC_{50}$ value in range of 50.01 to 100.0 nM and "C" refers to $IC_{50}$ values more than 100 nM.

TABLE 1

| Sr. No. | Example No. | Percentage inhibition at 1 μM | Percentage inhibition at 10 μM | $IC_{50}$ (nM) |
|---|---|---|---|---|
| 1 | Example-1 | 95.17 | 96.68 | A |
| 2 | Example-2 | 95.77 | 97.24 | A |
| 3 | Example-3 | 96.01 | 98.09 | A |
| 4 | Example-4 | 98.59 | 99.85 | A |
| 5 | Example-5 | 99.45 | 98.46 | A |
| 6 | Example-6 | 92.96 | 95.88 | B |
| 7 | Example-7 | 100 | 96.73 | A |
| 8 | Example-8 | 98.99 | 97.95 | A |
| 9 | Example-9 | 99.12 | 100.00 | A |
| 10 | Example-10 | 99.67 | 98.86 | A |
| 11 | Example-11 | 97.40 | 90.66 | A |
| 12 | Example-12 | 99.43 | 99.70 | A |
| 13 | Example-13 | 90.19 | 92.25 | A |
| 14 | Example-14 | 100 | 100 | A |
| 15 | Example-15 | 98.07 | 97.55 | A |
| 16 | Example-16 | 99.02 | 99.56 | A |
| 17 | Example-17 | 94.29 | 93.87 | A |
| 18 | Example-18 | 100 | 99.92 | A |
| 19 | Example-19 | 97.71 | 98.16 | A |
| 20 | Example-20 | 98.76 | 99.39 | A |
| 21 | Example-21 | 97.27 | 97.24 | A |
| 22 | Example-22 | 100 | 99.58 | A |
| 23 | Example-23 | 94.98 | 94.86 | A |
| 24 | Example-24 | 99.27 | 99.8 | A |
| 25 | Example-25 | 97.7 | 98.29 | A |
| 26 | Example-26 | 93.39 | 93.09 | A |
| 27 | Example-27 | 94.39 | 93.92 | A |
| 28 | Example-28 | 99.12 | 100 | A |
| 29 | Example-29 | 98.96 | 99.79 | A |
| 30 | Example-30 | 97.39 | 99.08 | A |
| 31 | Example-31 | 98.68 | 98.66 | A |
| 32 | Example-32 | 94.47 | 95.86 | A |
| 33 | Example-33 | 95.49 | 97.24 | A |
| 34 | Example-34 | 75.42 | 84.05 | C |
| 35 | Example-35 | 100 | 100 | A |
| 36 | Example-36 | 98.08 | 99.11 | A |
| 37 | Example-37 | 97.72 | 96.29 | A |
| 38 | Example-38 | 99.29 | 99.9 | A |
| 39 | Example-39 | 98.04 | 99.53 | A |
| 40 | Example-40 | 99.32 | 98.55 | A |
| 41 | Example-41 | 99 | 97.63 | A |
| 42 | Example-42 | 96.47 | 99.56 | A |
| 43 | Example-43 | 98.36 | 99.92 | A |
| 44 | Example-44 | 100 | 99.95 | A |
| 45 | Example-45 | 99.58 | 98.3 | A |
| 46 | Example-46 | 89.42 | 97.71 | A |
| 47 | Example-47 | 85.09 | 97.67 | C |
| 48 | Example-48 | 91.11 | 95.17 | A |
| 49 | Example-49 | 91.92 | 91.05 | A |
| 50 | Example-50 | 99.24 | 99.6 | A |
| 51 | Example-51 | 99.26 | 99.72 | A |

TABLE 1-continued

| Sr. No. | Example No. | Percentage inhibition at 1 μM | Percentage inhibition at 10 μM | $IC_{50}$ (nM) |
|---|---|---|---|---|
| 52 | Example-52 | 94.54 | 95.33 | A |
| 53 | Example-53 | 98.28 | 98.28 | A |
| 54 | Example-54 | 98.22 | 97.32 | A |
| 55 | Example-55 | 94.11 | 99.77 | A |
| 56 | Example-56 | 97.89 | 99.28 | B |
| 57 | Example-57 | 74.12 | 96.01 | C |
| 58 | Example-58 | 51.29 | 93.40 | — |
| 59 | Example-59 | 97.47 | 99.41 | A |
| 60 | Example-60 | 86.50 | 91.73 | C |
| 61 | Example-61 | 88.26 | 97.21 | C |
| 62 | Example-62 | 97.32 | 97.82 | A |
| 63 | Example-63 | 90.75 | 94.66 | A |
| 64 | Example-64 | 90.57 | 94.48 | A |
| 65 | Example-65 | 93.96 | 92.98 | A |
| 66 | Example-66 | 96.69 | 96.83 | A |
| 67 | Example-67 | 96.48 | 100.00 | A |
| 68 | Example-68 | 99.84 | 100.00 | A |
| 69 | Example-69 | 84.91 | 98.18 | A |
| 70 | Example-70 | 100.00 | 98.78 | A |
| 71 | Example-71 | 100.00 | 97.28 | A |
| 72 | Example-72 | 86.77 | 98.66 | B |
| 73 | Example-73 | 88.68 | 93.23 | A |
| 74 | Example-74 | 100.00 | 100.00 | A |
| 75 | Example-75 | 93.64 | 98.31 | A |
| 76 | Example-76 | 83.53 | 93.40 | B |
| 77 | Example-77 | 78.43 | 99.93 | A |
| 78 | Example-78 | 83.34 | 94.82 | A |
| 79 | Example-79 | 100.00 | 99.11 | A |
| 80 | Example-80 | 99.70 | 98.49 | A |

Screening for mPGES-1 Inhibitors Using the A549 Cell Based Assay

The inhibition of mPGES-1 enzyme in A549 cell line was monitored as inhibition of IL-1β induced $PGE_2$ release. A549 cells were maintained in DMEM medium with 10% FBS and 1% Penicillin-Streptomycin Solution in 5% $CO_2$ at 37° C. Cells were seeded 24 h prior to the assay in 96 well plates in DMEM containing 1% Penicillin-Streptomycin and 2% FBS so as to get ~40,000 cells per well on the day of experiment. The assay was carried out in a total volume of 200 μL. Test compounds were dissolved in dimethyl sulfoxide (DMSO) to prepare 2 mM stock solution and then diluted using plain DMEM. The final concentration of DMSO in the reaction was 0.55% (v/v). Cells were treated with test compounds for 30 minutes followed by addition of IL-1β at a final concentration of 10 ng/mL for 16-20 h. Plates were then centrifuged at 1000 rpm for 10 min at 4° C. Supernatants were collected & analyzed by the addition of $PGE_2$-D2 & anti-$PGE_2$ cryptate conjugate supplied by the CisBio HTRF kit in a 96 well half area Blackwell EIA/RIA plate. The assay plate was incubated overnight at 4-5° C. before being read in Artemis (K-101) (Japan) HTRF plate reader and levels of $PGE_2$ calculated by extrapolation from the standard curve.

The concentration response curves were plotted as % of maximal response obtained in the absence of test antagonist. The $IC_{50}$ value was calculated from the concentration response curve by nonlinear regression analysis using GraphPad PRISM software.

The invention claimed is:
1. A compound of formula (II):

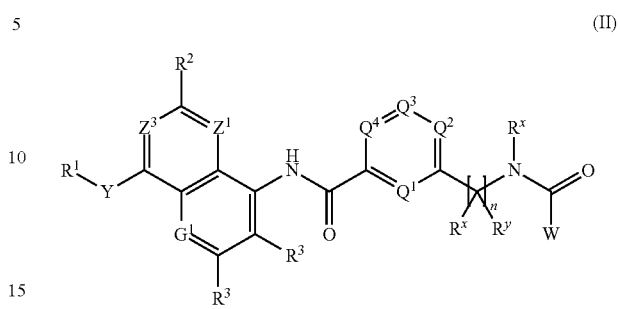

(II)

or a pharmaceutically acceptable salt thereof,
wherein
Y is O, NH or $NR^c$;
$Z^1$ and $Z^3$, which may be same or different, are independently selected from N and $CR^2$;
$G^1$ is selected from N and $CR^3$; with a proviso that at least one of $Z^1$, $Z^3$ and $G^1$ is N;
$Q^1$, $Q^2$, $Q^3$ and $Q^4$, which may be same or different, are independently selected from N, CH and $CR^4$; with a proviso that $Q^2$, $Q^3$ and $Q^4$ are not N simultaneously;
W is selected from substituted or unsubstituted $C_{1-8}$alkyl, substituted or unsubstituted $C_{1-8}$alkoxy$C_{1-8}$alkyl, substituted or unsubstituted halo$C_{1-8}$alkyl, substituted or unsubstituted hydroxy$C_{1-8}$alkyl, substituted or unsubstituted $C_{3-12}$cycloalkyl and substituted or unsubstituted tetrahydrofuryl or tetrahydrofuranyl;
$R^1$ is selected from substituted or unsubstituted $C_{1-8}$alkyl, substituted or unsubstituted $C_{1-8}$alkoxy$C_{1-8}$alkyl, substituted or unsubstituted halo$C_{1-8}$alkyl, substituted or unsubstituted hydroxy$C_{1-8}$alkyl, substituted or unsubstituted $C_{3-12}$cycloalkyl, substituted or unsubstituted $C_{6-14}$aryl, substituted or unsubstituted 3-15 membered heterocyclyl, and substituted or unsubstituted 5-14 membered heteroaryl;
each occurrence of $R^2$ and $R^3$, which may be the same or different, are independently selected from hydrogen, halogen, nitro, cyano, hydroxyl, substituted or unsubstituted $C_{1-8}$alkyl, substituted or unsubstituted $C_{1-8}$alkoxy, substituted or unsubstituted halo$C_{1-8}$alkyl, substituted or unsubstituted hydroxy$C_{1-8}$alkyl, substituted or unsubstituted $C_{3-12}$cycloalkyl and substituted or unsubstituted $C_{3-8}$cycloalkyl$C_{1-8}$alkyl;
at each occurrence, $R^4$ is independently selected from halogen, nitro, cyano, hydroxyl, substituted or unsubstituted $C_{1-8}$alkyl, substituted or unsubstituted $C_{1-8}$alkoxy, substituted or unsubstituted $C_{1-8}$alkoxy$C_{1-8}$alkyl, substituted or unsubstituted halo$C_{1-8}$alkyl, substituted or unsubstituted hydroxy$C_{1-8}$alkyl, substituted or unsubstituted $C_{3-12}$cycloalkyl and substituted or unsubstituted $C_{3-8}$cycloalkyl$C_{1-8}$alkyl:
at each occurrence, $R^c$ is independently selected from substituted or unsubstituted $C_{1-8}$alkyl and substituted or unsubstituted $C_{6-14}$aryl$C_{1-8}$alkyl; or $R^c$ and $R^1$, together with the N to which they are attached, form a morpholine ring;
each occurrence of $R^x$ and $R^y$, which may be the same or different, are independently selected from hydrogen, substituted or unsubstituted $C_{1-8}$alkyl and substituted or unsubstituted $C_{6-14}$aryl$C_{1-8}$alkyl; and
'n' is an integer ranging from 1 to 4, both inclusive.

2. The compound according to claim 1, wherein Y is O or NH.

3. The compound according to claim 1, wherein $Z^1$ is N, $Z^3$ is CH and $G^1$ is CH.

4. The compound according to claim 1, wherein $Z^1$, $Z^3$ are N and $G^1$ is CH.

5. The compound according to claim 1, wherein $Z^1$ is CH, $Z^3$ is N and $G^1$ is CH.

6. The compound according to claim 1, wherein $R^2$ is hydrogen, methyl or trifluoromethyl.

7. The compound according to claim 1, wherein $R^3$ is hydrogen or methyl.

8. The compound according to claim 1, wherein $Q^1$ is N, CH or $CR^4$, $Q^2$ is CH or $CR^4$, $Q^3$ is N or CH, and $Q^4$ is $CR^4$.

9. The compound according to claim 1, wherein $R^4$ is $OCH_3$, $CH_3$, $CHF_2$, Cl or F.

10. The compound according to claim 1, wherein $R^x$ and $R^y$ are hydrogen.

11. The compound according to claim 1, wherein 'n' is 1.

12. The compound according to claim 1, wherein $R^1$ is methyl, ethyl, isopropyl, tert-butyl, 2,2,2-trifluoroethyl, 3-(trifluoromethyl)phenyl, 4-(trifluoromethyl)phenyl, 2-fluoro-5-(trifluoromethyl)phenyl, 4-fluoro-3-(trifluoromethyl)phenyl, 2-fluoro-4-(trifluoromethyl)phenyl, 6-(trifluoromethyl)pyridin-3-yl, 4,4-difluorocyclohexyl, 4,4-dimethylcyclohexyl, 4-(trifluoromethyl)cyclohexyl, (1s,4s)-4-(trifluoromethyl)cyclohexyl or (1r,4r)-4-(trifluoromethyl)cyclohexyl.

13. The compound according to claim 1, wherein W is isopropyl, tert-butyl, 1-fluoro-2-methylpropan-2-yl, 1-hydroxy-2-methylpropan-2-yl, tetrahydrofuranyl or (S)-tetrahydrofuran-2-yl.

14. A compound of the formula (III):

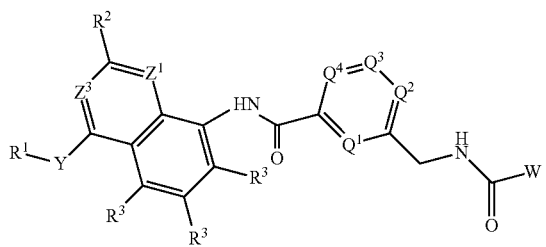

(III)

or a pharmaceutically acceptable salt thereof,
wherein
Y is selected from NH and O;
$Z^1$ and $Z^3$, which may be same or different, are independently selected from N and $CR^2$; with a proviso that at least one of $Z^1$ and $Z^3$ is N;
$Q^1$, $Q^2$, $Q^3$ and $Q^4$, which may be same or different, are independently selected from N, CH and $CR^4$; with a proviso that $Q^2$, $Q^3$ and $Q^4$ are not N simultaneously;
W is selected from substituted or unsubstituted $C_{1-8}$alkyl, substituted or unsubstituted $C_{1-8}$alkoxy$C_{1-8}$alkyl, substituted or unsubstituted halo$C_{1-8}$alkyl, substituted or unsubstituted hydroxy$C_{1-8}$alkyl, substituted or unsubstituted $C_{3-12}$cycloalkyl and substituted or unsubstituted tetrahydrofuryl or tetrahydrofuranyl;
$R^1$ is selected from substituted or unsubstituted $C_{1-8}$alkyl, substituted or unsubstituted $C_{1-8}$alkoxy$C_{1-8}$alkyl, substituted or unsubstituted halo$C_{1-8}$alkyl, substituted or unsubstituted hydroxy$C_{1-8}$alkyl, substituted or unsubstituted $C_{3-12}$cycloalkyl, substituted or unsubstituted $C_{6-14}$aryl, substituted or unsubstituted 3-15 membered heterocyclyl, and substituted or unsubstituted 5-14 membered heteroaryl;
each occurrence of $R^2$ and $R^3$, which may be the same or different, are independently selected from hydrogen, halogen, hydroxyl, substituted or unsubstituted $C_{1-8}$alkyl, substituted or unsubstituted $C_{1-8}$alkoxy and substituted or unsubstituted halo$C_{1-8}$alkyl; and
at each occurrence, $R^4$ is independently selected from halogen, nitro, cyano, hydroxyl, substituted or unsubstituted $C_{1-8}$alkyl, substituted or unsubstituted $C_{1-8}$alkoxy, substituted or unsubstituted halo$C_{1-8}$alkyl, and substituted or unsubstituted $C_{3-12}$cycloalkyl.

15. The compound according to claim 14, wherein $Z^1$ is N and $Z^3$ is CH or N.

16. The compound according to claim 14, wherein $Z^1$ is CH and $Z^3$ is N.

17. The compound according to claim 14, wherein $R^2$ is hydrogen, methyl or trifluoromethyl.

18. The compound according to claim 14, wherein $R^3$ is hydrogen or methyl.

19. The compound according to claim 14, wherein $Q^1$ is N, CH or $CR^4$, $Q^2$ is CH or $CR^4$, $Q^3$ is N or CH, and $Q^4$ is $CR^4$.

20. The compound according to claim 14, wherein $R^4$ is $OCH_3$, $CH_3$, $CHF_2$, Cl or F.

21. The compound according to claim 14, wherein $R^1$ is methyl, ethyl, isopropyl, tert-butyl, 2,2,2-trifluoroethyl, 3-(trifluoromethyl)phenyl, 4-(trifluoromethyl)phenyl, 2-fluoro-5-(trifluoromethyl)phenyl, 4-fluoro-3-(trifluoromethyl)phenyl, 2-fluoro-4-(trifluoromethyl)phenyl, 6-(trifluoromethyl)pyridin-3-yl, 4,4-difluorocyclohexyl, 4,4-dimethylcyclohexyl, 4-(trifluoromethyl)cyclohexyl, (1s,4s)-4-(trifluoromethyl)cyclohexyl or (1r,4r)-4-(trifluoromethyl)cyclohexyl.

22. The compound according to claim 14, wherein W is isopropyl, tert-butyl, 1-fluoro-2-methylpropan-2-yl, 1-hydroxy-2-methylpropan-2-yl, tetrahydrofuranyl or (S)-tetrahydrofuran-2-yl.

23. A compound selected from
6-Chloro-2-fluoro-3-(pivalamidomethyl)-N-(1-((3-(trifluoromethyl)phenyl)amino)isoquinolin-5-yl)benzamide;
3-Chloro-6-(pivalamidomethyl)-N-(1-((3-(trifluoromethyl)phenyl)amino)isoquinolin-5-yl)picolinamide;
2,6-Dimethyl-3-(pivalamidomethyl)-N-(1-((3-(trifluoromethyl)phenyl)amino)isoquinolin-5-yl)benzamide;
2-Chloro-5-(pivalamidomethyl)-N-(1-((3-(trifluoromethyl)phenyl)amino)isoquinolin-5-yl)benzamide;
6-Chloro-2-fluoro-3-(pivalamidomethyl)-N-(1-(3-(trifluoromethyl)phenoxy)isoquinolin-5-yl)benzamide;
3-Chloro-6-(pivalamidomethyl)-N-(1-(3-(trifluoromethyl)phenoxy)isoquinolin-5-yl)picolinamide;
2-Chloro-5-(pivalamidomethyl)-N-(1-(3-(trifluoromethyl)phenoxy)isoquinolin-5-yl)benzamide;
3-Chloro-6-(pivalamidomethyl)-N-(4-((3-(trifluoromethyl)phenyl)amino)quinazolin-8-yl)picolinamide;
3-Chloro-6-(pivalamidomethyl)-N-(4-(3-(trifluoromethyl)phenoxy)quinazolin-8-yl)picolinamide;
2-Chloro-5-(pivalamidomethyl)-N-(4-(3-(trifluoromethyl)phenoxy)quinazolin-8-yl)benzamide;
6-Chloro-2-fluoro-3-(pivalamidomethyl)-N-(4-(3-(trifluoromethyl)phenoxy)quinazolin-8-yl)benzamide;
6-Chloro-2-fluoro-3-(pivalamidomethyl)-N-(4-((3-(trifluoromethyl)phenyl)amino)quinazolin-8-yl)benzamide;
2-Chloro-5-(pivalamidomethyl)-N-(4-((3-(trifluoromethyl)phenyl)amino)quinazolin-8-yl)benzamide;

2-Chloro-N-(4-((4,4-difluorocyclohexyl)amino)quinazolin-8-yl)-5-(pivalamidomethyl)benzamide;
2-Chloro-N-(4-((4,4-dimethylcyclohexyl)oxy)quinazolin-8-yl)-5-(pivalamidomethyl)benzamide;
2-Chloro-5-(pivalamidomethyl)-N-(4-(3-(trifluoromethyl)phenoxy)quinolin-8-yl)benzamide;
3-Chloro-6-(pivalamidomethyl)-N-(4-(3-(trifluoromethyl)phenoxy)quinolin-8-yl)picolinamide;
6-Chloro-2-fluoro-3-(pivalamidomethyl)-N-(4-(3-(trifluoromethyl)phenoxy)quinolin-8-yl)benzamide;
2-Chloro-5-(pivalamidomethyl)-N-(8-((3-(trifluoromethyl)phenyl)amino)quinolin-4-yl)benzamide;
6-Chloro-N-(4-((4,4-difluorocyclohexyl)amino)quinazolin-8-yl)-2-fluoro-3-(pivalamidomethyl)benzamide;
6-Chloro-2-fluoro-N-(4-((2-fluoro-5-(trifluoromethyl)phenyl)amino)quinazolin-8-yl)-3-(pivalamidomethyl)benzamide;
6-Chloro-N-(4-((4,4-dimethylcyclohexyl)amino)quinazolin-8-yl)-2-fluoro-3-(pivalamidomethyl)benzamide;
(S)—N-(4-Chloro-2-fluoro-3-((4-((3-(trifluoromethyl)phenyl)amino)quinazolin-8-yl)carbamoyl)benzyl)tetrahydrofuran-2-carboxamide;
6-Chloro-N-(4-((4,4-dimethylcyclohexyl)oxy)quinazolin-8-yl)-2-fluoro-3-(pivalamidomethyl)benzamide;
6-Chloro-2-fluoro-N-(4-((4-fluoro-3-(trifluoromethyl)phenyl)amino)quinazolin-8-yl)-3-(pivalamidomethyl)benzamide;
6-Chloro-2-fluoro-3-(pivalamidomethyl)-N-(4-(((1s,4s)-4-(trifluoromethyl)cyclohexyl)oxy)quinazolin-8-yl)benzamide;
6-Chloro-2-fluoro-3-(pivalamidomethyl)-N-(4-(((1r,4r)-4-(trifluoromethyl)cyclohexyl)oxy)quinazolin-8-yl)benzamide;
6-Chloro-2-fluoro-N-(4-(2-fluoro-5-(trifluoromethyl)phenoxy)quinazolin-8-yl)-3-(pivalamidomethyl)benzamide;
6-Chloro-2-fluoro-N-(4-((2-fluoro-4-(trifluoromethyl)phenyl)amino)quinazolin-8-yl)-3-(pivalamidomethyl)benzamide;
6-Chloro-2-fluoro-3-(pivalamidomethyl)-N-(4-((6-(trifluoromethyl)pyridin-3-yl)amino)quinazolin-8-yl)benzamide;
6-Chloro-2-fluoro-3-(pivalamidomethyl)-N-(4-((3-(trifluoromethyl)phenyl)amino)quinolin-8-yl)benzamide;
6-Chloro-N-(4-((4,4-dimethylcyclohexyl)amino)-2-(trifluoromethyl)quinazolin-8-yl)-2-fluoro-3-(pivalamidomethyl)benzamide;
6-Chloro-2-fluoro-N-(2-methyl-4-((3-(trifluoromethyl)phenyl)amino)quinazolin-8-yl)-3-(pivalamidomethyl)benzamide;
6-Chloro-N-(1-((4,4-dimethylcyclohexyl)oxy)isoquinolin-5-yl)-2-fluoro-3-(pivalamidomethyl)benzamide;
6-Chloro-2-fluoro-3-(pivalamidomethyl)-N-(1-(((1r,4r)-4-(trifluoromethyl)cyclohexyl)amino)isoquinolin-5-yl)benzamide;
6-Chloro-2-fluoro-3-(pivalamidomethyl)-N-(4-(((1r,4r)-4-(trifluoromethyl)cyclohexyl)amino)quinazolin-8-yl)benzamide;
2-Chloro-5-(pivalamidomethyl)-N-(1-(((1r,4r)-4-(trifluoromethyl)cyclohexyl)oxy)isoquinolin-5-yl)benzamide;
2-Chloro-5-(pivalamidomethyl)-N-(4-(((1r,4r)-4-(trifluoromethyl)cyclohexyl)oxy)quinazolin-8-yl)benzamide;
6-Chloro-2-fluoro-N-(4-(2-fluoro-5-(trifluoromethyl)phenoxy)quinolin-8-yl)-3-(pivalamidomethyl)benzamide;
2-Chloro-N-(1-(2-fluoro-5-(trifluoromethyl)phenoxy)isoquinolin-5-yl)-5-(pivalamidomethyl)benzamide;
6-Chloro-2-fluoro-N-(7-methyl-4-((3-(trifluoromethyl)phenyl)amino)quinazolin-8-yl)-3-(pivalamidomethyl)benzamide;
6-Chloro-N-(4-ethoxyquinazolin-8-yl)-2-fluoro-3-(pivalamidomethyl)benzamide;
2-Chloro-N-(1-((2-fluoro-4-(trifluoromethyl)phenyl)amino)isoquinolin-5-yl)-5-(pivalamidomethyl)benzamide;
2-Chloro-5-(pivalamidomethyl)-N-(1-((4-(trifluoromethyl)phenyl)amino)isoquinolin-5-yl)benzamide;
2-Chloro-5-(pivalamidomethyl)-N-(1-(4-(trifluoromethyl)phenoxy)isoquinolin-5-yl)benzamide;
2-Chloro-5-(pivalamidomethyl)-N-(1-(((1s,4s)-4-(trifluoromethyl)cyclohexyl)oxy)isoquinolin-5-yl)benzamide;
2-Chloro-N-(1-(4-fluoro-3-(trifluoromethyl)phenoxy)isoquinolin-5-yl)-5-(pivalamidomethyl)benzamide;
6-Chloro-2-methoxy-3-(pivalamidomethyl)-N-(4-(3-(trifluoromethyl)phenoxy)quinazolin-8-yl)benzamide;
6-Chloro-2-fluoro-3-(pivalamidomethyl)-N-(1-(((1r,4r)-4-(trifluoromethyl)cyclohexyl)oxy)isoquinolin-5-yl)benzamide;
6-Chloro-2-fluoro-N-(4-(4-fluoro-3-(trifluoromethyl)phenoxy)quinolin-8-yl)-3-(pivalamidomethyl)benzamide;
6-Chloro-2-fluoro-N-(4-(4-fluoro-3-(trifluoromethyl)phenoxy)quinazolin-8-yl)-3-(pivalamidomethyl)benzamide;
6-Chloro-2-fluoro-3-(pivalamidomethyl)-N-(4-(4-(trifluoromethyl)phenoxy)quinolin-8-yl)benzamide;
6-Chloro-N-(4-((4,4-dimethylcyclohexyl)amino)-2-methylquinazolin-8-yl)-2-fluoro-3-(pivalamidomethyl)benzamide;
6-Chloro-2-fluoro-N-(2-methyl-4-(3-(trifluoromethyl)phenoxy)quinazolin-8-yl)-3-(pivalamidomethyl)benzamide;
6-Chloro-2-fluoro-N-(4-(isopropylamino)-2-methylquinazolin-8-yl)-3-(pivalamidomethyl)benzamide;
6-Chloro-2-fluoro-N-(2-methyl-4-morpholinoquinazolin-8-yl)-3-(pivalamidomethyl)benzamide;
6-Chloro-2-fluoro-N-(4-isopropoxyquinazolin-8-yl)-3-(pivalamidomethyl)benzamide;
6-Chloro-N-(4-((4,4-difluorocyclohexyl)amino)-2-methylquinazolin-8-yl)-2-fluoro-3-(pivalamidomethyl)benzamide;
6-Chloro-N-(4-(dimethylamino)quinazolin-8-yl)-2-fluoro-3-(pivalamidomethyl)benzamide;
N-(4-(tert-Butylamino)quinazolin-8-yl)-6-chloro-2-fluoro-3-(pivalamidomethyl)benzamide;
6-Chloro-N-(4-ethoxyquinolin-8-yl)-2-fluoro-3-(pivalamidomethyl)benzamide;
6-Chloro-2-fluoro-N-(4-(isopropylamino)quinazolin-8-yl)-3-(pivalamidomethyl)benzamide;
N-(4-(tert-Butylamino)-2-methylquinazolin-8-yl)-6-chloro-2-fluoro-3-(pivalamidomethyl)benzamide;
6-Chloro-2-fluoro-3-((3-hydroxy-2,2-dimethylpropanamido)methyl)-N-(4-(3-(trifluoromethyl)phenoxy)quinazolin-8-yl)benzamide;
N-(4-(tert-Butylamino)quinazolin-8-yl)-2-chloro-5-(pivalamidomethyl)benzamide;
N-(4-(tert-Butylamino)quinazolin-8-yl)-2,6-dimethyl-3-(pivalamidomethyl)benzamide;
N-(4-(tert-Butylamino)quinazolin-8-yl)-6-chloro-2-fluoro-3-((3-hydroxy-2,2-dimethylpropanamido)methyl)benzamide;
N-(4-(tert-Butylamino)quinazolin-8-yl)-6-chloro-2-fluoro-3-(isobutyramidomethyl)benzamide;

N-(4-(tert-Butylamino)quinazolin-8-yl)-2-chloro-4-fluoro-5-(pivalamidomethyl)benzamide;

N-(4-(tert-Butylamino)quinazolin-8-yl)-2-chloro-4-fluoro-3-(pivalamidomethyl)benzamide;

6-Chloro-2-fluoro-3-(isobutyramidomethyl)-N-(4-((2,2,2-trifluoroethyl)amino)quinazolin-8-yl)benzamide;

2-(Difluoromethyl)-5-(isobutyramidomethyl)-N-(4-(3-(trifluoromethyl)phenoxy)quinazolin-8-yl)nicotinamide;

N-(4-(tert-Butylamino)quinazolin-8-yl)-2-(difluoromethyl)-5-(isobutyramidomethyl)nicotinamide;

2-(Difluoromethyl)-5-(isobutyramidomethyl)-N-(4-(isopropylamino)quinazolin-8-yl)nicotinamide;

6-Chloro-2-fluoro-3-(isobutyramidomethyl)-N-(4-(isopropylamino)quinazolin-8-yl)benzamide;

2-(Difluoromethyl)-5-(isobutyramidomethyl)-N-(4-((2,2,2-trifluoroethyl)amino)quinazolin-8-yl)nicotinamide;

N-(4-(tert-Butylamino)quinazolin-8-yl)-6-chloro-2-fluoro-3-((3-fluoro-2,2-dimethylpropanamido)methyl)benzamide;

2-(Difluoromethyl)-N-(4-(4-fluoro-3-(trifluoromethyl)phenoxy)quinolin-8-yl)-5-(isobutyramidomethyl)nicotinamide;

and pharmaceutically acceptable salts thereof.

24. A compound of the formula

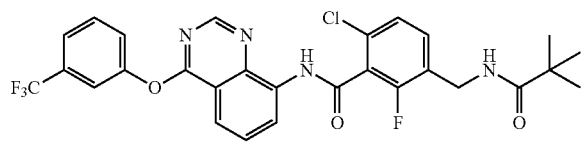

or a pharmaceutically acceptable salt thereof.

25. A compound of the formula

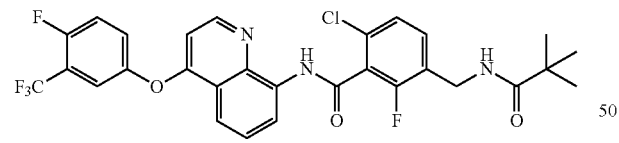

or a pharmaceutically acceptable salt thereof.

26. A compound of the formula

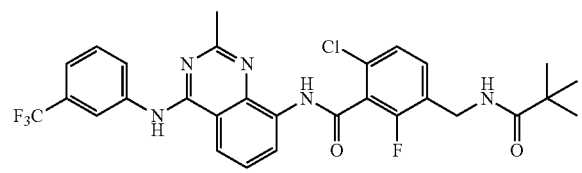 [SMILES: Cc1nc(Nc2cccc(C(F)(F)F)c2)c2cccc(NC(=O)c3c(Cl)ccc(CNC(=O)C(C)(C)C)c3F)c2n1]

or a pharmaceutically acceptable salt thereof.

27. A compound of the formula

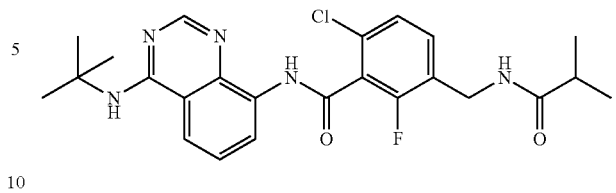

or a pharmaceutically acceptable salt thereof.

28. A compound of the formula

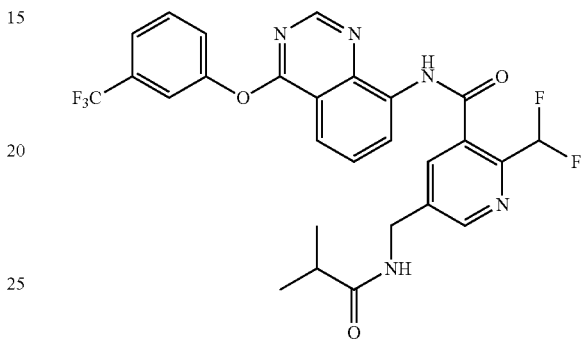

or a pharmaceutically acceptable salt thereof.

29. A compound of the formula

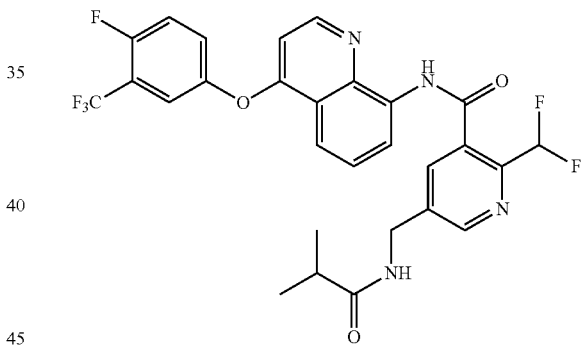

or a pharmaceutically acceptable salt thereof.

30. A compound selected from
 4-(3-(Trifluoromethyl)phenoxy)quinazolin-8-amine;
 $N^4$-(3-(Trifluoromethyl)phenyl)quinazoline-4,8-diamine;
 4-(4-Fluoro-3-(trifluoromethyl)phenoxy)quinolin-8-amine;
 2-Methyl-$N^4$-(3-(trifluoromethyl)phenyl)quinazoline-4,8-diamine;
and pharmaceutically acceptable salts thereof.

31. A compound selected from
 8-nitro-4-(3-(trifluoromethyl)phenoxy)quinazoline;
 8-nitro-N-(3-(trifluoromethyl)phenyl)quinazolin-4-amine;
 4-(4-fluoro-3-(trifluoromethyl)phenoxy)-8-nitroquinoline;
 2-methyl-8-nitro-N-(3-(trifluoromethyl)phenyl)quinazolin-4-amine;
and pharmaceutically acceptable salts thereof.

32. A compound selected from
 2-Chloro-6-fluoro-N-(4-((2-fluoro-5-(trifluoromethyl)phenyl)amino)quinazolin-8-yl)benzamide;

6-Chloro-2-fluoro-3-(pivalamidomethyl)-N-(quinolin-8-yl)benzamide;
tert-Butyl 4-chloro-2-fluoro-3-((4-((3-(trifluoromethyl)phenyl)amino)quinazolin-8-yl)carbamoyl)benzylcarbamate;
$N^1$-(3-(Trifluoromethyl)phenyl)isoquinoline-1,5-diamine;
5-Nitro-N-(3-(trifluoromethyl)phenyl)isoquinolin-1-amine;
1-(3-(Trifluoromethyl)phenoxy)isoquinolin-5-amine;
5-Nitro-1-(3-(trifluoromethyl)phenoxy)isoquinoline;
$N^4$-(3-(Trifluoromethyl)phenyl)quinazoline-4,8-diamine;
8-Nitro-N-(3-(trifluoromethyl)phenyl)quinazolin-4-amine;
4-(3-(Trifluoromethyl)phenoxy)quinazolin-8-amine;
8-Nitro-4-(3-(trifluoromethyl)phenoxy)quinazoline;
$N^4$-(4,4-Difluorocyclohexyl)quinazoline-4,8-diamine;
N-(4,4-Difluorocyclohexyl)-8-nitroquinazolin-4-amine;
4-((4,4-Dimethylcyclohexyl)oxy)quinazolin-8-amine;
4-((4,4-Dimethylcyclohexyl)oxy)-8-nitroquinazoline;
4-(3-(Trifluoromethyl)phenoxy)quinolin-8-amine;
8-Nitro-4-(3-(trifluoromethyl)phenoxy)quinoline;
$N^8$-(3-(Trifluoromethyl)phenyl)quinoline-4,8-diamine;
$N^4$-(4-Methoxybenzyl)-$N^8$-(3-(trifluoromethyl)phenyl)quinoline-4,8-diamine;
$N^4$-(2-Fluoro-5-(trifluoromethyl)phenyl)quinazoline-4,8-diamine;
N-(2-Fluoro-5-(trifluoromethyl)phenyl)-8-nitroquinazolin-4-amine;
$N^4$-(4,4-Dimethylcyclohexyl)quinazoline-4,8-diamine;
N-(4,4-Dimethylcyclohexyl)-8-nitroquinazolin-4-amine;
$N^4$-(4-Fluoro-3-(trifluoromethyl)phenyl)quinazoline-4,8-diamine;
N-(4-Fluoro-3-(trifluoromethyl)phenyl)-8-nitroquinazolin-4-amine;
8-Nitro-4-(((1s,4s)-4-(trifluoromethyl)cyclohexyl)oxy)quinazoline;
8-Nitro-4-(((1r,4r)-4-(trifluoromethyl)cyclohexyl)oxy)quinazoline;
4-(((1s,4s)-4-(Trifluoromethyl)cyclohexyl)oxy)quinazolin-8-amine;
4-(((1r,4r)-4-(Trifluoromethyl)cyclohexyl)oxy)quinazolin-8-amine;
4-(2-Fluoro-5-(trifluoromethyl)phenoxy)quinazolin-8-amine;
4-(2-Fluoro-5-(trifluoromethyl)phenoxy)-8-nitroquinazoline;
$N^4$-(2-Fluoro-4-(trifluoromethyl)phenyl)quinazoline-4,8-diamine;
N-(2-Fluoro-4-(trifluoromethyl)phenyl)-8-nitroquinazolin-4-amine;
$N^4$-(6-(Trifluoromethyl)pyridin-3-yl)quinazoline-4,8-diamine;
8-Nitro-N-(6-(trifluoromethyl)pyridin-3-yl)quinazolin-4-amine;
$N^4$-(3-(Trifluoromethyl)phenyl)quinoline-4,8-diamine;
8-Nitro-N-(3-(trifluoromethyl)phenyl)quinolin-4-amine;
$N^4$-(4,4-Dimethylcyclohexyl)-2-(trifluoromethyl)quinazoline-4,8-diamine;
N-(4,4-Dimethylcyclohexyl)-8-nitro-2-(trifluoromethyl)quinazolin-4-amine;
2-Methyl-$N^4$-(3-(trifluoromethyl)phenyl)quinazoline-4,8-diamine;
2-Methyl-8-nitro-N-(3-(trifluoromethyl)phenyl)quinazolin-4-amine;
1-((4,4-Dimethylcyclohexyl)oxy)isoquinolin-5-amine;
1-((4,4-Dimethylcyclohexyl)oxy)-5-nitroisoquinoline;
$N^1$-((1r,4r)-4-(Trifluoromethyl)cyclohexyl)isoquinoline-1,5-diamine;
5-Nitro-N-((1r,4r)-4-(trifluoromethyl)cyclohexyl)isoquinolin-1-amine;
$N^4$-((1r,4r)-4-(Trifluoromethyl)cyclohexyl)quinazoline-4,8-diamine;
8-Nitro-N-((1r,4r)-4-(trifluoromethyl)cyclohexyl)quinazolin-4-amine;
5-Nitro-1-(((1r,4r)-4-(trifluoromethyl)cyclohexyl)oxy)isoquinoline;
5-Nitro-1-(((1s,4s)-4-(trifluoromethyl)cyclohexyl)oxy)isoquinoline;
1-(((1r,4r)-4-(Trifluoromethyl)cyclohexyl)oxy)isoquinolin-5-amine;
1-(((1s,4s)-4-(Trifluoromethyl)cyclohexyl)oxy)isoquinolin-5-amine;
4-(2-Fluoro-5-(trifluoromethyl)phenoxy)quinolin-8-amine;
4-(2-Fluoro-5-(trifluoromethyl)phenoxy)-8-nitroquinoline;
1-(2-Fluoro-5-(trifluoromethyl)phenoxy)isoquinolin-5-amine;
1-(2-Fluoro-5-(trifluoromethyl)phenoxy)-5-nitroisoquinoline;
4-Ethoxyquinazolin-8-amine;
4-Ethoxy-8-nitroquinazoline;
$N^1$-(2-Fluoro-4-(trifluoromethyl)phenyl)isoquinoline-1,5-diamine;
N-(2-Fluoro-4-(trifluoromethyl)phenyl)-5-nitroisoquinolin-1-amine;
$N^1$-(4-(Trifluoromethyl)phenyl)isoquinoline-1,5-diamine;
5-Nitro-N-(4-(trifluoromethyl)phenyl)isoquinolin-1-amine;
1-(4-(Trifluoromethyl)phenoxy)isoquinolin-5-amine;
5-Nitro-1-(4-(trifluoromethyl)phenoxy)isoquinoline;
1-(4-Fluoro-3-(trifluoromethyl)phenoxy)isoquinolin-5-amine;
1-(4-fluoro-3-(trifluoromethyl)phenoxy)-5-nitroisoquinoline;
4-(4-Fluoro-3-(trifluoromethyl)phenoxy)quinolin-8-amine;
4-(4-Fluoro-3-(trifluoromethyl)phenoxy)-8-nitroquinoline;
4-(4-Fluoro-3-(trifluoromethyl)phenoxy)quinazolin-8-amine;
4-(4-Fluoro-3-(trifluoromethyl)phenoxy)-8-nitroquinazoline;
4-(4-(Trifluoromethyl)phenoxy)quinolin-8-amine;
8-Nitro-4-(4-(trifluoromethyl)phenoxy)quinoline;
$N^4$-(4,4-Dimethylcyclohexyl)-2-methylquinazoline-4,8-diamine;
N-(4,4-Dimethylcyclohexyl)-2-methyl-8-nitroquinazolin-4-amine;
2-Methyl-4-(3-(trifluoromethyl)phenoxy)quinazolin-8-amine;
2-Methyl-8-nitro-4-(3-(trifluoromethyl)phenoxy)quinazoline;
$N^4$-Isopropyl-2-methylquinazoline-4,8-diamine;
N-Isopropyl-2-methyl-8-nitroquinazolin-4-amine;
2-Methyl-4-morpholinoquinazolin-8-amine;
4-(2-Methyl-8-nitroquinazolin-4-yl)morpholine;
4-Isopropoxyquinazolin-8-amine;
4-Isopropoxy-8-nitroquinazoline;
$N^4$-(4,4-Difluorocyclohexyl)-2-methylquinazoline-4,8-diamine;

N-(4,4-Difluorocyclohexyl)-2-methyl-8-nitroquinazolin-4-amine;
$N^4$-(tert-Butyl)quinazoline-4,8-diamine;
N-(tert-Butyl)-8-nitroquinazolin-4-amine;
$N^4$-Isopropylquinazoline-4,8-diamine;
N-Isopropyl-8-nitroquinazolin-4-amine;
$N^4$-(tert-Butyl)-2-methylquinazoline-4,8-diamine;
N-(tert-Butyl)-2-methyl-8-nitroquinazolin-4-amine;
$N^4$-(2,2,2-Trifluoroethyl)quinazoline-4,8-diamine;
8-nitro-N-(2,2,2-trifluoroethyl)quinazolin-4-amine;
3-Chloro-6-(pivalamidomethyl)picolinic acid;
2,6-Dimethyl-3-(pivalamidomethyl)benzoic acid;
6-Chloro-2-methoxy-3-(pivalamidomethyl)benzoic acid;
and pharmaceutically acceptable salts thereof.

33. A pharmaceutical composition comprising a compound according to claim 1 and a pharmaceutically acceptable excipient.

34. The pharmaceutical composition according to claim 33, wherein the pharmaceutically acceptable excipient is a carrier or diluent.

35. A method of treating a mPGES-1 mediated disease, disorder or syndrome in a subject comprising administering an effective amount of a compound according to claim 1.

36. A method of treatment of disease, disorder, syndrome or condition selected from the group consisting of inflammation, asthma, chronic obstructive pulmonary disease, pulmonary fibrosis, inflammatory bowel disease, irritable bowel syndrome, pain, inflammatory pain, chronic pain, acute pain, fever, migraine, headache, low back pain, fibromyalgia, myofascial disorders, viral infections, influenza, common cold, herpes zoster, hepatitis C, AIDS, bacterial infections, fungal infections, dysmenorrhea, burns, surgical or dental procedures, malignancies hyperprostaglandin E syndrome, classic Bartter syndrome, synovitis, atherosclerosis, gout, arthritis, osteoarthritis, juvenile arthritis, rheumatoid arthritis, juvenile onset rheumatoid arthritis, rheumatic fever, ankylosing spondylitis, Hodgkin's disease, systemic lupus erythematosus, vasculitis, pancreatitis, nephritis, bursitis, conjunctivitis, iritis, scleritis, uveitis, wound healing, dermatitis, eczema, psoriasis, stroke, diabetes mellitus, cancer, neurodegenerative disorders such as Alzheimer's disease, Parkinson's disease, Amyotrophic lateral sclerosis and multiple sclerosis, autoimmune diseases, allergic disorders, rhinitis, ulcers, mild to moderately active ulcerative colitis, familial adenomatous polyposis, coronary heart disease, and sarcoidosis comprising administering a compound according to claim 1.

37. The method according to claim 36, wherein the disease, disorder, syndrome or condition is pain.

38. The method according to claim 36, wherein the disease, disorder, syndrome or condition is chronic or acute pain.

39. The method according to claim 36, wherein the disease, disorder, syndrome or condition is rheumatoid arthritic pain or osteoarthritic pain.

40. The method according to claim 36, wherein the disease, disorder, syndrome or condition is inflammation.

41. The method according to claim 36, wherein the disease, disorder, syndrome or condition is neurodegenerative disorders selected from Parkinson's disease, Alzheimer's disease and amyotrophic lateral sclerosis.

42. A method of treating, preventing or managing cancer comprising administering to a subject in need of such treatment an effective amount of a compound according to claim 1.

* * * * *